(12) United States Patent
Ahmed et al.

(10) Patent No.: US 12,064,217 B2
(45) Date of Patent: Aug. 20, 2024

(54) REMOTE PATIENT MANAGEMENT AND MONITORING SYSTEMS AND METHODS

(71) Applicant: Masimo Corporation, Irvine, CA (US)

(72) Inventors: Omar Ahmed, Mission Viejo, CA (US); Nicholas Evan Barker, Laguna Beach, CA (US); Keith Ward Indorf, Riverside, CA (US); Sungwhan Cha, Santiago (CL); Sebastian T. Frey, Laguna Niguel, CA (US); Hyejin Cho, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 126 days.

(21) Appl. No.: 17/207,447

(22) Filed: Mar. 19, 2021

(65) Prior Publication Data
US 2021/0290080 A1    Sep. 23, 2021

Related U.S. Application Data

(60) Provisional application No. 63/106,273, filed on Oct. 27, 2020, provisional application No. 63/065,961, (Continued)

(51) Int. Cl.
*A61B 5/00* (2006.01)
*A61B 5/01* (2006.01)
(Continued)

(52) U.S. Cl.
CPC ........ *A61B 5/02055* (2013.01); *A61B 5/0004* (2013.01); *A61B 5/0008* (2013.01);
(Continued)

(58) Field of Classification Search
CPC .............. A61B 5/02055; A61B 5/0816; A61B 5/14542; A61B 5/746
See application file for complete search history.

(56) References Cited

U.S. PATENT DOCUMENTS 4,960,128 A   10/1990   Gordon et al.
4,964,408 A   10/1990   Hink et al.
(Continued)

FOREIGN PATENT DOCUMENTS

JP    2017-518834      7/2017
WO    WO 2017/139761   8/2017
(Continued)

OTHER PUBLICATIONS

Jin YH, et al., A rapid advice guideline for the diagnosis and treatment of 2019 novel coronavirus (2019-nCoV) infected pneumonia (standard version). Mil Med Res. Feb. 6, 2020;7(1):4. doi: 10.1186/s40779-020-0233-6. PMID: 32029004; PMCID: PMC7003341. (Year: 2020).*

(Continued)

*Primary Examiner* — Evangeline Barr
(74) *Attorney, Agent, or Firm* — Knobbe, Martens, Olson & Bear, LLP

(57) ABSTRACT

Systems and methods are provided for remote patient management and monitoring. The patient is monitored with a wireless sensor system connected to an application executing on a patient user computing device. The system continuously monitors physiological parameters, such as, but not limited to, blood oxygen saturation ($SpO_2$), pulse rate, perfusion index, pleth variability index, and/or respiration rate from the photoplethysmograph. The system triggers alarms if the patient physiological data violates thresholds. Care providers review patient data and associated alarm(s) with graphical user interfaces.

13 Claims, 91 Drawing Sheets

Related U.S. Application Data filed on Aug. 14, 2020, provisional application No. 63/056,925, filed on Jul. 27, 2020, provisional application No. 63/049,478, filed on Jul. 8, 2020, provisional application No. 63/010,669, filed on Apr. 15, 2020, provisional application No. 62/992,779, filed on Mar. 20, 2020, provisional application No. 62/992,808, filed on Mar. 20, 2020.

(51) Int. Cl.

| | |
|---|---|
| *A61B 5/0205* | (2006.01) |
| *A61B 5/08* | (2006.01) |
| *A61B 5/145* | (2006.01) |
| *G06F 9/451* | (2018.01) |
| *G16H 10/60* | (2018.01) |
| *G16H 15/00* | (2018.01) |
| *G16H 40/20* | (2018.01) |
| *G16H 40/67* | (2018.01) |
| *G16H 50/20* | (2018.01) |
| *G16H 50/30* | (2018.01) |
| *G16H 50/70* | (2018.01) |
| *G16H 50/80* | (2018.01) |
| *H04B 17/318* | (2015.01) |
| *H04W 4/021* | (2018.01) |
| *A61B 5/024* | (2006.01) |
| *A61B 5/026* | (2006.01) |
| *A61B 5/1455* | (2006.01) |
| *G06F 3/04842* | (2022.01) |

(52) U.S. Cl.
CPC .......... *A61B 5/002* (2013.01); *A61B 5/0022* (2013.01); *A61B 5/01* (2013.01); *A61B 5/0205* (2013.01); *A61B 5/08* (2013.01); *A61B 5/0816* (2013.01); *A61B 5/14542* (2013.01); *A61B 5/6801* (2013.01); *A61B 5/6814* (2013.01); *A61B 5/6823* (2013.01); *A61B 5/6824* (2013.01); *A61B 5/6826* (2013.01); *A61B 5/7275* (2013.01); *A61B 5/7282* (2013.01); *A61B 5/7435* (2013.01); *A61B 5/746* (2013.01); *A61B 5/7465* (2013.01); *A61B 5/747* (2013.01); *A61B 5/7475* (2013.01); *G06F 9/451* (2018.02); *G16H 10/60* (2018.01); *G16H 15/00* (2018.01); *G16H 40/20* (2018.01); *G16H 40/67* (2018.01); *G16H 50/20* (2018.01); *G16H 50/30* (2018.01); *G16H 50/70* (2018.01); *G16H 50/80* (2018.01); *H04B 17/318* (2015.01); *H04W 4/021* (2013.01); *A61B 5/024* (2013.01); *A61B 5/026* (2013.01); *A61B 5/14551* (2013.01); *A61B 2562/0271* (2013.01); *G06F 3/04842* (2013.01)

(56) References Cited

U.S. PATENT DOCUMENTS

| | | |
|---|---|---|
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| 5,441,047 A | 8/1995 | David et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,544,649 A | 8/1996 | David et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,710,551 A | 1/1998 | Ridgeway |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,163,281 A | 12/2000 | Torch |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,611,206 B2 | 8/2003 | Eshelman et al. |
| 6,611,707 B1 | 8/2003 | Prausnitz et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |

(56) References Cited

U.S. PATENT DOCUMENTS

| | | |
|---|---|---|
| RE38,476 E | 3/2004 | Diab et al. |
| RE38,492 E | 4/2004 | Diab et al. |
| 6,723,046 B2 | 4/2004 | Lichtenstein |
| 6,738,652 B2 | 5/2004 | Mattu et al. |
| 6,760,607 B2 | 7/2004 | Ai-Ali |
| 6,767,341 B2 | 7/2004 | Cho |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,936,007 B2 | 8/2005 | Quy |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,976,958 B2 | 12/2005 | Quy |
| 6,985,524 B1 | 1/2006 | Borchers |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,156,809 B2 | 1/2007 | Quy |
| 7,220,000 B2 | 5/2007 | Alster et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,733,224 B2 | 6/2010 | Tran |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,839,266 B2 | 11/2010 | Hoglund et al. |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 7,999,685 B2 | 8/2011 | Sanchez et al. |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,135,227 B2 | 3/2012 | Lewis et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,390,694 B2 | 3/2013 | Ryan et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Ai-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,591,430 B2 | 11/2013 | Amurthur et al. |
| 8,603,384 B2 | 12/2013 | Luttge et al. |
| 8,615,408 B2 | 12/2013 | Ryan |
| 8,622,922 B2 | 1/2014 | Banet et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |

(56) References Cited

U.S. PATENT DOCUMENTS

| | | |
|---|---|---|
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | Macneish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,968,195 B2 | 3/2015 | Tran |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,186,075 B2 | 11/2015 | Baker, Jr. et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,283,150 B2 | 3/2016 | Bujalski et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,405,135 B2 | 8/2016 | Sweis et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,495,881 B2 | 11/2016 | Christmas et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,554,706 B2 | 1/2017 | Soomro et al. |
| 9,560,996 B2 | 2/2017 | Kiani |
| 9,579,039 B2 | 2/2017 | Jansen et al. |
| 9,597,004 B2 | 3/2017 | Hughes et al. |
| 9,615,792 B2 | 4/2017 | Raptis et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,700,222 B2 | 7/2017 | Quinlan et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,820,699 B2 | 11/2017 | Bingley et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,887,650 B2 | 2/2018 | Maekawa et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| 10,008,091 B2 | 6/2018 | Mason et al. |
| D822,215 S | 7/2018 | Al-Ali et al. |
| D822,216 S | 7/2018 | Barker et al. |
| 10,010,276 B2 | 7/2018 | Al-Ali et al. |
| 10,039,445 B1 | 8/2018 | Torch |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 * | 3/2019 | Al-Ali .................. A61B 5/1121 |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,292,906 B1 | 5/2019 | Gershoni et al. |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,623 B2 | 6/2019 | Edwards et al. |
| 10,332,630 B2 | 6/2019 | Al-Ali |
| 10,339,500 B2 | 7/2019 | Hussam |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |

(56) References Cited

U.S. PATENT DOCUMENTS

| | | |
|---|---|---|
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| 10,691,777 B2 | 6/2020 | Dettinger et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,916,336 B2 | 2/2021 | Fiedler et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,285,121 B2 | 3/2022 | Chang et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| 11,872,156 B2 | 1/2024 | Telfort et al. |
| 11,879,960 B2 | 1/2024 | Ranasinghe et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0022973 A1 | 2/2002 | Sun et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2004/0106858 A1 | 6/2004 | Say et al. |
| 2004/0152961 A1* | 8/2004 | Carlson .............. A61B 5/6816 128/904 |
| 2005/0055276 A1 | 3/2005 | Kiani et al. |
| 2005/0227929 A1 | 10/2005 | Masferrer |
| 2005/0234317 A1 | 10/2005 | Kiani |
| 2005/0240444 A1 | 10/2005 | Wooten et al. |
| 2006/0073719 A1 | 4/2006 | Kiani |
| 2006/0140502 A1 | 6/2006 | Tseng et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0293781 A1 | 12/2007 | Sims et al. |
| 2007/0299694 A1 | 12/2007 | Merck |
| 2008/0008745 A1 | 1/2008 | Stinchcomb et al. |
| 2008/0064965 A1 | 3/2008 | Jay et al. |
| 2008/0094228 A1 | 4/2008 | Welch et al. |
| 2008/0097795 A1 | 4/2008 | Sasai et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0094220 A1 | 4/2010 | Mandro |
| 2010/0099964 A1 | 4/2010 | O'Reilly et al. |
| 2010/0131482 A1 | 5/2010 | Linthicum et al. |
| 2010/0234718 A1 | 9/2010 | Sampath et al. |

(56) References Cited

U.S. PATENT DOCUMENTS

| | | |
|---|---|---|
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0054924 A1 | 3/2011 | Mitchell et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0137680 A1 | 6/2011 | Sweeney |
| 2011/0172498 A1 | 7/2011 | Olsen et al. |
| 2011/0192744 A1 | 8/2011 | Parker et al. |
| 2011/0230733 A1 | 9/2011 | Al-Ali |
| 2012/0041279 A1 | 2/2012 | Freeman et al. |
| 2012/0044070 A1 | 2/2012 | Putrino |
| 2012/0084101 A1 | 4/2012 | Qadri |
| 2012/0101847 A1 | 4/2012 | Johnson et al. |
| 2012/0123231 A1 | 5/2012 | O'Reilly |
| 2012/0136232 A1 | 5/2012 | Jeong et al. |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0033485 A1 | 2/2013 | Kollin et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096819 A1 | 4/2013 | Tarnok |
| 2013/0172759 A1 | 7/2013 | Melker et al. |
| 2013/0183923 A1* | 7/2013 | Brackett ............... H04W 4/90 455/404.1 |
| 2013/0187774 A1 | 7/2013 | Muecke et al. |
| 2013/0222135 A1 | 8/2013 | Stein et al. |
| 2013/0296672 A1 | 11/2013 | O'Neil et al. |
| 2013/0345921 A1 | 12/2013 | Al-Ali et al. |
| 2014/0164022 A1 | 6/2014 | Reed et al. |
| 2014/0166076 A1 | 6/2014 | Kiani et al. |
| 2014/0173674 A1 | 6/2014 | Wolman et al. |
| 2014/0180160 A1 | 6/2014 | Brown et al. |
| 2014/0187973 A1 | 7/2014 | Brown et al. |
| 2014/0228657 A1 | 8/2014 | Palley et al. |
| 2014/0257852 A1 | 9/2014 | Walker et al. |
| 2014/0275871 A1 | 9/2014 | Lamego et al. |
| 2014/0275872 A1 | 9/2014 | Merritt et al. |
| 2014/0275890 A1 | 9/2014 | Meehan et al. |
| 2014/0278536 A1 | 9/2014 | Zhang et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2014/0350966 A1 | 11/2014 | Khatana et al. |
| 2014/0353328 A1 | 12/2014 | Makhalfeh et al. |
| 2014/0376789 A1 | 12/2014 | Xu et al. |
| 2015/0005600 A1 | 1/2015 | Blank et al. |
| 2015/0011907 A1 | 1/2015 | Purdon et al. |
| 2015/0050633 A1 | 2/2015 | Christmas et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0100343 A1 | 4/2015 | Siedlecki et al. |
| 2015/0134107 A1 | 5/2015 | Hyde et al. |
| 2015/0134345 A1 | 5/2015 | Hyde et al. |
| 2015/0141910 A1 | 5/2015 | Francis et al. |
| 2015/0173674 A1 | 6/2015 | Hayes et al. |
| 2015/0244878 A1 | 8/2015 | Macauley et al. |
| 2015/0317891 A1 | 11/2015 | Day et al. |
| 2015/0367071 A1 | 12/2015 | Donnellan et al. |
| 2016/0019360 A1 | 1/2016 | Pahwa et al. |
| 2016/0071392 A1 | 3/2016 | Hankey et al. |
| 2016/0098536 A1 | 4/2016 | Dettinger et al. |
| 2016/0129182 A1 | 5/2016 | Schuster et al. |
| 2016/0166766 A1 | 6/2016 | Schuster et al. |
| 2016/0189317 A1 | 6/2016 | Papandrea |
| 2016/0196388 A1 | 7/2016 | Lamego |
| 2016/0212404 A1 | 7/2016 | Maiello et al. |
| 2016/0263317 A1 | 9/2016 | Arefieg |
| 2016/0328993 A1 | 11/2016 | Brogioli |
| 2016/0360971 A1* | 12/2016 | Gross ................. A61B 5/4833 |
| 2016/0367173 A1 | 12/2016 | Dalvi et al. |
| 2016/0371833 A1 | 12/2016 | Prasad et al. |
| 2017/0024748 A1 | 1/2017 | Haider |
| 2017/0042488 A1 | 2/2017 | Muhsin |
| 2017/0084133 A1 | 3/2017 | Cardinali et al. |
| 2017/0094450 A1 | 3/2017 | Tu et al. |
| 2017/0172522 A1 | 6/2017 | Insler et al. |
| 2017/0173632 A1 | 6/2017 | Al-Ali |
| 2017/0246390 A1 | 8/2017 | Tchao et al. |
| 2017/0251974 A1 | 9/2017 | Shreim et al. |
| 2017/0262604 A1 | 9/2017 | Francois |
| 2017/0287316 A1 | 10/2017 | Wildman et al. |
| 2017/0293727 A1 | 10/2017 | Klaassen et al. |
| 2017/0311891 A1 | 11/2017 | Kiani et al. |
| 2017/0332952 A1 | 11/2017 | Desborough et al. |
| 2017/0358242 A1 | 12/2017 | Thompson et al. |
| 2017/0366627 A1 | 12/2017 | Chan et al. |
| 2017/0372018 A1 | 12/2017 | Rosenblatt et al. |
| 2018/0032699 A1 | 2/2018 | Carrender et al. |
| 2018/0035101 A1 | 2/2018 | Osterhout |
| 2018/0098698 A1 | 4/2018 | Marcus et al. |
| 2018/0103874 A1 | 4/2018 | Lee et al. |
| 2018/0110923 A1 | 4/2018 | Kaplan et al. |
| 2018/0137932 A1 | 5/2018 | Fiedler et al. |
| 2018/0147343 A1 | 5/2018 | Tyson |
| 2018/0174261 A1 | 6/2018 | Brabazon |
| 2018/0200433 A1 | 7/2018 | Cirit |
| 2018/0206733 A1 | 7/2018 | Kasan et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0264242 A1 | 9/2018 | Hoffman et al. |
| 2018/0300919 A1 | 10/2018 | Muhsin et al. |
| 2018/0308569 A1 | 10/2018 | Luellen |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0350455 A1 | 12/2018 | Rosen |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0209084 A1 | 7/2019 | Bryant et al. |
| 2019/0216317 A1 | 7/2019 | Grande |
| 2019/0216321 A1 | 7/2019 | Grande |
| 2019/0221320 A1 | 7/2019 | Amini et al. |
| 2019/0239787 A1 | 8/2019 | Pauley et al. |
| 2019/0320906 A1 | 10/2019 | Olsen |
| 2019/0336085 A1 | 11/2019 | Kayser et al. |
| 2019/0365315 A1 | 12/2019 | Ramabadran |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0054250 A1 | 2/2020 | Joseph et al. |
| 2020/0054278 A1 | 2/2020 | Joseph et al. |
| 2020/0060869 A1 | 2/2020 | Telfort et al. |
| 2020/0066415 A1 | 2/2020 | Hettig et al. |
| 2020/0101166 A1 | 4/2020 | Jenkins et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0129117 A1 | 4/2020 | Henderson |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0262864 A1 | 8/2020 | Barbut et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |

(56) References Cited

U.S. PATENT DOCUMENTS

| | | |
|---|---|---|
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2020/0357513 A1 | 11/2020 | Katra |
| 2020/0390402 A1* | 12/2020 | Fernando ............. A61B 5/6816 |
| 2021/0020307 A1 | 1/2021 | Bhimavarapu et al. |
| 2021/0022628 A1 | 1/2021 | Telfort et al. |
| 2021/0074142 A1 | 3/2021 | Payment |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0247393 A1 | 8/2021 | Chorny et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0345974 A1 | 11/2021 | Chung |
| 2021/0386382 A1 | 12/2021 | Olsen et al. |
| 2021/0398667 A1 | 12/2021 | Fujioka |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0105289 A1 | 4/2022 | Lancaster |
| 2022/0151521 A1 | 5/2022 | Krishnamani et al. |
| 2022/0189594 A1 | 6/2022 | Cohen et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Ai-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0240532 A1 | 8/2023 | Brown et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |

FOREIGN PATENT DOCUMENTS

| | | |
|---|---|---|
| WO | WO 2018/065284 | 4/2018 |
| WO | WO 2018/094520 | 5/2018 |
| WO | WO 2018/110510 | 6/2018 |
| WO | WO 2018/020911 | 7/2018 |
| WO | WO 2019/236759 | 12/2019 |
| WO | WO 2021/189007 | 9/2021 |

OTHER PUBLICATIONS

A "Second Chance" to Prevent Opioid Deaths, Technology Networks, Informatics News, This App Uses Sonar to Detect Opioid Overdoses, University of Washington, Jan. 10, 2019, in 3 pages, https://www.technologynetworks.com/informatics/news/a-second-chance-to-prevent-opioid-deaths-313744.

Announcing the Winner of the 2016 FDA Naloxone APP Competition, U.S. Food & Drug Administration, dated 2016, in 2 pages. https://www.fda.gov/news-events/public-health-focus/announcing-winner-2016-fda-naloxone-app-competition.

Blair, Andre, Monitoring For Opioid Overdoses: HopeBand Can Save People's Life, Advocator, dated Dec. 28, 2018 in 2 pages. https://advocator.ca/news/monitoring-for-opioid-overdoses-hopeband-can-save-peoples-life.

England, Rachel, "Wearable Sensor Can Detect Imminent Opioid Overdose, The low-cost device gives wearers the opportunity to administer life-saving drugs", Engadget, https://www.engadget.com/2018/12/28/wearable-sensor-opioid-overdose/?guccounter=1, Dec. 28, 2018, in 3 pages.

Hsu, Jeremy, Wristband That Detects Opioid Overdose Joins U.S. Race for Tech Solutions, IEEE Spectrum's Biomedical Engineering Blog, dated Dec. 26, 2018, in 2 pages.

International Search Report and Written Opinion received in PCT Application No. PCT/US2019/035664, dated Nov. 6, 2019 in 17 pages.

Mckibben, Justin, OD Help App Could Make Getting Naloxone Like Getting an Uber, Palm Partners Drug Rehab Center, 2018, in 7 pages. https://www.palmpartners.com/od-help-app-naloxone-uber/.

Middlebrook, Hailey, OD Help app wins FDA's competition to help fight heroin overdose, CNN, dated Dec. 19, 2016, in 4 pages. http://www.cnn.com/2016/09/22/health/fda-heroin-app-competition/index.html.

Muoio, Dave, "Robert Wood Johnson Foundation Names Winners of $50,000 AI, Opioid Challenges", Mobihealthnews, dated Sep. 19, 2018, in 13 pages. https://www.mobihealthnews.com/content/robert-wood-johnson-foundation-names-winners-50000-ai-opioid-challenges.

Opioid Overdose, SAMHSA—Substance Abuse and Mental Health Services Administration, retrieved Jul. 2, 2019, in 2 pages. http://www.samhsa.gov/medication-assisted-treatment/treatment/opioid-overdose.

"OD Help", PwrdBy, published Nov. 7, 2016, https://www.youtube.com/watch?v=wiiNvSLbUgo in 1 page.

Singer, "Pill dispenser that's set by timer may stop opioid addiction before it starts" https://www.democratandchronicle.com, May 8, 2018, in 6 pages.

Young, Grace, "NALNOW—2016 FDA Naloxone App Competition", Nov. 7, 2016, retrieved from https://www.youtube.com/watch?v=DKsHBJm90Nc&feature=youtu.be.

Al-Taee et al., "Web-of-Things Inspired e-Health Platform for Integrated Diabetes Care Management",2013 IEEE Jordan Conference on Applied Electrical Engineering and Computing Techologies, Dec. 2013, pp. 6.

Halo: Assessing Global Patient Status with the Halo Index™, in 8 pages, Whitepaper, 2011, https://www.masimo.co.uk/siteassets/uk/documents/pdf/clinical-evidence/whitepapers/lab4158a_whitepapers_masimo_halo_index.pdf.

International Search Report and Written Opinion received in PCT Application No. PCT/US2021/023336, dated Jun. 25, 2021 in 12 pages.

(56) References Cited

OTHER PUBLICATIONS

Nandakumar et al., "Opioid Overdose Detection Using Smartphones", Science Translational Medicine, vol. 11, No. 474, Research Article, Jan. 9, 2019, pp. 10.

* cited by examiner

Data View

Alan Smith

☐ All

Alan Smith

☐ All
- 🏃 Fitness
- ♡ Heart
- 🩺 Vitals
- ⚕ Body Measurements
- 🏥 Results

∿ View Chart   ⟳ Refresh

⊞ PATIENT LIST  ⌂ HOME  ⓘ HELP  Ⓜ ME

< JAN 01, 2020 – DEC 31, 2020 >

Samples | Showing samples from all categories

Filter by                                                       🔍

| Name ↓ | Value | Measurement Date |
|---|---|---|
| 🏋 Weight | 100 lbs | Jan 01–Nov 29, 2020 > |
| 🐾 Walking Heart Rate Average | Monthly 101 bpm | Feb 01–Nov 29, 2020 > |
| 👣 Steps | Daily Average 2,670 Steps | Jan 01–Nov 29, 2020 > |
| ♥ Resting Heart Rate | Monthly 76 bpm | Mar 01–Nov 29, 2020 > |
| ⦵ Respiratory Rate | Monthly 7.87 breaths/mn | May 01, 2020 > |
| 💧 Peripheral Perfusion Index | Monthly 11.42% | May 01–Nov 29, 2020 > |
| ◯ Oxygen Saturation | Monthly Oxygen Saturation 90.17% | Jan 01–Nov 29, 2020 > |
| ⇧ Height | 54" | Jan 01–Nov 29, 2020 > |
| ♡ Heart Rate Variability | Monthly 66 Milliseconds | Jan 01–Nov 29, 2020 > |

Page: 1 ▽  Rows per page: 1 ▽   1–10 of 16 < >

FIG. 20

2442
Please confirm that you would like to notify an Ambulance
Call Now
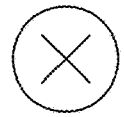
Never mind
FIG. 24V

REMOTE PATIENT MANAGEMENT AND MONITORING SYSTEMS AND METHODS

INCORPORATION BY REFERENCE TO ANY PRIORITY APPLICATIONS

This application claims the benefit of priority of U.S. Patent Application No. 63/106,273, titled "WEARABLE DEVICE FOR NONINVASIVE BODY TEMPERATURE MEASUREMENT," filed Oct. 27, 2020, U.S. Patent Application No. 63/056,925, titled "WEARABLE DEVICE FOR NONINVASIVE BODY TEMPERATURE MEASUREMENT," filed Jul. 27, 2020, U.S. Patent Application No. 63/065,961, titled "HEALTH SCREENING AND MONITORING SYSTEM," filed Aug. 14, 2020, U.S. Patent Application No. 63/049,478, titled "REMOTE PATIENT MANAGEMENT AND MONITORING SYSTEMS AND METHODS," filed Jul. 8, 2020, U.S. Patent Application No. 62/992,808, titled "REMOTE PATIENT MANAGEMENT AND MONITORING," filed Mar. 20, 2020, U.S. Patent Application No. 62/992,779, titled "OPIOID OVERDOSE MONITORING USER INTERFACE," filed Mar. 20, 2020, and U.S. Patent Application No. 63/010,669, titled "REMOTE PATIENT MANAGEMENT AND MONITORING," filed Apr. 15, 2020. All of the above-mentioned applications are hereby incorporated by reference herein in their entireties.

Any and all applications for which a foreign or domestic priority claim is identified in the Application Data Sheet as filed with the present application are hereby incorporated by reference under 37 CFR 1.57.

FIELD

This application relates broadly to patient management and/or monitoring system that can assist care providers to provide remote care for patients.

BACKGROUND

In a medical context, a patient may be given a plan to manage health condition(s) or recover from health condition(s). The plan can include instructions for the patient. The patient can be asked to implement their plan outside of a hospital, such as in their home. A patient may be asked to self-monitor and/or track their own health condition, which can include taking their own physiological measurements. Patients can also be tested for health conditions.

In the medical field, instead of extracting material from a patient's body for testing, light or sound energy may be caused to be incident on the patient's body and transmitted (or reflected) energy may be measured to determine information about the material through which the energy has passed. This type of non-invasive measurement is more comfortable for the patient and can be performed more quickly than invasive measurement techniques. Blood pressure and the body's available supply of oxygen, or the blood oxygen saturation, can be monitored. Measurements such as these are often performed with non-invasive techniques where assessments are made by measuring the ratio of incident to transmitted (or reflected) light through a portion of the body, for example a digit such as a finger, or an earlobe, foot, or forehead.

In a computer/software context, frameworks exist for developing applications, such as smart phone applications. Application development using such frameworks typically requires developers with programming skills and technical expertise. In some cases, significant updates to the applications require recompiling and republishing of the updated executable applications.

The COVID-19 pandemic is creating increased demand across the globe for home-based monitoring and patient engagement solutions. As current CDC and WHO guidelines require monitoring a suspected and/or confirmed COVID-19 patient's temperature, respiration rate, and oxygen saturation and due to the highly contagious nature of the virus and/or the limited healthcare resources such as the availability of hospital beds, there is an increased need to provide remote monitoring and patient engagement solutions in multiple settings via a secure remote solution. Various systems and methods have been proposed or implemented to provide wireless communication links between patients and remotely-located care providers, allowing patients to receive care while reducing the risk of being infected from or infecting other patients, and/or the risk of infecting the care providers.

SUMMARY

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

According to various embodiments of the present disclosure, a method for remote patient care and monitoring can include causing presentation of a patient care configuration user interface. A patient care user interface can be made available in a patient care application, such as an application executing on a patient user computing device. The patient care user interface can be tailored towards particular health condition(s), such as, but not limited to, COVID-19, diabetes, sleep apnea, one or more addictions, one or more cardiac diseases, obesity, and/or one or more respiratory diseases. An administrator can configure a patient care user interface with the patient care configuration user interface and without programming. The patient care configuration user interface can include one or more configuration user interface elements. The method can further include receiving, via the patient care configuration user interface, a request to create or edit a first patient care user interface; and one or more selections of the configuration user interface elements. The one or more selections can indicate: a graphical layout configuration of the first patient care user interface; a patient care action item configuration; and a patient sensor item configuration. The method can further include generating, for the first patient care user interface, a first client configuration package. The first client configuration package can include the graphical layout configuration, the patient sensor item configuration, and the patient care action item configuration. The method can further include transmitting, to a patient user computing device, the first client configuration package. A patient care application, executing on the patient user computing device, can be configured to receive the first client configuration package. Upon receiving the first client configuration package, the patient care application can be caused to arrange a graphical layout of the first patient care user interface according to the graphical layout configuration. The patient care application can be further caused to present a patient care action item according to the patient care action item configuration. The patient care application can be further caused to interface, according to the patient sensor item configuration, with a patient sensor device capable of capturing physiological parameters from a patient. The patient care application can implement the first client configuration package, which can cause presentation of the first patient care user interface on the patient user computing device. The patient care application can implement the first client configuration package and/or present the first patient care user interface without or before recompiling of the patient care application. The method can further include receiving, from the patient user computing device, a first physiological parameter value generated by the patient sensor device. The method can further include causing presentation, on a clinician user computing device, a patient monitoring user interface including: (i) information associated with the patient; and (ii) a visual representation based at least in part on the physiological parameter value.

According to various embodiments of the present disclosure, a system for remote patient care and monitoring can include a memory device configured to store instructions and a hardware processor. The system, such as the hardware processor of the system, can cause presentation of a patient care configuration user interface. A patient care user interface can be made available in a patient care application, such as an application executing on a patient user computing device. The patient care user interface can be tailored towards particular health condition(s), such as, but not limited to, COVID-19, diabetes, one or more addictions, one or more cardiac diseases, and/or one or more respiratory diseases. An administrator can configure a patient care user interface with the patient care configuration user interface and without programming. The patient care configuration user interface can include one or more configuration user interface elements. The system can receive, via the patient care configuration user interface, a request to create or edit a first patient care user interface; and one or more selections of the configuration user interface elements. The one or more selections can indicate: a patient care action item configuration and a patient sensor item configuration. The system can generate, for the first patient care user interface, a first client configuration package. The first client configuration package can include the patient sensor item configuration and the patient care action item configuration. The system can transmit, to a patient user computing device, the first client configuration package. A patient care application, executing on the patient user computing device, can be configured to receive the first client configuration package. Upon receiving the first client configuration package, the patient care application can be caused to present a patient care action item according to the patient care action item configuration. The patient care application can be further caused to interface, according to the patient sensor item configuration, with a patient sensor device capable of capturing physiological parameters from a patient. The patient care application can implement the first client configuration package, which can cause presentation of the first patient care user interface on the patient user computing device. The patient care application can implement the first client configuration package and/or present the first patient care user interface without or before recompiling of the patient care application. The system can receive, from the patient user computing device, a physiological parameter value generated by the patient sensor device. The system can cause presentation, on a clinician user computing device, a patient monitoring user interface including: (i) information associated with the patient; and (ii) a visual representation based at least in part on the physiological parameter value.

In various embodiments, the system can transmit, to the patient user computing device, multiple client configuration packages. Each client configuration package can be configured to cause the patient care application to present a patient care user interface different from the first patient care user interface.

In various embodiments, the system can transmit, to the patient user computing device, a second client configuration package. The second client configuration package can be configured to cause the patient care application to present a second patient care user interface different from the first patient care user interface.

In various embodiments, the system can receive, from the patient user computing device, multiple physiological parameter values. The system can identify, from the first physiological parameter value and the other physiological parameter values, a subset of physiological parameter values for a period of time. The system can determine that the subset of physiological parameter values for the period of time violates a threshold. In response to determining that the subset of physiological parameter values violates the threshold, the system can transmit an alert.

In various embodiments, the patient care action item can include a prompt. The system can receive, from the patient user computing device, response data associated with the prompt.

In various embodiments, the system can select, from a first threshold and a second threshold, the first threshold. Selecting the first threshold can include: applying the response data as input to conditional threshold logic and identifying the first threshold as output from the conditional threshold logic. The system can determine an alert based at least in part on the physiological parameter value and the first threshold. The system can transmit the alert.

In various embodiments, the system can receive, via the patient care configuration user interface, a definition of the conditional threshold logic customized for the first patient care user interface.

In various embodiments, the patient care action item can include at least one of a boolean input field, a numeric input field, a text input field, a data input field, or a time input field.

In various embodiments, a data type of the response data corresponds to the at least one of the boolean input field, the numeric input field, the text input field, the data input field, or the time input field.

In various embodiments, the patient care application is capable of implementing the first client configuration package without recompiling the patient care application.

In various embodiments, the patient sensor device includes a pulse oximeter.

In various embodiments, the physiological parameter value measures at least one of oxygen saturation, respiration rate, pulse rate, or a perfusion index.

In various embodiments, the one or more selections further indicate a graphical layout configuration of the first patient care user interface. The first client configuration package can further cause the patient care application to: arrange a graphical layout of the first patient care user interface according to the graphical layout configuration.

In various embodiments, the system can receive via the patient care configuration user interface: a second request to edit the first patient care user interface; and user input comprising program instructions in an interpreted language; generate, for the first patient care user interface, an updated first client configuration package comprising the program instructions in the interpreted language; and transmit, to the patient user computing device, the updated first client configuration package.

In various embodiments the interpreted language can include JavaScript.

In various embodiments, the patient care application, executing on the patient user computing device, can receive the updated first client configuration package that causes the patient care application to execute the program instructions without recompiling the patient care application.

According to various embodiments of the present disclosure, a method establishing a monitoring environment for a user suspected of having a contagious respiratory infection where the user is to be monitored remotely from a care provider, said monitoring environment including one or more sensors worn by the user, a wearable device worn by the user configured to communicate with the one or more sensors and to process information responsive to output from the one or more sensors, a user computing device configured to wirelessly communicate with the wearable device and to communicate with a remote care provider system over a network, the care provider system configured to be monitored by the care provider, can include providing a user monitoring kit to the user, said user monitoring kit including said wearable device and at least some of said one or more sensors, said wearable device configured to process sensor signals to determine measurement values of blood oxygen saturation of the user over a monitoring period. The method can further include providing a user a first software application for said user computing device, said first software application configured to aggregate medical information of said user, said medical information including received said measurement values of said blood oxygen saturation and received one or more measurement values of a temperature of said user. The method can further include providing a care provider a second software application for said care provider system, said second software application configured to receive medical information from said first software application, to process said medical information and to output to a display viewable by said care provider indicia responsive to said measurement values of said blood oxygen saturation and temperature of said user during said monitored period, said indicia including a variance from a baseline for said user at least when said user should receive further screening for said contagious respiratory infection.

In various embodiments, said providing said user monitoring kit to the user can further include providing said kit including said one or more sensors including a disposable battery and disposable sensor and a reusable processor and reusable wireless device.

According to various embodiments of the present disclosure, a method of treating a contagious respiratory infection using a wearable sensor can include providing a remote monitoring kit to a patient, said remote monitoring kit including a reusable device and a disposable device, wherein the reusable device is configured to engage the disposable device to form a wearable sensor assembly, said wearable sensor assembly configured to measure blood oxygen saturation of the patient over a monitoring period. The remote monitoring kit can be used at the patient's place of residence. The method can further include providing, to the patient, a first software application that is configured to be installed on a patient user computing device, said wearable sensor assembly configured to wirelessly connect with the patient user computing device. The method can further include providing a second software application to a care provider, wherein the said second software application enables the care provider to view the patient's blood oxygen saturation and temperature measurements over the monitoring period. The method can further include treating the patient based at least on the patient's measured blood oxygen saturation and the temperature measurements over the monitoring period.

In various embodiments, the remote monitoring kit further can further include a connectivity hub device configured to transmit the patient's blood oxygen saturation and the temperature measurements over the monitoring period to the care provider.

In various embodiments, the wearable sensor assembly can be further configured to measure the patient's respiratory rate over the monitoring period.

In various embodiments, treating the patient can further include ordering mechanical ventilation for the patient.

In various embodiments, treating the patient can further include prescribing a drug to the patient. The drug can further include at least one of: remdesivir, dexamethasone, azithromycin, tocilizumab, lopinavir, ritonavir, or oseltamivir.

In various embodiments, the first software application can be further configured to provide an alert based at least on the patient's blood oxygen saturation and the temperature measurements over the monitoring period.

In various embodiments, the second software application can be further configured to provide an alert based at least on the patient's measured blood oxygen saturation and the temperature measurements over the monitoring period.

In various embodiments, the wearable sensor assembly can be further configured to be disposed on at least one of the patient's finger, wrist, chest, or forehead.

According to various embodiments of the present disclosure, a method of managing surge capacity in a hospital during an infectious disease outbreak can include providing each of a plurality of patients having symptoms of an infectious disease a wearable device in a non-clinical space, said wearable device configured to measure blood oxygen saturation over a monitoring period. The method can further include providing a connectivity hub device that is configured to (i) wirelessly connect with respective wearable devices of the plurality of patients and (ii) transmit the measured blood oxygen saturation over the monitoring period. The method can further include providing a first software application to a care provider, wherein said first software application enables the care provider to monitor the patient's physiological condition over the monitoring period without coming in close proximity with the patient. The method can further include determining based at least on the patient's measured blood oxygen saturation over the monitoring period that the patient needs to be moved to a clinical space for treatment of a contagious respiratory infection.

In various embodiments, the method can further include diagnosing the patient with a respiratory virus. The respiratory virus can include at least one of severe acute respiratory syndrome coronavirus 2 (SARS-COV-2), severe acute respiratory syndrome-related coronavirus (SARS-COV), or influenza.

In various embodiments, the method can further include providing each of the plurality of patients a second software application that is configured to be installed on a respective patient user computing device, said wearable device configured to wirelessly connect with respective patient user computing devices.

In various embodiments, the first software application can be further configured to provide an alert based at least on the patient's measured blood oxygen saturation over the monitoring period.

In various embodiments, the method can further include treating the patient based at least on the patient's measured blood oxygen saturation over the monitoring period.

In various embodiments, the method can further include notifying emergency medical services based at least on the patient's measured blood oxygen saturation over the monitoring period.

In various embodiments, the wearable device can be further configured to measure the patient's respiratory rate over the monitoring period.

In various embodiments, the first software application can be further configured to provide an alert based at least on the patient's measured blood oxygen saturation over the monitoring period.

In various embodiments, the method can further include causing the care provider to contact the patient.

According to various embodiments of the present disclosure, a method of detecting a respiratory health condition using a wearable sensor can include providing a pulse oximetry sensor device to a patient, wherein the pulse oximetry sensor device is configured to measure blood oxygen saturation of the patient over a monitoring period. The method can further include providing, to the patient, a software application that is configured to be installed on a patient user computing device, said pulse oximetry sensor device configured to wirelessly connect with the patient user computing device. The method can further include receiving, from the patient user computing device, the patient's blood oxygen saturation and temperature measurements over the monitoring period. The method can further include diagnosing a contagious respiratory infection based at least on the patient's measured blood oxygen saturation and the temperature measurements over the monitoring period.

In various embodiments, the method can further include notifying emergency medical services based at least on the patient's measured blood oxygen saturation and the temperature measurements over the monitoring period.

In various embodiments, the software application can be further configured to provide an alert based at least on the patient's blood oxygen saturation and the temperature measurements over the monitoring period.

According to various embodiments of the present disclosure, a system for remote detecting and monitoring of a respiratory health condition can include a pulse oximetry sensor device, wherein the pulse oximetry sensor device is configured to measure blood oxygen saturation of a patient over a monitoring period, and wherein the pulse oximetry sensor device is configured to wirelessly connect with a patient user computing device. The system can further include a memory device configured to store instructions; and a hardware processor. The hardware processor can be configured to execute the instructions to: receive, from the patient user computing device, the patient's blood oxygen saturation and temperature measurements over the monitoring period; and diagnose a contagious respiratory infection based at least on the patient's measured blood oxygen saturation and the temperature measurements over the monitoring period.

In various embodiments, the contagious respiratory infection can be caused by at least one of severe acute respiratory syndrome coronavirus 2 (SARS-COV-2), severe acute respiratory syndrome-related coronavirus (SARS-COV), or influenza.

In various embodiments, the hardware processor can be further configured to execute further instructions to: notify emergency medical services based at least on the patient's measured blood oxygen saturation and the temperature measurements over the monitoring period.

In various embodiments, the hardware processor can be further configured to execute further instructions to: provide an alert based at least on the patient's blood oxygen saturation and the temperature measurements over the monitoring period.

According to various embodiments of the present disclosure, a remote monitoring kit can include a package, wherein the package is configured to be mailed and a pulse oximetry sensor device. The pulse oximetry sensor device can include a wireless communications device; a memory device configured to store instructions; and a hardware processor. The hardware processor can be configured to execute the instructions to pair, via the wireless communications device, with a patient user computing device through a downloadable application. The pulse oximetry sensor device can be disposed within the package.

In various embodiments, the remote monitoring kit can further include a scannable code. The scannable code can encode a link to download the downloadable application. The downloadable application can be configured to receive input data associated with the scannable code. Receipt of the input data by the downloadable application can cause the downloadable application to initiate pairing with the pulse oximetry sensor device.

In various embodiments, the pulse oximetry sensor device can further include a removable chip, and wherein the removable chip comprises the wireless communications device, the memory device, and the hardware processor.

In various embodiments, the remote monitoring kit can further include a second sensor, wherein the second sensor is configured to receive the removable chip, and wherein the second sensor is disposed within the package.

In various embodiments, the patient user computing device can include a smart phone or a tablet.

In various embodiments, the remote monitoring kit can further include a connectivity hub device, wherein the connectivity hub device is configured to communicate with the pulse oximetry sensor device and a remote server, and wherein the connectivity hub device is disposed within the package.

In various embodiments, the pulse oximetry sensor device can be configured to be disposed on at least one of the patient's finger, wrist, chest, or forehead.

In various embodiments, the pulse oximetry sensor device can be further configured to measure the patient's respiratory rate over the monitoring period.

According to various embodiments of the present disclosure, a method of treating opioid addiction using a wearable sensor can include providing a remote monitoring kit to a patient, said remote monitoring kit including a reusable device and a disposable device, wherein the reusable device is configured to engage the disposable device to form a wearable sensor assembly, said wearable sensor assembly configured to measure blood oxygen saturation of the patient over a monitoring period at the patient's place of residence. The method can further include providing, to the patient, a first software application that is configured to be installed on a patient user computing device, said wearable sensor assembly configured to wirelessly connect with the patient user computing device. The method can further include providing a second software application to a care provider, wherein the said second software application enables the care provider to view the patient's blood oxygen saturation over the monitoring period. The method can further include treating the patient for an opioid overdose based at least on the patient's measured blood oxygen saturation over the monitoring period.

In various embodiments, treating the patient can include applying medication to the patient.

In various embodiments, the remote monitoring kit can further include a connectivity hub device configured to transmit the patient's blood oxygen saturation over the monitoring period to the care provider.

In various embodiments, the wearable sensor assembly can be further configured to measure the patient's respiratory rate over the monitoring period.

In various embodiments, the second software application can be further configured to provide an alert based at least on the patient's measured blood oxygen saturation over the monitoring period.

In various embodiments, the wearable sensor assembly can be configured to be disposed on at least one of the patient's finger, wrist, chest, or forehead.

In various embodiments, the remote monitoring kit can further include a medication applicator device, wherein the first software application, based at least on the patient's blood oxygen saturation over the monitoring period, is configured to instruct the medication applicator device to administer medication to the patient.

According to various embodiments of the present disclosure, a method of managing an opioid epidemic can include providing each of a plurality of patients having symptoms of an opioid addiction a wearable device in a non-clinical space, said wearable device configured to measure blood oxygen saturation over a monitoring period. The method can further include providing a connectivity hub device that is configured to (i) wirelessly connect with respective wearable devices of the plurality of patients and (ii) transmit the measured blood oxygen saturation over the monitoring period. The method can further include providing a first software application to a care provider, wherein the said first software application enables the care provider to monitor the patient's physiological condition over the monitoring period from the non-clinical space. The method can further include determining based at least on the patient's measured blood oxygen saturation over the monitoring period that the patient needs to be moved to a clinical space for treatment of an opioid overdose.

In various embodiments, the method can further include diagnosing the patient with an opioid addiction.

In various embodiments, the method can further include notifying emergency medical services based at least on the patient's measured blood oxygen saturation over the monitoring period.

In various embodiments, the method can further include providing each of the plurality of patients a second software application that is configured to be installed on a respective user computing device, said wearable device configured to wirelessly connect with respective user computing devices.

In various embodiments, the first software application can be further configured to provide an alert based at least on the patient's blood oxygen saturation over the monitoring period.

In various embodiments, the method can further include treating the patient based at least on the patient's measured blood oxygen saturation over the monitoring period.

In various embodiments, the connectivity hub device can be further configured to transmit patient temperature measurements over the monitoring period.

In various embodiments, the wearable device can be further configured to measure the patient's respiratory rate over the monitoring period.

In various embodiments, the method can further include causing the care provider to contact the patient.

In various embodiments, the method can further include providing a medication applicator device, wherein the first software application, based at least on the patient's blood oxygen saturation over the monitoring period, is configured to instruct the medication applicator device to administer medication to the patient.

Various combinations of the above and below recited features, embodiments, and aspects are also disclosed and contemplated by the present disclosure.

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

According to an aspect of the present disclosure, a patient management and monitoring system can include a network server and a processor. The network server can establish wireless communication with one or more user devices and one or more care provider devices. The processor can execute program instructions to cause the patient management and monitoring system to receive patient health data from the one or more user devices and transmit the patient health data to a remote care provider via wireless communication.

The one or more user devices can be in wireless communication with one or more sensor systems. The one or more sensors configured to collect the patient health data and wirelessly transmit the patient health data to the one or more user devices. The processor of the patient management and monitoring system can further cause the patient and monitoring system to generate a graphical user interface and display indicators associated with the patient health data via the graphical user interface. The graphical user interface can be displayed on the one or more care provider devices. The patient data may allow care providers to track compliance, thereby allowing the care providers to identify when intervention is needed. Additionally, the patient data may allow care providers to prioritize patients.

BRIEF DESCRIPTION OF THE DRAWINGS

FIGS. 18, 19A-19B, and 20 illustrate example patient monitoring user interfaces, according to some embodiments of the present disclosure.

FIG. 30 illustrates example graphical user interfaces providing patients with descriptions of the digital home-care plan and initial questions, according to some embodiments of the present disclosure.

DETAILED DESCRIPTION

Introduction

Figure 1A:
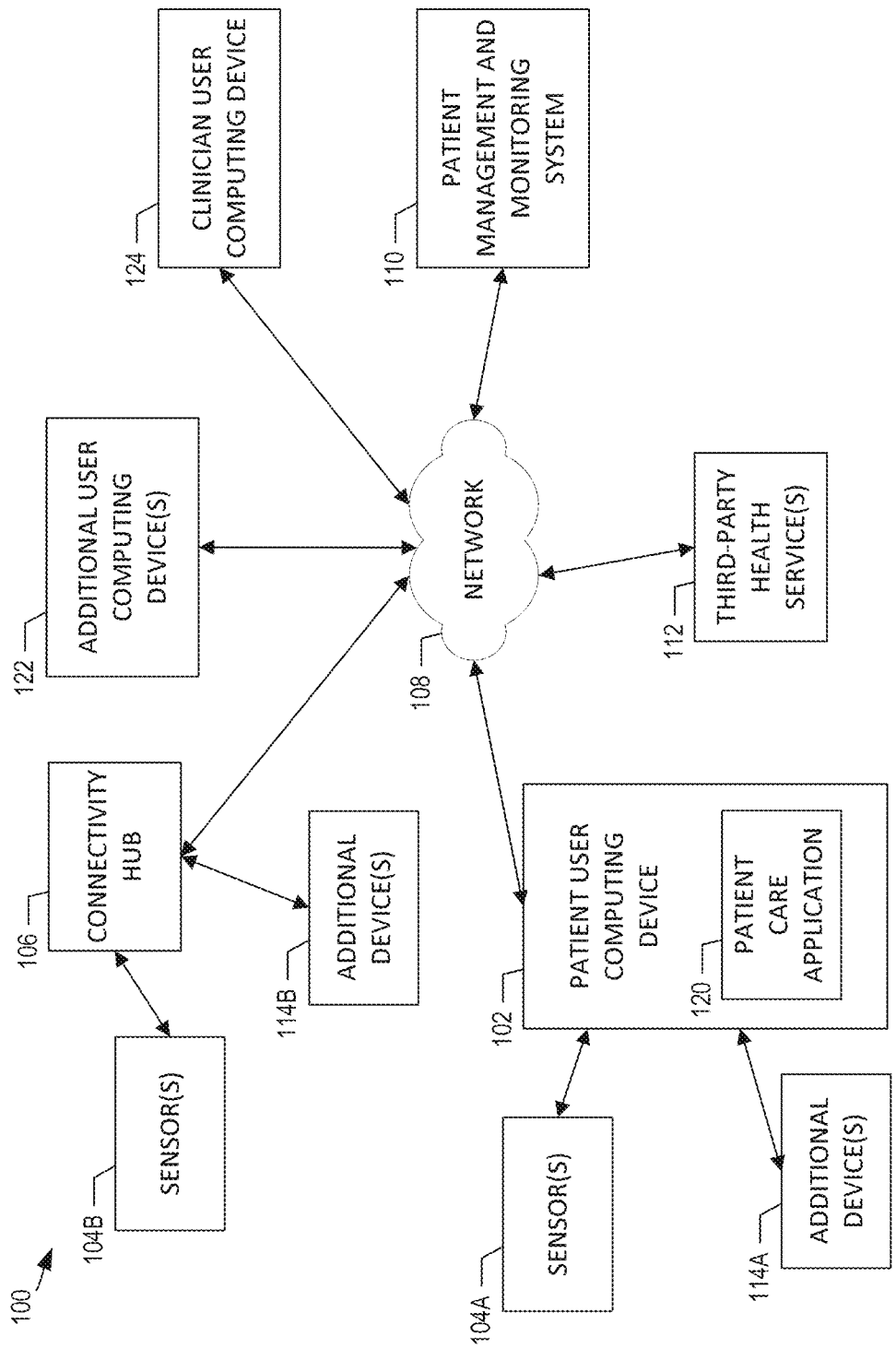
FIGS. 1A-1B are block diagrams illustrating network environments for a patient management and monitoring system, according to some embodiments of the present disclosure.

Patients are cared for and/or treated in healthcare facilities. Some existing healthcare facilities have patient sensors and devices to capture physiological data regarding patients. Clinicians can respond to alarms associated with the physiological data. As described herein, some patients can be discharged from a healthcare facility (such as when a patient is and sent home) and given plans to continue their recovery at their new location. In many cases, patients are sent home with written instructions for self-care. In other cases, temporary health care facilities (such as an emergency medical tents) can be setup where having portable medical equipment can be advantageous. Improved and/or easily expandable/extensible patient monitoring, care, and management may advantageously improve a patient's recovery, patient health, and/or save patient lives.

Disclosed herein are embodiments of remote patient management and monitoring systems and methods. Some or all of the patient sensor devices described herein can be sent to and used in nearly any environment. Those patient sensor devices can be connected to user computing devices and/or ancillary devices to securely transmit physiological data to a backend system. The system can enable care providers to configure and push customized patient care user interfaces to patient care applications executing on the user computing devices. A configuration package can define a patient care user interface. The patient care user interfaces can address and/or be tailored to particular health condition(s). Customized configuration packages for the patient care user interfaces can include configurations for sensors that streamline remote patient monitoring. The system can continuously monitor physiological parameters, such as, but not limited to, blood oxygen saturation ($SpO_2$), pulse rate, perfusion index, pleth variability index, and/or respiration rate from the photoplethysmograph. The patient can be monitored with a wireless sensor system connected to an application executing on a patient user computing device or other device that transmits patient data to the backend. The customized patient care user interfaces can include prompts to elicit patient responses and patient engagement (such as a reminder for the patient to take their temperature or for the patient to exercise), and the patient's responses can be shared with the backend system. Patients can also specify additional recipients (such as friends or family) that can be authorized to view their patient data. Care providers can review the patient data and associated alarm(s) with graphical user interfaces.

A monitoring kit can be provided to a patient. The monitoring kit can include various devices for remote patient monitoring. For example, a wearable device can be worn by a patient that captures physiological parameters for the patient. The wearable device can wirelessly connect with a software application on the patient's user computing device. The patient's user computing device can transmit the physiological parameters to a patient management and monitoring system, which can include a software application for a care provider. As described herein, the patient management and monitoring system and/or a clinician can use the physiological parameters for the patient. For example, a clinician can treat, diagnose, and/or respond to physiological parameters for the patient.

The remote patient management and monitoring systems and methods described herein can be used to address communicable diseases, such as respiratory, influenza, and/or influenza-like virus outbreaks, and in particular the severe acute respiratory syndrome coronavirus 2 (SARS-COV-2 or novel coronavirus) and the coronavirus disease 2019 (COVID-19) global pandemic. The solutions described herein can allow extensible and/or remote patient monitoring and patient engagement. Such solutions can be crucial to expanding healthcare services and/or allowing suspected or confirmed, novel coronavirus patients to remain quarantined, which can be crucial to slowing a virus' spread so that fewer people need to seek treatment at any given time, which is known as "flattening the curve." The solutions described herein can enable remote-monitoring of patient physiological parameters, such as, but not limited to, a patient's temperature, respiration rate, and/or oxygen saturation. An example remote patient management and monitoring system is Masimo SafetyNet™ by Masimo Corporation, Irvine, CA.

Some existing methods for diagnosing a communicable disease can include administering a test. For example, in the context of SARS-COV-2, a viral or an antibody test can be administered to a patient. In some cases, such tests can take several days to get results, some of which may include false positive or negative results. Testing for the novel coronavirus or other communicable diseases can involve inserting a long swab, e.g., a six-inch swab, into the cavity between the nose and mouth. The solutions described herein can provide additional or alternative methods of diagnosing a health condition, such as the novel coronavirus. As described herein, a patient can use a patient sensor device, such as a wearable device, which captures physiological parameters and a system and/or a clinician can use the physiological parameters to diagnose a health condition. For example, the novel coronavirus or other communicable diseases can be diagnosed as possibly being present in a patient based at least on one or more physiological parameters, such as blood oxygen saturation, pulse rate, perfusion index, respiration rate, pleth variability index, and/or temperature.

In some embodiments, the wireless sensor system may be a tetherless pulse oximetry sensor with respiration rate monitoring. An example tetherless pulse oximetry sensor can use Masimo SET® measure-through-motion technology. The tetherless single-patient-use sensor can provide continuous respiration rate and oxygen saturation monitoring. Patient data can be sent securely via Bluetooth® to a computing device, such as, for example, a computing device executing the Masimo Safety Net mobile application.

Creation and implementation of customized patient care user interfaces and applications by care providers may be impractical or difficult with some existing systems. As described above, frameworks exist for developing applications, such as smart phone applications. However, application development using such frameworks typically requires developers with programming skills and technical expertise to prepare and configure user interfaces. Such barriers can make it difficult or prohibitive for care providers to develop such applications since the providers typically lack such resources and competencies. Moreover, significant updates to the applications typically require recompiling and republishing of the updated executable applications.

Various embodiments of the present disclosure provide improvements to various technologies and technological fields, and practical applications of various technological features and advancements. For example, as described above, some existing systems are limited in various ways, and various embodiments of the present disclosure provide significant improvements over such systems, and practical applications of such improvements. For example, embodiments of the present disclosure can allow care providers to create customized patient care user interfaces without programming skills and/or technical expertise. Care providers can use configuration user interfaces to configure patient care user interfaces. The configurations of the patient care user interfaces can be stored in client configuration packages that can be received by patient care applications. The patient care applications can then implement the client configuration packages to present customized patient care user interfaces. As described herein, the patient care user interfaces can be customized for particular health conditions(s). The patient care applications can receive and/or implement new or updated client configuration packages to present new or updated patient care user interfaces without or before recompiling the patient care applications. Accordingly, the systems and techniques described herein can result in improvements to computer application development technologies. Thus, various embodiments of the present disclosure can be inextricably tied to, and provide practical applications of, computer technology.

Advantageously, the systems and techniques described herein can result in improvements to graphical user interfaces. For example, existing methods for pairing devices may be cumbersome for users. As described herein, the client configuration packages can include sensor configurations to facilitate configuring sensor devices that capture patient physiological parameters. The predefined sensor configurations can enable a faster pairing processes with fewer user input clicks or selections. The client configuration packages may facilitate other configurations of a patient care application. Thus, various embodiments of the present disclosure can result in more efficient graphical user interfaces.

Various embodiments of the present disclosure can interface with sensor technology, such as non-invasive patient sensor devices. Such features and others are intimately tied to, and enabled by, computer sensor technology, and would not exist except for computer sensor technol1efined below. The terms defined below, as well as other terms used herein, should be construed broadly to include the provided definitions, the ordinary and customary meaning of the terms, and/or any other implied meaning for the respective terms. Thus, the definitions below do not limit the meaning of these terms, but only provide example definitions.

Client Configuration Package:

Data and/or software instructions that define a patient care user interface. An administrator configures a patient care user interface with a configuration user interface and the output of the configuration user interface is a client configuration package. The client configuration package can be received by a patient care application that causes the patient care application to present the patient care user interface. The client configuration package can include configurations for a graphical layout of a patient care user interface, action items, and/or sensor items.

Patient Care User Interface:

A graphical user interface of an application that addresses and/or is tailored to particular health condition(s). The graphical user interface can include action items for a patient and/or prompts to elicit user input, which are related to health condition(s). Example action items can be tasks for a patient associated with the health condition(s), such as medication reminder(s) and/or physical activity or physical therapy reminder(s) or goal(s). The graphical user interface can integrate with patient sensor(s) to present physiological parameters and can include elements to configure patient sensor items. The graphical user interface can present particular action(s) and/or prompts based on configured schedule(s). As described herein, an administrator can configure the patient care user interface with a configuration user interface and can make the patient care user interface available on an application. As used herein, the terms "CareProgram" or "care program" can refer to a configured patient care user interface, which can be embodied in a client configuration package.

Overview

FIG. 1A illustrates a network environment 100 that includes a patient management and monitoring system 110. The network environment 100 can further include a network 108, one or more patient sensor devices 104A and/or one or more additional devices 114A in communication with a patient user computing device 102, and one or more patient sensor devices 104B and/or one or more additional devices 114B in communication with a connectivity hub device 106. The one or more patient sensor devices 104A, 104B and/or additional devices 114A, 114B can wirelessly communicate (e.g., over Bluetooth) with the patient user computing device 102 and/or the connectivity hub device 106. Example patient sensor devices 104A, 104B can include, but are not limited to, a tetherless pulse oximetry sensor/pulse oximetry device with respiration rate monitoring, which can be described in further detail below with respect to FIGS. 2A-2B. Example additional devices 114A, 114B can include, but are not limited to, a device capable of administering one or more medications. The patient user computing device 102 and/or the connectivity hub device 106 can transmit patient data, such as captured patient physiological data, to the patient management and monitoring system 110 over the network 108.

The patient user computing device 102, the additional user computing device 122, and/or the clinician user computing device 124 can include any computing device capable of communicating with patient management and monitoring system 110 over the network 108. Example computing devices include a smartphone, hybrid PDA/mobile phone, mobile phone, tablet computer, laptop, desktop computer, and/or a personal digital assistant (PDA). The patient user computing device 102 can execute a patient care application 120 that is configured to present patient care user interfaces and/or to communicate with the patient management and monitoring system 110 over the network 108. In particular, the patient care application 120 can communicate (such as interface) with the one or more patient sensor devices 104A, 104B and/or additional devices 114A, 114B. A patient can authorize their health data to be shared with third-party health service(s) 112. The patient user computing device 102 can share patient data with third-party health service(s) 112.

A patient can authorize their health data to be shared with additional user computing device(s) 122. For example, a patient can specify one or more contacts, such as friends or family, that are authorized to view the patient-associated data. Thus, the authorized additional user computing device(s) 122 can implement a patient care application 120 or otherwise have access to the shared patient data. For example, the authorized additional user computing device(s) 122 can receive an alert if an alarm is triggered, such as a patient's oxygen saturation alarm being triggered.

As described herein, the patient management and monitoring system 110 can provide graphical user interfaces and alerts associated with the patient to the clinician user computing device 124.

Figure 1B:
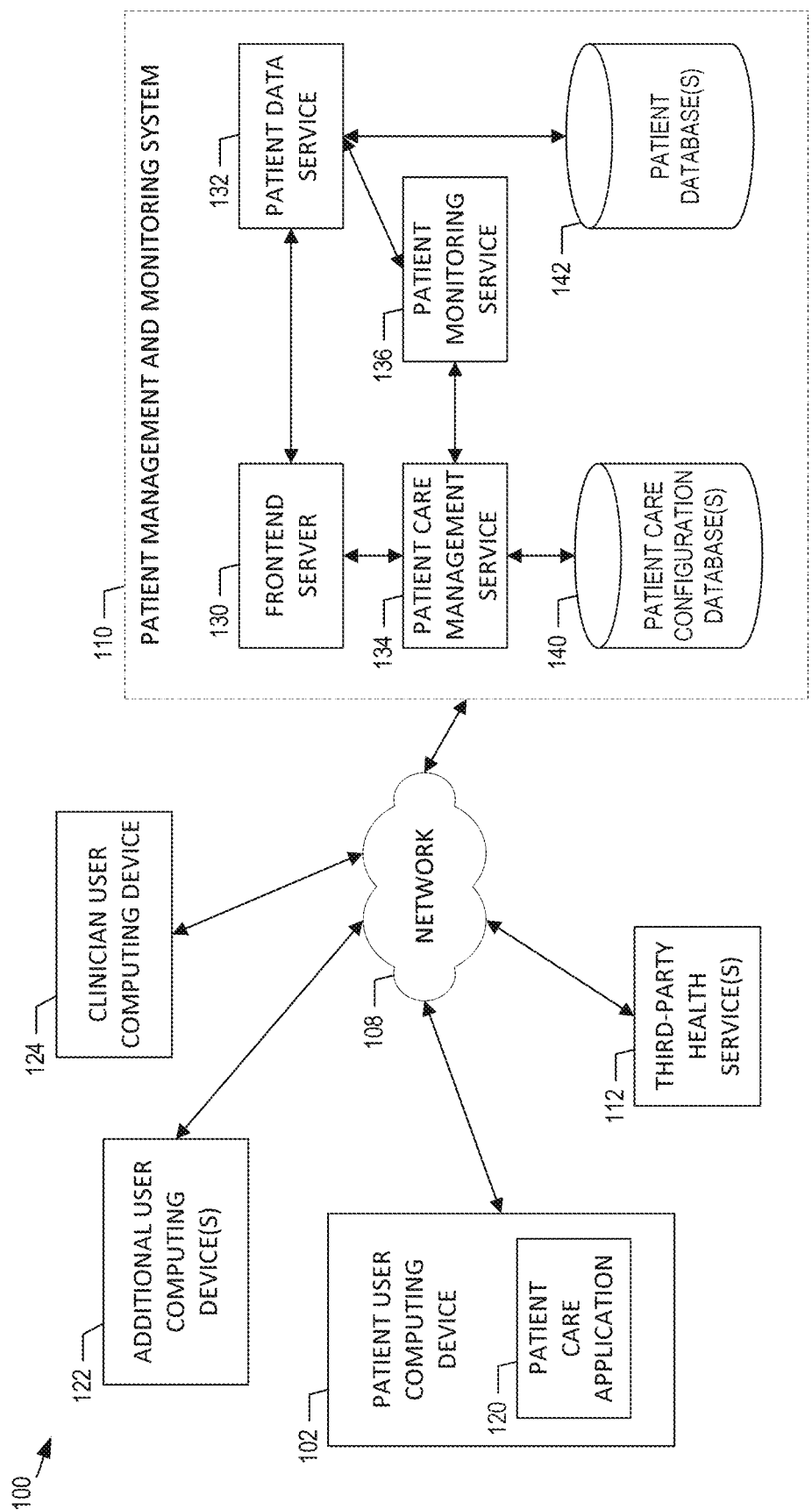

FIG. 1B illustrates components of the patient management and monitoring system 110 in the network environment 100. The network environment 100 of FIG. 1B can be similar or identical to the network environment 100 of FIG. 1A. For example, the network environment 100 of FIG. 1B can include the patient user computing device 102, the connectivity hub device 106 (not illustrated), patient sensor devices 104A, 104B and/or additional devices 114A, 114B (not illustrated), additional user computing devices 122, third-party health services 112, and/or the clinician user computing device 124.

The patient management and monitoring system 110 can include a frontend server 130, a patient care management service 134, a patient data service 132, and/or a patient monitoring service 136. The patient data service 132 can receive patient data from the patient user computing device 102 and/or the connectivity hub device 106. The patient data service 132 can store patient data in the patient database(s) 142. Example patient data can include, but is not limited to, temperature, blood pressure, pulse rate, respiratory rate (RRa), total hemoglobin (SpHb®), carboxyhemoglobin (SpCO®), methemoglobin (SpMet®), oxygen content (SpOC™), oxygen saturation (SpO2), pulse rate (PR), perfusion index (Pi), pleth variability index (PVi®), and/or electroencephalogram (EEG) data, some of which can be collected by the patient sensor device(s) 104A, 104B.

In some embodiments, the patient sensor device(s) 104A, 104B, the additional device(s) 114A, 114B, and/or the patient user computing device 102 can include one or more sensors that can obtain information associated with position, acceleration, orientation, and/or movement of a patient. Example one or more sensors can include, but are not limited to, an accelerometer, a gyroscope, and/or a magnetometer. The patient user computing device 102 and/or the connectivity hub device 106 can process the sensor information to determine a position, acceleration, orientation, and/or movement of the patient (such as the patient's position and/or orientation in three-dimensional space). For example, the patient user computing device 102 and/or the connectivity hub device 106 can determine whether the patient is upright based on the sensor information.

The frontend server 130 can provide patient care configuration user interfaces that allow a care provider administrator to configure a patient care user interface. Upon receiving administrator user selections, the frontend server 130 can cause client configuration packages to be created or updated via the patient care management service 134. The patient care management service 134 can store configurations in the patient care configuration database 140. The patient care management service 134 can also be responsible for maintaining patient monitoring alarms, which can be customized for a particular patient care user interface. The patient monitoring service 136 can communicate with the patient care management service 134 to receive alarm configurations. The patient monitoring service 136 can communicate with the patient data service 132 to monitor patient data, trigger patient alarms, and/or to send alerts regarding a patient. The frontend server 130 can further provide graphical user interfaces to the clinician user computing device 124. A clinician can view patient data and/or alerts via the provided graphical user interfaces.

In some embodiments, the patient management and monitoring system 110 and/or components thereof are implemented by one or more virtual machines implemented in a hosted computing environment. The hosted computing environment may include one or more rapidly provisioned and/or released computing resources. The computing resources may include hardware computing, networking and/or storage devices configured with specifically configured computer-executable instructions. Hosted computing environments can be referred to as "cloud computing" environments.

Patient Sensor Device

Wirelessly transmitting physiological data may have some limitations. Sensors capable of wirelessly transmitting patient physiological data may include internal power source (for example, battery) that may be limited in size and/or capacity. Since continuous data collection and wireless transmission can require significant power usage, operation time duration of such sensors can be limited. Therefore, such wireless sensors and/or batteries may need to be replaced and/or recharged regularly. Although such wireless patient monitoring sensors may utilize rechargeable batteries, having rechargeable batteries may not be suitable where it may not be ideal for a patient to wait for the battery to recharge in time of need. Accordingly, it can be advantageous to provide a sensor system that is compatible with existing sensors and monitors and is capable of wireless communication as discussed herein.

Figure 2A:
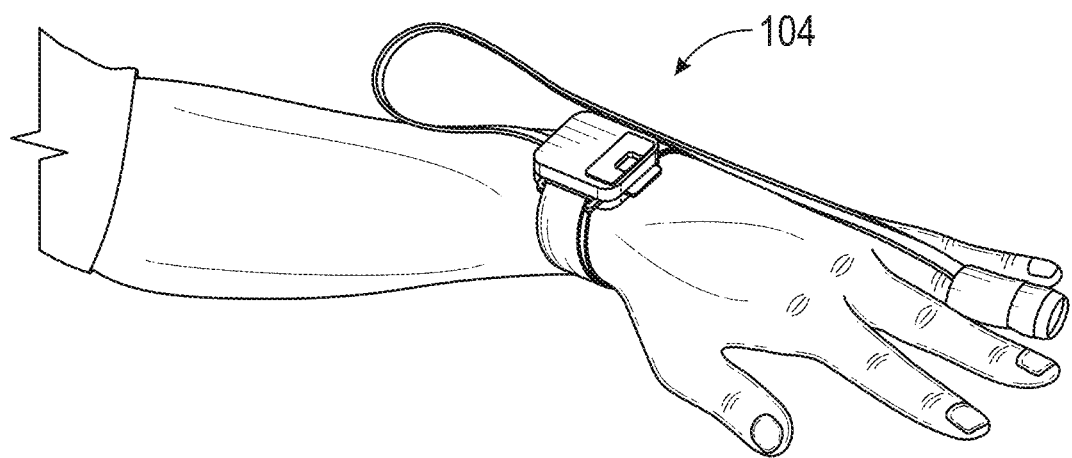
FIG. 2A is a perspective view of an example patient sensor device on a patient, according to some embodiments of the present disclosure.

FIG. 2A illustrates an example patient sensor device 104 attached to a wrist of a patient. The patient sensor device 104 can be attached to a patient with a strap. The patient sensor device 104 does not have to be physically attached to a monitoring device. Therefore, a patient may be able to move around, for example, in their home, hospital room, hotel room, outdoor tent, or outdoor area (for example, parks, beaches, and malls), without having to worry about cables or cords limiting their range of movement. As such, the patient sensor device 104 can establish wireless communication with nearby devices to securely transmit physiological data the patient sensor device 104 collects from a patient. The patient sensor device 104 can be an example pulse oximetry device. An example patient sensor device 104 can be a wearable sensor assembly. As described herein, a reusable device can be configured to engage a disposable device to form a wearable sensor assembly.

The patient sensor device 104 can be disposed on various locations of a patient's body. For example, instead of the patient sensor device 104 being attached to the wrist of a patient as illustrated in FIG. 2A, the patient sensor device 104 can be disposed on a patient's chest. The patient sensor device 104 can be disposed on other locations on a patient including, but not limited to, torso, back, shoulder, arms, legs, neck, or head. Various means can be used to attach the patient sensor device 104 to a patient. For example, the patient sensor device 104 can be attached to, for example, the skin of a patient with an adhesive. In another example, the patient sensor device 104 can be attached to a patient with a fastener, such as tape, laid over at least a portion of the patient sensor device 104. Alternatively, the patient sensor device 104 can be attached to a patient via one or more straps, such as the strap(s) shown in FIG. 2A.

Figure 2B:
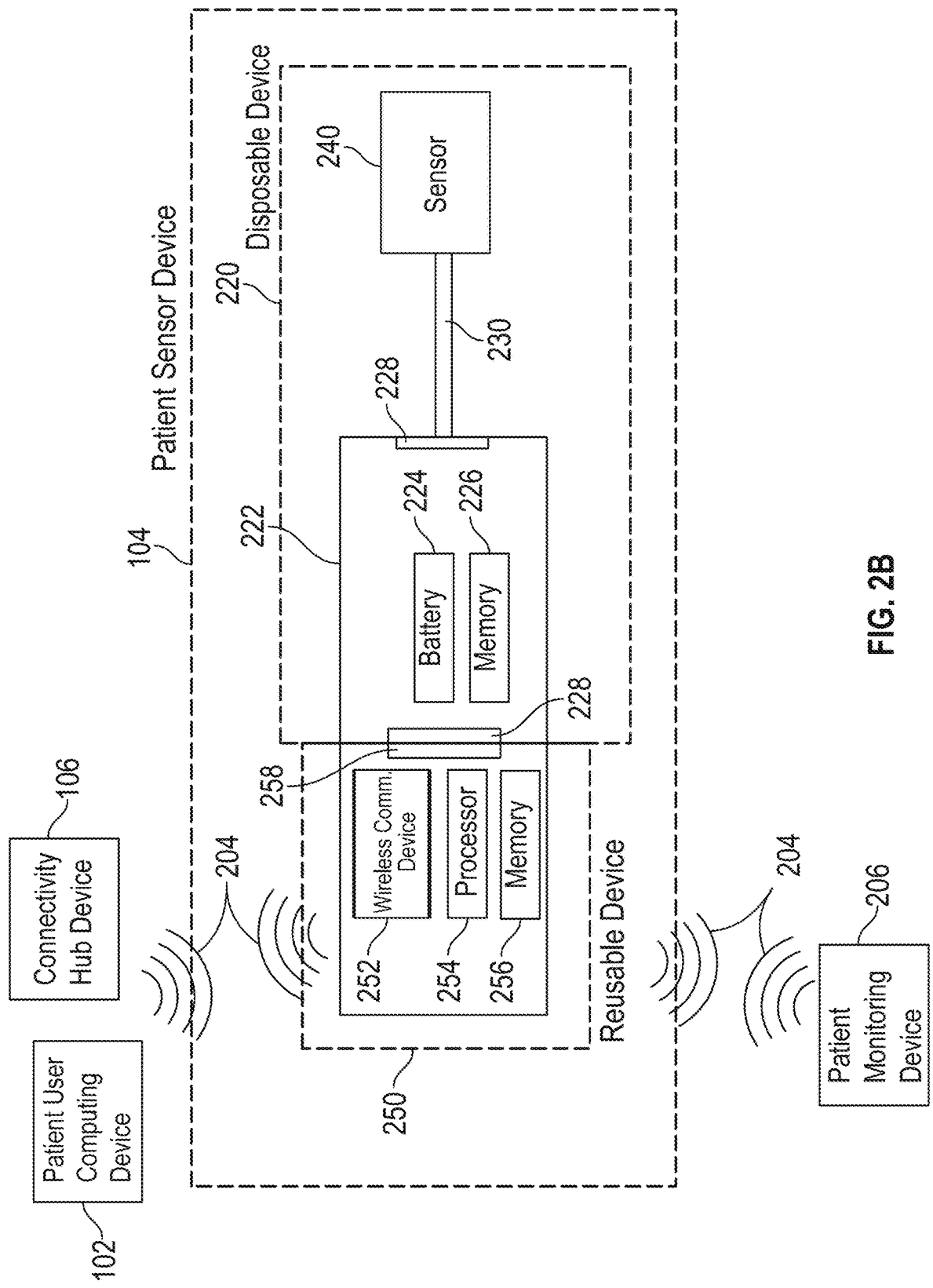
FIG. 2B is a block diagram illustrating a patient sensor device and other devices, and communications between the devices, according to some embodiments of the present disclosure.

FIG. 2B is an example block diagram illustrating an example patient sensor device 104 including a disposable device 220 and a reusable device 250. As used herein, the terms "disposable" and "reusable" refer to an expected length of use for respective portions of the patient sensor device 104. For example, the sensor 240 of the disposable device 220 may come into physical contact physical contact with a patient, and, therefore, may be discarded after some period of use by the patient. As another example, the battery 224 of the disposable device 220 may not be a rechargeable battery, and the disposable device 220 may be discarded after the battery loses charge. In contrast to the disposable device 220, the reusable device 250 may be designed to be disinfected easily and its intended use may be to be used with multiple disposable devices. However, in some embodiments, the disposable device 220 can be used multiple times and/or over multiple days or weeks. The expected period of use for the reusable device 250 may be longer than the expected period of use of the disposable device 220. In other embodiments, some patient sensor devices 104 do not have "disposable" portions in the sense that those devices may not have portions that have expected shorter lifespans that other portions of the same device.

The disposable device 220 can collect physiological data from a patient and transmit the data to the reusable device 250. The reusable device 250 can receive the physiological data from the disposable device 220 and wirelessly transmit the data to the patient user computing device 102, the connectivity hub device 106, and/or the patient monitoring device 206. In some embodiments, the patient monitoring device 206 can be used as part of a hospital patient monitoring system, which can include various types of monitors capable of displaying patient health data. An example patient monitoring device 206 includes a Root® Platform, a patient monitoring and connectivity hub by Masimo Corporation, Irvine, CA. A mobile physiological parameter monitoring system usable with the cable is described in U.S. Pat. No. 9,436,645, issued on Sep. 6, 2016, titled "MEDICAL MONITORING HUB," which is hereby incorporated by reference in its entirety.

The disposable device 220 can include a dock 222, a battery (or batteries) 224, a memory 226, one or more sensors 240, and one or more cable assemblies 230. As used herein, the disposable device 220 can be referred to herein as a "sensor." The battery 224 can provide power for the reusable device 250. The battery 224 can be housed within the dock 222 of the disposable device 220. The battery 224 can provide power for the disposable device 220 and the reusable device 250 when the reusable device 250 is coupled with the disposable device 220. The reusable device 250 may use the power from the battery 224 to, for example, receive and/or retrieve physiological data from the disposable device 220, process the physiological data, and transmit the processed physiological data to, for example, the patient user computing device 102 and/or the connectivity hub device 106.

When the battery 224 is depleted, a patient may discard the disposable device 220 with the depleted battery 224 and use a new disposable device 220 with a charged battery 224. This can advantageously allow users, for example, care providers, to continue remote monitoring and/or managing patients without having to use multiple reusable devices 250. This can prevent or reduce the need to reestablish wireless communication between the reusable device 250 and, for example, a nearby device such as the patient user computing device 102 and/or the connectivity hub device 106.

The memory 226 can be housed within the dock 222 of the disposable device 220. The memory 226 can store physiological data collected by the sensor 240. In some embodiments, the memory 226 may be optional. For example, the physiological data collected by the sensor 240 may be transmitted to the reusable device 250 without first being stored. This can advantageously prevent or reduce the likelihood of physiological data being thrown away when replacing the disposable device 220.

The dock 222 can removably couple with the reusable device 250. Once the reusable device 250 is coupled with the dock 222, the reusable device 250 can communicate with the disposable device 220 to transmit data therebetween. For example, the reusable device 250 can transmit sensor signal to the disposable device 220 to operate the sensor 240 to collect physiological data from a patient. The collected physiological data can then be transmitted to the reusable device 250.

The cable 230 can be flexible or non-flexible. The cable 230 can be a thin film including electrical circuitries. The cable 230 can be surrounded by different types of electrical insulating material. The cable 230 can be substantially flat or round.

The sensor 240 can collect various types of physiological data for the patient sensor device 104. The various types of physiological data can include, but not limited to, blood pressure, respiratory rate (RRa), total hemoglobin (SpHb), carboxyhemoglobin (SpCO), methemoglobin (SpMet), oxygen content (SpOC), oxygen saturation (SpO$_2$), pulse rate (PR), perfusion index (Pi), and pleth variability index (PVi), and/or electroencephalogram (EEG). An example sensor 240 can include, but is not limited to, a RD rainbow SET Sensor™ Rainbow® sensor, Rainbow Acoustic Monitoring® sensor, Radius PPG™, RD SET™ sensor, LNCS® sensor, and/or SofTouch™ sensor, by Masimo Corporation, Irvine, CA.

The data collected by the sensor 240 may be in a raw data format. As such, a processor 254 of the reusable device 250 may process the raw data and transmit the processed data to the patient user computing device 102, the connectivity hub device 106, and/or the patient monitoring device 206. Additionally or alternatively, the sensor 240 can process the raw physiological data and send processed physiological data to the reusable device 250. When the reusable device 250 wirelessly transmits processed physiological data, power consumption of the reusable device 250 can be reduced since processed physiological data can be smaller in size than unprocessed, raw physiological data.

As described herein, the reusable device 250 can, for example, receive and/or retrieve physiological data from the disposable device 220, process the physiological data, and wirelessly transmit the processed physiological data to, for example, with the patient user computing device 102 and/or the connectivity hub device 106. The reusable device 240 can include a wireless communication device 252, a processor 254, and a memory 256. As described herein, the reusable device 250 can receive physiological data from the disposable device 220 when the reusable device 250 is coupled to the disposable device 220, for example, via the dock 222. The reusable device 250 can transmit the physiological data received from the disposable device 220 to nearby devices. For example, as shown in FIG. 2B, the reusable device 250 can establish wireless communication 204 with the patient user computing device 102 and/or the connectivity hub device 106. The wireless communication 204 may be established via the wireless communication device 252.

The wireless communication device 252 can include an RFID (radio-frequency identification) antenna. Additionally or alternatively, the wireless communication device 252 can include a Bluetooth antenna. The wireless communication device 252 can include multiple antennae. A first antenna can be a receiving antenna and a second antenna can be a transmitting antenna. In other embodiments, both the first antenna and the second antenna can each receive and transmit data. In some embodiments, the first antenna can be a passive antenna while the second antenna can be an active antenna. An active antenna can include a built-in amplifier that can amplify certain spectrum or frequency of signals.

In some embodiments, the wireless communication device 252 can include multiple antennae for establishing different types of wireless communication. For example, the wireless communication device 252 may include a first antenna for establishing an RFID-based or NFC-based (near field communication) wireless communication with nearby devices, and a second antenna for establishing a Bluetooth-based wireless communication with nearby devices. In some embodiments, both the first and the second antenna are capable of establishing RFID-based and/or Bluetooth-based wireless communication.

The memory 256 can be computer hardware integrated circuits that store information for immediate use for a computer (for example, the processor 254). The memory 256 can store the patient physiological data received from the sensor 240. The memory 256 can be volatile memory. For example, the memory 256 can be a dynamic random access memory (DRAM) or a static random access memory (SRAM). The memory 256 can be a non-volatile memory. For example, the memory 256 can be a flash memory, ROM (read-only memory), PROM (programmable read-only memory), EPROM (erasable programmable read-only memory), and/or EEPROM (electrically erasable programmable read-only memory).

The memory 256 of the reusable device 250 can store patient physiological data received from the sensor 240. The memory 256 can store instructions that, when accessed, can prompt the processor 254 to receive or retrieve patient physiological data from the disposable device 220. When the reusable device 250 is not wirelessly connected with other devices, for example, the patient user computing device 102 and/or the connectivity hub device 106, the reusable device 250 may store the physiological data in the memory 256. When the reusable device 250 is wirelessly connected with other devices, for example, the patient user computing device 102 and/or the connectivity hub device 106, the reusable device 250 may wirelessly transmit the physiological data to the other devices.

In some embodiments, the memory 256 can store patient physiological data regardless of whether the reusable device 250 has established wireless communication with other devices. For example, the physiological data may be stored in the memory 256 regardless of whether the reusable device 250 is in wireless communication with other devices.

In some embodiments, the patient sensor device 104 can optimize how data is stored. For example, in order to maximize the life of the memory 256, the memory 256 may store a health-related event (for example, an event representing high blood pressure and low blood oxygen level) but not a series of individual physiological data items (for example, individual blood pressure and blood oxygen readings). For example, the information related to a health-related event can be a time stamp when an event occurred or it can be a snapshot of data taken before, during, and/or after an event. In some embodiments, the memory 256 can store a window of data, such as, for example, one, two, three, five, or seven days of data.

In some embodiments, the coupling between the reusable device 250 and the dock 222 of the disposable device 220 can be waterproof or shockproof. The disposable device 220 and/or the reusable device 250 can be shockproof and/or waterproof. The disposable device 220 and the reusable device 250 can be durable under various types of environments. For example, the reusable device 250 can be fully enclosed, allowing it to be washed, sanitized, and reused.

Further details regarding the patient sensor device 104 can be found in U.S. application Ser. No. 16/599,017, filed Oct. 10, 2019, titled "SYSTEM FOR TRANSMISSION OF SENSOR DATA USING DUAL COMMUNICATION PROTOCOL" (hereinafter the "Dual Communication reference"), which is hereby incorporated by reference in its entirety.

Figure 2C:
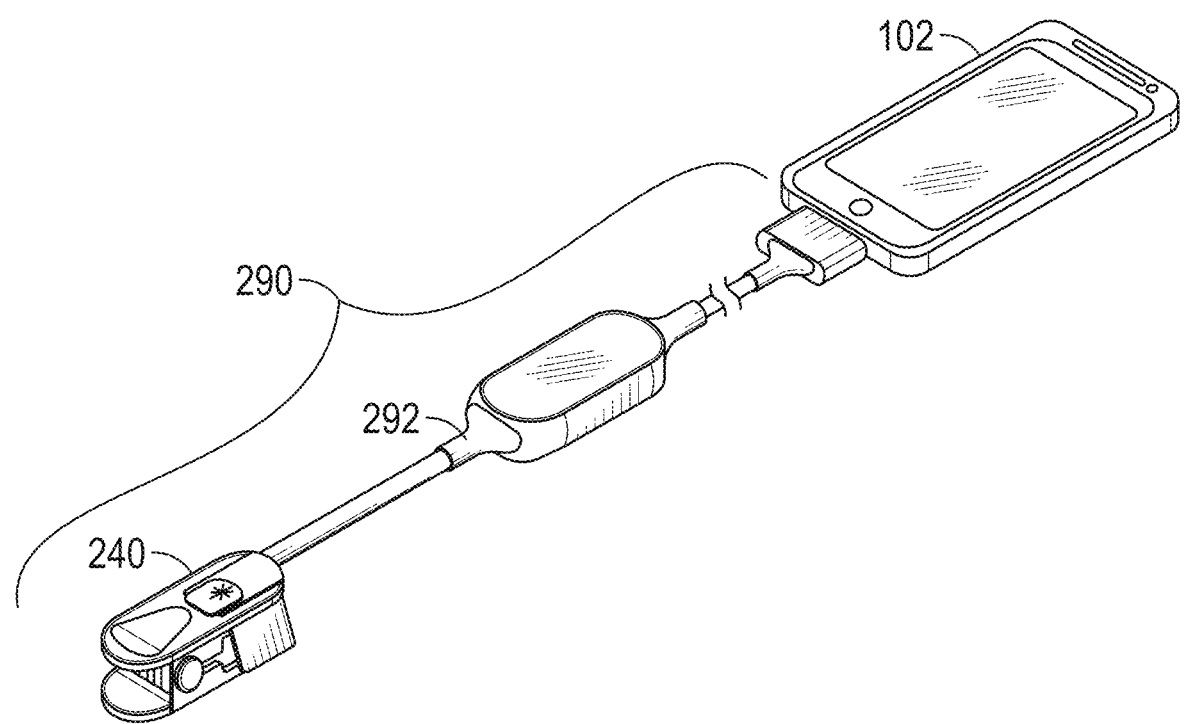
FIGS. 2C-2H illustrate additional example patient sensor devices, according to some embodiments of the present disclosure.

FIG. 2C illustrates another example patient sensor device 290. The patient sensor device 290 can include a sensor 240 and a cable assembly 292. As shown, the sensor 240 can be coupled to the patient user computing device 102 via the cable assembly 292. Accordingly, the patient user computing device 102 may receive patient physiological data from the sensor 240 via the cable assembly 292.

The example patient sensor device 290 can have some advantages. For example, the sensor 240 can be powered by a power source of the patient user computing device 102, which may have greater capacity than the battery 224 of the disposable device 220. As such, the configuration of the patient sensor device 290 and the patient user computing device 102 can collect physiological data for a longer period of time relative to some other sensor configurations. Patient physiological data can be transmitted to the patient user computing device 102 via the cable assembly 292, which may have some security advantages over wireless data transmission methods.

Figure 2D:
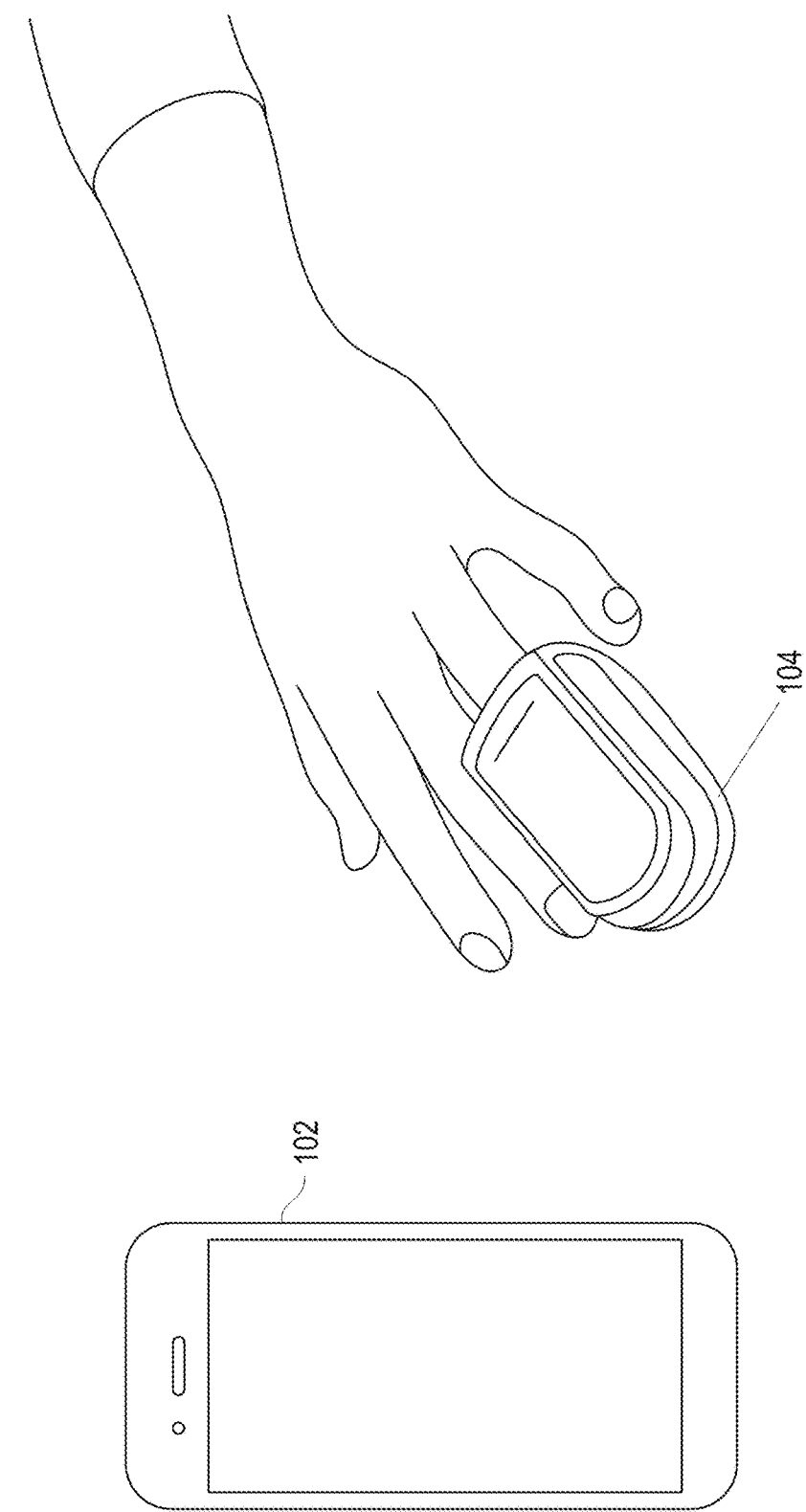

In FIG. 2D, the environment 251 includes an example patient sensor device 104 and a patient user computing device 102. The patient sensor device 104 of FIG. 2D can be a pulse oximeter that is designed to non-invasively monitor patient physiological parameters from a fingertip. The patient sensor device 104 of FIG. 2D can include a display and a touchpad and/or touchscreen. Example physiological parameters that the patient sensor device 104 of FIG. 2D can measure can include, but is not limited to, blood oxygen saturation, pulse rate, perfusion index, respiration rate, and/or pleth variability index. As described herein, the patient sensor device 104 of FIG. 2D can be wirelessly connected to the patient user computing device 102. An example patient sensor device 104 includes a MightySat® fingertip pulse oximeter by Masimo Corporation, Irvine, CA.

Figure 2E:
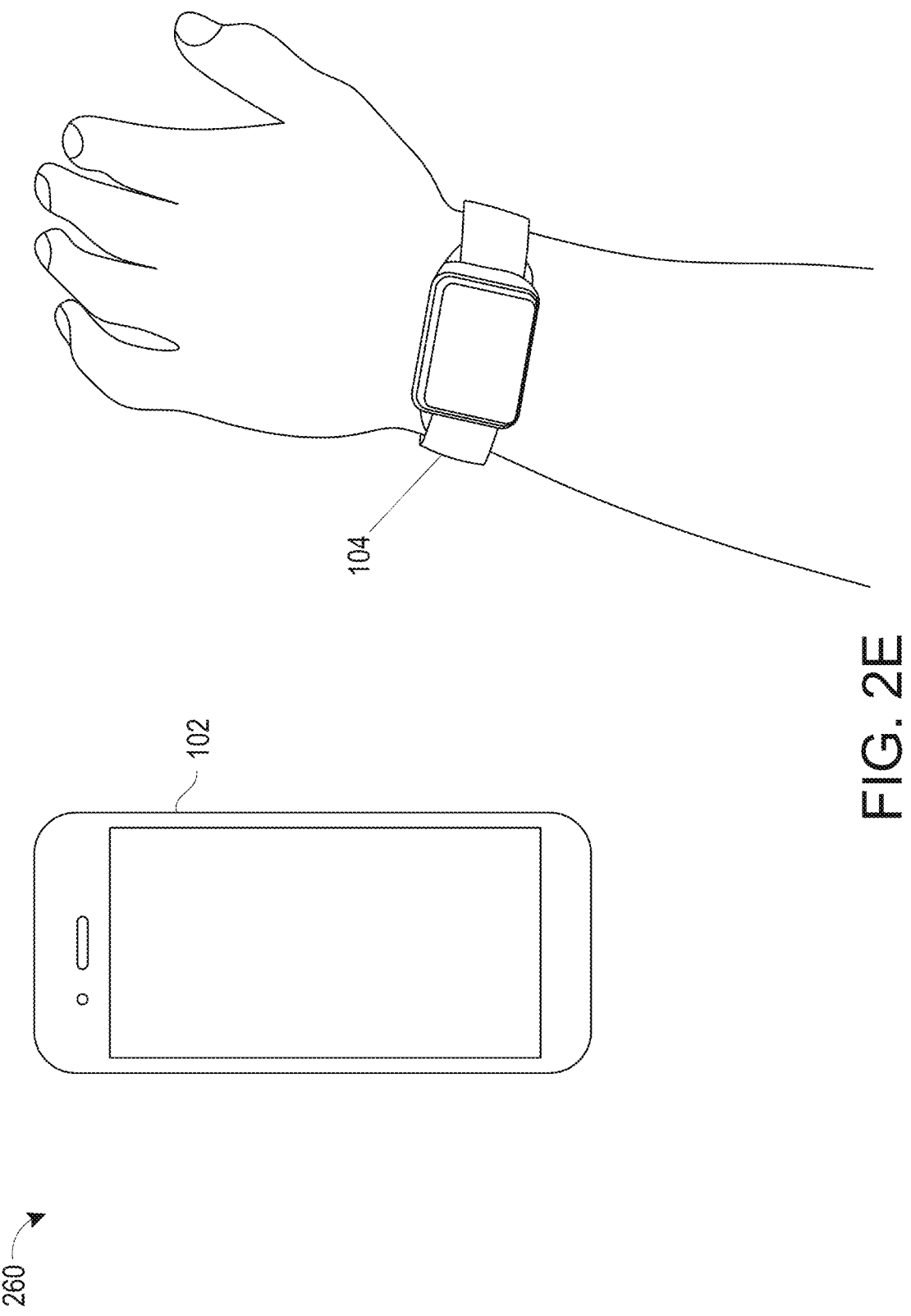

In FIG. 2E, the environment 260 includes an example patient sensor device 104 and a patient user computing device 102. The patient sensor device 104 of FIG. 2E can be configured to be worn on a patient's wrist to non-invasively monitor patient physiological parameters from a fingertip. The patient sensor device 104 of FIG. 2E can include a display and/or touchscreen. In some embodiments, the patient sensor device 104 of FIG. 2E can present a graphical user interface, which is designed to be presented on a wrist-worn display. Example physiological parameters that the patient sensor device 104 of FIG. 2E can measure can include, but is not limited to, blood oxygen saturation, pulse rate, perfusion index, respiration rate, and/or pleth variability index. As described herein, the patient sensor device 104 of FIG. 2E can be wirelessly connected to the patient user computing device 102. In some embodiments, the patient sensor device 104 of FIG. 2E can be a smartwatch.

Figure 2F:
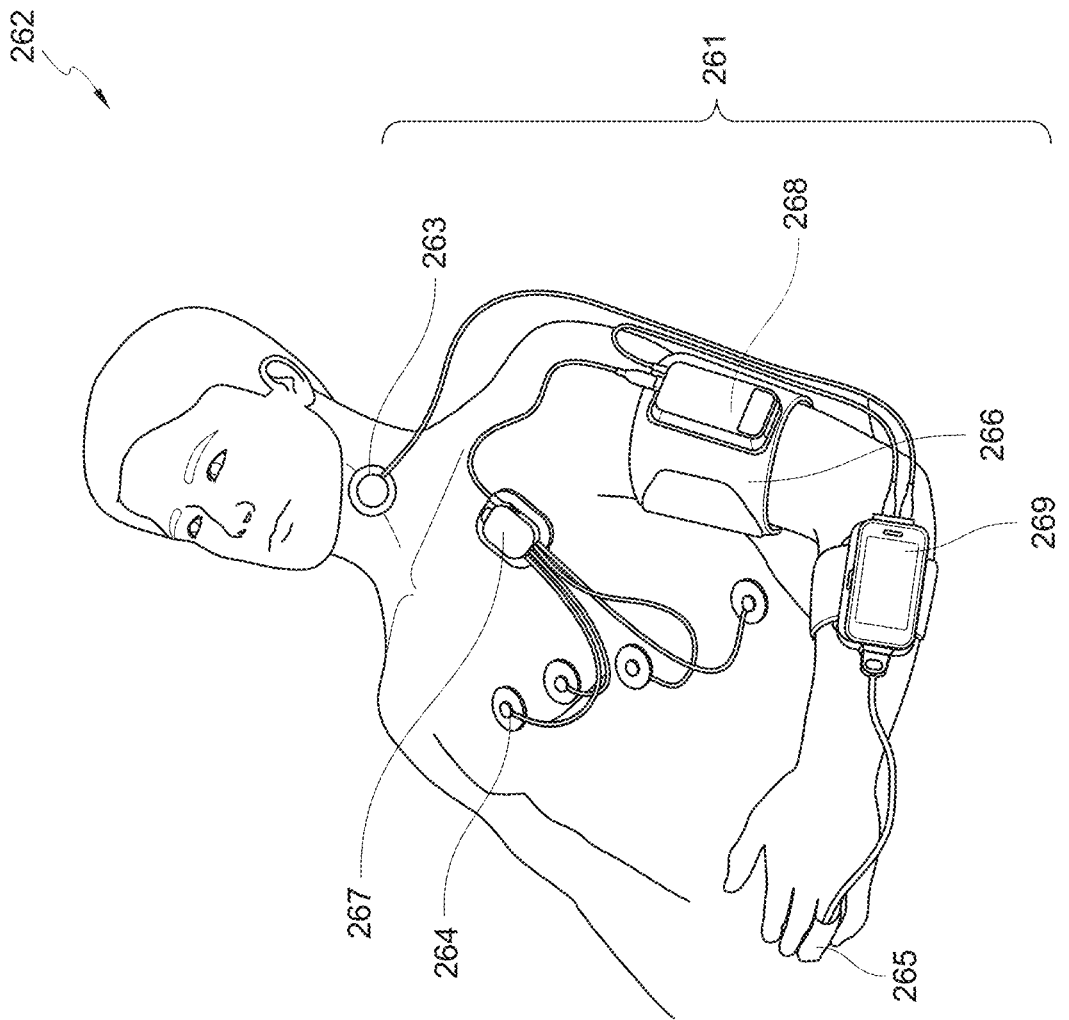

In FIG. 2F, the environment 262 includes an example patient sensor system 261. The patient sensor system 261 can include an acoustic sensor 263, an electrode 264, an optical sensor 265, a blood pressure cuff 266, an electrocardiogram (ECG) device 267, a blood pressure monitor 268, and/or a patient monitor 269. Any or all of the sensors/cuffs/monitors 263, 264, 265, 266, 267, 268 can be reusable, disposable, or resposable. Resposable devices can include devices that are partially disposable and partially reusable. For example, the acoustic sensor 263 can include both reusable electronics and a disposable contact surface (such as an adhesive) where the sensor 263 comes in to contact with a skin of the patient. As another example, the ECG device 267 can include a reusable portion and a disposable portion. In some embodiments, the patient sensor system 261 (such as the patient monitor 269 and/or individual sensors of the patient sensor system 261) can communicate with the patient user computing device 102 and/or the connectivity hub device 106.

The ECG device 267 can be connected to the electrodes 112 and to the blood pressure monitor 268. The blood pressure monitor 268 can be connected to the patient monitor 269. The acoustic sensor 263 can be connected to the patient monitor 269. The optical sensor 265 can be connected to the patient monitor 269. The ECG device 267 can be secured to a chest of the patient. The blood pressure monitor 269 can be secured to an arm of the patient and/or a blood pressure cuff 266 can be secured to the arm.

The electrocardiogram (ECG) device 267 can be used to monitor electrical activity of the heart of the patient. The ECG device 267 can be coupled to the one or more electrodes 264. The ECG device 267 can include one, two, three, four, five, six or seven or more electrodes 264. The blood pressure monitor 268 and the blood pressure cuff 266 can be used to measure the blood pressure of the patient. The blood pressure cuff 266 can inflate and/or deflate. The blood pressure cuff 266 can be an oscillometric cuff that is actuated electronically (e.g., via intelligent cuff inflation and/or based on a time interval) to obtain blood pressure information of the patient. The blood pressure monitor 268 can transmit the blood pressure data to the patient monitor 269.

The optical sensor 265 can include one or more emitters and one or more detectors for obtaining physiological information indicative of one or more physiological parameters for the patient. These parameters can include various blood analytes such as oxygen, carbon monoxide, methemoglobin, total hemoglobin, glucose, proteins, glucose, lipids, a percentage thereof (e.g., concentration or saturation), and the like. The optical sensor 265 can also be used to obtain a photoplethysmograph, a measure of plethysmograph variability, pulse rate, a measure of blood perfusion, and the like. The optical sensor 265 can obtain information such as oxygen saturation (SpO2), pulse rate, a plethysmograph waveform, perfusion index (PI), pleth variability index (PVI), methemoglobin (MetHb), carboxyhemoglobin (CoHb), total hemoglobin (tHb), and/or glucose and data related to such information can be transmitted to the patient monitor 269. The optical sensor 265 can be a pulse oximeter, for example.

The acoustic sensor 263 can include an acoustic transducer, such as a piezoelectric element. The acoustic sensor 263 can connect to the patient monitor 269. The acoustic sensor 263 can detect respiratory and other biological sounds of a patient and provide signals reflecting these sounds to the patient monitor 269. An example acoustic sensor 263 can be a piezoelectric sensor that obtains physiological information reflective of one or more respiratory parameters of the patient. These parameters can include, for example, respiratory rate, inspiratory time, expiratory time, inspiration-to-expiration ratio, inspiratory flow, expiratory flow, tidal volume, minute volume, apnea duration, breath sounds, rales, rhonchi, stridor, and/or changes in breath sounds such as decreased volume or change in airflow. In addition, in some cases the acoustic sensor 263 can measure other physiological sounds such as heart rate (e.g., to help with probe-off detection), heart sounds (for example, S1, S2, S3, S4, and murmurs), and changes in heart sounds such as normal to murmur or split heart sounds indicating fluid overload. In some implementations, a second acoustic sensor can be provided over the chest of the patient for additional heart sound detection.

Figure 2G:
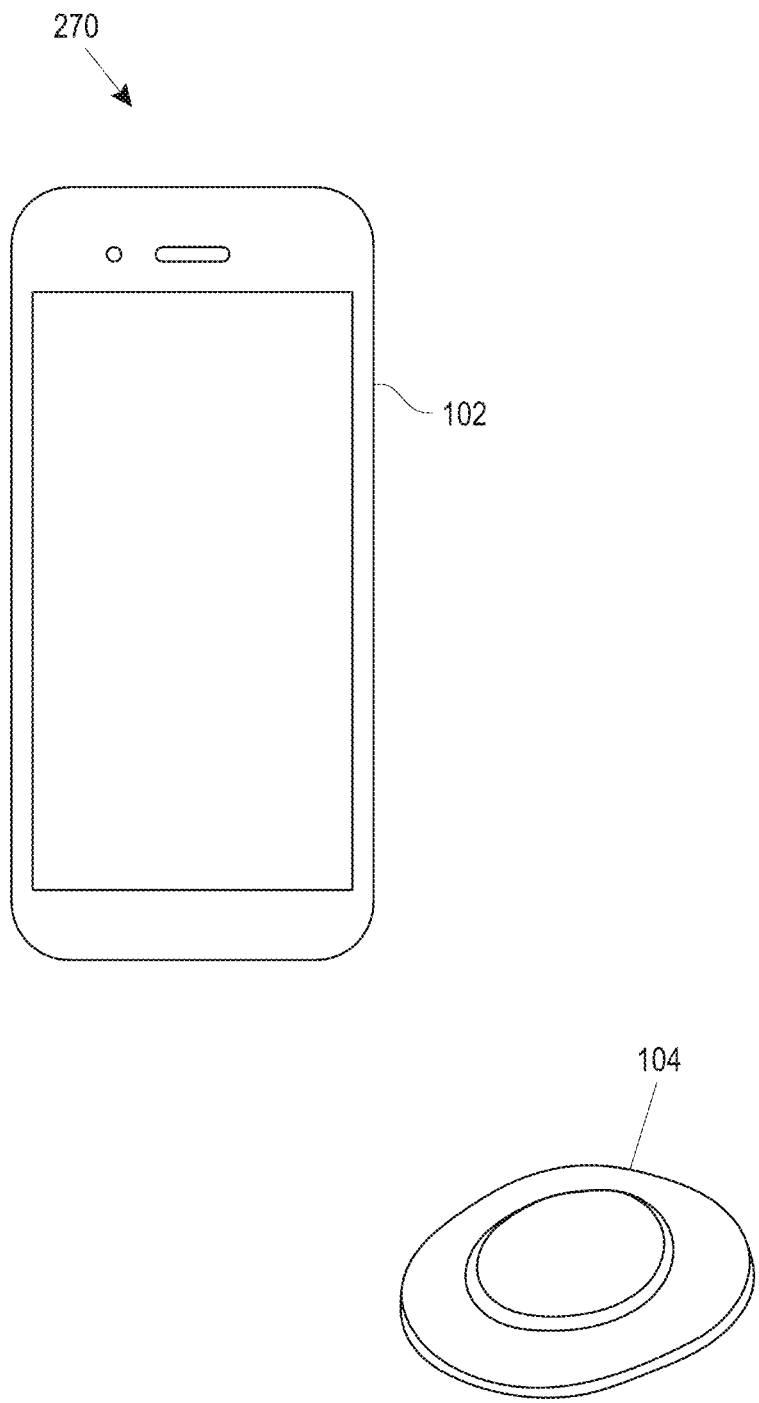

In FIG. 2G, the environment 270 includes an example patient sensor device 104 and a patient user computing device 102. The patient sensor device 104 of FIG. 2D can be a temperature sensor that is designed to non-invasively monitor physiological parameters of a patient. In particular, the temperature sensor 104 can measure a temperature of the patient. As described herein, the temperature sensor 104 can be wirelessly connected to the patient user computing device 102. The temperature sensor 104 of FIG. 2G can be described in further detail below with respect to FIG. 2H.

Figure 2H:
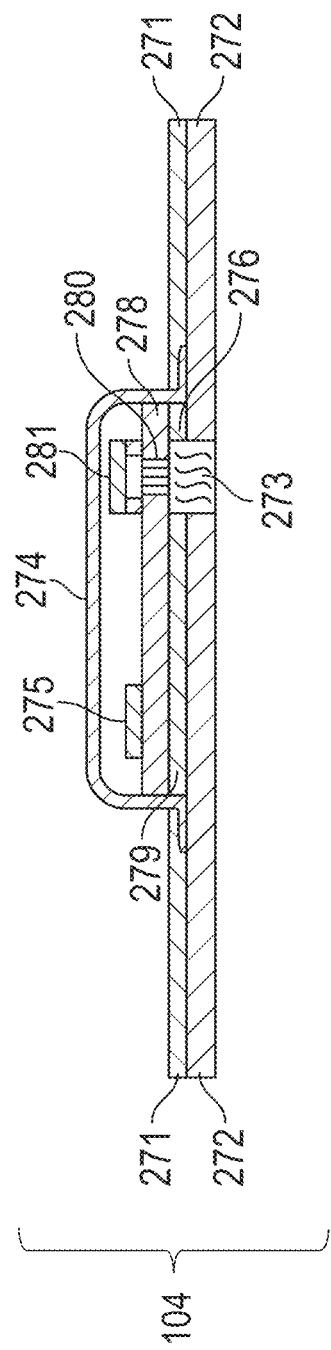

In FIG. 2H, the patient sensor device 104 can be a temperature sensor assembly. FIG. 2H can depict a schematic cross-sectional view of the temperature sensor assembly 104. In the assembly, the top surface of the bottom base 272 can be in contact with and adhered to the bottom surface of the top base 271. A rim of the housing 274 can be sandwiched between the two bases 271, 272 to secure the housing 274. The housing 274 can protrude through a cut-out of the top base 271. Within the housing 274, a battery 279 and a mounting frame 276 can be adjacent the top surface of the bottom base 272.

A temperature device 281 can be mounted on the circuit board 278. The temperature device 281 can be in thermal contact with the patient's skin to sense the temperature of the patient. Inputs to the temperature device 281 can be thermally connected to multiple through-hole vias 280 located in the circuit board 278. A through-hole vias can be a small vertical opening or pathway in the circuit board 278 through which thermally and/or electrically conductive material can be placed, thereby permitting transmission of thermal and/or electrical energy from one side of the circuit board 278 to the other side. Under the through-hole vias 280 is an aperture or opening that extends through the mounting frame 276 (to form a mounting frame aperture) and through the bottom base 272 of the temperature sensor assembly 104. The aperture can provide access from the temperature sensor 281 to the patient's skin when the temperature sensor assembly 104 is disposed on the patient. The aperture and the through-hole vias 280 are filled with thermally conductive material 273. Thermally conductive materials can include, by way of non-limiting example, thermally conductive elastomers, polymers, and resins, to name a few. The temperature sensor assembly 104 can be affixed to the patient's skin. The thermally conductive material 273, which can be exposed to the patient's skin, can transmit thermal energy from the patient's body through the aperture and the through-hole vias 273 to arrive at the inputs to the temperature device 281.

Advantageously, the temperature sensor 104 can measure the patient's body core temperature (an established and useful vital sign) from the skin surface. In the human body, there is a natural heat flux between the body core and the skin surface because the body core temperature is typically at a higher temperature than that of the skin surface. The bottom base 272 and top base 271 of the temperature sensor 104, which is in contact with the patient's skin, can possess thermal insulation properties. Illustratively, by way of non-limiting example, the bottom base 272 and top base 271 can be made of thermally insulating materials including polyurethane foam, polystyrene foam, neoprene foam, neoprene rubber, polyester (Mylar), polytetrafluoroethylene (PTFE), silicone foam, silicone rubber, or the like.

In some embodiments, a patient sensor device 104 can include a processor and a temperature sensor. A temperature sensor may capture one or more physiological signals related to a patient's temperature, such as a body core temperature. The processor can process the one or more physiological signals to measure the patient's body core temperature, which is a vital sign used by clinicians to monitor and manage patients' conditions. The temperature sensor can include a thermocouple, a temperature-measuring device having two dissimilar conductors or semiconductors that contact each other at one or more spots. A temperature differential can be experienced by the different conductors. The thermocouple can produce a voltage when the contact spot differs from a reference temperature. Thermocouples may be self-powered and therefore may not require an external power source for operation. In some embodiments, the temperature sensor can include a thermistor. A thermistor is a type of resistor whose resistance value can vary depending on its temperature. Thermistors typically offer a high degree of precision within a limited temperature range.

In some embodiments, a patient sensor device 104 can include an acoustic respiration sensor. The acoustic respiration sensor may capture one or more physiological signals related to vibrational motion from the patient's body (e.g., the patient's chest) that are indicative of various physiologic parameters and/or conditions, including without limitation, heart rate, respiration rate, snoring, coughing, choking, wheezing, and respiratory obstruction (e.g., apneic events). Additional details regarding an example acoustic respiration sensor are described in U.S. Pat. No. 8,771,204, titled "ACOUSTIC SENSOR ASSEMBLY," which is hereby incorporated by reference in its entirety.

In some embodiments, a patient sensor device 104 can include a processor and an electrocardiogram (ECG) sensor. The ECG sensor may capture one or more physiological signals related to cardiac activity. The processor can process the one or more physiological signals to measure the patient's cardiac activity. In some embodiments, the patient management and monitoring system 110 can process the ECG parameter values to detect arrhythmias, such as bradycardia, tachyarrhythmia, or ventricular fibrillation.

Additional temperature sensor embodiments (also referred to as "wearable devices") are described in U.S. patent application Ser. No. 17/206,907, titled "WEARABLE DEVICE FOR NONINVASIVE BODY TEMPERATURE MEASUREMENT," filed on Mar. 19, 2021 ("the '907 Application"), which is hereby incorporated by reference in its entirety. For example, the '907 Application describes example wearable devices and aspects thereof in paragraphs [0005]-[0020] and [0043]-[0124], among others.

Additional example patient sensor devices 104 can include blood pressure monitors and/or digital weight scales. Blood pressure monitors and/or digital weight scales can be used to diagnose and/or treat health conditions as described herein. For example, a patient's blood pressure and/or weight can be used in combination with other patient physiological data to diagnose and/or treat health conditions related to COVID-19, diabetes, sleep apnea, one or more addictions, one or more cardiac diseases, obesity, and/or one or more respiratory diseases.

Medical Applicator Device

In an opioid medical context, it can be important to administer an opioid medication, such as an opioid receptor antagonist (e.g., Naloxone), to victims of opioid overdoses as soon as possible. Often it can be a matter of life or death for the overdose victim. It can be advantageous for a medication applicator device to administer medication without user or responder action. It can be further advantageous for a device to provide assistance to first responders in the event of an opioid overdose event, such as visual or auditory indicators and/or instructions. For example, a patient can wear a wrist band that changes color to indicate an opioid overdose event.

Figure 2I:
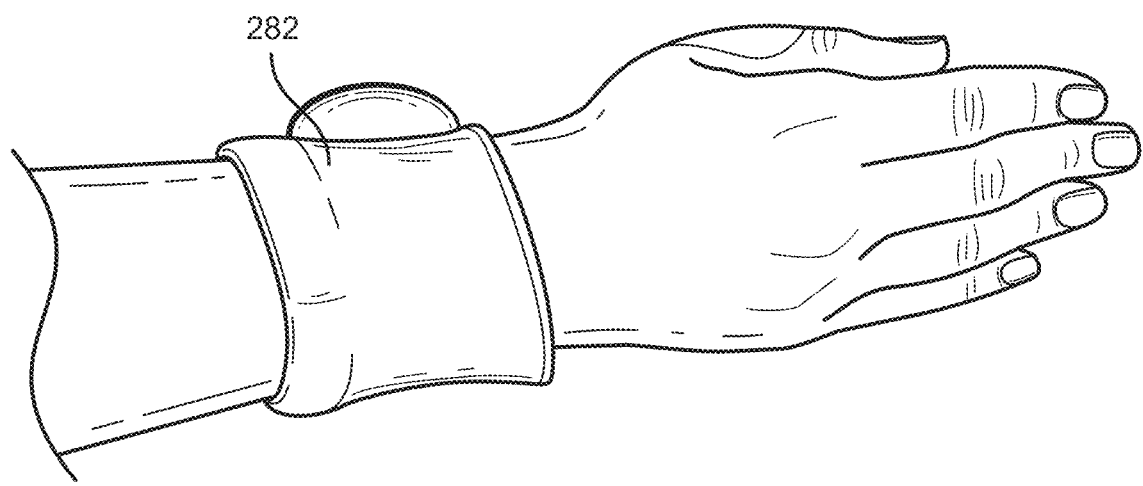
FIG. 2I illustrates an example medication applicator device, according to some embodiments of the present disclosure.

FIG. 2I illustrates a medication applicator device 282. The medication applicator device 282 can be an example of an additional device 114A, 114B, as described herein. The medication applicator device 282 can be configured to apply topical medication to reverse or reduce the effects of an opioid overdose. The medication applicator device 282 can include an actuator and medication in a gel form. The gel can be contained in a pouch or container with frangible seals. The actuator can receive an actuation signal from the connectivity hub device 106 and/or the patient user computing device 102 to initiate the actuation process. An antenna in the medication applicator device 282 can receive the actuation signal. The medication applicator device 282 can receive the actuation signal and the actuator can actuate to dispense the gel onto the skin of the patient. For example, the actuator can include a gas squib that, when activated, creates a pressurized gas or fluid that is in fluid contact with the gel via one or more conduits. The pressurized fluid can force the gel to break frangible seals next to the tissue that can cause the gel to be applied to surface tissue.

Additionally or alternatively, the medication applicator device 282 can include a vial or container of injectable medication, an actuator, and/or a needle. The needle can be a microneedle. The actuator can receive the actuation signal from the connectivity hub device 106 and/or the patient user computing device 102 to initiate the actuation process. Once the medication applicator device 282 receives the actuation signal, the actuator can actuate to force injectable medication through the needle. The needle can be configured to inject the medication into tissue under the pressure generated by the actuator.

Connectivity Hub Device

In addition to or in place of a patient user computing device 102, a connectivity hub device 106 may be used to facilitate wireless transmission of physiological data from the patient sensor device 104. Also as described herein, another example context for a patient management and monitoring system can be situations where medicine may need to be administered, such as in the case of home opioid monitoring and patient care.

Figure 3:
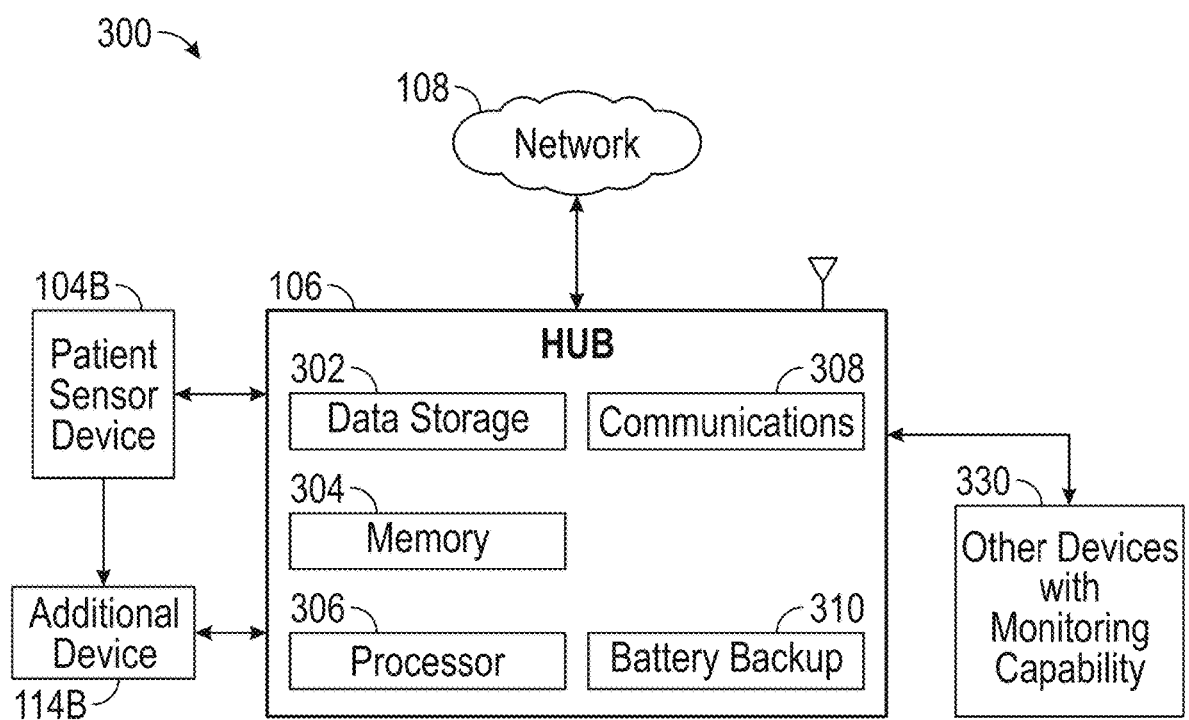
FIG. 3 is a block diagram illustrating a connectivity hub device and other devices, and communications between the devices, according to some embodiments of the present disclosure.

FIG. 3 illustrates a block diagram of a network environment 300 that includes the patient sensor device 104B, the additional device 114B, the connectivity hub device 106, and the network 108. In some embodiments, the network environment 300 can further include other devices 330. The patient sensor device 104B may collect patient physiological data and the additional device 114B may, for example, deliver a dose of a medicine based at least in part on the physiological data. The dosage may be predetermined. The additional device 114B may be a delivery device that can be self-administrating or user-activated (for example, activated by a patient, a care provider, or an emergency responder). The patient sensor device 104B may or may not be integrated with the additional device 114B.

The connectivity hub device 106 can receive patient physiological data, for example, from the patient sensor device 104B, and transmit the patient physiological data via the network 108. The connectivity hub device 106 can include a communications device 308 to communicate with one or more additional devices 114B, the patient sensor device 104B, the network 108, and other devices 330 with monitoring capabilities. Communications can be over Bluetooth or Wi-Fi, for example. The connectivity hub device 106 can further include data storage 302, memory 304, and a processor 306. In some embodiments, one or more applications may be stored within the data storage 302 and loaded into the memory 304. The data storage 302 can store physiological data received from the patient sensor device 104.

The connectivity hub device 106 can be powered by an AC current. In some implementations, as shown in FIG. 3, the connectivity hub device 106 can include a backup battery 310 that can supply power for the connectivity hub device 106 when AC power is no longer available. The connectivity hub device 106 can be powered through a USB port, using a charger connected to an AC outlet. The connectivity hub device 106 can generate a notification for a battery-low condition. For example, the notification for a battery-low condition may be visual and/or auditory.

The patient sensor device 104B can collect a patient's physiological data and transmit the physiological data to the additional device 114B and/or the connectivity hub device 106. The patient sensor device 104B may communicate with the additional device 114B and/or the connectivity hub device 106 via wired or wireless communication. Optionally, the patient sensor device 104B can transmit raw sensor data to the connectivity hub device 106 and/or the additional device 114B, via wired or wireless communication. The additional device 114B and/or the connectivity hub device 106 can process the raw sensor data to, for example, determine when a user of the patient sensor device 104B (for example, a patient) needs a care provider's attention or a critical health-related event is imminent or occurring. Additionally or alternatively, the connectivity hub device 106 can transmit the raw physiological data via the network 108. Accordingly, a patient management and monitoring system 110 (not illustrated) can receive the data and determine when the patient may require a care provider's attention or a critical health-related event is imminent or occurring. When the patient management and monitoring system 110 determines that a critical health-related event (for example, inability to breathe, an opioid overdose, heart attack, and the like) is imminent or occurring, the system 110 can communicate with other devices to address the critical health-related event. For example, the patient management and monitoring system 110 can generate and transmit to the additional device 114B via the connectivity hub device 106 instructions to, for example, administer one or more medications. The patient management and monitoring system 110 can generate and transmit notifications to user-authorized contacts, such as friends, family, emergency personnel, caregivers, police, ambulance services, other addicts or patients, and/or hospitals. The patient management and monitoring system 110 can generate and transmit notifications to a patient's user computing device. In some embodiments, the connectivity hub device 106 can send the additional device 114B instructions to, for example, activate and deliver medication.

To avoid false-positive indications, the additional device 114B can provide an indicator or a notification before administrating medication when a critical health-related event is detected to inform the user that medicine will be administered. Example notifications can include, but are not limited to, a low-voltage electric shock or haptic feedback. The notification intensity can incrementally escalate until a threshold is reached or a user applies a manual override. In response to a notification, the user can employ a manual override to indicate that the user is not in need of the medication or is not experiencing a critical health-related event. The override can be a button, switch, or other user input on the additional device 114B, the patient user computing device 102, and/or the connectivity hub device 106. The additional device 114B, the patient user computing device 102, and/or the connectivity hub device 106 can wait for the user input for a period of time before triggering the release of the medicine. The period of time can be less than 1 minute, less than 5 minutes, less than 10 minutes, between 1 minute and 5 minutes, between 1 minute and 10 minutes, and the like.

In some embodiments, to receive additional indicators of any critical health-related events, the connectivity hub device 106 can receive data from other devices with some monitoring capability 330. Example devices with monitoring capabilities include, but are not limited to, smartphones, smart speakers, video cameras (such as an indoor home security camera), and/or Internet of Things (IOT) devices. For example, many homes have household cameras which provide a video feed. As another example, a smartphone can listen to breathing and generate respiration data. Intelligent personal assistants, such as Amazon's Alexa® Google's Google Assistant®, Apple's Siri®, and the like, can control devices that have monitoring capabilities (such as microphones or cameras). Many IoT household appliances, such as refrigerators, washing machines, coffee makers, and the like, can include monitoring capabilities. Other medical monitoring devices such as ECGs may also provide additional data. Data from one or more of these devices can be stored in the data storage 302 and used by the connectivity hub device 106 and/or sent to the patient management and monitoring system. The data from the devices 330 can be used to detect that a critical health-related event is imminent or occurring. The connectivity hub device 106 can identify if any other monitoring devices 330 are available and can connect to the devices 330 to receive data.

The connectivity hub device 106 can interface with an internet filter, such as a Circle® internet filter that connects to a home network to monitor content. Using the filter, the connectivity hub device 106 can determine which network data is directed to the user's well-being and store the well-being data. The data can comprise text messages, voice recordings, video, and the like. Because of privacy concerns, the connectivity hub device 106 can determine which small portions of data are helpful to determining the user's physical condition and store only those portions of data.

Because the connectivity hub device 106 can sometimes fail to connect to the network 108, it can be advantageous to have redundant systems to report or transmit patient physiological data for detecting critical health-related events. In the event that the connectivity hub device 106 fails to connect to the network 108, other networked devices can provide an internet connection. For example, the connectivity hub device 106 can transmit patient physiological data to another device 330, such as a user computing device that can transmit the patient physiological data to the network 108. The patient sensor device 104B or the additional devices 114B can wirelessly communicate with other devices 330 when the connectivity hub device 106 fails to communicate with the network 108.

While some aspects of FIG. 3 are described herein as being performed by the connectivity hub device 106, some of those aspects may additionally or alternatively be performed by the patient user computing device 102. For example, in some embodiments, the patient user computing device 102 can communicate with and cause the additional device 114B to administer medicine.

Patient Sensor Device Pairing

Figure 4A:
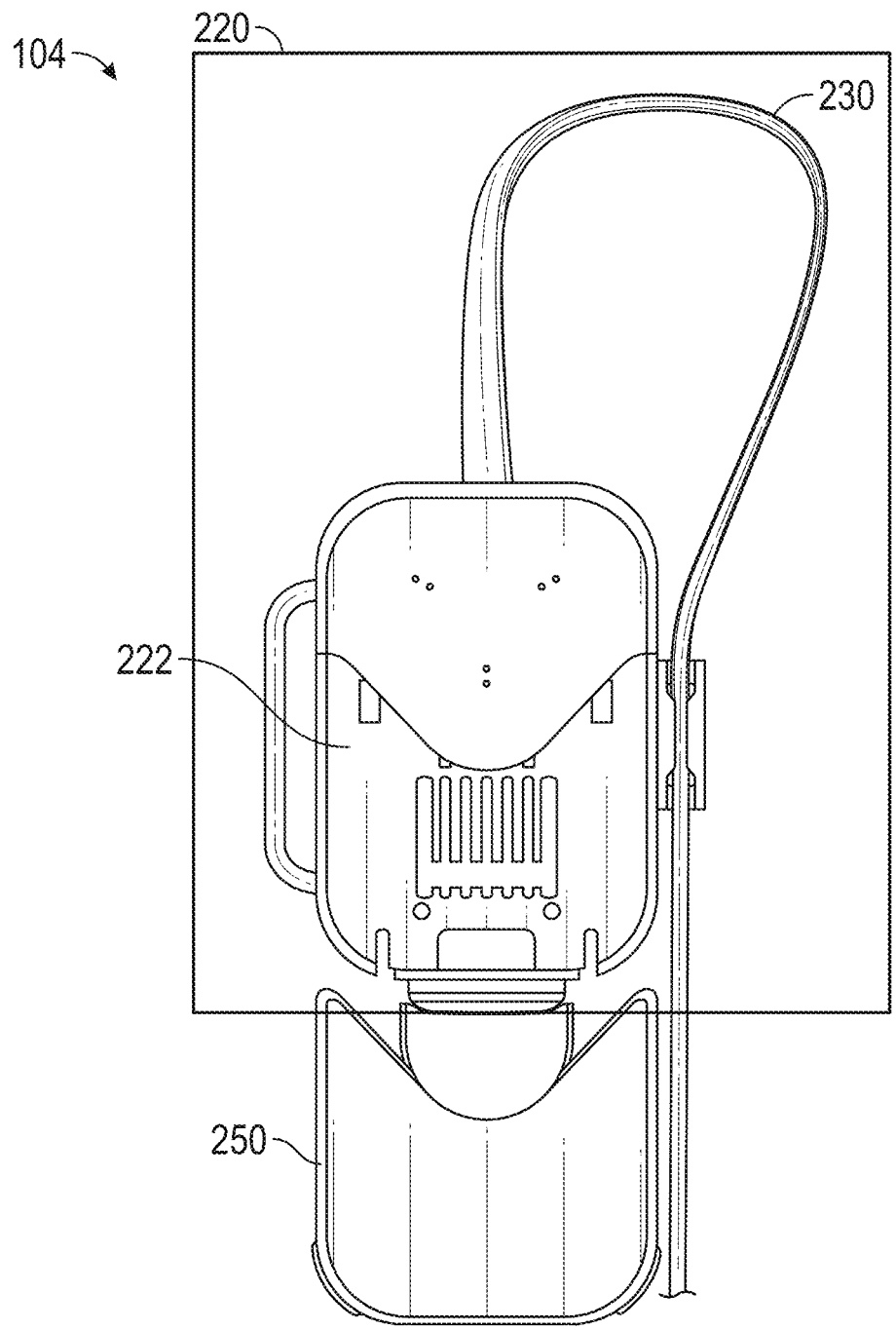
FIGS. 4A-4D illustrate a pairing process between a patient sensor device and another device, according to some embodiments of the present disclosure.

FIGS. 4A-4D illustrate an example pairing process between a patient sensor device 104 and another device. In FIG. 4A, an example patient sensor device 104 is shown. The patient sensor device 104 includes a reusable device 250 and disposable device 220. As shown, the reusable device 250 can detach from the disposable device 220. The disposable device 104 can include the dock 222. The dock 222 can be coupled to one or more sensors 240 (not shown) via the cable 230. The dock 222 can receive and couple with the reusable device 250. As part of the setup/pairing process, the reusable device 250 can be inserted into the dock 222, which can cause the patient sensor device 104 to power on.

Figure 4B:
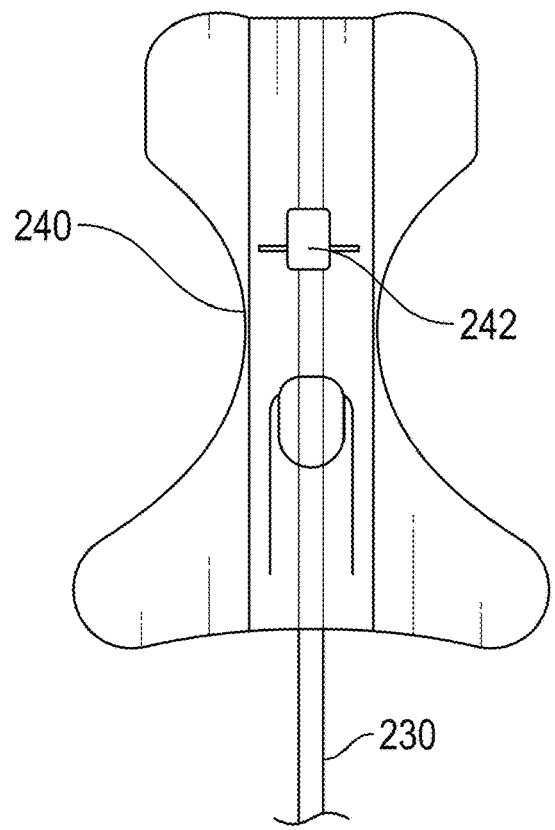

In FIG. 4B, an example sensor 240 is shown. The sensor 240 can be designed to be placed on a patient's finger. As described herein, a sensor can be disposed on different parts of a patient's body including, but not limited to, torso, legs, arms, neck, back, shoulder, and the like. The sensor 240 can include an indicator 242 that can indicate that the patient sensor device 104 is powered on. The indication can be auditory and/or visual. For example, when the patient sensor device 104 is powered on (such as when the reusable device 250 is coupled to the disposable device 220), the indicator 242 may generate a light. The sensor 240 may receive power from the battery 224 of the disposable device 220. In some embodiments, the sensor 240 may not draw power from the battery 224 until the reusable device 250 is coupled with the disposable device 220, for example, via the dock 222. The sensor 240 may not be powered or may not operate until it receives a sensor signal from the processor 254 of the reusable device 250. This can advantageously conserve the power stored in the battery 224 by allowing the sensor 240 to draw power from the battery 224 when the reusable device 250 is powered and ready to wirelessly transmit patient physiological data to nearby devices. In other embodiments, the sensor 240 may receive power from the battery 224 regardless of whether the reusable device 250 is coupled to the disposable device 220. In some embodiments, the sensor 240 may not be operational (for example, not collect physiological data) even though it receives power from the battery 224.

Figure 4C:
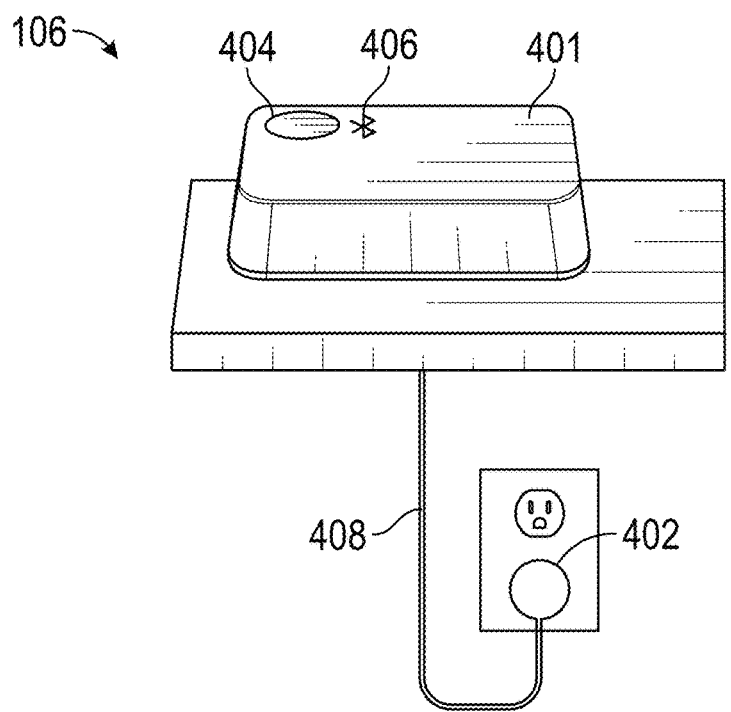

In FIG. 4C, an example connectivity hub device 106 powered by an AC power source is shown. The connectivity hub device 106 can include a body 401, a power connector 402, a network connect button 404, a network status indicator 406, and a cable assembly 408. The body 401 can house the data storage 302, the memory 303, the processor 306, the communications device 308, and the backup battery 310.

The connectivity hub device 106 can receive power from a power source, for example, a standard power outlet on a wall, via the power connector 402. The power connector may vary in shape, size, and/or orientation based least in part on voltage, current, and/or power ratings associated with the connectivity hub device 106. The power connector 402 can be coupled to the body 401 of the connectivity hub device 106 via the cable assembly 408 such that the connectivity hub device 106 can receive power from a power source via the power connector 402 and the cable assembly 408. As part of the setup/pairing process, the connectivity hub device 106 can be connected to a power source, which can cause the connectivity hub device 106 to power on.

Selection of the network connect button 404 (such as pressing the button for five seconds) can cause the connectivity hub device 106 to connect with nearby devices (such as the patient sensor device 104). The connectivity hub device 106 may wirelessly pair with another device, such as the patient sensor device 104, over a communication protocol, such as, but not limited to, Bluetooth. In particular, selection of the network connect button 404 can cause the connectivity hub device 106 to enter a pairing mode.

In some embodiments, the network connect button 404 may be pressed for a predetermined length of time before the connectivity hub device 106 is caused to search for nearby devices with wireless communication capabilities. In other embodiments, the network connect button 404 may be pressed in a predetermined manner to cause the connectivity hub device 106 to search for nearby devices with wireless communication capabilities. For example, the network connect button 404 may be pressed three times consecutively to cause the processor 306 of the connectivity hub device 106 to search for nearby devices with wireless communication capabilities.

The network status indicator 406 can be disposed on the body 401 of the connectivity hub device 106. For example, the network status indicator 406 can be positioned on a top surface of the body 401 such that users, for example, care providers or patients, can easily monitor the network status indicator 406 and determine network connectivity status for the connectivity hub device 106.

Figure 4D:
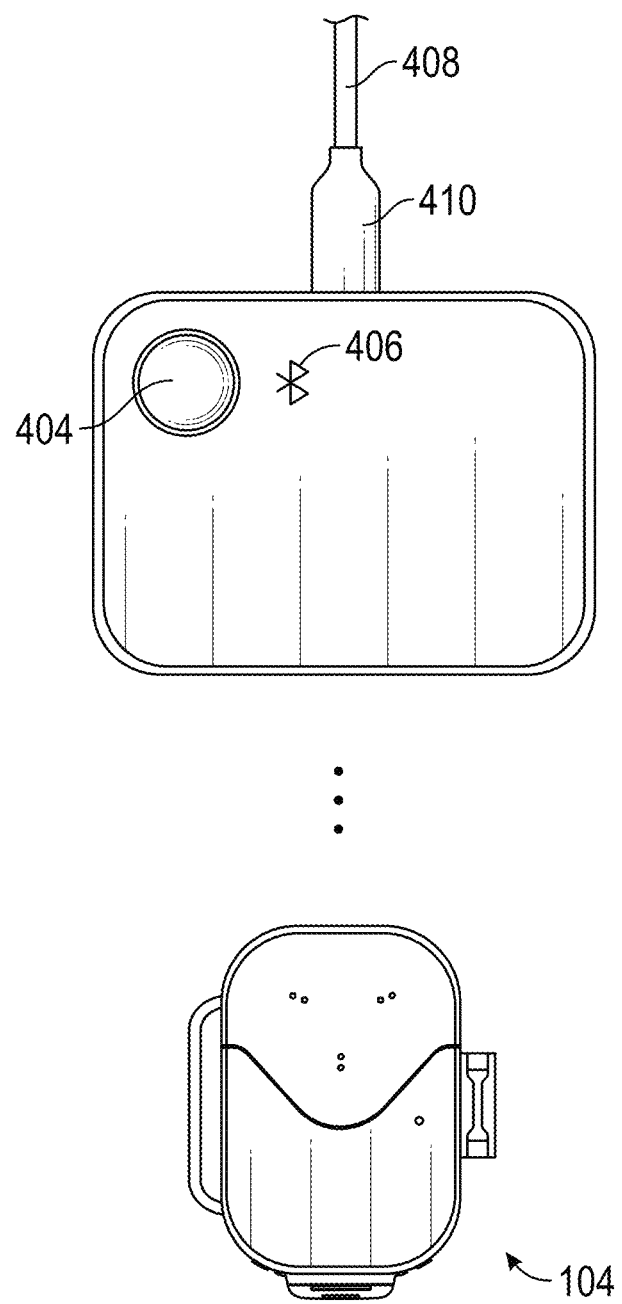

In FIG. 4D, the patient sensor device 104 can be paired with the connectivity hub device 106. As described herein, the patient sensor device 104 and/or the connectivity hub device 106 can be caused to enter a pairing mode. As shown, a wireless device (such as the patient sensor device 104) can connect with the connectivity hub device 106 when the wireless is proximate to the connectivity hub device 106 in a pairing mode.

Figure 5:
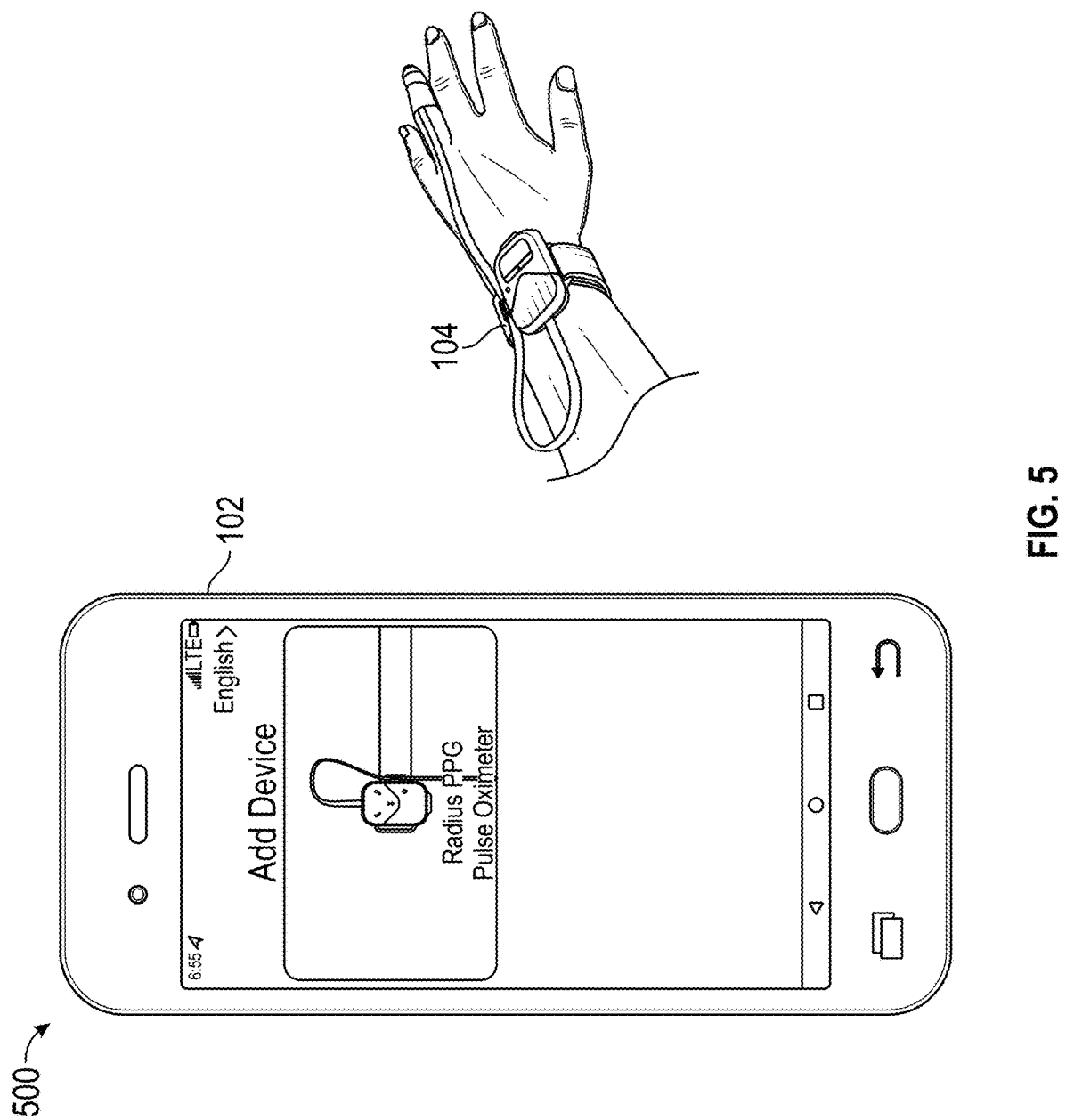
FIG. 5 illustrates pairing between a patient sensor device and a patient user computing device, according to some embodiments of the present disclosure.

In FIG. 5, the environment 500 can include a patient user computing device 102 and a patient sensor device 104. In the environment 500, the patient sensor device 104 can be paired with the patient user computing device 102. As described herein, the patient sensor device 104 and/or the patient user computing device 102 can be caused to enter a pairing mode. As shown, an application executing on the patient user computing device 102 can include a user interface that enables pairing between the patient sensor device 104 and the patient user computing device 102

Figure 6:
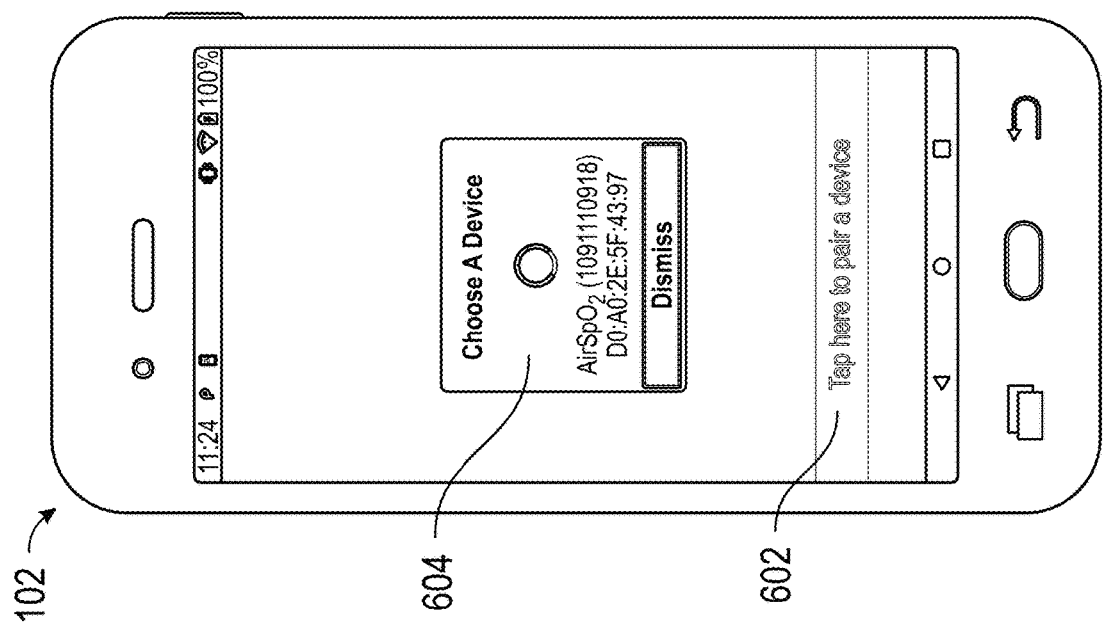
FIG. 6 illustrates a pairing graphical user interface, according to some embodiments of the present disclosure.

In FIG. 6, an example graphical user interface on a patient user computing device 102 is shown. The graphical user interface can enable a user to pair with other devices. For example, a user can select the user interface element 602 to cause the executing application to search for nearby devices, such as a patient sensor device 104. Once the application identifies one or more nearby patient sensor devices 104, the application can generate the device information display 604 that provides information associated with the nearby patient sensor device 104. As shown, example information can include, but is not limited to, sensor type information, sensor identification/serial number, and/or device access control information (for example, a media access control (MAC) address). Additionally or alternatively, the application may search for nearby devices without any user intervention or input.

Figure 7B:
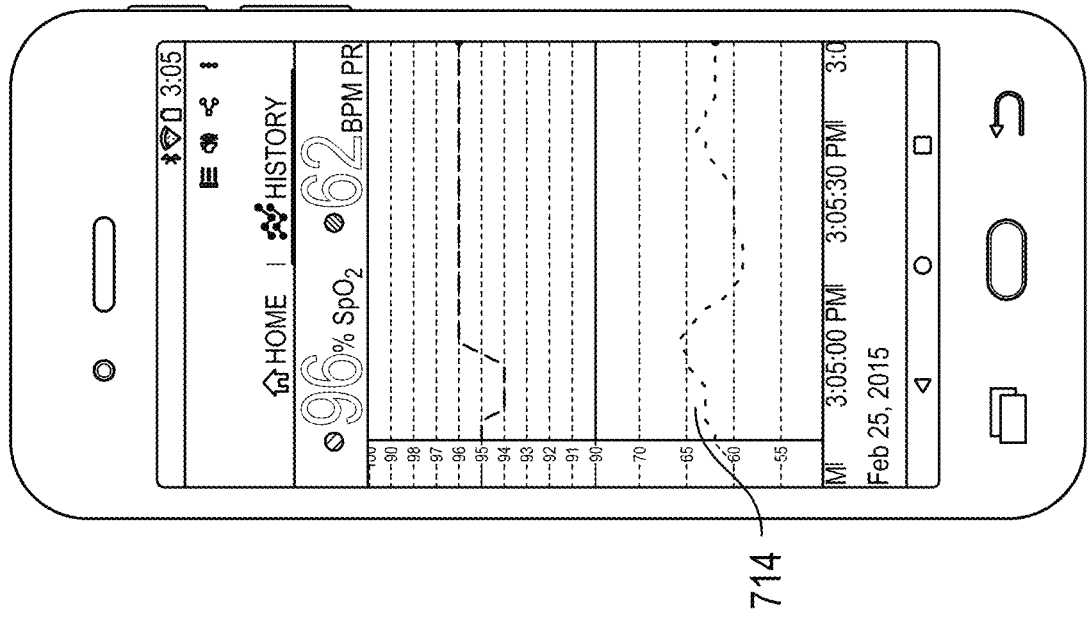
FIGS. 7A-7B illustrate graphical user interfaces for a patient user computing device connected to a patient sensor device, according to some embodiments of the present disclosure.
Figure 7A:
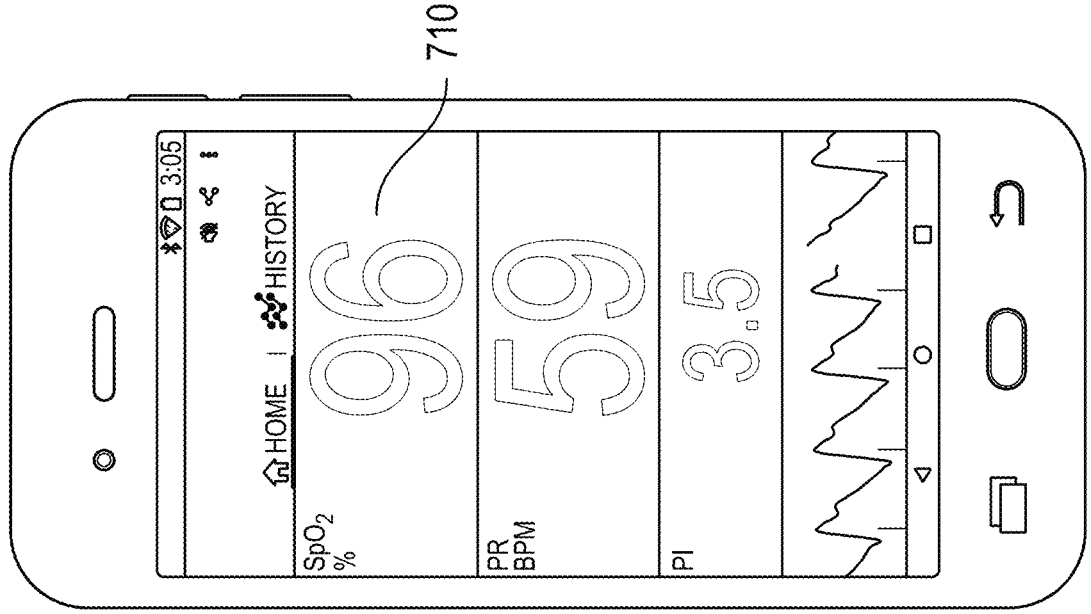

A graphical user interface can present physiological parameters that are received from paired patient sensor device(s) 104. FIGS. 7A-7B illustrate example graphical user interfaces for presenting physiological parameters received from paired device. In FIG. 7A, the depicted graphical user interface includes patient physiological parameter values 710. As shown, example physiological parameters 710 can include blood oxygen saturation (SpO$_2$), pulse rate (PR), and/or perfusion index (PI). In some embodiments, the physiological parameters 710 can update in substantially real-time.

In FIG. 7B, another graphical user interface is depicted that includes patient physiological parameters. The graphical user interface of FIG. 7B can further include historical data. In particular, the graphical user interface can include a visualization 714 that presents historical trends of patient physiological parameters. As shown, the visualization 714 can include one or more graphs with an x-axis of time and a y-axis of parameter values. The underlying historical data can originally be generated, at least in part, by the one or more patient sensor devices 104.

Remote Monitoring Kit

The solutions described herein can enable remote patient monitoring with remote monitoring kits. A remote monitoring kit can be mailed or otherwise made available to a patient. A remote monitoring kit can include a package, such as a box and/or packaging configured to hold the contents of the kit. In the case of communicable or other diseases, it can be advantageous for the package to be configured to be mailed. For example, a package can be under a certain weight, can be under a certain total length and girth, and/or include a sturdy box. As described herein, the contents of the remote monitoring kit can advantageously facilitate monitoring and/or patient care. As used herein, the terms "remote monitoring kit" and "user monitoring kit" can be used interchangeably.

Figure 7C:
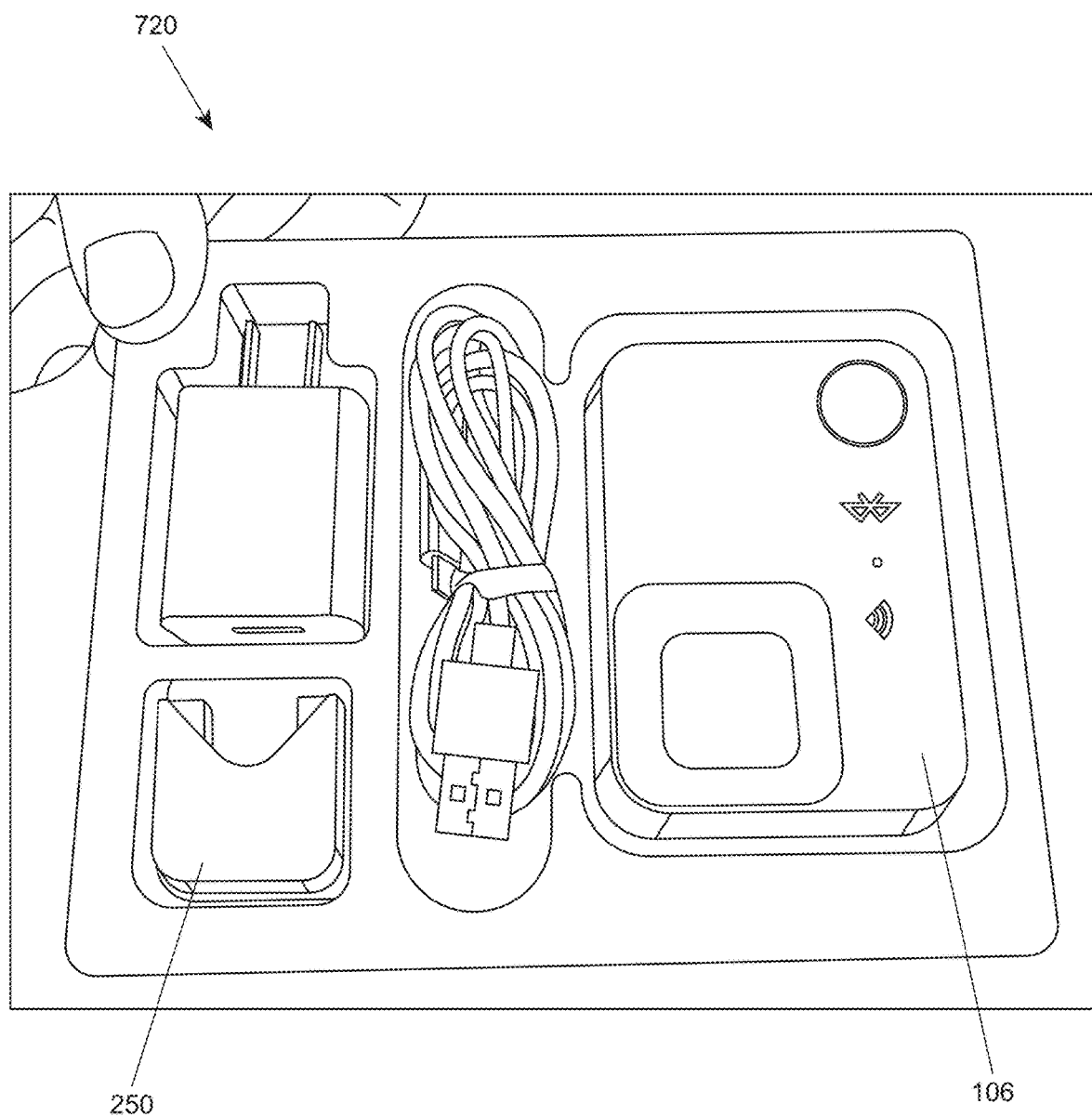
FIG. 7C illustrates an example remote monitoring kit, according to some embodiments of the present disclosure.

FIG. 7C illustrates an example remote monitoring kit 720. The remote monitoring kit 720 can include a connectivity hub device 106 and sensor and/or sensor-related devices, such as the reusable device 250. The remote monitoring kit 720 can further include a charging adapter and/or a cord. In some embodiments, the kit 720 can include other sensor and/or sensor-related devices, such as a disposable device 220 and/or sensors 240. Example remote monitoring kits can include different combinations of devices, such as any of the devices described herein.

For example, another remote monitoring kit can include a pulse oximetry device. The remote monitoring kit can further include a package. The package can be configured to be mailed. The pulse oximetry device can be disposed within the packaged. Example pulse oximetry devices are described herein, such as the above description of the patient sensor device 104 of FIGS. 2A-2B. The pulse oximetry device can include a wireless communications device, such as a Bluetooth device. A hardware processor of the pulse oximetry device can be configured to pair, via the wireless communications device, with a patient user computing device 102 through a downloadable application, such as the patient care application 120. In some embodiments, the remote monitoring kit can include a connectivity hub device 106. The connectivity hub device 106 can be configured to communicate with the pulse oximetry sensor device and a remote server, such as a server of the patient management and monitoring system 110. The connectivity hub device 106 can be disposed within the package.

In some embodiments, a pulse oximetry device can include a reusable device 250 (such as a removable chip). As described above with respect to FIG. 2B, the reusable device 250 can include a wireless communication device 252, a hardware processor 254, and a memory device 256.

A remote monitoring kit can include a sensor, such as the disposable device 220 described above with respect to FIG. 2B. The sensor can be disposed within a package. The sensor can be configured to receive the removable chip. For example, a reusable device 250 (such as a removable chip) can be docked into the dock 222 of the disposable device 220.

A remote monitoring kit can include a scannable code. An example scannable code can include, but is not limited to, a Quick Response (QR) code. The scannable code can encode a link to download the downloadable application. In other embodiments, the downloadable application can be configured to receive input data associated with the scannable code. For example, the patient user computing device 102 can include a camera and the downloadable application can receive input data associated with the scannable code (such as an image of the scannable code) via the camera. Receipt of the input data by the downloadable application can cause the downloadable application to initiate pairing with a patient sensor device 104, such as the pulse oximetry sensor.

In some embodiments, a remote monitoring kit can include any number of sensors, hubs, and/or other devices, such as a medication applicator device 282. For example, a remote monitoring kit can include a reusable device 250, a disposable device 220, and multiple sensors 240. As another example, a remote monitoring kit can include one or more of the following: the patient sensor device 290 of FIG. 2C, the patient sensor device 104 of FIGS. 2D, 2E, 2G, 2H, and/or the patient sensor system 261 of FIG. 2F.

Methods of Pairing, Collecting Data, and Transmitting Data

Figure 8A:
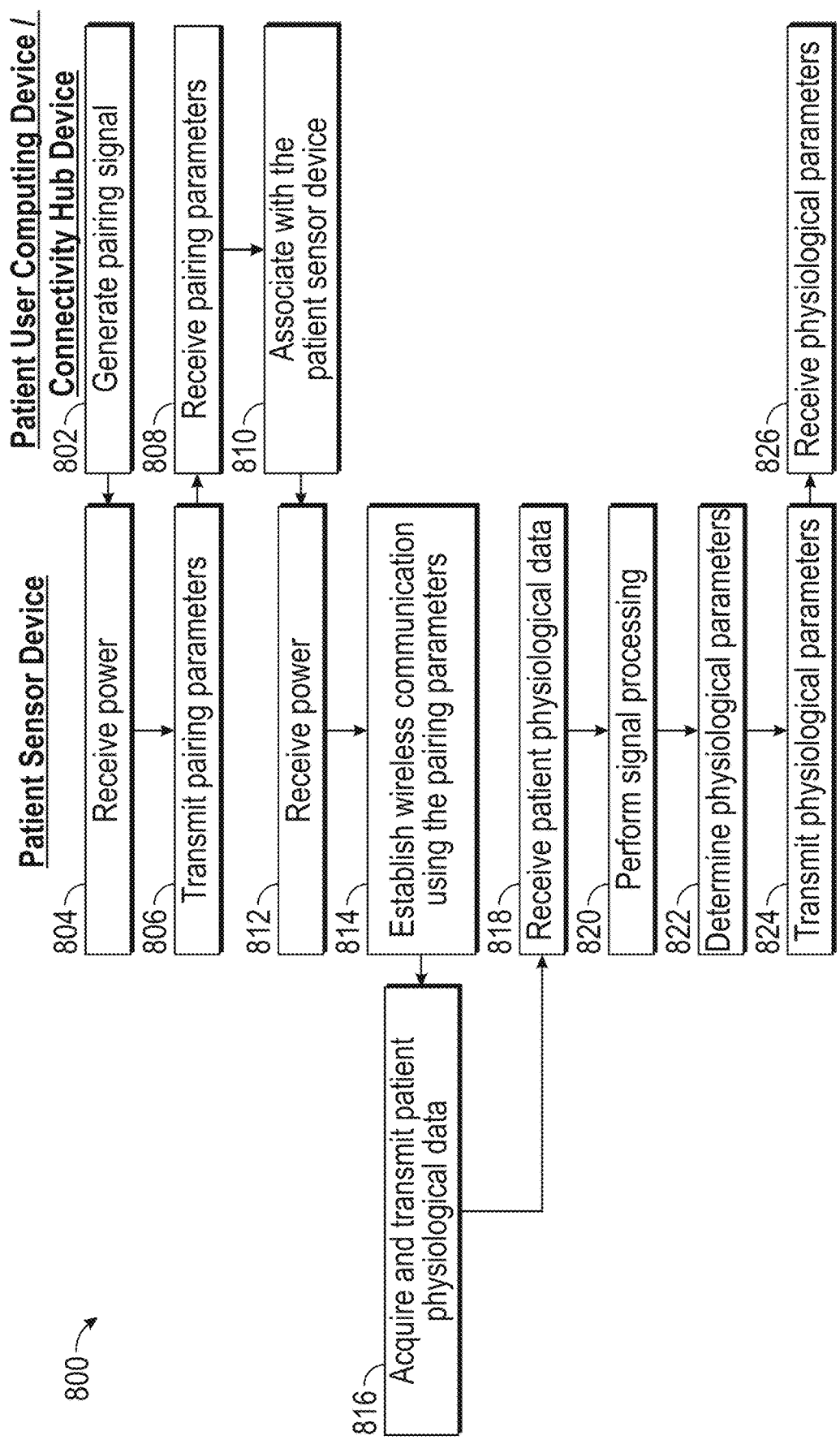
FIGS. 8A-8B are flowcharts of methods for pairing a patient sensor device and a connectivity hub device and/or a patient user computing device, according to some embodiments of the present disclosure.
Figure 8B:
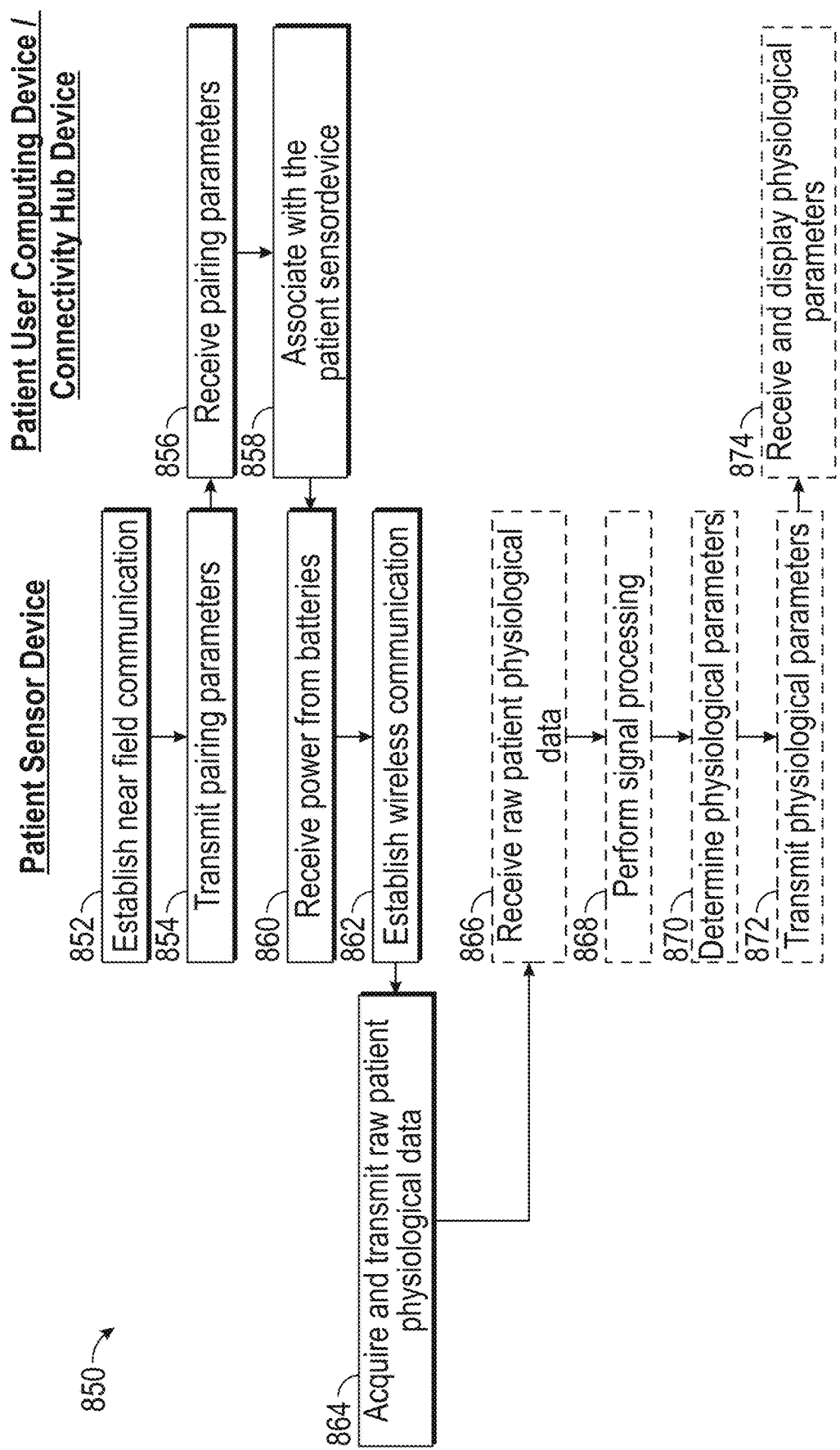

FIGS. 8A-8B are flowcharts of methods for pairing a patient sensor device 104 with another device. The below description of the FIGS. 8A-8B may discuss pairing a patient sensor device 104 with a patient user computing device 102 and/or a connectivity hub device 106. However, in some embodiments, the techniques for pairing a patient sensor device 104 may also apply to pairing with a device that is different than the patient user computing device 102 and the connectivity hub device 106, such as a patient monitoring device 206.

FIG. 8A illustrates a method 800 of establishing wireless communication between a patient sensor device 104 and another device, determining patient physiological parameters, and/or transmitting the physiological parameters. As described herein, an example patient sensor device 104 can include a reusable device 250 and a disposable device 220.

Beginning at block 802, a pairing signal can be generated. In particular, the patient user computing device 102 and/or the connectivity hub device 106 can generate and transmit a pairing signal. Generating the transmitting the pairing signal can be done automatically or manually. An example pairing signal can be a radio signal. A component of the patient sensor device 104, such as the reusable device 250, can be configured such that, upon receiving the signal, the patient sensor device 104 is triggered to transmit identification information back to the patient user computing device 102 and/or the connectivity hub device 106 in response. The pairing signal can include energy sufficient to enable nearby devices to transmit pairing parameters in response to the pairing signal, which is discussed in further detail below. The patient user computing device 102 and/or the connectivity hub device 106 can vary the strength of the pairing signal.

In some embodiments, generating and transmitting the pairing signal can be done by a device coupled to the connectivity hub device 106. For example, a dongle attached to the connectivity hub device 106 can generate and transmit the pairing signal. Additional details regarding the dongle and/or pairing can be found in the Dual Communication reference.

At block 804, power can be received. In particular, a component of the patient sensor device 104, such as the reusable device 250, can receive power from the pairing signal generated by the connectivity hub device 106. The pairing signal can be a high-frequency alternating current which can be used to create a voltage potential. A component of the patient sensor device 140, such as the reusable device 250, may receive the pairing signal of the connectivity hub device 106 when the component of the patient sensor device 104 is within a threshold distance from the connectivity hub device 106. In some embodiments, physical contact between the connectivity hub device 106 and the patient sensor device 104 can cause the patient sensor device 104 to receive the power from the pairing signal. In some embodiments, by receiving power from the pairing signal, the wireless communication device 252 of the reusable device 250 may not need to draw power from the battery 224 of the disposable device 220.

At block 806, pairing parameters can be transmitted. In particular, the patient sensor device 104 can transmit pairing parameters to the patient user computing device 102 and/or the connectivity hub device 106. In some embodiments, a component of the patient sensor device 104, such as the reusable device 250, can use the power received from the pairing signal to transmit identification information to the patient user computing device 102 and/or the connectivity hub device 106. Example pairing parameters can include an identifier for the patient sensor device 104, such as a serial number that identifies the patient sensor device 104. Additional example identification information can include, but is not limited to, a stock number, lot number, batch number, production date, or other information.

At block 808, the pairing parameters can be received. In particular, the patient user computing device 102 and/or the connectivity hub device 106 can receive the identification information from the patient sensor device 104.

At block 810, a device can be associated with the patent sensor device 104. In particular, the patient user computing device 102 and/or the connectivity hub device 106 can associate with the patent sensor device 104, which allows the wireless communication to be established between the patent sensor device 104 and the patient user computing device 102 and/or the connectivity hub device 106. In some embodiments, association between the patient sensor device 104 and the patient user computing device 102 and/or the connectivity hub device 106 can include a user input step. For example, upon receiving the pairing parameters from the patient sensor device 104, the patient user computing device 102 and/or the connectivity hub device 106 can generate a notification prompting a user to allow or disallow association with the patient sensor device 104. If allowed, the patient user computing device 102 and/or connectivity hub device 106 can associate with the patient sensor device 104. If rejected, the patient user computing device 102 and/or the connectivity hub device 106 may not associate with the patient sensor device 104 and the patient sensor device 104 may not establish a wireless communication 204 with the patient user computing device 102 and/or the connectivity hub device 106.

At block 812, the patent sensor device 104 can receive power. For example, in the context of the patient sensor device 104 of FIG. 2B, the reusable device 250 can mate with the dock 222 and can receive power from the battery 224.

At block 814, wireless communication can be established. In particular, the patient sensor device 104 can establish wireless communication 204 with the patient user computing device 102 and/or the connectivity hub device 106. The wireless communication can be established using the pairing parameters. Example wireless communication can be via Bluetooth, as described herein. The wireless communication can be one-way or two-way communication between the patient sensor device 104 and the patient user computing device 102 and/or the connectivity hub device 106. For example, the patient sensor device 104 can transmit processed physiological data to the patient user computing device 102 and/or the connectivity hub device 106. The patient user computing device 102 and/or the connectivity hub device 106, in turn, can transmit a confirmation signal back to the patient sensor device 104 indicating that the processed physiological data was received. The patient sensor device 104 can audibly or visually (for example, a light-emitting diode or other light source can generate light) indicate that wireless communication has been established, such as when the patient sensor device 104 receives the confirmation signal from the patient user computing device 102 and/or the connectivity hub device 106.

At block 816, raw patient physiological data can be acquired and physiological data can be transmitted. For example, in the context of the patient sensor device 104 of FIG. 2B, the sensor 240 can acquire raw patient physiological data, which can be received by the disposable device 220. In the context of the device 104 from FIG. 2B, the reusable device 250 can receive raw physiological data from the disposable device 220. As described herein, one or more example sensors 240 can include, but are not limited to, an acoustic sensor, ECG sensor, EEG sensor, respiratory acoustic sensor (RAS), and/or a $SpO_2$ sensor.

At block 818, the patient physiological data can be received. For example, in the context of the patient sensor device 104 of FIG. 2B, the processor 254 of the reusable device 250 can receive the raw patient physiological data from the disposable device 220. The raw patient physiological data can be stored in the memory 256 of the reusable device 250.

At block 820, signal processing can be performed on the raw physiological data. In particular, the patient sensor device 104 can perform signal processing on the raw physiological data. For example, in the context of the patient sensor device 104 of FIG. 2B, the processor 254 of the reusable device 250 can perform signal processing on the raw physiological data. Various types of signal processing can be used on the raw physiological data. Further details regarding signal processing can be found in the Dual Communication reference.

At block 822, physiological parameters can be determined. In particular, the patient sensor device 104 can determine physiological parameters. For example, in the context of the patient sensor device 104 of FIG. 2B, the processor 254 of the reusable device 250 can determine patient physiological parameters by processing the raw physiological data. The processor 254 can then store the processed data and the calculated parameters in the memory 256 before transmitting the parameters. As described herein, example physiological parameters can include, but are not limited to, temperature, blood pressure, respiratory rate (RRa), total hemoglobin (SpHb), carboxyhemoglobin (SpCO), methemoglobin (SpMet), oxygen content (SpOC), oxygen saturation ($SpO_2$), pulse rate (PR), perfusion index (Pi), pleth variability index (PVi), and/or electroencephalogram (EEG) data.

At block 824, the physiological parameters can be transmitted. In particular, the patient sensor device 104 can transmit the physiological parameters to the patient user computing device 102 and/or the connectivity hub device 106. For example, in the context of the patient sensor device 104 of FIG. 2B, the reusable device 250 can transmit the patient physiological parameters. The patient sensor device 104 can advantageously transmit the physiological parameters (for example, 60% $SpO_2$) as opposed to transmitting the raw physiological data to the computing device 206. For example, the raw physiological data can be larger in size than corresponding physiological parameters, and, therefore, can use greater bandwidth to transmit to the patient sensor device 104 and/or the connectivity hub device 106. Conversely, physiological parameters can be much smaller in size and can use less bandwidth to transmit. Accordingly, transmitting patient physiological parameters instead of raw physiological data can lead to decreased energy consumption and/or longer battery life. The patient sensor device 104 can wirelessly transmit the physiological parameters via NFC and/or Bluetooth. Additionally or alternatively, the patient sensor device 104 can transmit the physiological parameters via a cable.

At block 826, the physiological parameters can be received. In particular, the patient user computing device 102 and/or the connectivity hub device 106 can receive the patient physiological parameters. As described herein, the patient user computing device 102 and/or the connectivity hub device 106 can transmit the patient physiological parameters to the patient management and monitoring system 110.

FIG. 8B illustrates another method 850 of establishing wireless communication between a patient sensor device 104 and another device, determining patient physiological parameters, and/or transmitting the physiological parameters. The method 850 of FIG. 8B can be similar to the method of FIG. 8A. However, the method 850 of FIG. 8B can use communication protocol(s) that are different from the communication protocol(s) used by the method of FIG. 8A. For example, the method 850 of FIG. 8B can use near field communication (NFC) protocol(s).

At block 852, an NFC connection can be established. In particular, the patient sensor device 104 can establish an NFC connection with the patient user computing device 102 and/or the connectivity hub device 106. For example, in the context of the patient sensor device 104 of FIG. 2B, the reusable device 250 can establish an NFC connection by being placed near the patient user computing device 102 and/or the connectivity hub device 106 (such as by making physical contact between the devices).

At block 854, pairing parameters can be transmitted. In particular, the patient sensor device 104 can transmit pairing parameters to the patient user computing device 102 and/or the connectivity hub device 106 using NFC. At block 856, the pairing parameters can be received. In particular, the patient user computing device 102 and/or the connectivity hub device 106 can receive the pairing parameters from the patient sensor device 104 via NFC.

At block 858, a device can be associated with the patent sensor device 104. In particular, the patient user computing device 102 and/or the connectivity hub device 106 can associate with the patient sensor device 104 can using the pairing parameters. Once associated, the patient user computing device 102 and/or the connectivity hub device 106 may wait for the wireless communication 204 from the patient sensor device 104. As described herein, the wireless communication 204 can be made over Bluetooth.

The remaining blocks 860, 862, 864, 866, 868, 870, 872 of FIG. 8B can be similar to the blocks 812, 814, 816, 818, 820, 822, 824, 826 of FIG. 8A regarding receiving physiological data and generating and transmitting physiological parameters.

At block 860, power may be received. For example, in the context of the patient sensor device 104 of FIG. 2B, the reusable device 250 can receive power from the batteries 224 of the disposable device 220.

At block 862, wireless communication can be established. For example, in the context of the patient sensor device 104 of FIG. 2B, the reusable device 250 can establish wireless communication with patient user computing device 102 and/or the connectivity hub device 106. As described herein, the patient sensor device 104 can use the pairing parameters to establish wireless communication with the connectivity hub device 106.

At block 864, raw patient physiological data can be acquired and physiological data can be transmitted. In particular, a component of the patient sensor device 104 can acquire the raw patient physiological data and transmit the data.

The remaining blocks 866, 866, 868, 870, 872 can be optional in some embodiments. In other embodiments, other blocks can be optional. At block 866, patient physiological data can be received. For example, in the context of the patient sensor device 104 of FIG. 2B, the reusable device 250 can receive the patient physiological data from the disposable device 220. At block 868, signal processing can be performed. In particular, the patient sensor device 104 can perform signal processing on the patient physiological data. At block 870, patient physiological parameters can be determined using the processed physiological data. In particular, the patient sensor device 104 can determine patient physiological parameters using the processed physiological data. At block 872, the patient physiological parameters can be transmitted. In particular, the patient sensor device 104 can transmit the physiological parameters to the patient user computing device 102 and/or the connectivity hub device 106 using the wireless communication 204, such as Bluetooth. At block 874, the patient physiological parameters can be received. In particular, the patient user computing device 102 and/or the connectivity hub device 106 can receive the patient physiological parameters.

Configuration Graphical User Interfaces

FIGS. 9, 10A-10C, 11, and 12 illustrate example patient care configuration user interfaces, according to some embodiments of the present disclosure. In various embodiments, aspects of the user interfaces may be rearranged from what is shown and described below, and/or particular aspects may or may not be included. As described herein, the patient care configuration user interfaces of FIGS. 9, 10A-10C, 11, and 12 can enable a user to create or edit patient care user interfaces. An administrator can interact with the graphical user interfaces of FIGS. 9, 10A-10C, 11, and 12 on the clinician user computing device 124. The graphical user interfaces of FIGS. 9, 10A-10C, 11, and 12 may have similar user interface elements and/or capabilities.

Figure 9:
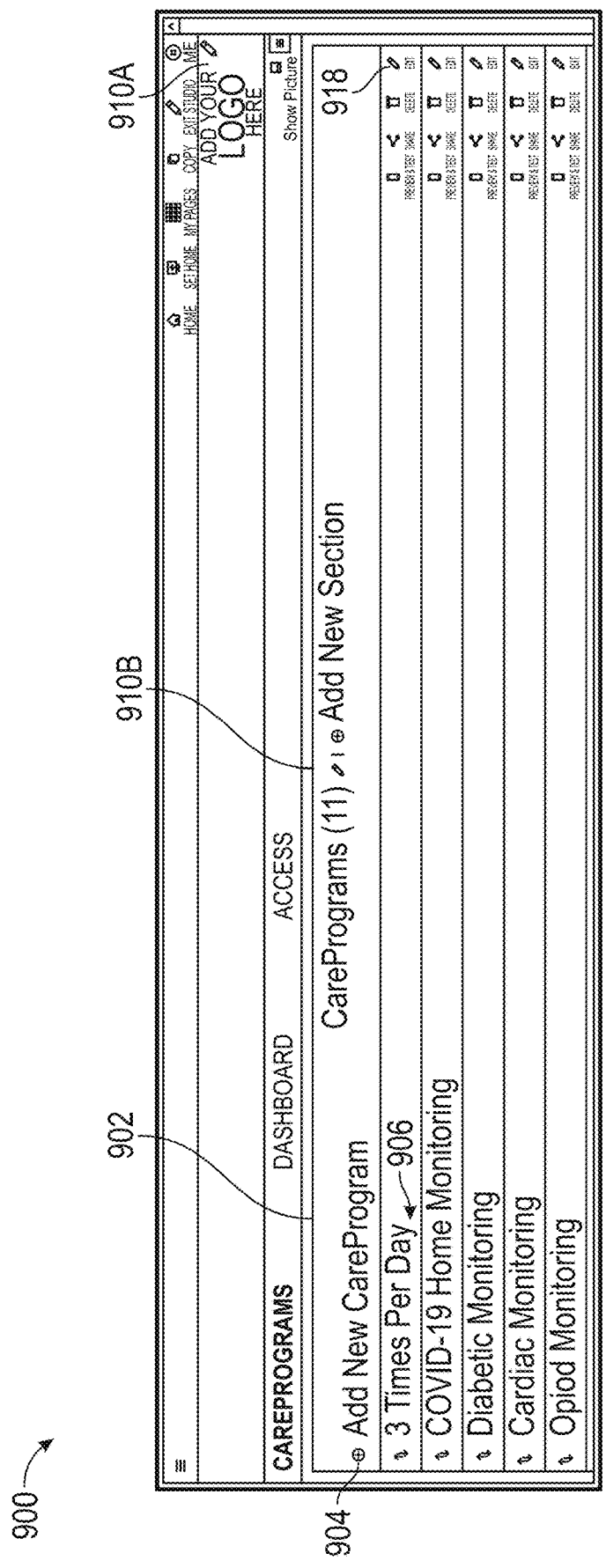
FIGS. 9, 10A-10C, 11, and 12A-12C illustrate example patient care configuration user interfaces, according to some embodiments of the present disclosure.

In FIG. 9, an example patient care configuration user interface 900 is depicted. The patient care configuration user interface 900 can include a patient care user interface list area 902 that can present patient care user interfaces for configuration. For example, a first patient care user interface 906 (here "3 Times Per Day") in the area 902 can be edited by an administrator in response to a user selection of the edit element 918 associated with the first patient care user interface 906. An administrator can request to create a new patient care user interface by selecting the new element 904.

In some embodiments, the patient care configuration user interface 900 of FIG. 9 can be configurable. The patient care configuration user interface 900 can further include the edit elements 910A, 910B. The edit elements 910A, 910B (here represented by the pen icon) can be selected by an administrator to configure the patient care configuration user interface 900. For example, the first edit element 910A can be selectable to allow an administrator to update a logo or text associated with the patient care configuration user interface 900.

Figure 10A:
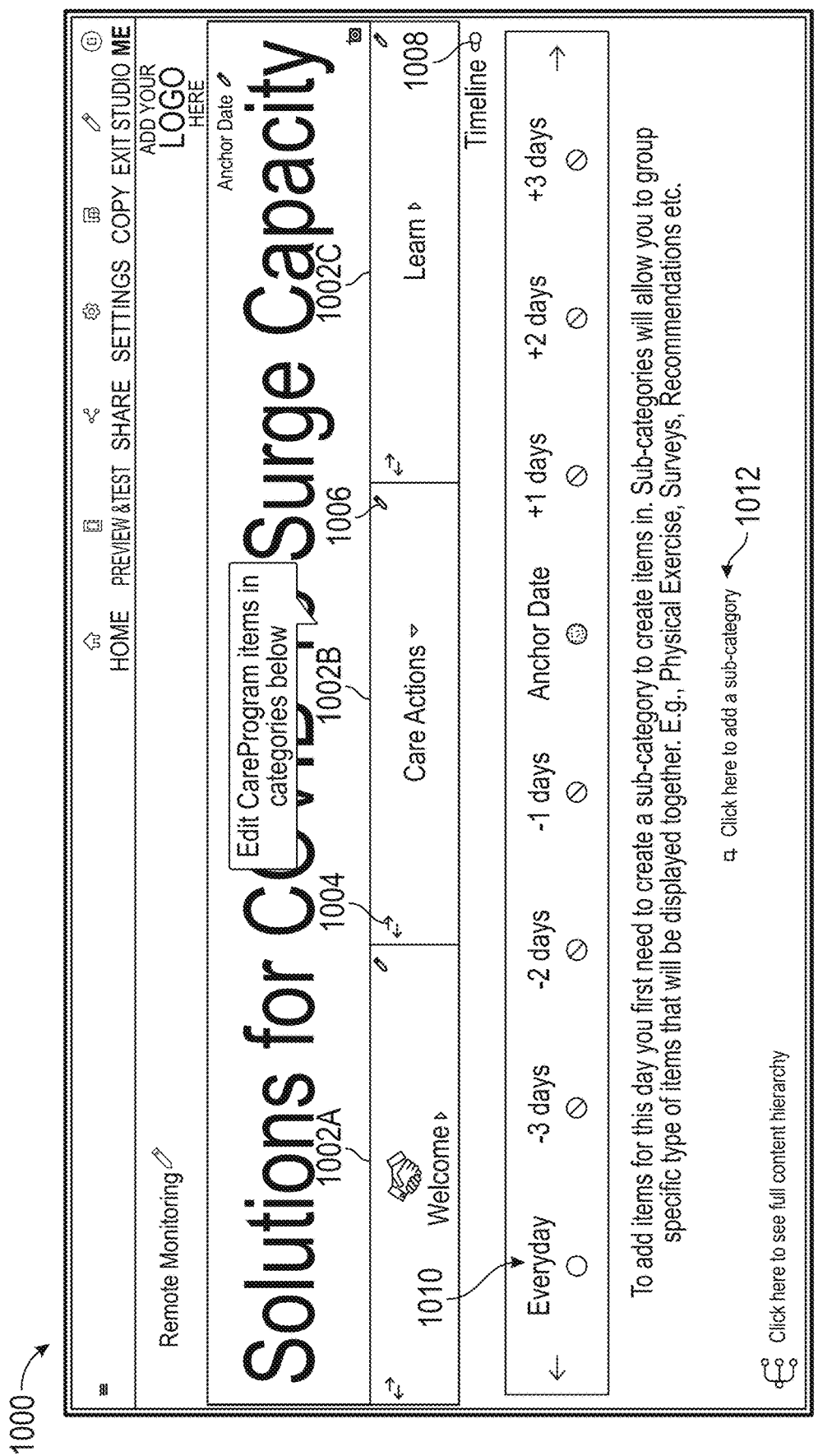

In FIG. 10A, another example patient care configuration user interface 1000 is depicted. An administer can create a patient care user interface (here the "Remote Monitoring" user interfaces) with the patient care configuration user interface 1000. The patient care configuration user interface 1000 can include multiple configuration user interface elements. For example, the patient care configuration user interface 1000 can include multiple sections 1002A, 1002B, 1002C. Each section can be assigned one or more items. The presentation of the sections (in a patient care user interface) can be edited with the elements 1004, 1006. In particular, the text and/or image(s) of a section can be edited and/or the graphical layout of the section(s) can be edited. For example, an administrator can delete, add, or rename sections, as well as reorder the arrangement of the sections. The patient care configuration user interface 1000 can include an element 1008 that enables an administrator to add or remove a timeline 1010. If configured, the timeline 1010 can allow for presentation of different items in the patient care user interface based on a schedule.

In some embodiments, items in a patient care user interface can be associated with one or more categories. In the patient care configuration user interface 1000, an administrator can select the add-category element 1012 to create a new category. As described herein, example items can include action items for a patient, prompts to elicit user input, and/or patient sensor items.

Figure 10B:
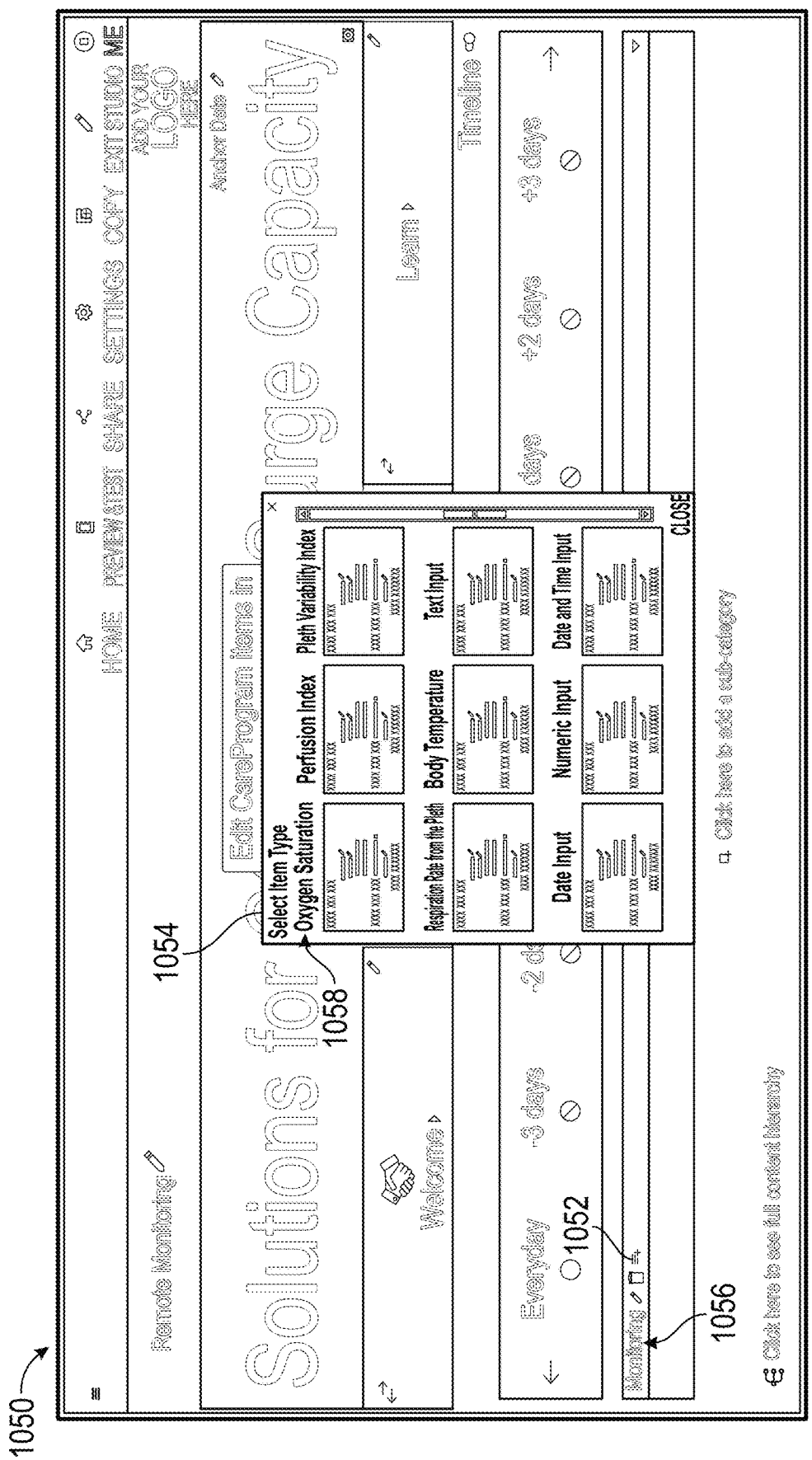

In FIG. 10B, another example patient care configuration user interface 1050 is depicted. The patient care configuration user interface 1000 can include an add-item element 1052. An administrator can select the add-item element 1052, which can cause presentation of the item-type selection area 1054. The item-type selection area 1054 can include multiple template item types. As described herein, items in a patient care user interface can be associated with one or more categories. Accordingly, the item being created in the patient care configuration user interface 1050 of FIG. 10B can be associated with the category 1056 (here a "Monitoring" category). The administrator, via the patient care configuration user interface 1050, can configure the patient care user interface to have an additional item by using the item-type selection area 1054.

Example item types can include patient sensor items, such as, but not limited to, an oxygen saturation sensor item type, a perfusion index sensor item type, a pleth variability index sensor item type, a respiration rate from pleth sensor item type, a body temperature sensor item type, a pulse rate sensor item type, a step count (e.g., pedometer) sensor item type, a blood glucose sensor item type, and/or a blood pressure sensor item type. An administrator can select a patient sensor item type that causes a corresponding patient sensor item to be added to the patient care user interface. The patient sensor items can be configured with example prompts such as, but not limited to, "What is oxygen saturation ($SpO_2$)?", "What is your temperature?", or "What is your respiration rate?" In some embodiments, a patient sensor item can reduce the number of steps to pair a patient sensor with the patient care application 120 that includes the patient care user interface. An advantage of configuring patient sensor items in a patient care user interface is that such configurations can improve graphical user interfaces for monitoring patient physiological parameters by enabling a user to more quickly associate patient sensor(s) with their patient care user interface, as described herein. Once a patient sensor is associated/paired, the value for a physiological parameter in the patient sensor item can auto-populate. Additionally or alternatively, some patient sensor items may allow a user (for example, a patient or a care provider) to manually input a value. For example, in some embodiments, a patient can manually input the value for the patient sensor item.

Additional example item types can be generic and can allow an administrator to further customize items in a patient care user interface. Additional example item types (some of which are shown in the item-type selection area 1054 of FIG. 10B) can include, but are not limited to, a text input item type, a date input item type, a numeric input item type, a date and time input item type, a text item type, a uniform resource location item type, a weight input item type, a height input item type, a yes/no item type, a rating item type, a slider item type, a single select item type, and/or a multi-select item type. The input items can be configured with example prompts such as, but not limited to, "What is your age?", "Do you have any pre-existing conditions?", "Are you experiencing any symptoms?", or "Have you been in contact with anyone who has texted positive for the novel coronavirus?"

For example, with the text input item type, an administrator can configure a text input item to receive text input from a user (for example, a patient or a care provider). With the date input item type, an administrator can configure a date input item to receive date input from a user. With the numeric input item type, an administrator can configure a numeric input item to receive numeric input from a user. With the date and time input item type, an administrator can configure a date and time input item to receive date and time input from a user. With the text item type, an administrator can configure a text item to present text to a user. With the uniform resource location (URL) item type an administrator can configure a uniform resource location (URL) item to present a URL and/or the contents of a URL to a user. With the weight input item type, an administrator can configure a weight input item to receive a weight value from a user. With the height input item type, an administrator can configure a height input item to receive a height value from a user. With the yes/no item type, an administrator can configure a yes/no item type to receive yes/no input from a user. With the rating item type, an administrator can configure a rating item to receive rating input from a user. With the slider item type, an administrator can configure a slider item to receive slider input from a user. With the single select item type, an administrator can configure a single select item to receive a user selected option from a variety of options (such as options in a drop-down menu or list). With the multi-select item type, an administrator can configure a multi-select item to receive multiple user selected options from a variety of options (such as options in a drop-down menu or list).

Figure 10C:
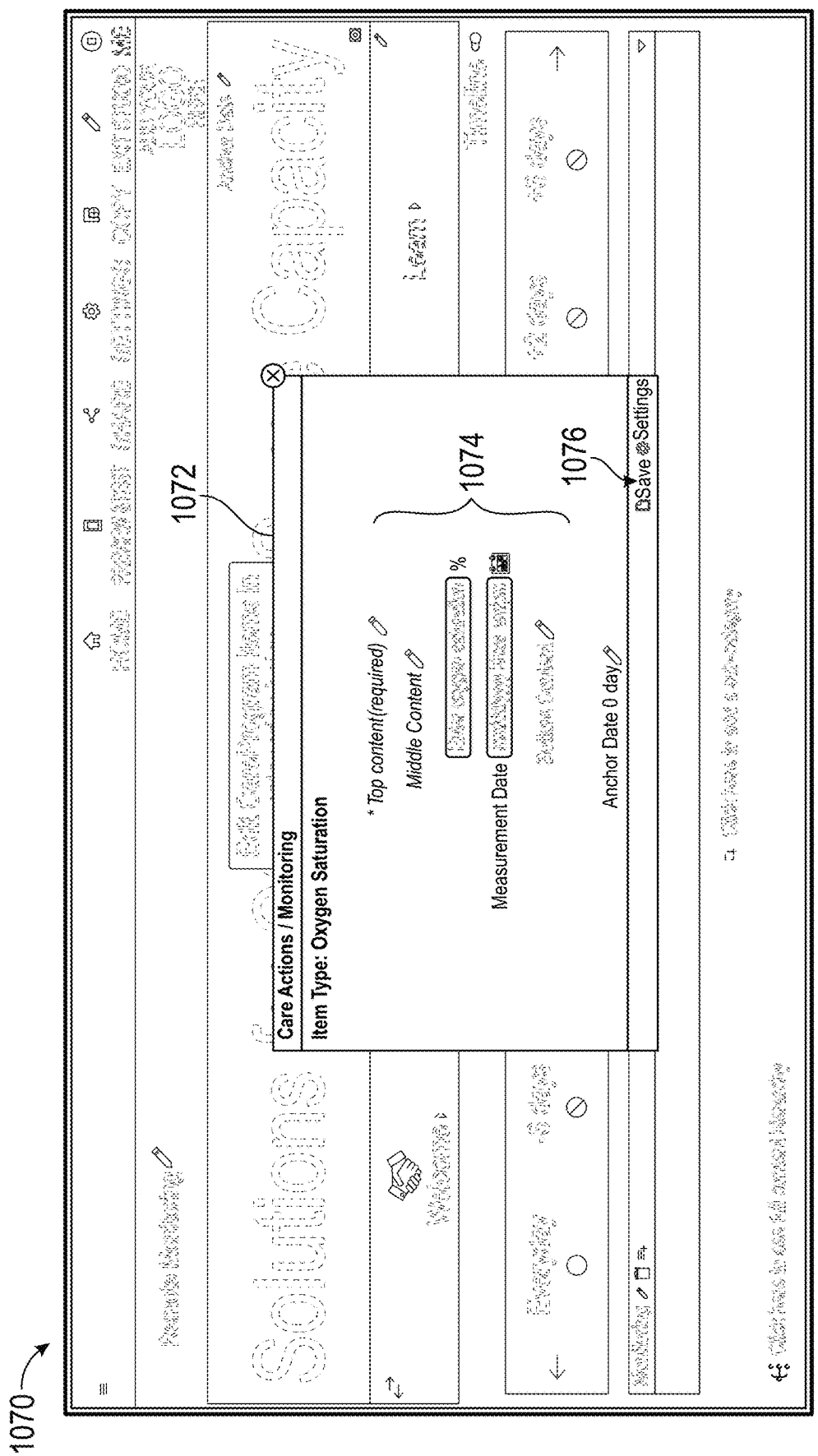

In FIG. 10C, yet another example patient care configuration user interface 1070 is depicted. The patient care configuration user interface 1070 can include an item configuration area 1072. In particular, with respect to FIG. 10B, an administrator can select the item type 1058 (here an oxygen saturation item type), which can cause presentation of the item configuration area 1072 corresponding to the item type 1058. The item configuration area 1072 can include editable fields 1074 that allow an administrator to configure the item (here a patient sensor item for oxygen saturation). The patient sensor item can be configured to interface with particular patient sensor devices (such as a tetherless pulse oximetry sensor device) and can include a particular physiological parameter type, such as, but not limited to, an oxygen saturation parameter type or a pulse rate parameter type. In some embodiments, a single patient sensor device 104 can output multiple types of physiological parameters. An administrator can add the item to the patient care user interface by selecting a complete element 1076 from the item configuration area 1072. An output of the patient care configuration user interface 1070 can be a patient sensor item configuration, which is further included in an output client configuration package. The patient sensor item configuration can include configuration information that facilitates the interface between the patient care application 120 and a patient sensor device 104. Example configuration information can include a device type (such as a tetherless pulse oximetry sensor device type) that allows the patient care application 120 to detect a patient sensor device 104 has already been connected to the patient user computing device 102 and/or to initiate a pairing process between the patient sensor device 104 and the patient user computing device 102. In some embodiments, the device type(s) in the configuration information can include specific model(s) of patient sensor devices 104.

Figure 11:
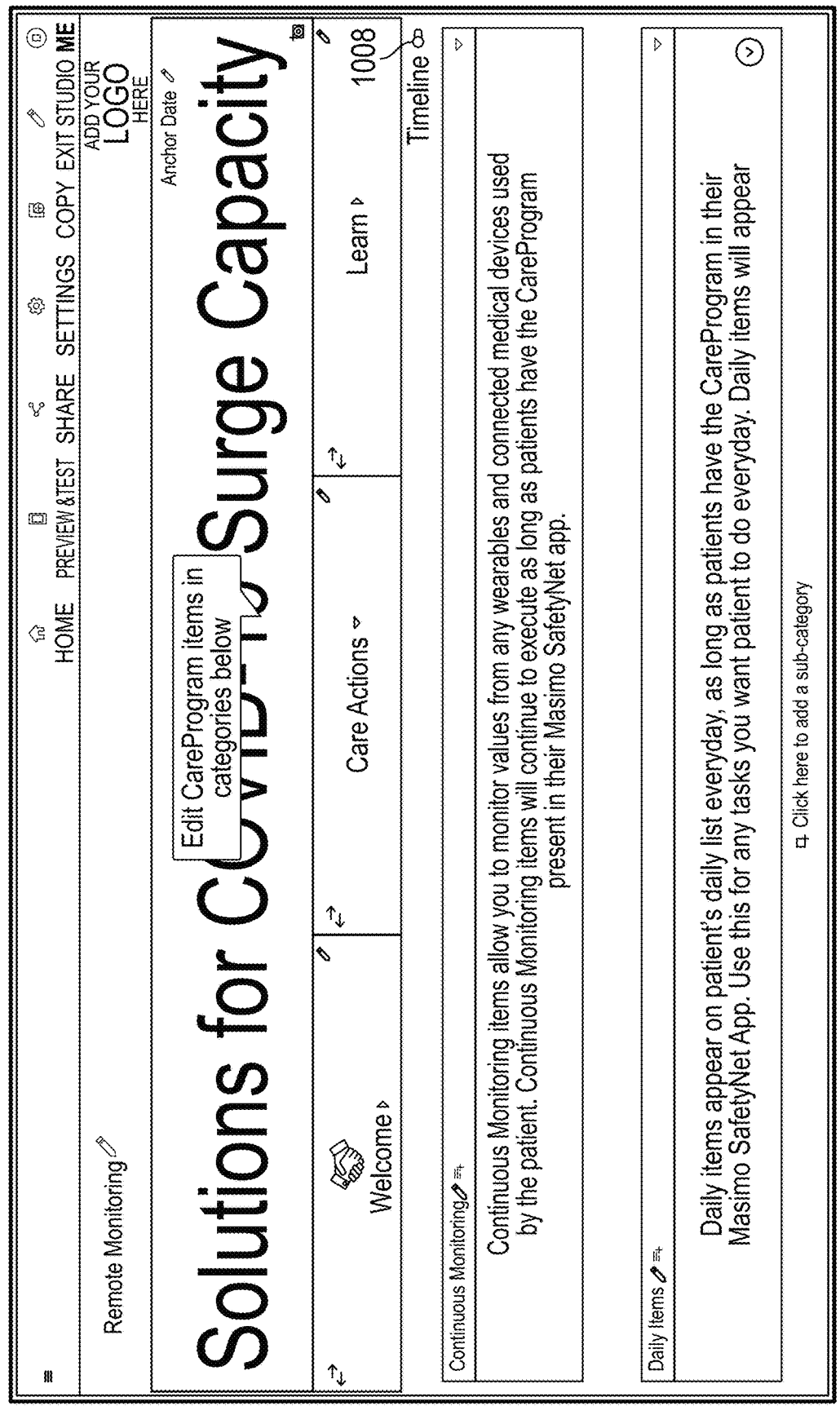

In FIG. 11, yet another example patient care configuration user interface 1100 is depicted. The patient care configuration user interface 1100 of FIG. 11 can be similar to the patient care configuration user interface 1000 of FIG. 10A. However, unlike the element 1008 of the patient care configuration user interface 1000 of FIG. 10A that was selected, the element 1108 of the patient care configuration user interface 1100 of FIG. 11 may be unselected. Accordingly, unlike the patient care configuration user interface 1000 of FIG. 10A that includes a timeline 1010 in its layout, the patient care configuration user interface 1100 of FIG. 11 may not include a timeline in its layout. In some embodiments, without a timeline, the patient care configuration user interface 1100 may not have a schedule and/or different items per day, but rather the same daily items.

Figure 12A:
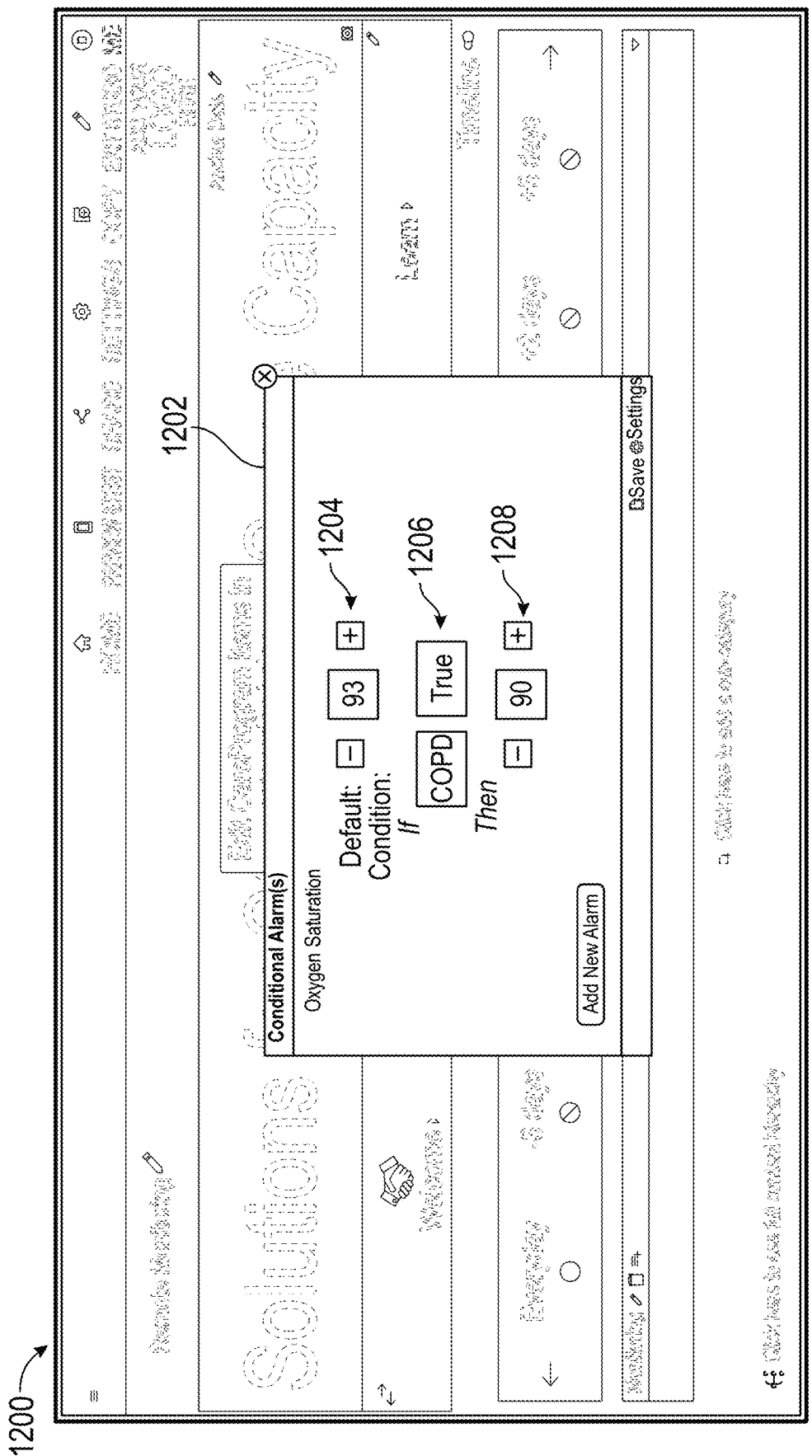

In FIG. 12A, yet another example patient care configuration user interface 1200 is depicted. The patient care configuration user interface 1200 can include an alarm configuration area 1202. As described herein, a patient care user interface can have customized alarms. For example, a first patient care user interface can have first alarms that are different from second alarms of a second patient care user interface. The alarm configuration area 1202 can be associated with a particular physiological parameter (here an oxygen saturation physiological parameter). The alarm configuration area 1202 can allow an administrator to configure conditional threshold logic. For example, the alarm configuration area 1202 can include a first condition 1204 (here a default condition) and a second condition 1206 (here a chronic obstructive pulmonary disease (COPD) condition). The first condition 1204 can include a first threshold and the second condition 1206 can include a second threshold. An administrator can configure each of the conditions 1204, 1206. As described herein, a patient monitoring service 136 can apply the second condition 1206 based on response data from a patient. For example, as configured, the patient monitoring service 136 can apply the second condition 1206 if a patient has indicated that they have chronic obstructive pulmonary disease, then the patient monitoring service 136 can use the second threshold (here a 90% oxygen saturation threshold). Otherwise, the patient monitoring service 136 can apply the first default condition 1204 that uses a first threshold (here a 93% oxygen saturation threshold).

Figure 12B:
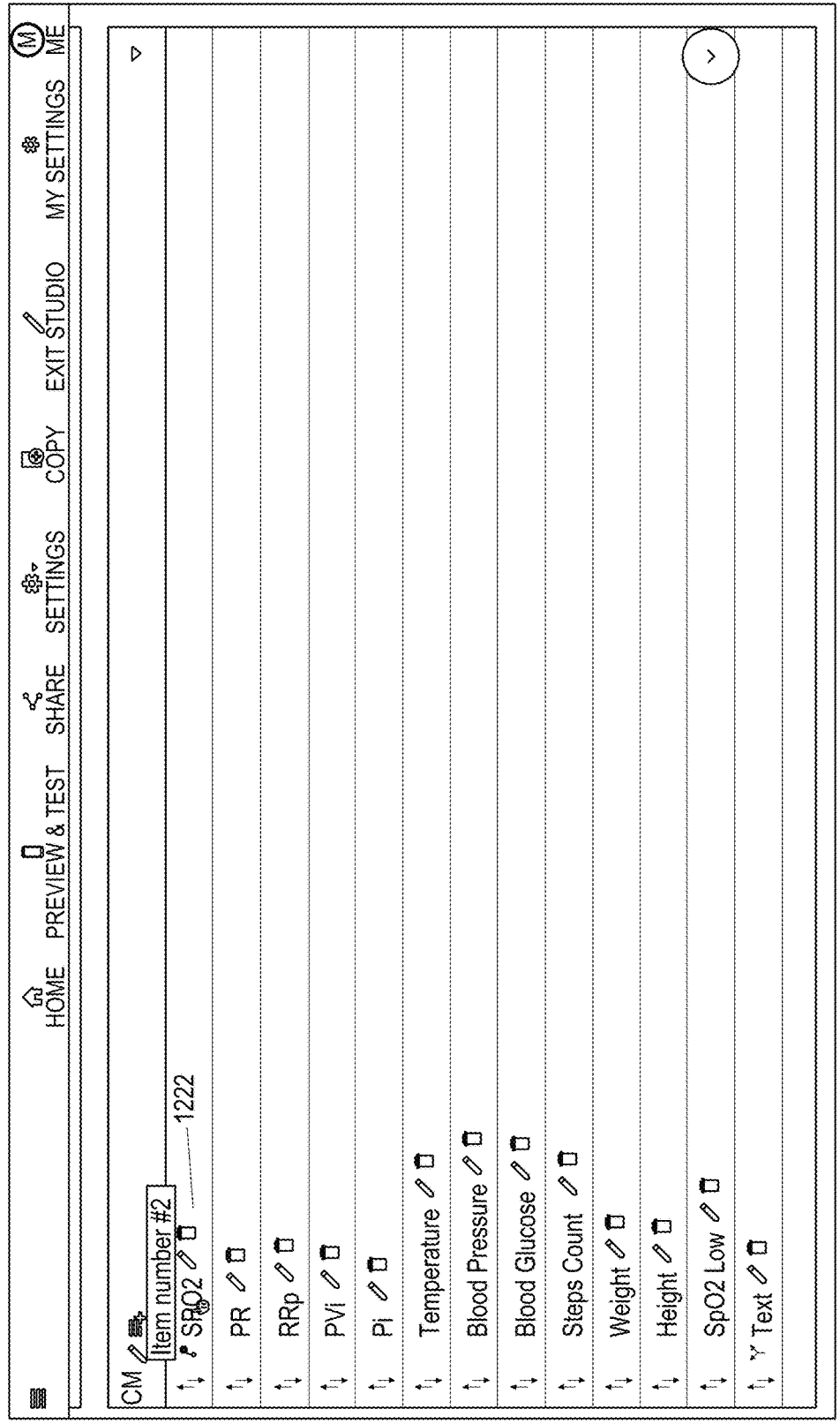

In FIG. 12B, yet another example patient care configuration user interface 1220 is depicted. The patient care configuration user interface 1220 can include a list of patient sensor items and/or items, such as the patient sensor item 1222 for blood oxygen saturation (SpO2). As shown, an administrator can select an item, such as the patient sensor item 1222.

Figure 12C:
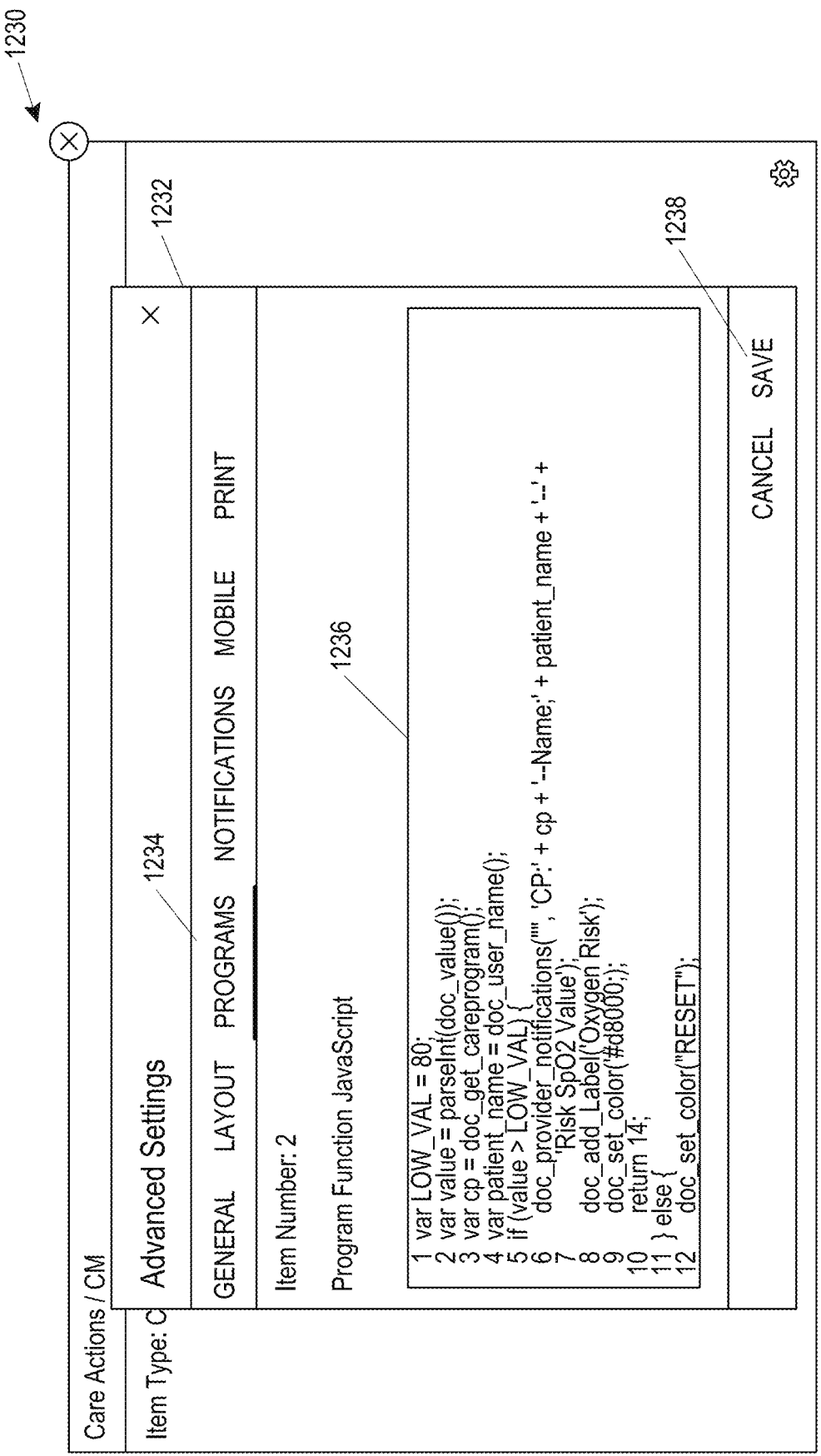

In FIG. 12C, yet another example patient care configuration user interface 1230 is depicted. The patient care configuration user interface 1230 can include a settings area 1232, which can be presented in response to the selection of an item, such as the patient sensor item 1222 described above with respect to FIG. 12B. The settings area 1234 can include a program instructions area 1234. The program instructions area 1234 can include a program instructions input area 1236. An administrator can submit user input in the input area 1236, such as the depicted program instructions that can be in an interpreted language (such as JavaScript). As shown, the program instructions can include customized logic related to an item, such as generating an alert, which can be transmitted to a patient user computing device 102 in a client configuration package. As described herein, using an interpreted language for the program instructions can advantageously have the benefit of providing and/or changing behavior in the patient care application 120 without or before recompiling of the patient care application 120. An administrator can submit user input including the program instructions by selecting the save element 1238. Additionally or alternatively, some embodiments can allow administrators to configure customized logic and/or application behavior without writing program instructions in an interpreted language. For example, graphical user interface can be provided that allow similar customization of logic and/or behavior with graphical elements, such as the graphical elements described above with respect to FIG. 12A.

Client Graphical User Interfaces

FIGS. 13, 14, and 15A-15C illustrate example graphical user interfaces of a patient care application 120, according to some embodiments of the present disclosure. In various embodiments, aspects of the user interfaces may be rearranged from what is shown and described below, and/or particular aspects may or may not be included. The patient care application 120 can execute on the patient user computing device 102 to present the graphical user interfaces of FIGS. 13, 14, and 15A-15C. The graphical user interfaces of FIGS. 13, 14, and 15A-15C may have similar user interface elements and/or capabilities.

Figure 13:
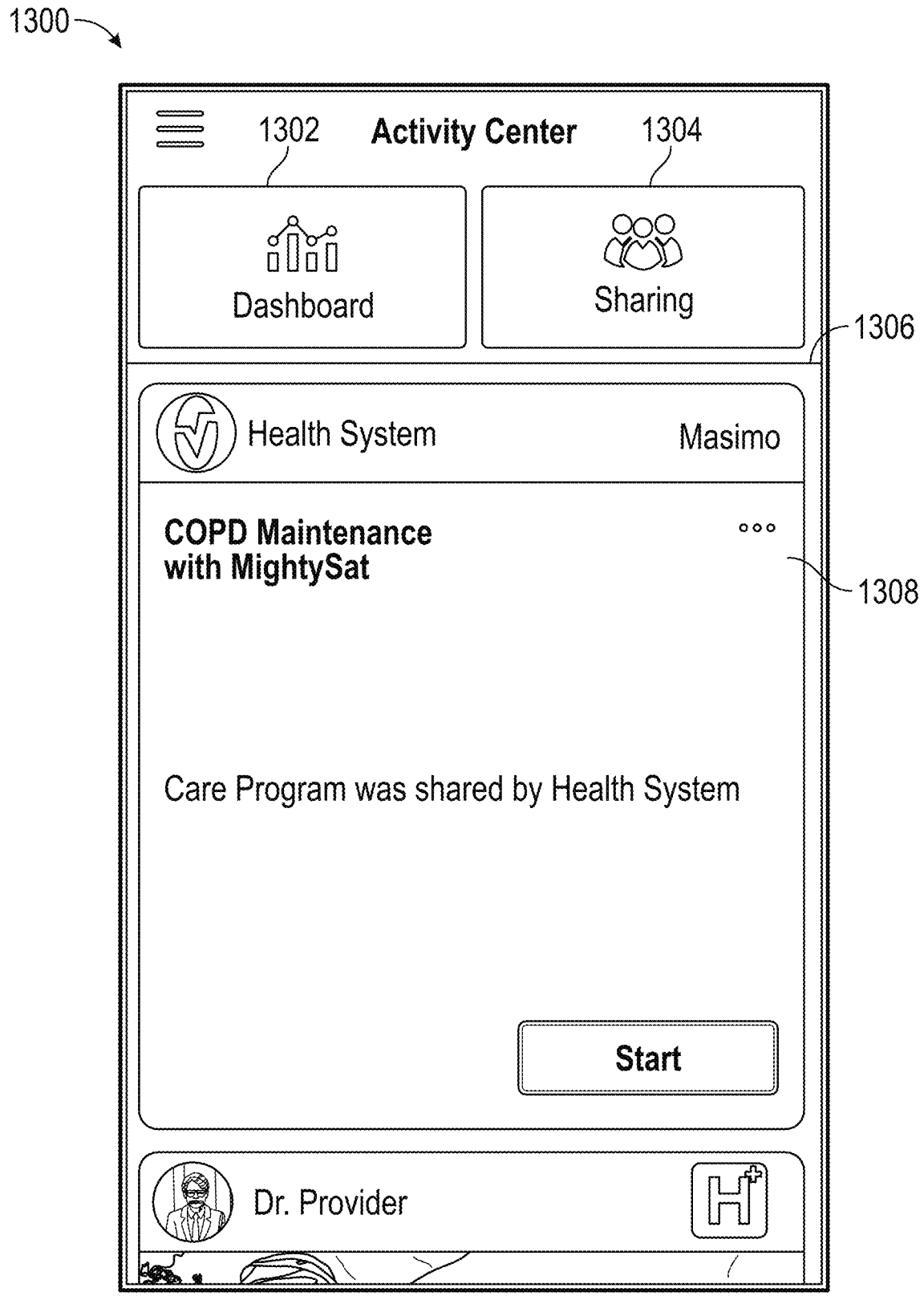
FIGS. 13, 14, and 15A-15C illustrate example graphical user interfaces of a patient care application, according to some embodiments of the present disclosure.

FIG. 13 illustrates a graphical user interface 1300 of the patient care application 120. The graphical user interface 1300 can include a feed 1306, which can present the patient care user interface option(s) 1308 that correspond to a patient care user interface that has been shared with the patient user (here the "COPD Maintenance with MightySat" user interface/CareProgram). The graphical user interface 1300 can provide further access to the user (for example, a patient or a care provider) to other aspects of the patient care application 120. For example, the user can access a dashboard user interface, which can present patient physiological parameters, via the dashboard element 1302. An example dashboard user interface is described in further detail below with respect to FIG. 14. As another example, the user can access a sharing configuration user interface via the sharing element 1304. As described herein, a sharing configuration user interface can allow a user to modify their sharing permissions, such as by identifying and/or modifying the other users that are permissioned to view at least some the patient's data/receive alerts regarding the patient.

Figure 14:
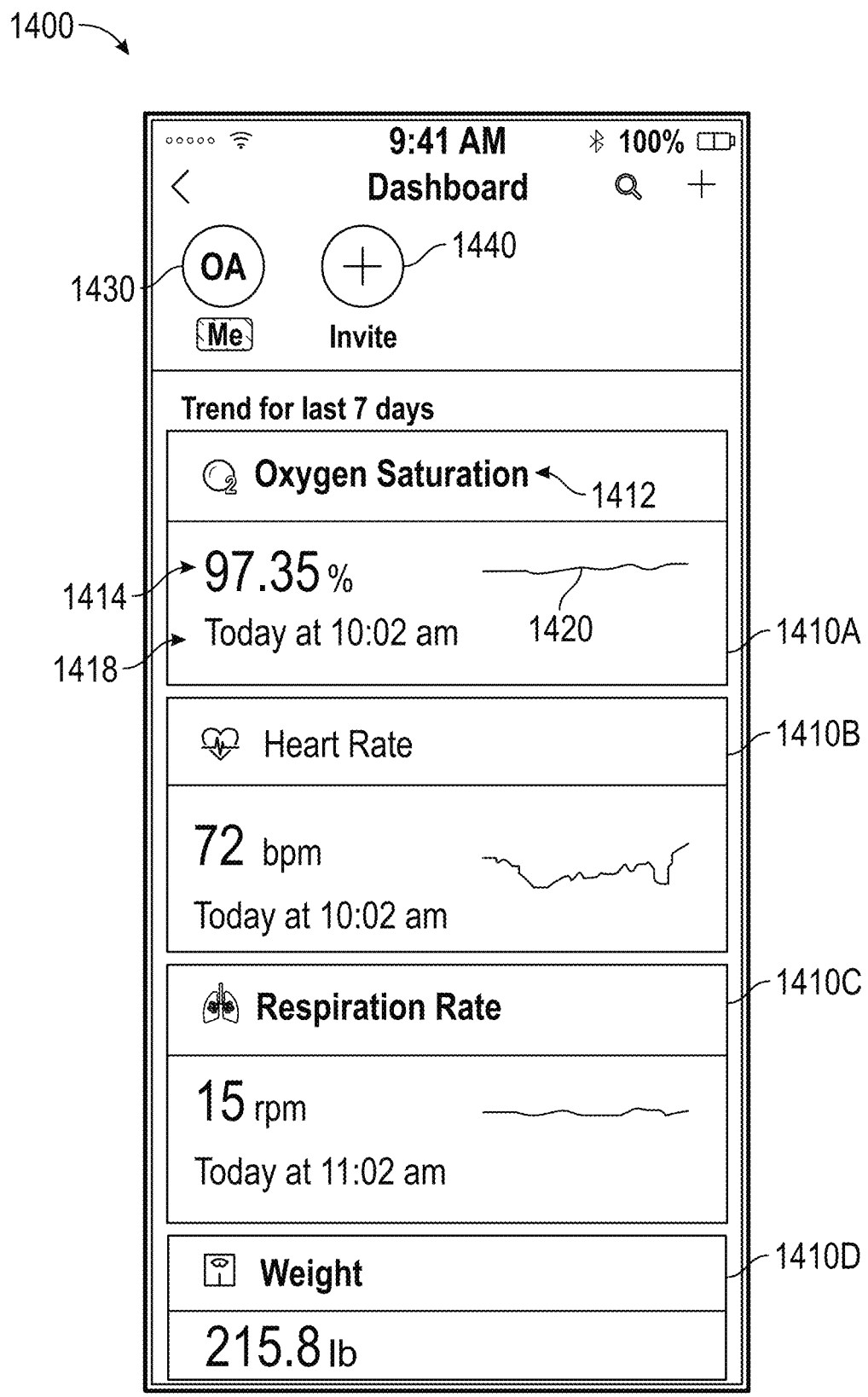

FIG. 14 illustrates an example dashboard user interface 1400 of the patient care application 120. The dashboard user interface 1400 can include one or more physiological parameter summaries 1410A, 1410B, 1410C, 1410D. As shown in FIG. 14, each of the example physiological parameter summaries 1410A, 1410B, 1410C, 1410D can be associated with different physiological parameters. The dashboard user interface 1400 can include more or less physiological parameter summaries based on the particular configuration or embodiment. The physiological parameter summaries 1410A, 1410B, 1410C, 1410D can allow a user (for example, a patient or a care provider) to review patient physiological parameters. The one or more physiological parameter summaries 1410A, 1410B, 1410C, 1410D can be associated with physiological parameters including, but not limited to, blood pressure, blood oxygen saturation, heart rate, respiration rate, body weight, or body temperature. A user can select the one or more physiological parameter summaries 1410A, 1410B, 1410C, 1410D to access additional details related to the physiological parameter associated with the selected physiological parameter summary 1410A, 1410B, 1410C, 1410D.

The physiological parameter summary 1410A can include a physiological parameter name 1412, a physiological parameter value 1414, and a visualization 1420. The physiological parameter value 1414 (here an oxygen saturation value) can be associated with a date and/or time 1418, such as when the measurement was taken. An example visualization 1420 can be a graph of physiological parameter values, such as a trend graph.

The visualization 1420 can display an overall trend of the parameter associated with the physiological parameter summary 1410A. The visualization 1420 may be based on physiological data from one or more sensors that collect data from a patient. Additionally or alternatively, the visualization 1420 can be based on measurements taken by care providers.

The dashboard user interface 1400 can include one or more elements 1430 that indicate users that are authorized to view and/or access patient data, such as the physiological parameter summaries 1410A, 1410B, 1410C, 1410D. Accordingly, a user of the patient care application 120 can readily identify who has access to the physiological parameter summaries 1410A, 1410B, 1410C, 1410D. A user may add other users as authorized users via the add user element 1440. Once added as authorized users, those other users may be able to view and/or access the physiological parameter summaries 1410A, 1410B, 1410C, 1410D associated with the user. User selection of the add user element 1440 may cause the patient care application 120 to present a graphical user interface that can allow the user to identify one or more users to be added as authorized users.

Figure 15A:
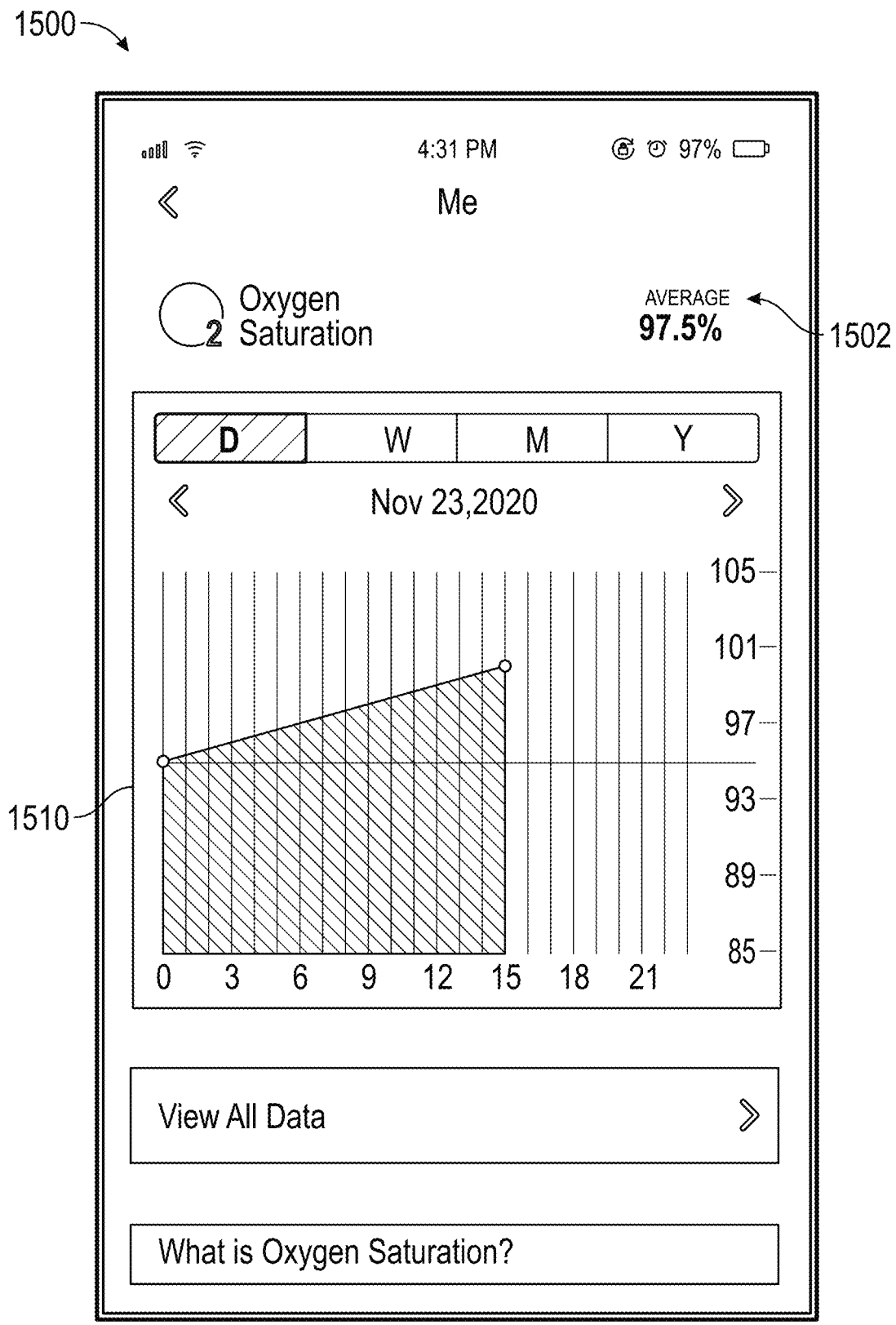
Figure 15B:
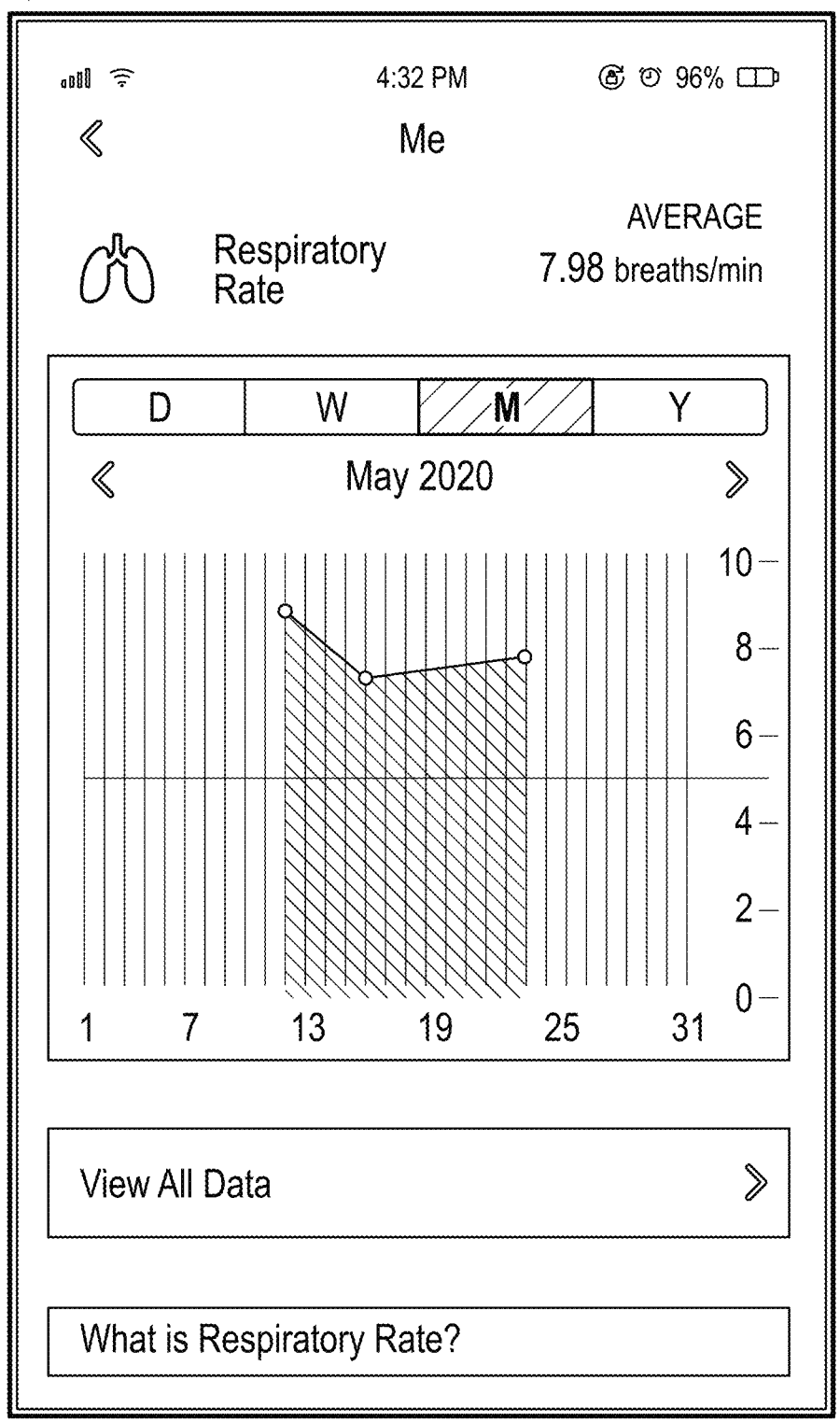
Figure 15C:
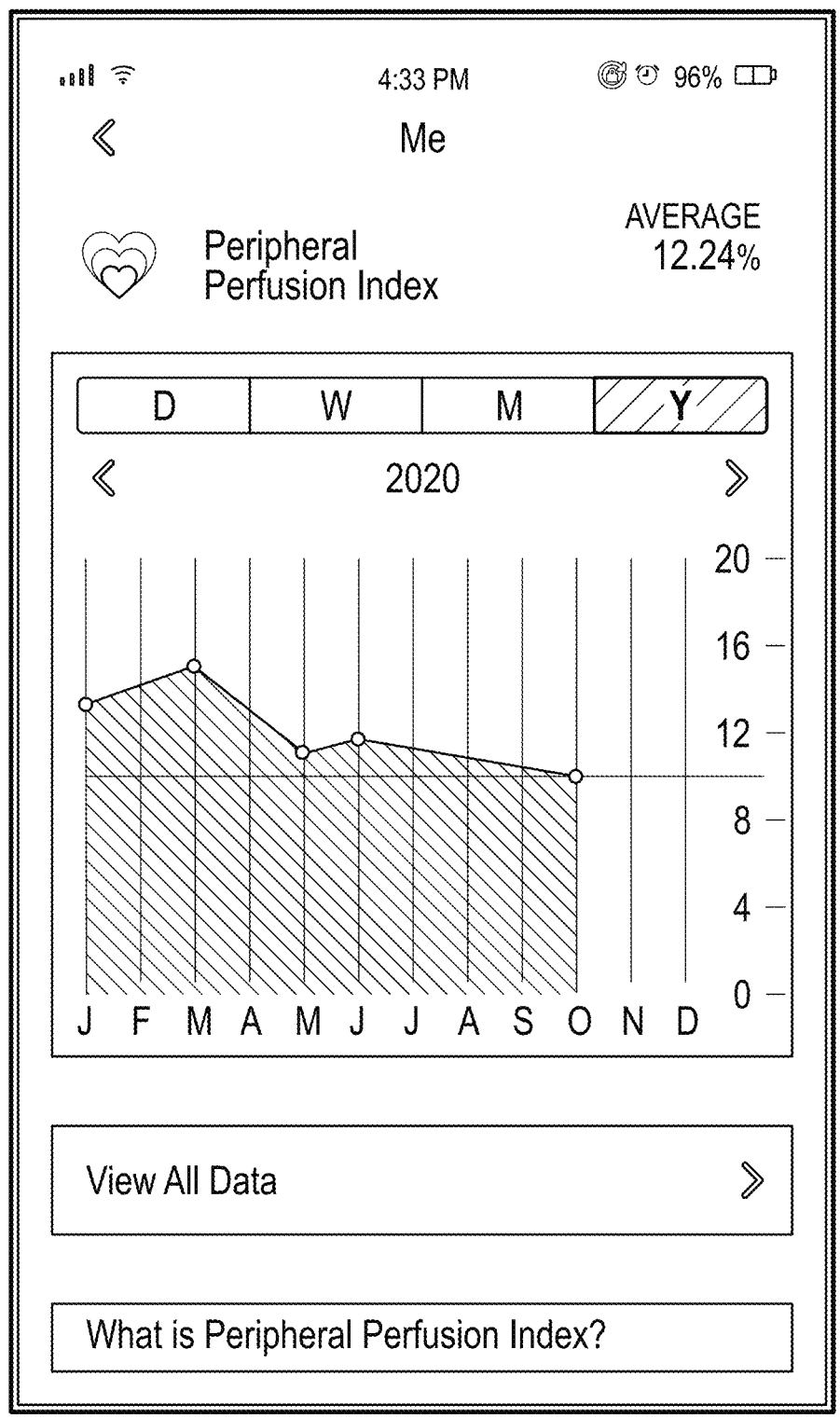

FIGS. 15A-15C illustrate example physiological parameter detail user interface of the patient care application 120. In particular, FIG. 15A illustrates a physiological parameter detail user interface 1500 associated with blood oxygen saturation. The physiological parameter detail user interface 1500 can include a statistical measurement value 1502, such as an average physiological parameter value (here an average blood oxygen saturation of 97.5 percent). The physiological parameter detail user interface 1500 can include a visualization 1510, such as a graph showing blood oxygen saturation values over time. As shown, the visualization 1510 can include user interface elements that allow a user to interact with the visualization 1510, such as by changing the time period associated with the visualization. Additional example visualizations (not shown) can include, but are not limited to, a bar graph, scatter plot, pie chart, etc.

In some embodiments, the visualization 1510 can use different indicators to display different data points in. For example, the visualization 1510 can use the color green for data points within a predetermined range, the color yellow for data points within a different predetermined range, and the color red for data points outside of those predetermined ranges. Care providers can configure the predetermined range(s).

FIG. 15B illustrates another physiological parameter detail user interface 1520 associated with respiratory rate. FIG. 15C illustrates yet another physiological parameter detail user interface 1540 associated with peripheral perfusion index. The physiological parameter detail user interfaces 1520, 1540 of FIGS. 15B and 15C can be similar to the physiological parameter detail user interface 1500 of FIG. 15A, such as by including similar user interface elements and/or operating in a similar manner. For example, the physiological parameter detail user interfaces 1520, 1540 of FIGS. 15B and 15C can each include a visualization. However, the physiological parameter detail user interfaces 1520, 1540 of FIGS. 15B and 15C can have different selected time periods than the selected time period of the physiological parameter detail user interface 1500 of FIG. 15A.

Patient Care User Interfaces

FIGS. 16A-16C and 17 illustrate example patient care user interfaces of a patient care application 120, according to some embodiments of the present disclosure. In various embodiments, aspects of the user interfaces may be rearranged from what is shown and described below, and/or particular aspects may or may not be included. The patient care application 120 can execute on the patient user computing device 102 to present the patient care user interfaces of FIGS. 16A-16C and 17. As described herein, the patient care application 120 can receive a respective client configuration package that causes the presentation the patient care user interfaces of FIGS. 16A-16C and 17. The graphical user interfaces of FIGS. 16A-16C and 17 may have similar user interface elements and/or capabilities.

Figure 16A:
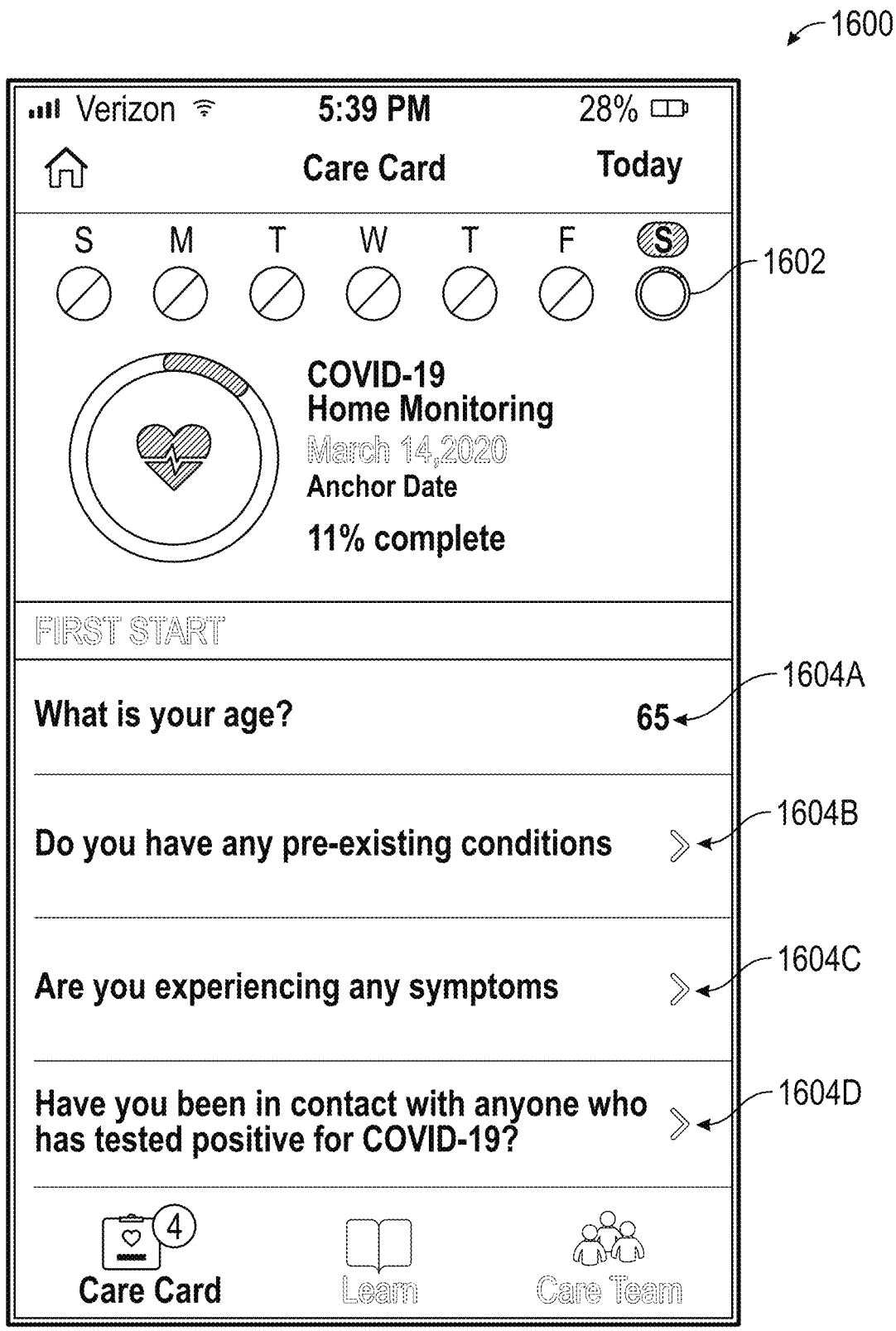
FIGS. 16A-16C and 17 illustrate example patient care user interfaces, according to some embodiments of the present disclosure.
Figure 16B:
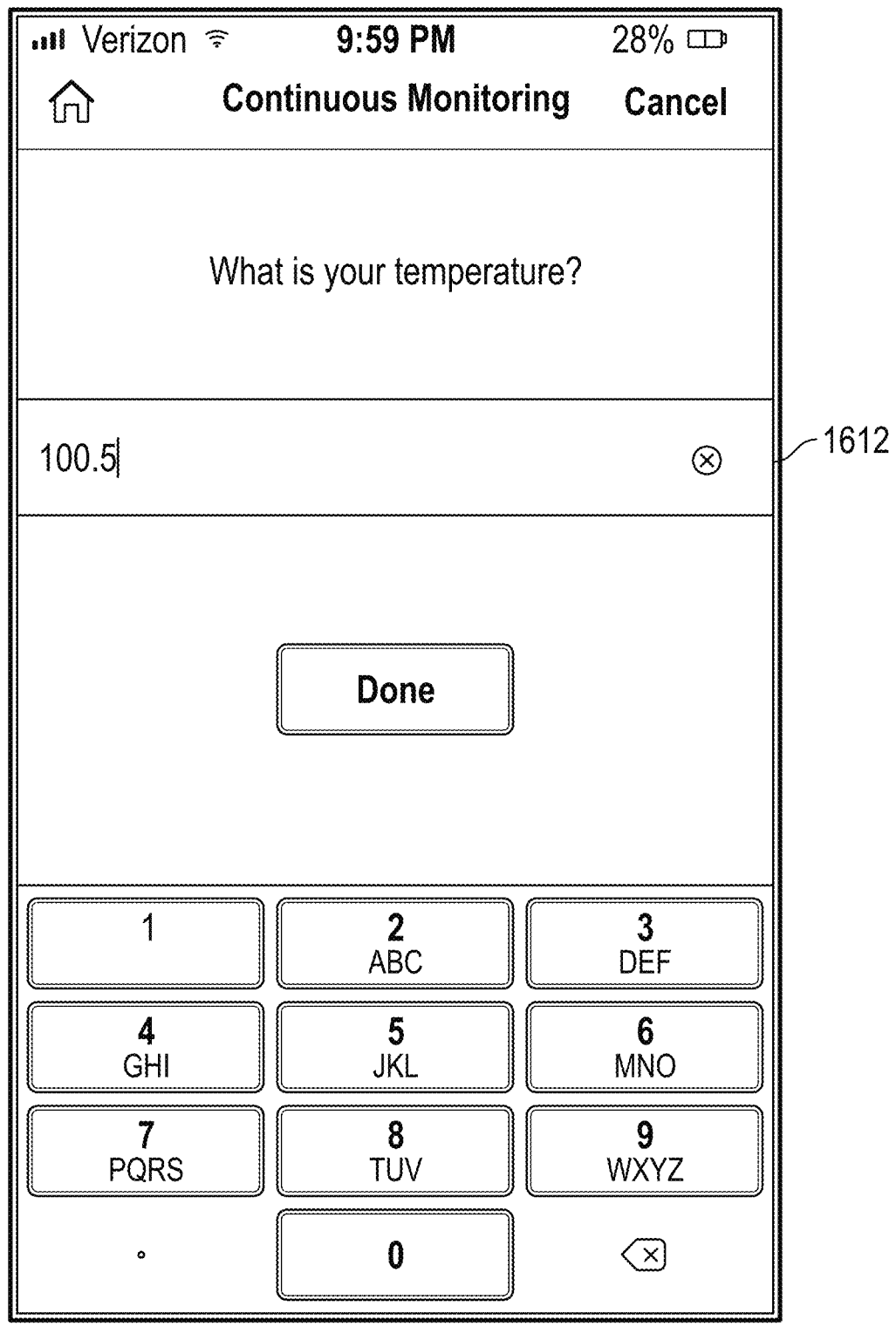
Figure 16C:
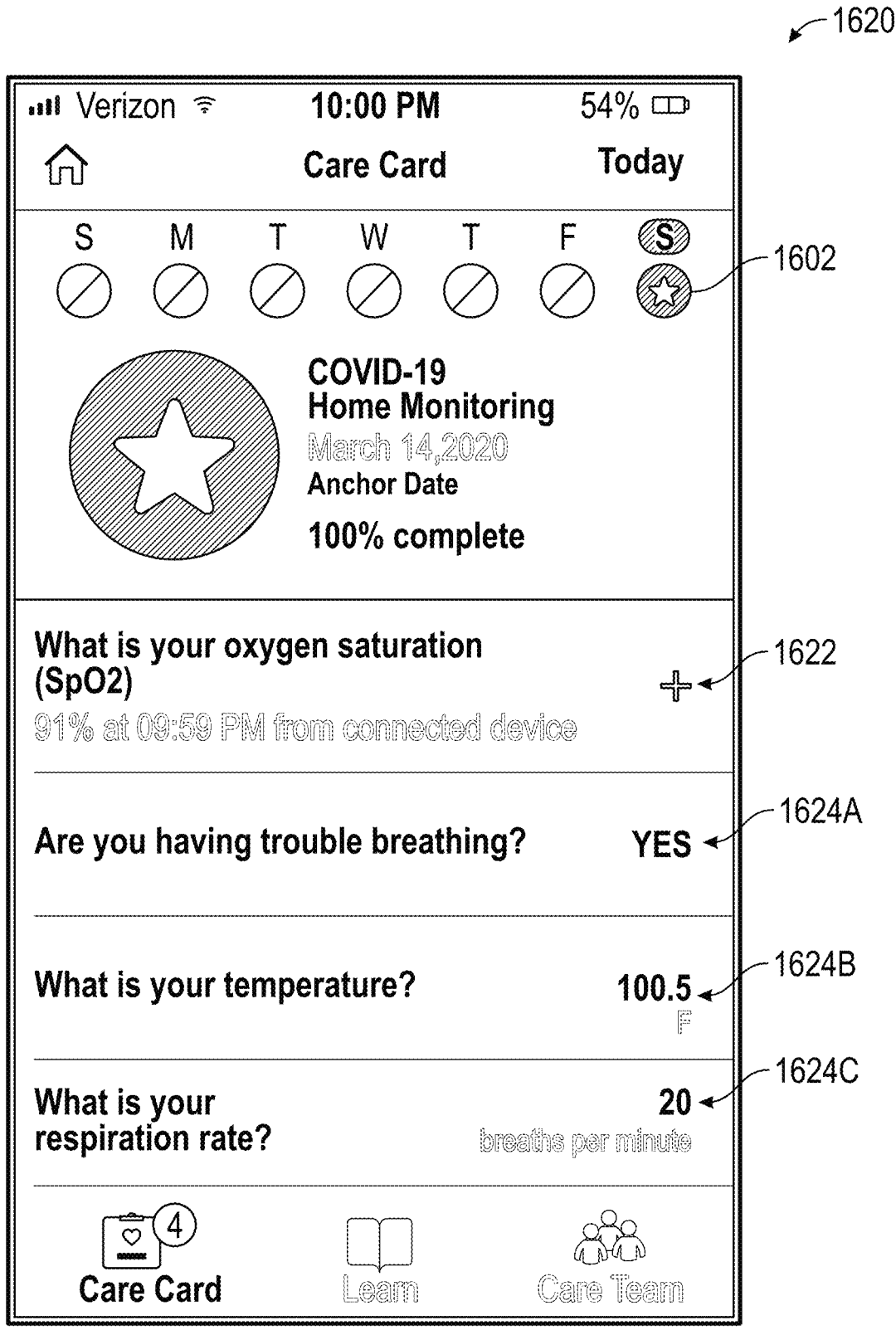

Turning to FIGS. 16A-16C, the patient care user interface of FIGS. 16A-16C can be directed towards the novel coronavirus and/or COVID-19 health condition(s). FIG. 16A illustrates an example patient care user interface 1600. In FIG. 16A, the graphical user interface 1600 includes a timeline 1602. As shown, the current day in the timeline 1602 has several items 1604A, 1604B, 1604C, 1604D to be completed by a user. The example items 1604A, 1604B, 1604C, 1604D can be patient care action items, such as questions to be completed by the user. The items 1604A, 1604B, 1604C, 1604D can include prompts that elicit user responses. The items 1604A, 1604B, 1604C, 1604D can correspond to an initial questionnaire for particular health condition(s). In the case of the novel coronavirus and/or COVID-19 and/or other use cases, example questions/prompts can include: "What is your age?", "Do you have pre-existing conditions", "Are you experiencing any symptoms", or "Have you been in contact with anyone who has test positive for COVID-19?" The responses to the questions can be used by clinicians and/or care providers.

FIG. 16B illustrates another example patient care user interface 1610. The patient care user interface 1610 can include an input area 1612 for a patient care action item (here an item to receive a patient's temperature as user input). As shown, a user can input a temperature value. Alternatively, in some embodiments, instead of being received via manual user input, a patient care user interface can receive the patient temperature value from a patient sensor device 104. The patient care action item of FIG. 16B can be defined by a patient care action item configuration of a client configuration package.

FIG. 16C illustrates yet another example patient care user interface 1620. The patient care user interface 1620 of FIG. 16C can be similar to the patient care user interface 1600 of FIG. 16A. In particular, the patient care user interface 1620 of FIG. 16C can represent a progression of completed items from the patient care user interface 1600 of FIG. 16A. For example, the patient care user interface 1620 of FIG. 16C can include indicators of the patient's progress (such as a visual icon representing a completed status for a particular day in the timeline 1602, such as a visual star icon, and/or the text "100% complete").

The patient care user interface 1620 can include a visual representation 1622 of a patient sensor item configuration, which also can be referred to as a patient sensor item. As described herein, a patient sensor item configuration can be included in a client configuration package, as configured by an administrator. The patient sensor item configuration can facilitate the interface between the patient care application 120 and a patient sensor device 104 capable of capturing physiological parameters from a patient. For example, the patient care application 120 can use the patient sensor item configuration to detect that a patient sensor device 104 has already been connected to the patient user computing device 102. As another example, the patient care application 120 can use the patient sensor item configuration to initiate a pairing process between the patient sensor device 104 and the patient user computing device 102. The example visual representation 1622 for the patient sensor item configuration includes an oxygen saturation physiological parameter received from a connected patient sensor device 104 that measured the patient's oxygen saturation.

The patient care user interface 1620 can further include several items 1624A, 1624B, 1624C. The example items 1624A, 1624B, 1624C can be patient care action items, which can be completed by the user. For example, the first patient care action item 1624A with the prompt (such as "Are you having trouble breathing?") can elicit a yes/no response to be provided from the user. The user can select the second item 1624B that can cause presentation of the patient care user interface 1610 of FIG. 16B. In some embodiments, the third item 1624C (shown as a respiration rate item) can be an item that can receive user input. In other embodiments, the third item 1624C can be a patient sensor item that receives the respiration rate physiological parameter from a patient sensor device 104. Similar to the items 1604A, 1604B, 1604C, 1604D of FIG. 16A that can be directed towards the novel coronavirus and/or COVID-19, the items 1622, 1624A, 1624B, 1624C of FIG. 16C can likewise be directed towards the novel coronavirus and/or COVID-19. For example, the items 1622, 1624A, 1624B, 1624C of FIG. 16C can be directed towards the symptoms of COVID-19 or any other respiratory disease (that can potentially be very dangerous) such as low oxygen saturation, high body temperature, difficulty breathing, and/or too low or too high of a respiration rate. As described herein, the items 1622, 1624A, 1624B, 1624C of the patient care user interface 1620 and associated response data/physiological parameter values can be monitored by authorized users (such as a clinician or family or friends) and/or used to alert the authorized user if the response data/physiological parameter values trigger an alarm. Such monitoring and alarms can save lives, since emergency personnel or family or friends can response to the alarm/alert.

Figure 17:
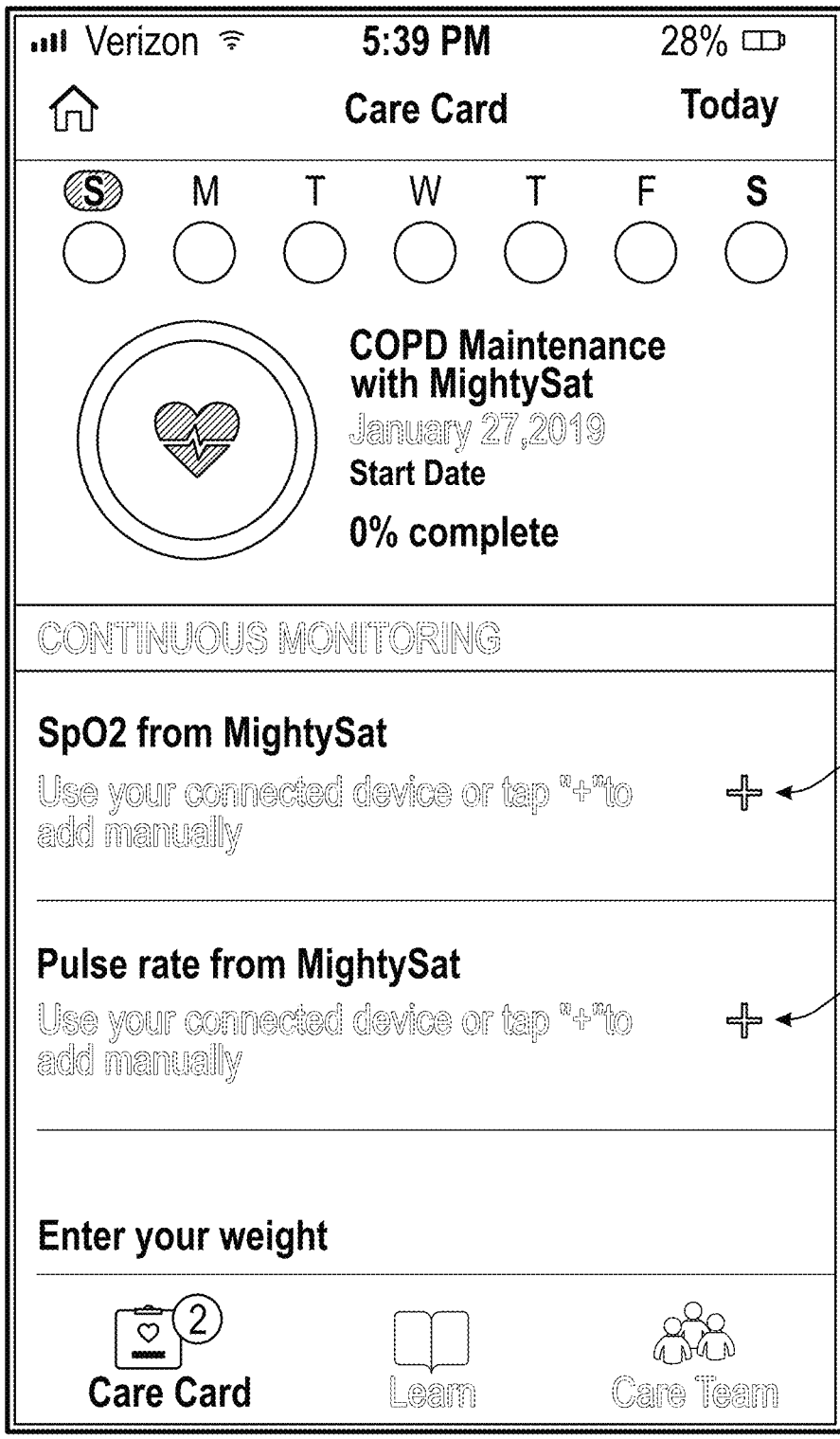

FIG. 17 illustrates yet another example patient care user interface 1700. The patient care user interface 1700 of FIG. 17 can be similar to the patient care user interfaces 1600, 1620 of FIGS. 16A and 16C. As described herein, while the patient care user interfaces 1600, 1620 of FIGS. 16A and 16C can be directed towards the novel coronavirus and/or COVID-19, the patient care user interface 1700 of FIG. 17 can be directed towards chronic obstructive pulmonary disease (COPD). Moreover, the patient care user interface 1700 of FIG. 17 can include items 1702A, 1702B, which can be similar to the item 1622 of FIG. 16C. Each of the items 1702A, 1702B can relate to a patient sensor item configuration for particular physiological parameters. For example, the items 1702A, 1702B, each of which are associated with one of an oxygen saturation or a pulse rate, respectively, can be configured to interface with a particular type of patent sensor device 104 (here the "MightySat" device).

Additional patient care user interfaces can be directed towards different types of health condition(s). For example, some patient care user interfaces can be directed towards heart disease. Example symptoms of heart disease can include, but are not limited to, abnormal heart rhythms, shortness of breath, high blood pressure (for example, pulmonary hyperextension), and/or shortness of breath. Accordingly, in some patient care user interfaces, one or more patient sensor items and/or items can monitor physiological parameters such as respiratory rate, heart rate, blood pressure, ECG trends, and/or blood oxygen saturation ($SpO_2$). Thus, as a result of the patient care user interface, the patient user computing device 102 can transmit physiological parameter values related to the patient management and monitoring system 110 to monitor for heart disease. For example, if a patient suffers from a sudden increase in respiratory rate (which may indicate shortness of breath), sudden decrease in blood oxygen saturation (which may indicate impaired heart function), and/or arrhythmia, the system 110 may generate and send a notification (or an alert) to a care provider, an emergency contact, and/or to the patient user computing device 102. Moreover, the patient management and monitoring system 110 can make the patient data related to heart disease available to clinicians in one or more patient monitoring user interfaces.

Some patient care user interfaces can be directed towards sleep apnea. Example symptoms of sleep apnea can include, but are not limited to, night sweats that may be indicated higher than normal body temperature, high blood pressure, irregular heartbeats, and/or irregular breathing. Example sleep-apnea-related complications can include, but are not limited to, cardiovascular problems such as a heart attack, unusual heart rhythms, and/or low blood oxygen levels. Accordingly, in some patient care user interfaces, one or more patient sensor items and/or items can monitor physiological parameters such as temperature, blood pressure, ECG trends, and/or blood oxygen saturation. For example, if a sleeping patient suffers from irregular respiratory rate, irregular heartbeat, and/or higher than normal body temperature, the system 110 may generate and send a notification (or an alert) to a care provider, an emergency contact, and/or to the patient user computing device 102. Moreover, the patient management and monitoring system 110 can make the patient data related to sleep apnea available to clinicians in one or more patient monitoring user interfaces.

Some patient care user interfaces can be directed towards chronic lower respiratory diseases such as chronic obstructive pulmonary disease, asthma, pulmonary hypertension, and the like. Example symptoms of chronic lower respiratory diseases can include, but are not limited to, shortness of breath, chronic cough, unintended weight loss, swelling in ankles, feet, or legs, and/or frequent respiratory infections. Example chronic-lower-respiratory-disease-related complications can include, but are not limited to, heart-related events (for example, heart attack) and/or high blood pressure. Accordingly, in some patient care user interfaces, one or more patient sensor items and/or items can monitor physiological parameters such as respiratory rate, patient temperature, blood oxygen saturation, and/or ECG trends. For example, if the patient's respiratory rate falls below a certain threshold (which can indicate that a patient is having difficulty breathing), the patient's blood oxygen saturation is below a threshold, the patient's temperature is higher than a certain threshold (which can indicate that a patient might have an infection), and/or blood pressure is above a certain threshold, the system 110 may generate and send a notification (or an alert) to a care provider, an emergency contact, and/or to the patient user computing device 102. Moreover, the patient management and monitoring system 110 can make the patient data related to chronic lower respiratory diseases available to clinicians in one or more patient monitoring user interfaces.

Patient Monitoring User Interfaces

FIGS. 18, 19A-19B, and 20 illustrate example patient monitoring user interfaces, according to some embodiments of the present disclosure. In various embodiments, aspects of the user interfaces may be rearranged from what is shown and described below, and/or particular aspects may or may not be included. The patient management and monitoring system 110 can provide the patient monitoring user interfaces of FIGS. 18, 19A-19B, and 20, which can be accessed by a clinician user computing device 124. The patient monitoring user interfaces of FIGS. 18, 19A-19B, and 20 can update substantially in real-time based on received data. The graphical user interfaces of FIGS. 18, 19A-19B, and 20 may have similar user interface elements and/or capabilities.

Figure 18:
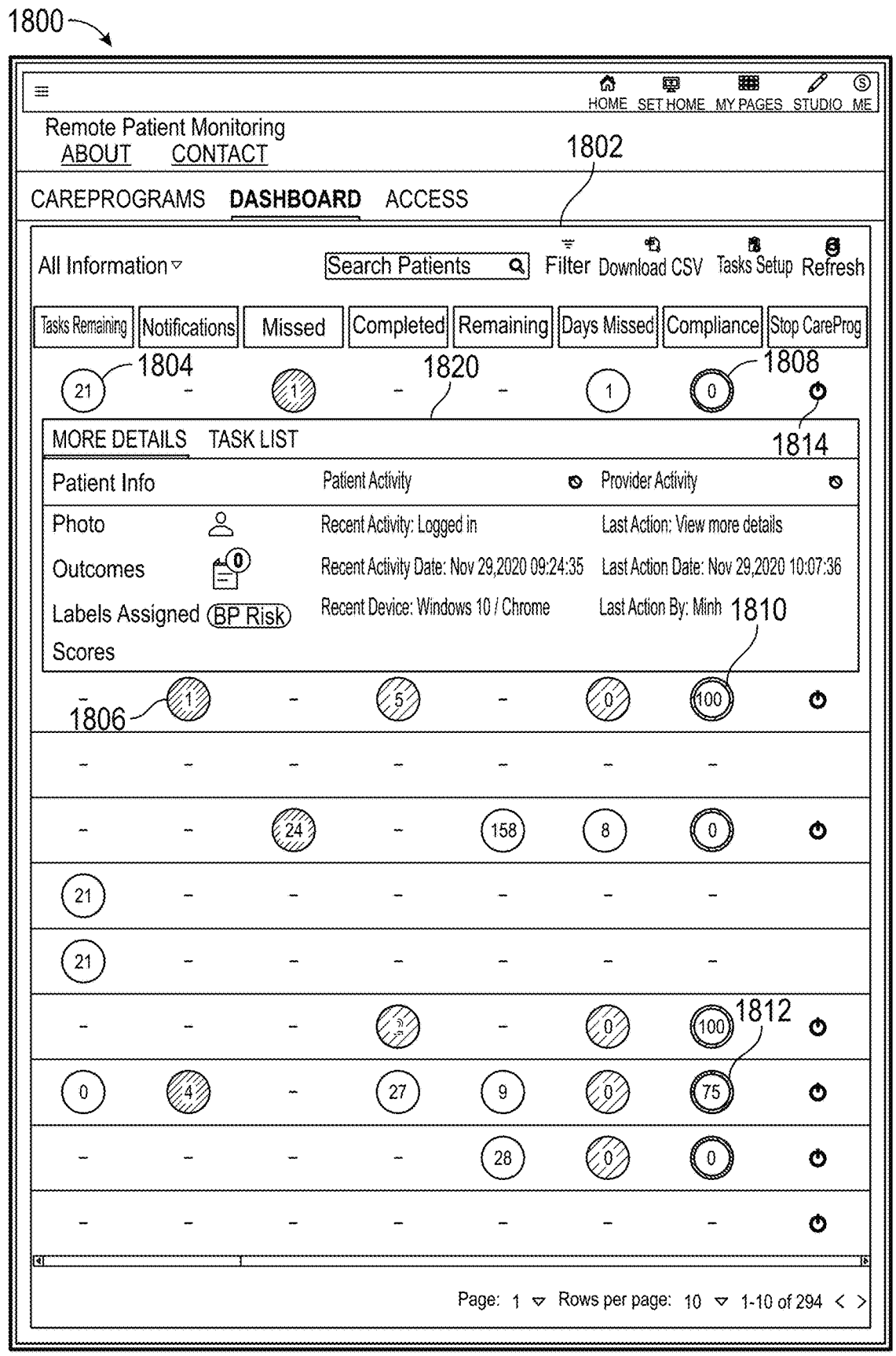

FIG. 18 depicts an example patient monitoring user interface 1800 that can allow care providers to monitor patients. The patient monitoring user interface 1800 includes a dashboard 1802. Generally, the patient monitoring user interface 1800 can allow a care provider to review information regarding patients, search for patients, and/or configure items (such as tasks) for patients. The patient management and monitoring system 110 can receive data from a patient care application 120 and/or a patient care user interface executing on a patient user computing device 102. As shown, the example dashboard 1802 can include a table with columns, column headings, and rows. In the example dashboard 1802, each row can correspond to a particular patient. The dashboard 1802 can include a patient detail area 1820, which can further provide details regarding a particular patient, such as patient identifying information, patient activity, provider activity, etc. In some embodiments, user selection of a row associated with a particular patient in the dashboard 1802 can cause presentation of the patient detail area 1820 for the particular patient. With respect to the dashboard 1802, user selection of the user interface element 1814 in the "Stop CareProgram" can cause a corresponding patient care user interface to pause or end, which can remove the patient care user interface from the patient care application 120 executing on a patient user computing device 102. In other embodiments, user selection of the user interface element 1814 in the "Stop CareProgram" can cause a corresponding patient care user interface presented from a patient care application 120 executing on a patient user computing device 102 to cease from presenting new items.

The patient management and monitoring system 110 can use the received data to generate summary metadata. The dashboard 1802 can include the summary metadata for multiple patients. Example summary metadata can be related to the headings shown in the dashboard 1802: "Tasks Remaining," "Notifications," "Missed," "Completed," "Remaining," "Days Missed," and "Compliance." As described herein, a patient care user interface can include items associated with a patient and/or can assist in collecting patient physiological data, which can trigger notifications/alarms. Example items can be associated with schedules, such as daily schedules.

The patient management and monitoring system 110 can generate summary data for each patient, which can be shown as indicators in the dashboard 1802. A "Tasks Remaining" indicator can indicate that there are items (such as tasks) remaining for a patient. For example, a first indicator 1804 in the "Tasks Remaining" column with the number "21" can indicate that there are twenty-one remaining items (such as tasks) for a first patient associated with one or more patient care user interfaces. A "Notifications" indicator can indicate that there are notifications for a patient. For example, a second indicator 1806 in the "Notifications" column with the number "1" can indicate that there is one notification for a second patient associated with one or more patient care user interfaces. The second indicator 1806 can further indicate a status level, such as by being color coded. For example, a red indicator can indicate an urgent status, a yellow indicator can indicate a warning status, and a green indicator can indicate a nominal status. "Missed," "Completed," and "Remaining" indicators can indicate that a patient has missed, completed, and remaining items (such as tasks), respectively. A "Compliance" indicator can indicate a level of compliance for items (such as tasks) associated with a patient. For example, the compliance indicators 1808, 1810, 1812 (with the numbers "0," "100," and "75," respectively) can represent non-compliance, total compliance, and partial compliance, respectively, for respective patients.

Figure 19A:
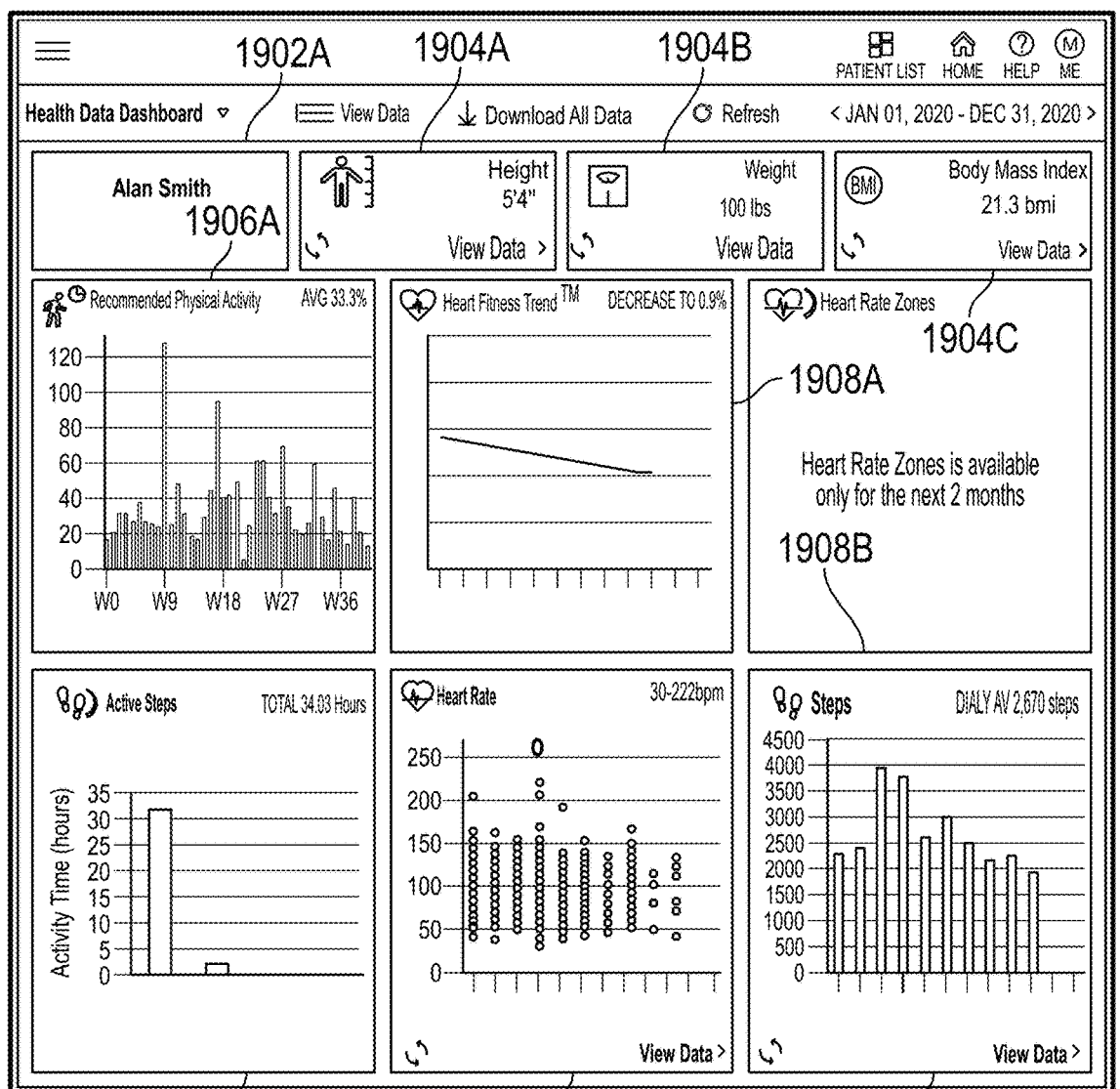
Figure 19B:
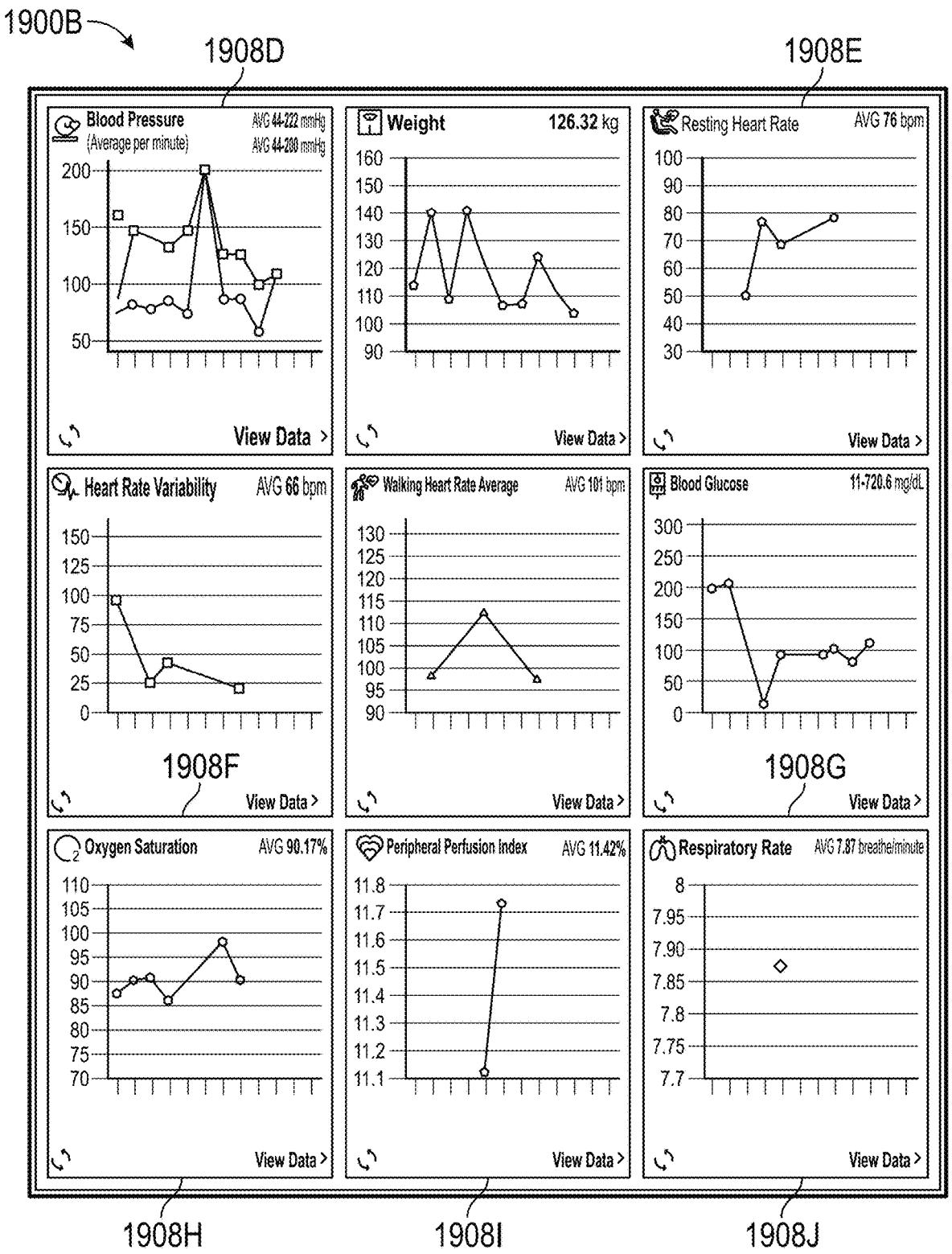

FIGS. 19A-19B depict additional example patient monitoring user interfaces 1900A, 1900B that can allow care providers to monitor a patient. In particular, FIG. 19A depicts a patient monitoring user interface 1900A with a dashboard 1902A. The dashboard 1902A can be specific to a particular patient and can include one or more patient attribute areas 1904A, 1904B, 1904C, physical activity areas 1906A, 1906B, 1906C, and physiological parameter areas 1908A, 1908B, 1908C. As described herein, the information in the areas 1904A, 1904B, 1904C, 1906A, 1906B, 1906C, 1908A, 1908B, 1908C can be received from a patient care user interface. As shown, the areas within the dashboard 1902A can be represented as tiles. The patient attribute areas 1904A, 1904B, 1904C can provide patient attributes, such as, but not limited to, height weight, body mass index, etc. The physical activity areas 1906A, 1906B, 1906C can be associated with physical activity data, such as a number of steps taken by the patient. As shown, the example physiological parameter areas 1908A, 1908B, 1908C can be associated with heart physiological parameters. Additional example physiological parameter areas can be described in further detail below with respect to FIG. 19B. As shown, some of the areas 1906A, 1906B, 1906C, 1908A, 1908C can include visualizations, such as graphs, plots, and/or bar graphs. The visualizations can allow a care provider to quickly analyze patient data and/or monitor a patient.

The data in the dashboard 1902A can be associated with a date and time range. In some embodiments, the data in the dashboard 1902A can update in response to a change of the date and time range. For example, the patient's weight of "100 lbs" in the area 1904B can be for a date and time within the date and time range.

FIG. 19B depicts a patient monitoring user interface 1900B with another dashboard 1902B. The dashboard 1902B of FIG. 19B can be similar to the dashboard 1902A of FIG. 19A. In particular, the dashboard 1902B of FIG. 19B can be a continuation of the same dashboard 1902A of FIG. 19A for the same patient. The dashboard 1902A can include physiological parameter areas 1908D, 1908E, 1908F, 1908G, 1908H, 1908I, 1908J. As described herein, example physiological parameters can include, but are not limited to, blood pressure, resting heart rate, heart rate variability, blood glucose, blood oxygen saturation, peripheral perfusion index, and/or respiratory rate, which can be captured by patient sensor devices 104. Some of the physiological parameter areas 1908H, 1908I, 1908J can be similar to and/or have some overlap with the physiological parameter detail user interfaces 1500, 1520, 1540 described above with respect to FIGS. 15A, 15B, and 15C.

FIG. 20 depicts another patient monitoring user interface 2000 that can allow care providers to monitor a patient. The patient monitoring user interface 2000 of FIG. 20 can be similar to the patient monitoring user interfaces 1900A, 1900B of FIGS. 19A-19B. For example, similar to the patient monitoring user interfaces 1900A, 1900B of FIGS. 19A-19B, the patient monitoring user interface 2000 of FIG. 20 can be specific to a particular patient. Moreover, much like the patient monitoring user interfaces 1900A, 1900B of FIGS. 19A-19B, the patient monitoring user interface 2000 of FIG. 20 can present values for patient data, such as, but not limited to, amount of time spent for physical activity, heart rate, active steps, total number of steps, blood pressure, weight, heart rate variability, walking heart rate, resting heart rate, blood glucose, blood oxygen saturation, peripheral perfusion index, and/or respiratory rate. However, instead of presenting visualizations of patient data, like in the patient monitoring user interfaces 1900A, 1900B of FIGS. 19A-19B, the patient monitoring user interface 2000 can present patient data in a data view. As shown, the patient monitoring user interface 2000 includes a patient data area 2002 with patient data values. In some embodiments, the patient data values shown in the patient data area 2002 can be sampled from the current date and time range.

The patient monitoring user interface 2000 can be interactive. The patient data value types (such as blood glucose, blood oxygen saturation, peripheral perfusion index, respiratory rate, physical activity, etc.) can each be associated with a category (such as a fitness category, a heart category, a vitals category, a body measurement category, or a results category). A clinician can select one or more categories from the filter area 2004, which can cause the patient monitoring user interface 2000 to update the data value types in the patient data area 2002 based on the category filter(s). A clinician can select a date and time range in the patient monitoring user interface 2000, which can cause the patient monitoring user interface 2000 to update the data values in the patient data area 2002 based on the selected date and time range.

Patient Care User Interface Configuration Methods

Figure 21:
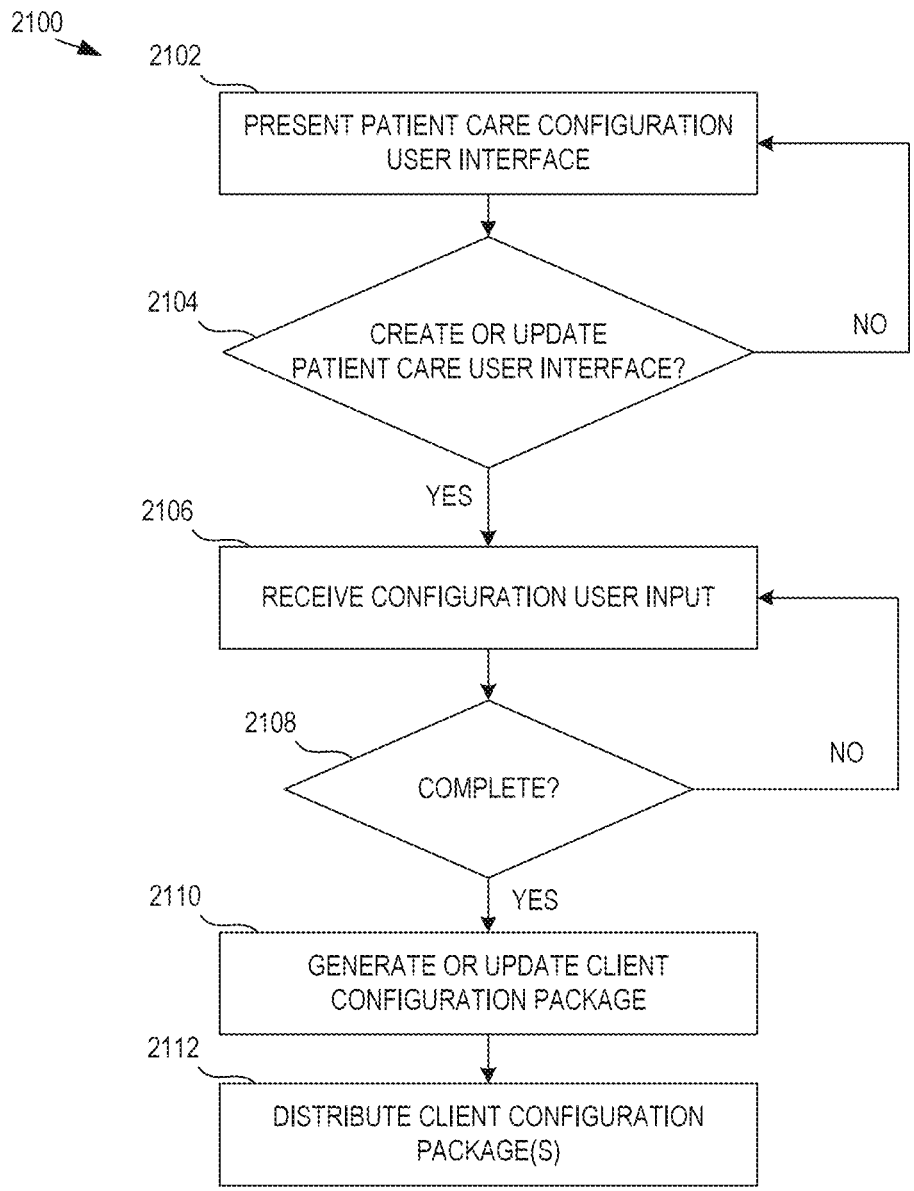
FIG. 21 is a flowchart of a method for configuring patient care user interfaces, according to some embodiments of the present disclosure.

FIG. 21 is a flowchart of a method 2100 for configuring patient care user interfaces, according to some embodiments of the present disclosure. The method 2100 provides example approaches regarding configuring patient care user interfaces. As described herein, the patient management and monitoring system 110 of FIG. 1B may include various devices, services, and/or applications, some of which may implement aspects of the method 2100 as described herein. Depending on the embodiment, the method 2100 may include fewer or additional blocks and/or the blocks may be performed in order different than is illustrated.

Beginning at block 2102, a patient care configuration user interface can be presented. In particular, the frontend server 130 can present a patient care configuration user interface. The frontend server 130 can present the patient care user interfaces that are available for configuration. An example patient care configuration user interface is the patient care configuration user interface 900 of FIG. 9, which includes a patient care user interface list area 902. The frontend server 130 can further present a patient care configuration user interface that includes an option to create a new patient care user interface. As described herein, an advantage of a frontend server 130 that presents patient care configuration user interfaces is that an administrator can be enabled to add, remove, or edit patient care user interfaces without programming experience. Additional details regarding some patient care configuration user interfaces are described above in further detail with respect to FIG. 9.

At block 2104, it can be determined whether to create or update a patient care user interface. In particular, the frontend server 130, via a patient care configuration user interface, can receive a request to create or update a patient care user interface. For example, if the frontend server 130 presents a list of patient care user interfaces in a patient care configuration user interface, an administrator can select a particular patient care user interface to edit. The frontend server 130 can further present an option to create a new patient care user interface. Thus, if the frontend server 130 receives a request to edit or create a patient care user interface, the method 2100 can proceed to the block 2106 for receiving configuration user input 2106.

However, if the frontend server 130 does not receive a request to edit or create a patient care user interface, the method 2100 can return to the previous block 2102 to continue present a patient care configuration user interface. For example, in some cases, an administrator can view existing patient care user interfaces without making a change to an existing patient care user interface.

At block 2106, configuration user input can be received. In particular, the frontend server 130 can receive configuration user input. Example configuration user input can include one or more selections of configuration user interface elements in a patient care configuration user interface. In particular, the one or more selections can indicate graphical layout configuration for a patient care user interface. As described above with respect to FIGS. 10A and 11, user selection of an element in patient care configuration user interface can add or remove a timeline to or from the graphical layout of a patient care user interface. Additional example graphical layout changes can include rearranging the order or placement of elements of a patient care user interface. The frontend server 130 can also receive configuration user input related to item configuration, which can be described in further detail above and below, such as with respect to FIGS. 10A-10C.

An additional example user selection can indicate a patient care action item configuration. As described herein, example patient care action items can be tasks for a patient associated with the health condition(s), such as medication reminder(s) and/or physical activity, physical therapy reminder(s) or goal(s). A patient care action item configuration can define a patient care action item. As defined by its configuration, a patient care action item can include at least one of a user selected boolean input field, a numeric input field, a text input field, a data input field, or a time input field.

An additional example user selection can indicate a patient sensor item configuration. A patient sensor item configuration can define a patient sensor item, which can include one of a sensor type and/or a physiological parameter type. Example patient sensor item configurations can relate to a physiological parameter such as oxygen saturation, a perfusion index, a pleth variability index, a respiration rate from pleth, a body temperature, a pulse rate, a blood glucose, and/or blood pressure. The user selections for a patient sensor item configuration can indicate particular model(s) of patient sensor devices 104. As described herein, a patient sensor item can reduce the number of steps to pair a patient sensor with the patient care application 120 that includes the patient care user interface. An advantage of the frontend server 130 allowing configurations of patient sensor items in a patient care user interface is that such configurations can improve graphical user interfaces for monitoring patient physiological parameters by enabling a user to more quickly associate patient sensor(s) with their patient care user interface. Thus, a patient care user interface can receive physiological parameters from a sensor based on the patient sensor item configuration that can include configuration information associated with a patient sensor device 104. An example patient sensor item configuration is described above with respect to FIGS. 10A-10C where a patient sensor item configuration is defined for oxygen saturation.

An additional example user selection can indicate one or more alarms or conditional alarms associated with a patient care user interface. The frontend server 130 can receive, via the patient care configuration user interface, alarm configurations, such as a definition of conditional threshold logic customized for a patient care user interface. Additional details regarding user input for configuring alarms or conditional alarms are described in further detail above with respect to FIG. 12A.

Additional example configuration user input can include program instructions. As described herein, the program instructions can be in an interpreted language, such as JavaScript. The frontend server 130 can receive the program instructions. Due to the nature of program instructions, an administrator can modify and customize the behavior of a patient care user interface in an open-ended manner. For example, an administrator can submit program instructions that can access patient data, such as a patient physiological parameter, an answer to a questionnaire, etc. Moreover, the program instructions can send notifications, set attributes, and/or control the pathway or flow of what happens next in the patient care user interface in a programmatic and/or conditional manner. Additional details regarding user input for program instructions are described in further detail above with respect to FIGS. 12B-12C. Additionally or alternatively, instead of text-based program instructions, some user input can be submitted via graphical elements that allow administrators to customize logic and/or behavior without programming skills or knowledge.

At block 2108, it can be determined whether configuration of the patient care user interface is complete. In particular, the frontend server 130 can receive user input that indicates that configuration of the patient care user interface is complete. For example, in the patient care user interfaces of FIGS. 10 and 11, an administrator can select the "EXIT STUDIO" user interface element to complete editing of the patient care user interface. In other embodiments, there can be a save or close user interface element. If configuration of the patient care user interface is complete, then the method 2100 proceeds to the block 2110 for generating or updating a client configuration package. However, if the frontend server 130 has not received user input that configuration of the patient care user interface is complete, then the method 2100 can return to block 2106 to allow the frontend server 130 to continue receiving additional configuration user input. Accordingly, an administrator can continue to add or change items and/or the layout of the patient care user interface.

At block 2110, a client configuration package can be generated or updated. In particular, the patient care management service 134 can generate or update a client configuration package that corresponds to the configured patient care user interface. An example client configuration package can include a graphical layout configuration of the patient care user interface, a patient care action item configuration, and/or a patient sensor item configuration. An example client configuration package can include at least some configuration in a configuration format such as, but not limited to, JavaScript Object Notation (JSON), Extensible Markup Language (XML), and/or YAML. For example, each of the graphical layout configuration of the patient care user interface, patient care action item configuration, and/or patient sensor item configuration can be represented in the configuration format. The patient care management service 134 can store the client configuration package in the patient care configuration database 140.

At block 2112, a client configuration package can be distributed. In particular, the patient care management service 134 can distribute one or more client configuration packages to a patient user computing device 102. An administrator can specify which patient care user interfaces should be provided to particular end-users. For example, an administrator can specific which of the patient care user interfaces listed in the user interface 900 of FIG. 9 should be shared and which end users should receive the specified patient care user interfaces. The patient care management service 134 can identify client configuration packages that correspond to the specified patient care user interfaces. The patient care management service 134 can transmit the identified client configuration package(s) over the network 108 to a patient user computing device 102. The patient care management service 134 can transmit multiple client configuration packages to the patient user computing device 102. Each client configuration package from the multiple client configuration packages can be configured to cause the patient care application to present a different, respective patient care user interface. The patient care management service 134 can cause updated patient care user interface(s) to be presented on the patient user computing device 102 by transmitting updated client configuration package(s) to the device 102.

In some embodiments, the method 2100 for configuring user interfaces can also be applied to a health monitoring system that can assist organizations to manage infectious diseases. Additional health monitoring systems and use cases are described in U.S. patent application Ser. No. 17/206,794, titled "HEALTH MONITORING SYSTEM FOR LIMITING THE SPREAD OF AN INFECTION IN AN ORGANIZATION," filed on Mar. 19, 2021 ("the '794 Application"), which is hereby incorporated by reference in its entirety. For example, the user interfaces that are configured by the method 2100 can be described in paragraphs [0103], [0150]-[0151], [0205]-[0219], and among others, of the health monitoring application.

Figure 22:
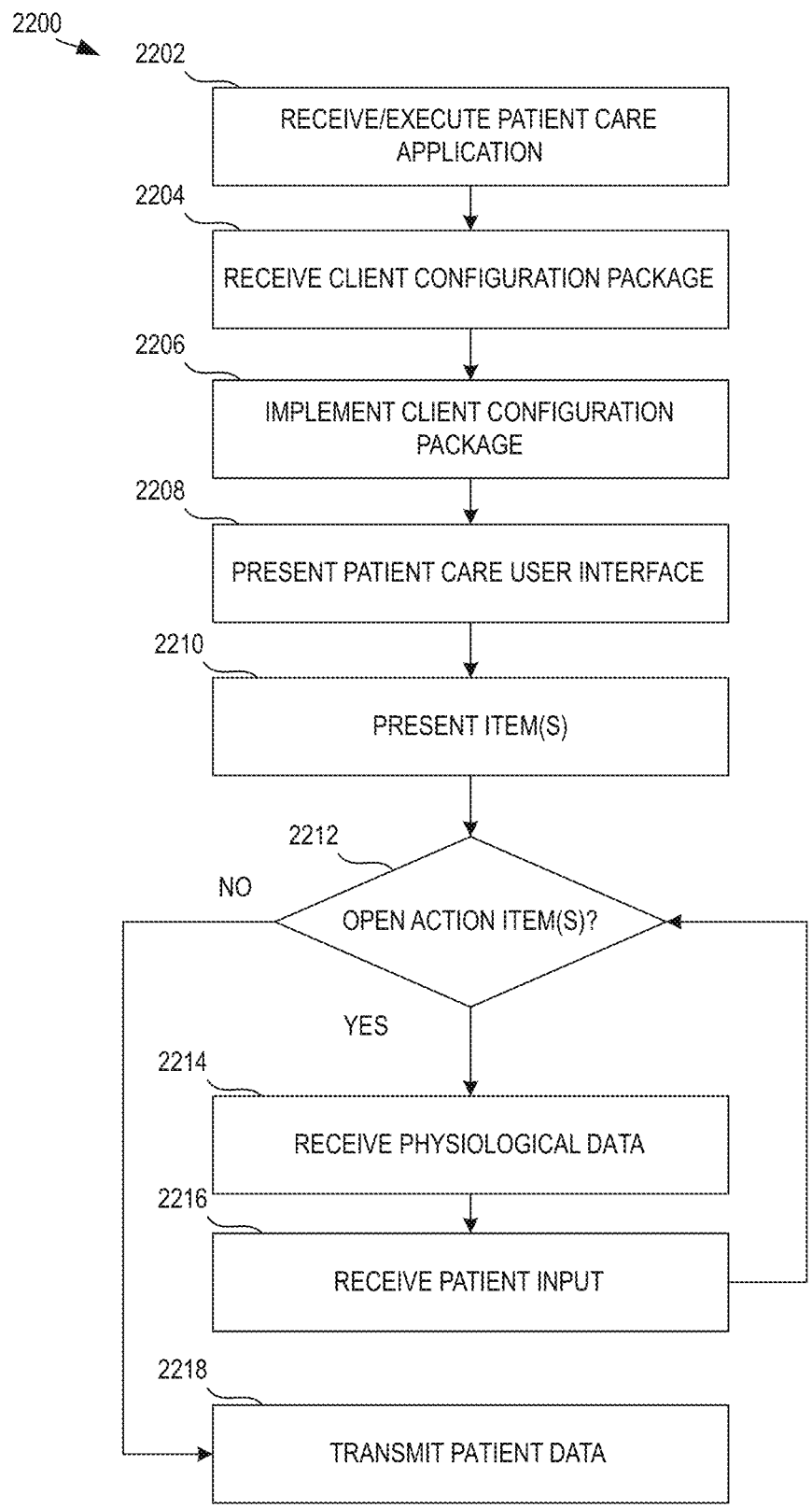
FIG. 22 is a flowchart of a method for implementing a patient care user interface and receiving patient data, according to some embodiments of the present disclosure.

FIG. 22 is a flowchart of a method 2200 for implementing a patient care user interface and receiving patient data, according to some embodiments of the present disclosure. The method 2200 provides example approaches regarding implementing patient care user interfaces and receiving patient data. As described herein, the patient user computing device 102 and/or the connectivity hub device 106 may implement aspects of the method 2200 as described herein. Depending on the embodiment, the method 2200 may include fewer or additional blocks and/or the blocks may be performed in order different than is illustrated.

Beginning at block 2202, a patient care application 120 can be received. In particular, the patient user computing device 102 can receive a file that can be executed as the patient care application 120. In some embodiments, a user can download and install an executable file for the patient care application 120. The patient user computing device 102 can execute the patient care application 120, which can cause the presentation of one or more user interfaces. In particular, the patient user computing device 102 can execute the patient care application 120 to cause presentation of any of the user interfaces 1300, 1400, 1500, 1520, 1540 described above in further detail with respect to FIGS. 13, 14, and 15A-15C.

At block 2204, a client configuration package can be received. In particular, the patient user computing device 102 and/or the patient care application 120 can receive the client configuration package. For example, while the patient care application 120 is executing on the patient user computing device 102, the patient care application 120 can receive a client configuration package from the patient management and monitoring system 110 over the network 108. As described herein, in some embodiments, an administrator can specify which client configuration packages can be made available to end users.

At block 2206, the client configuration package can be implemented. In particular, the patient care application 120, executing on the patient user computing device 102, can implement the received client configuration package. The patient care application 120 can be configured to receive the client configuration package as input. The patient care application 120 can be configured to use the configurations in the client configuration package and output a patient care user interface, as discussed in further detail herein with respect to the block 2208 for presenting a patient care user interface. In some embodiments, advantages of the patient care application 120 implementing client configuration packages can include that presentation of corresponding patient care user interfaces can occur without or before recompiling of the patient care application 120. For example, some patient care applications, executing on the patient user computing device 102, can be configured to receive new or updated client configuration packages that cause the patient care application 120 to execute program instructions without recompiling the patient care application. As described herein, such behavior can be achieved by using interpreted languages where the program instructions can be executed without or before recompiling respective applications 120.

In some embodiments, implementation of the client configuration package by the patient care application 120 can include interfacing with a patient sensor device 104. For example, the client configuration package implemented by the patient care application 120 can include a patient sensor item configuration. The patient care application 120 can interface, according to the patient sensor item configuration, with the patient sensor device 104. The patient care application 120 can use a sensor device type in the patient sensor item configuration to facilitate pairing the patient user computing device 102 with the patient sensor device 104. The patient care application 120 can be configured to receive physiological parameters from the patient sensor device 104 based on a physiological parameter type specified in the patient sensor item configuration.

At block 2208, a patient care user interface can be presented. In particular, the patient care application 120, executing on the patient user computing device 102, can present a patient care user interface. In some embodiments, a user (such as a patient) can select a user interface option to initiate a patient care user interface (such as the option 1308 and the "COPD Maintenance with MightySat" patient care user interface). As described herein, the patient care user interface can be defined by the client configuration package. The patient care application 120 can arrange a graphical layout of the patient care user interface according to the graphical layout configuration in the client configuration package. Additional details regarding example patient care user interfaces are described in further detail above with respect to FIGS. 16A-16C and 17.

At block 2210, one or more items can be presented. In particular, the patient care application 120 can present one or more items. For example, the patient care application 120 can present one or more patient care action items according to respective patient care action item configurations in the client configuration package. The patient care application 120 can present one or more patient sensor items according to respective patient sensor item configurations in the client configuration package. The patient care application 120 can present a patient care user interface that includes items such as a patient sensor item for oxygen saturation and patient care action items for the patient's breathing, their temperature, and/or respiration, which can be relevant to monitoring of patients under a COVID-19 program. Additional details regarding example items in patient care user interfaces are described in further detail above with respect to FIGS. 16A-16C and 17.

At block 2212, it can be determined whether there are any open action item(s). In particular, the patient care application 120 can determine whether any action item(s) are incomplete. For example, the patient care application 120 can determine that a physiological parameter value for a patient sensor item has not been received or that user input in response to a prompt has not been received. If there are open action item(s), the method 2200 can proceed to the blocks 2214, 2216 for receiving physiological data/patient input and the patient care application 120 can receive input for the open action item(s). However, if there are no open action item(s), the method 2200 can proceed to the block 2218 and the patient care application 120 can transmit patient data.

At block 2214, physiological data can be received. In particular, the patient care application 120 can receive physiological parameter values generated from one or more patient sensor devices 104. The patient care application 120 can receive physiological parameter values, such as, but not limited to, blood oxygen saturation ($SpO_2$), pulse rate, perfusion index, pleth variability index, and/or respiration rate. For example, as reflected in FIG. 16C described above, the patient care application 120 can receive an oxygen saturation value of 91% that was generated by the patient sensor device 104.

At block 2216, patient input can be received. In particular, the patient care application 120 can receive patient input. For example, the patient care application 120 can receive user input such as, but not limited to, a value for the patient's temperature, a value for the patient's age, a value for the patient's respiration rate, a value for the patient's weight, and/or a yes or no answer in response to a prompt (such as, "Are you having trouble breathing?"). Additional details regarding receiving patient input are described in further detail above with respect to FIGS. 16A-16C. The method 2200 can return to block 2212 to cause the patient care application 120 to check for additional open action item(s) until there are no open action item(s) left.

At block 2218, patient data can be transmitted. In particular, the patient care application 120, executing on the patient user computing device 102, can cause the patient user computing device 102 to transmit patient data. As described herein, example patient data can include, but is not limited to, physiological parameter values generated by the patient sensor device 104 and patient user input. The patient user computing device 102 can be configured to transmit patient data over the network 104 using one or more security protocols, such as various encryption methods, to the patient management and monitoring system 110.

In some embodiments, the method 2200 for implementing user interfaces and receiving health data can also be applied to a health monitoring system that can assist organizations to manage infectious diseases. As described herein, additional health monitoring systems and use cases are described in the health monitoring application. For example, the user interfaces that are implemented by and/or health data that is received by the method 2200 can be described in paragraphs [0103], [0150]-[0151], [0205]-[0219], and [0228], among others, of the '794 Application.

Patient Monitoring Methods

Figure 23:
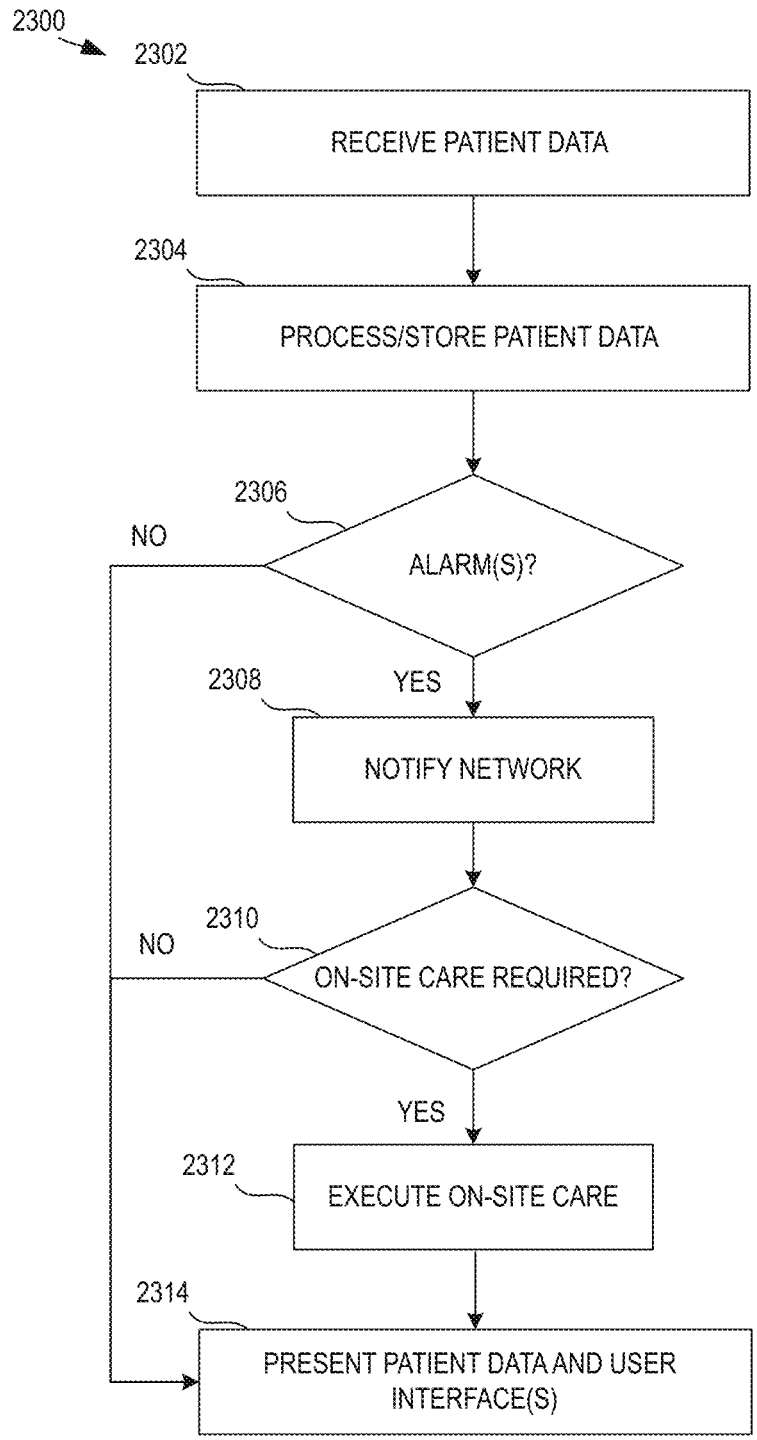
FIG. 23 is a flowchart of a method for patient monitoring, according to some embodiments of the present disclosure.

FIG. 23 is a flowchart of a method 2300 for patient monitoring, according to some embodiments of the present disclosure. The method 2300 provides example approaches regarding patient monitoring. As described herein, the patient management and monitoring system 110 of FIG. 1B may include various devices, services, and/or applications, some of which may implement aspects of the method 2300 as described herein. Depending on the embodiment, the method 2300 may include fewer or additional blocks and/or the blocks may be performed in order different than is illustrated.

At block 2302, patient data can be received. In particular, the patient data service 132 can receive patient data from the patient user computing device 102, the connectivity hub device 106, and/or the patient monitoring device 206. As described herein, example patient data can include, but is not limited to, temperature, blood pressure, respiratory rate (RRa), total hemoglobin (SpHb), carboxyhemoglobin (SpCO), methemoglobin (SpMet), oxygen content (SpOC), oxygen saturation (SpO2), pulse rate (PR), perfusion index (Pi), pleth variability index (PVi), and/or electroencephalogram (EEG) data. The patient data service 132 can receive the patient data in an encrypted format. The patient data service 132 can receive patient data, such as physiological parameter values, in a continuous stream, which can allow continuous monitoring, as described herein.

At block 2304, the patient data can be processed. In particular, the patient data service 132 can process the received patient data. The patient data service 132 can group the patient data by patient and/or by category. For example, the patient data service 132 can identify the type of physiological parameter (such as oxygen saturation (SpO2), pulse rate (PR), perfusion index (Pi), pleth variability index (PVi), etc.) for the patient data that includes physiological parameter values. The patient data service 132 can identify patient response data in the patient data, such as yes/no responses to prompts from the patient care user interface. The patient data service 132 can store the patient data in the patient database(s) 142, which can be encrypted.

At block 2306, it can be determined whether any applicable alarm(s) are triggered. In particular, the patient monitoring service 136 can determine whether any applicable alarm(s) are triggered. As described herein, a patient care user interface and/or a patient can be associated with one or more alarms. For example, the patient monitoring service 136 can identify a set of physiological parameter values for a patient. From the set, the patient monitoring service 136 can identify a subset of physiological parameter values for a period of time for the patient. For example, the patient monitoring service 136 can identify oxygen saturation values over one minute for the patient. The patient monitoring service 136 can determine that the subset of physiological parameter values for the period of time violates a threshold. For example, the patient monitoring service 136 can trigger an alarm if the oxygen saturation values go below 90% for one minute, such as by having an average oxygen saturation value under 90%. If an alarm is triggered, the method 2300 can proceed to the block 2308 for transmitting notifications. Otherwise, if an alarm is not triggered, the method 2300 can proceed to the block 2314 for presenting patient data and user interface(s).

In some embodiments, the patient monitoring service 136 can apply conditional alarms. A patient care user interface can be associated with a conditional alarm, such as the conditional alarm described in further detail above with respect to FIG. 12A. As described herein, the conditionality of an alarm can be based on response data received through the patient care user interface (for example, a patient can respond "Yes" to a prompt asking if the patient has a chronic obstructive pulmonary disease (COPD) condition). In the case of a conditional alarm, the patient monitoring service 136 can select, from a first threshold and a second threshold, the first threshold for alarm purposes. In particular, the patient monitoring service 136 can apply the response data as input to conditional threshold logic and output from the conditional threshold logic can identify the first threshold. For example, as described in further detail above with respect to FIG. 12A, conditional threshold logic can be based on the presence of a COPD condition; if the patient has response data indicating COPD "yes," then a first threshold (such as 90% oxygen saturation) can be used; however, if the patient has response data indicating COPD "no," then a second, default threshold can be used (such as 93% oxygen saturation). As described herein, an administrator can configure the conditional threshold logic and/or conditional alarm(s) with a patient care configuration user interface. After identifying the conditional threshold, the patient monitoring service 136 can determine that the alarm should be triggered based at least in part on the physiological parameter value and the first threshold (for example, if one or more physiological parameter values exceeds or is below the first threshold).

In some embodiments, the patient monitoring service 136 can compare each of the monitored physiological parameters with a threshold that indicates a minimum or maximum acceptable level for the respective physiological parameter. For example, the patient monitoring service 136 can compare the patient's heart rate in beats per minute with the acceptable range of approximately 50 beats per minute to approximately 195 beats per minute. The patient monitoring service 136 can compare the patient's respiration rate in breaths per minute with the acceptable range of approximately 6 breaths per minute to approximately 30 breaths per minute. The patient monitoring service 136 can compare the patient's pleth with the acceptable range of approximately 5 to approximately 40 and the patient's perfusion index to a minimum acceptable perfusion index of approximately 0.3.

The one or more physiological parameters can be weighted and when the combination of weighted parameters falls below a threshold, the patient monitoring service 136 can trigger an alarm. The one or more physiological parameters can be weighted based on trends in the patient's physiological parameters (such as the patient's parameters during opioid use) and when the combination of weighted parameters falls below a threshold, the patient monitoring service 136 can trigger an alarm.

At block 2308, a network can be notified. In particular, the patient monitoring service 136 can notify the patient's network, which can include the patient user computing device 102. An example patient network can include one or more person(s), emergency personnel, friends, family, caregivers, doctors, hospitals selected to be notified. The notification can inform the network of an alarm being triggered. For example, the selected person(s) can receive a notification on their user computing device(s). In some embodiments, the patient monitoring service 136 can alert emergency services. Accordingly, in response to the patient monitoring service 136 determining that an alarm has been triggered, the patient monitoring service 136 can transmit an alert.

At block 2310, it can be determined whether on-site care is required. In particular, the patient monitoring service 136 can determine whether on-site care is required. For example, in the case of patient care user interfaces directed towards opioid-related health conditions, the patient monitoring service 136 can monitor the physiological parameters for indications of an opioid overdose. The patient physiological parameters can include the physiological parameters that are most likely affected by an overdose condition, such as one or more of the oxygen saturation, heart rate, respiration rate, pleth variability, perfusion index, etc. The patient monitoring service 136 can determine whether the physiological parameters indicate that the patient needs on-site care. A blood oxygen saturation level below a threshold can indicate a heath condition, such as an opioid overdose condition. For example, the patient monitoring service 136 can monitor the oxygen saturation of the user and trigger an alarm when the oxygen saturation falls below a threshold. The patient monitoring service 136 can compare the user's current oxygen saturation level with a threshold that can indicate a minimum acceptable blood oxygen saturation level. An oxygen saturation level below the minimum acceptable blood oxygen saturation level can be an indication of a health condition, such as an overdose event. For example, an oxygen saturation level below approximately 88 can indicate respiratory distress. If on-site care is required, the method 2300 can proceed to the block 2312 for executing on-site care. Otherwise, if on-site care is not required, the method 2300 can proceed to the block 2314 for presenting patient data and user interface(s).

At block 2312, on-site care can be executed. In particular, emergency personnel and/or care providers can provide on-site care. In some embodiments, some additional devices 114A, 114B can administer medication on-site. In some embodiments, the additional device(s) 114A, 114B can include a delivery device to deliver medication in response to the indication of health event, such as an opioid overdose event. In some embodiments, the delivery device can administer an opioid receptor antagonist in response to the indication of an opioid overdose event. The delivery device can include a patch that includes a reservoir with the medication, a needle, and a battery. Additional details regarding patient monitoring and on-site care for opioid overdoses can be found in U.S. Provisional Application No. 62/992,779, filed Mar. 20, 2020, titled "OPIOID OVERDOSE MONITORING USER INTERFACE."

At block 2314, patient data and/or user interface(s) can be presented. In particular, the frontend server 130 can present patient data and/or user interface(s) to clinician user computing device(s) 124. The frontend server 130 can present a patient monitoring user interface comprising. The patient monitoring user interface can include (i) information associated with the patient and (ii) a visual representation based at least in part on a physiological parameter value. Example patient monitoring user interfaces that the frontend server 130 can present are described in further detail above with respect to FIGS. 18, 19A-19B, and 20. Accordingly, a clinician can review data received via the patient care user interfaces in a patient monitoring user interface.

In some embodiments, the method 2300 for health monitoring can also be applied to a health monitoring system that can assist organizations to manage infectious diseases. As described herein, additional health monitoring systems and use cases are described in the health monitoring application. For example, the health monitoring user interfaces that are presented by the method 2300 can be described in paragraphs [0220]-[0227], and [0229]-[0230], among others, of the '794 Application.

Patient Monitoring Graphical User Interfaces

FIGS. 24A-24Y and 25A-25J illustrate example patient monitoring graphical user interfaces of a patient user computing device 102, according to some embodiments of the present disclosure. In various embodiments, aspects of the user interfaces may be rearranged from what is shown and described below, and/or particular aspects may or may not be included. In some embodiments, the patient care application 120 can execute on the patient user computing device 102 to present the graphical user interfaces of FIGS. 24A-24Y and 25A-25J. The graphical user interfaces of FIGS. 24A-24Y and 25A-25J may have similar user interface elements and/or capabilities.

Figure 24A:
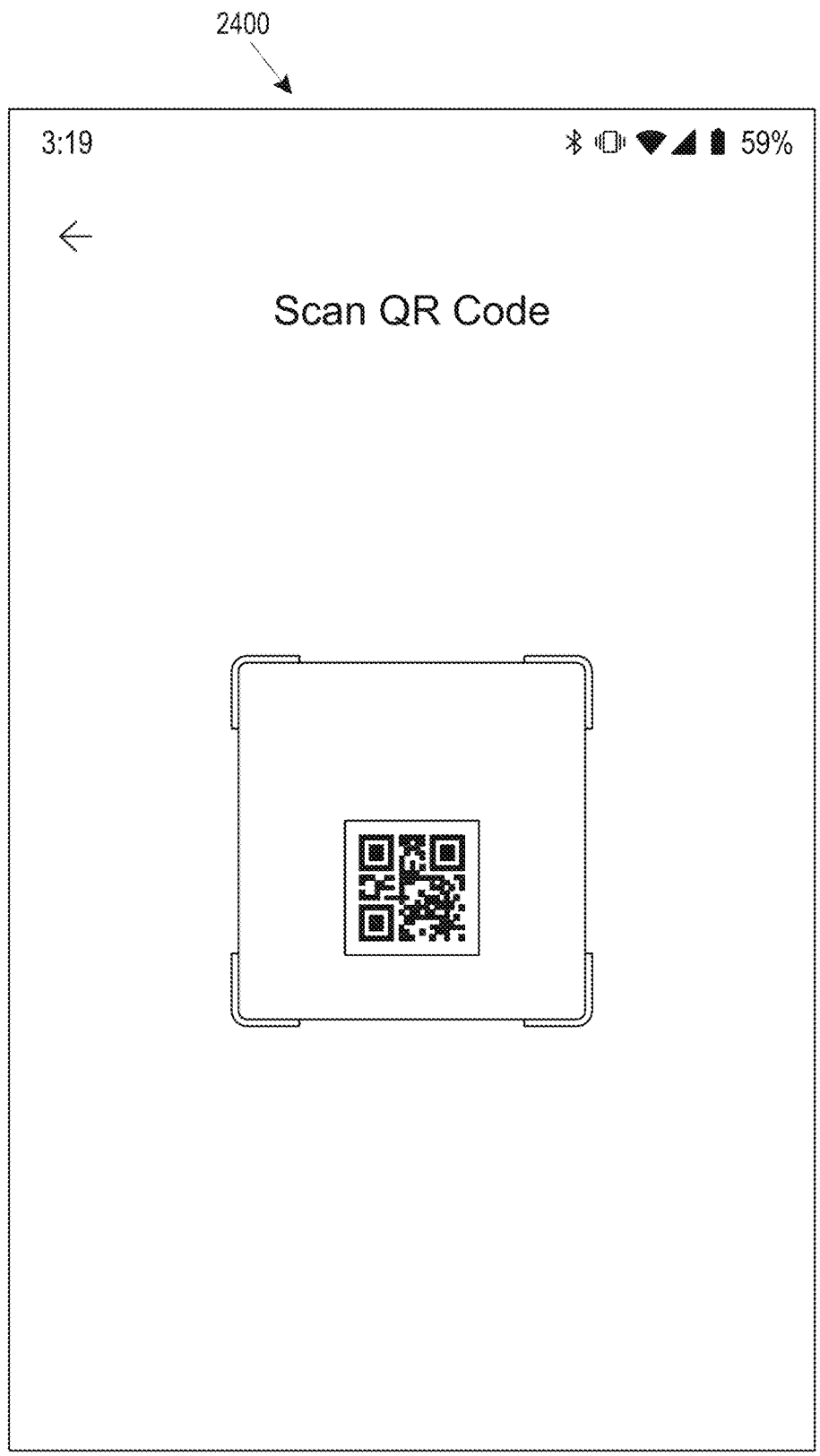
FIGS. 24A-24Y and 25A-25J illustrate additional patient monitoring graphical user interfaces for a patient user computing device, according to some embodiments of the present disclosure.

FIG. 24A illustrates a graphical user interface 2400 of the patient user computing device 102 for receiving an image of a scannable code. The graphical user interface 2400 can be configured to receive an image of a scannable code, such as the example QR code shown. Receipt of the image of the scannable code by the application of the graphical user interface 2400 can cause the application to initiate pairing with a patient sensor device 104. The example scannable code shown in FIG. 24A can be included in a remote monitoring kit.

Figure 24B:
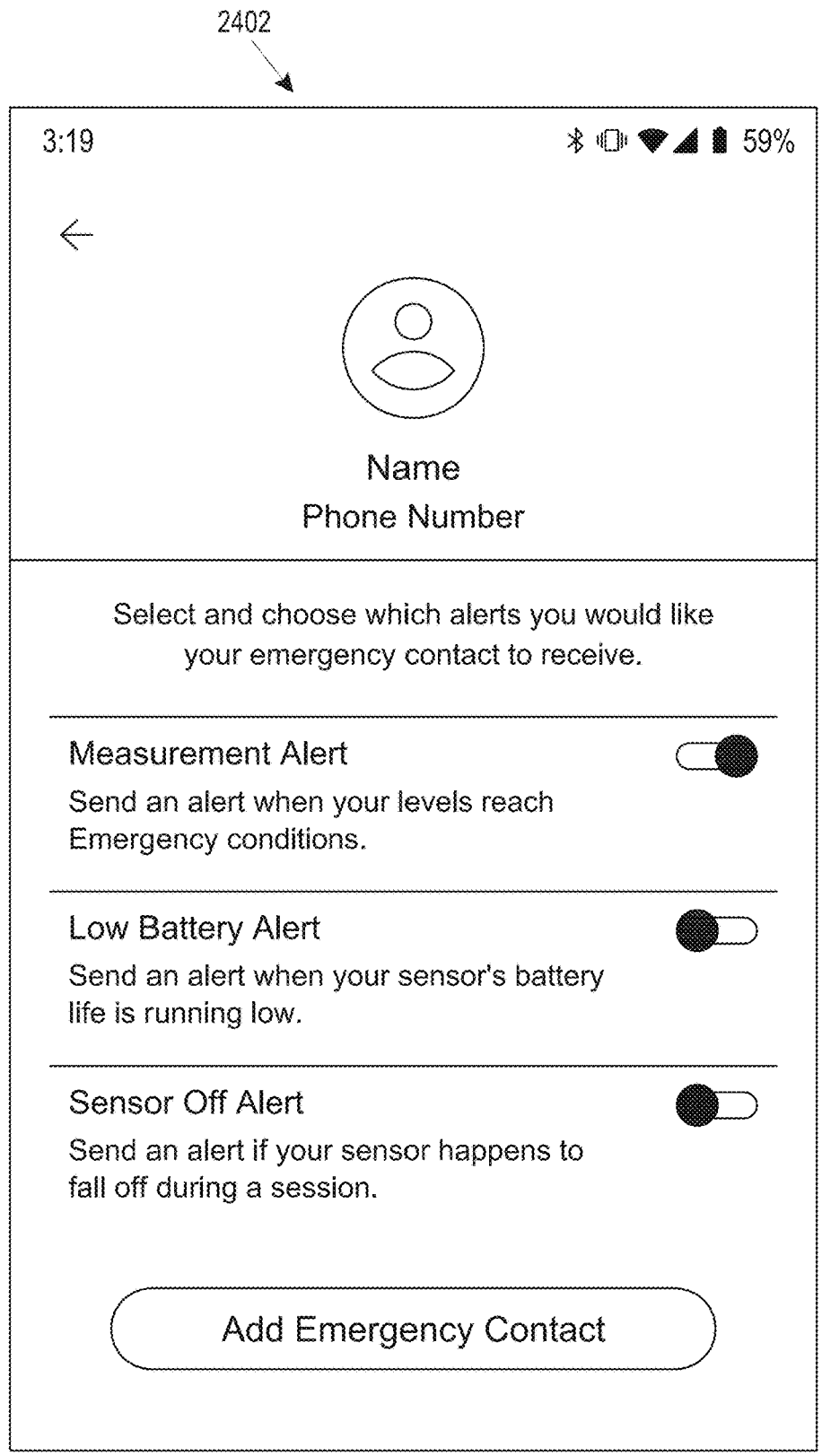

FIG. 24B illustrates a graphical user interface 2402 of the patient user computing device 102 for configuring alerts. The graphical user interface 2402 can allow a user to specify which alerts a recipient should receive. As shown, the recipient, "Brandon DeBord," can be an emergency contact for the user. Example alerts can include measurement alerts (such as alerts associated with physiological parameter values for a user), low battery alerts, and/or sensor off alerts.

Figure 24C:
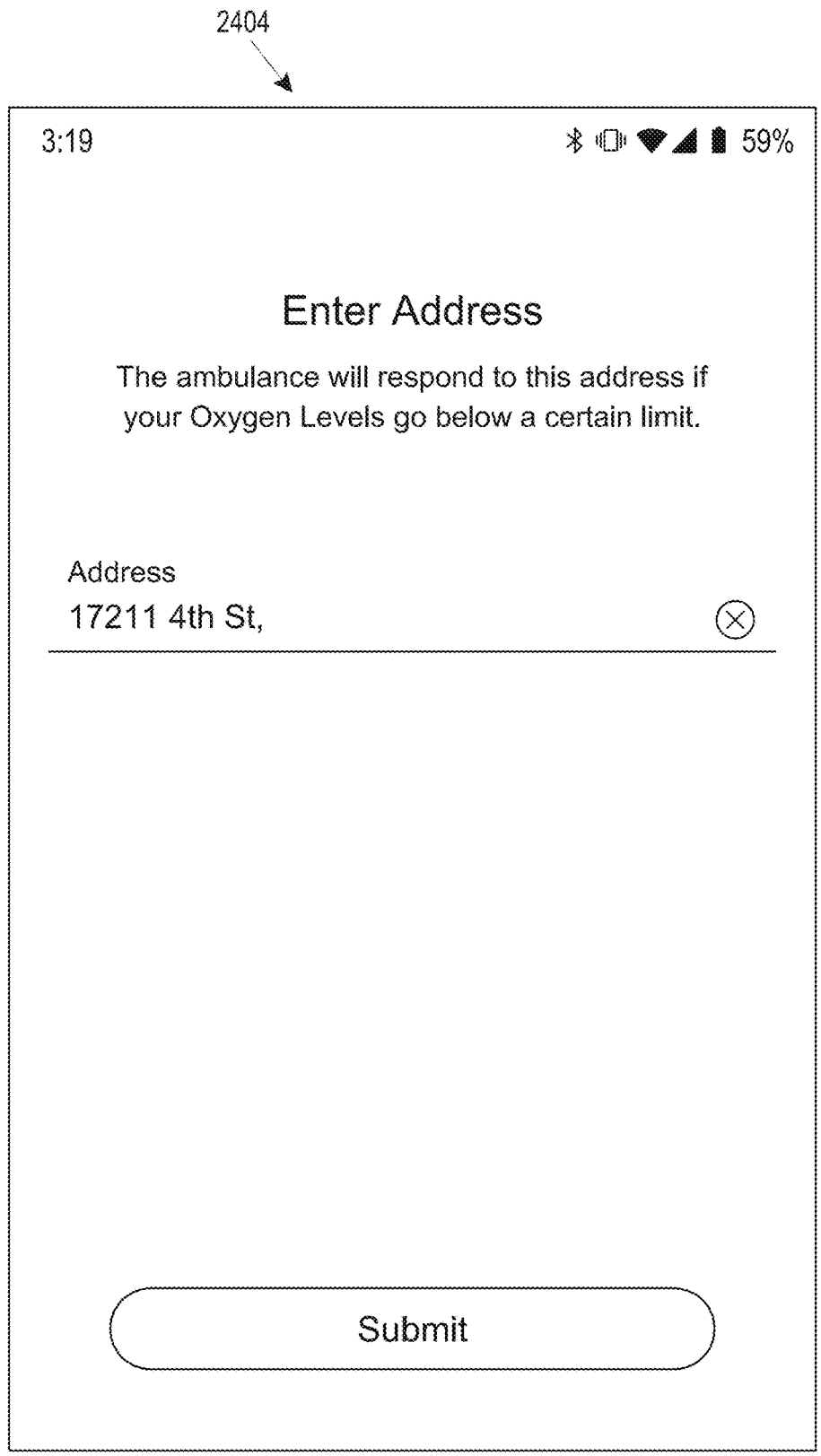

FIG. 24C illustrates a graphical user interface 2404 of the patient user computing device 102 for receiving geolocation-related input data. The graphical user interface 2404 can allow a user to provide an address as user input. Additionally or alternatively, the patient user computing device 102 can provide a current location using geolocation technique(s). For example, the graphical user interface 2404 can allow a user to authorize use of location services on the patient user computing device 102. In some embodiments, the patient user computing device 102 and/or the connectivity hub device 106 can provide a location to emergency services (e.g., emergency personnel, caregivers, police, or ambulance services) or to friends or family.

Figure 24D:
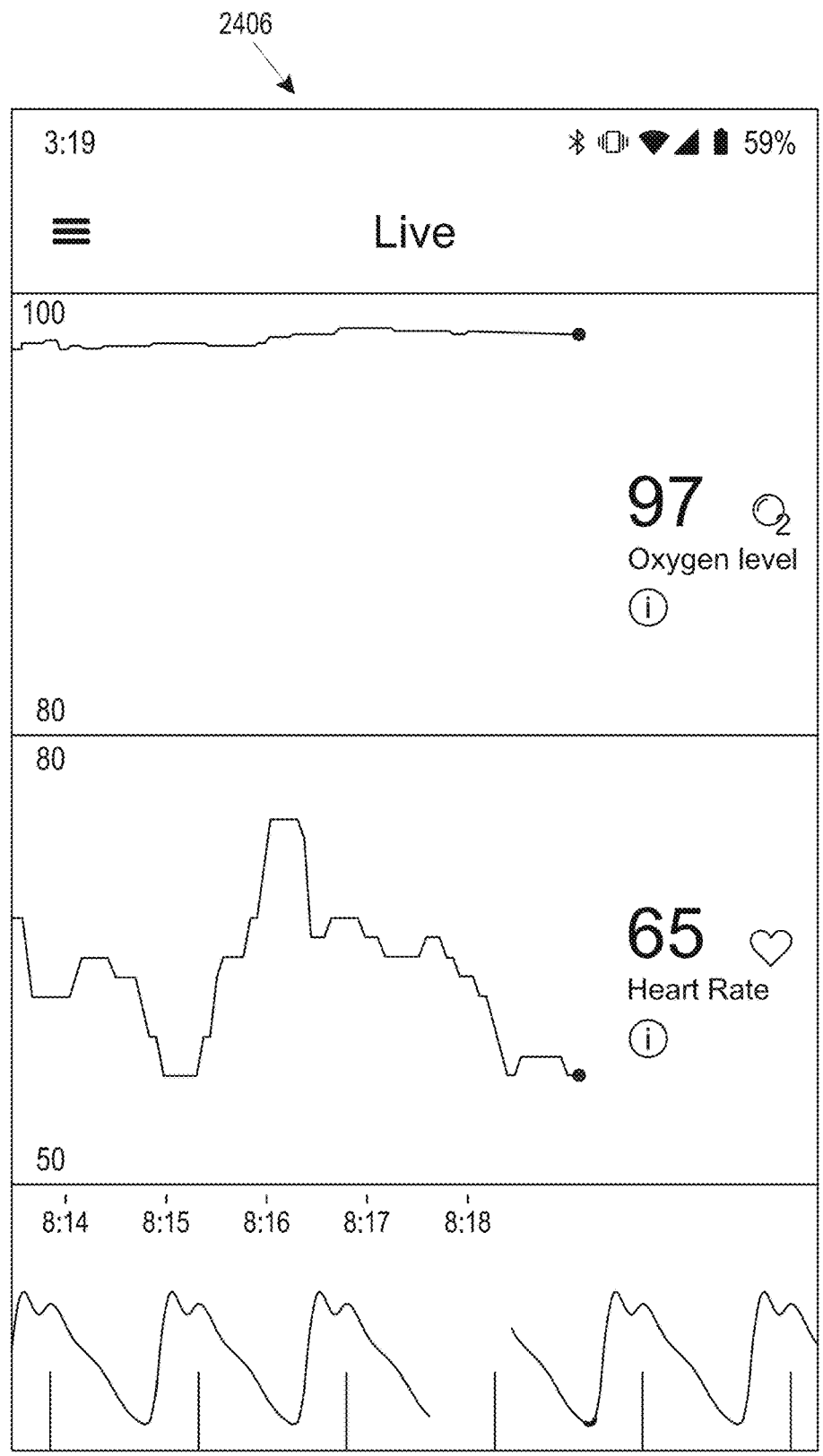

In FIG. 24D, another graphical user interface 2406 of the patient user computing device 102 is depicted that includes patient physiological parameters. The graphical user interface 2406 can further include historical data. In particular, the graphical user interface 2406 can include a visualization(s) that present historical trends of patient physiological parameters. As shown, the visualization(s) can include one or more graphs with an x-axis of time and a y-axis of parameter values. The underlying historical data can originally be generated, at least in part, by the one or more patient sensor devices 104.

Figure 24E:
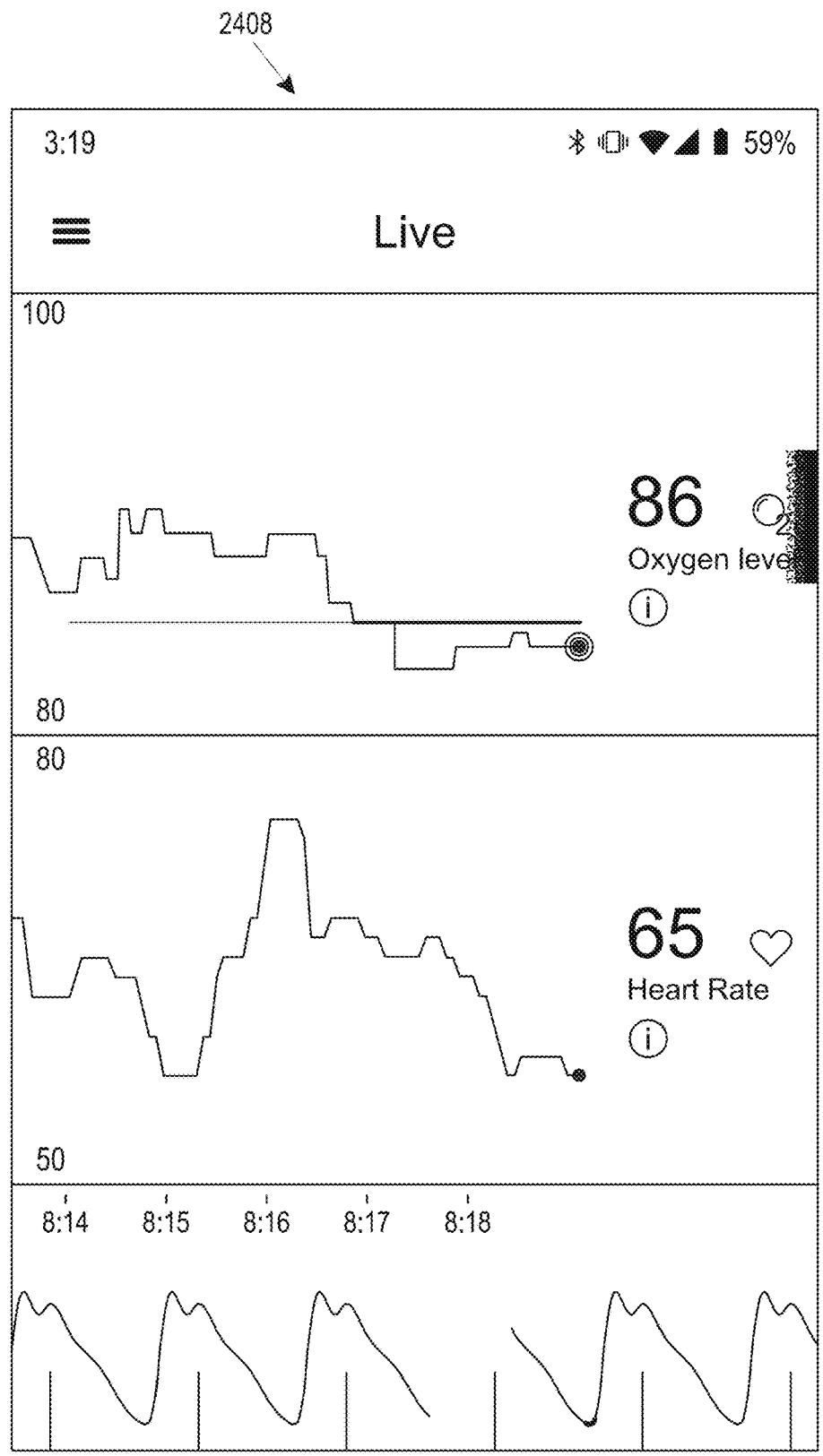

In FIG. 24E, yet another graphical user interface 2408 of the patient user computing device 102 is depicted that includes patient physiological parameters. The graphical user interface 2408 of FIG. 24E can be similar to the graphical user interface 2406 of FIG. 24D. However, in addition to the presentation of the patient physiological parameters shown in the graphical user interface 2406 of FIG. 24D, the graphical user interface 2408 of FIG. 24E can include alert indicator(s). For example, in the graphical user interface 2408 of FIG. 24E, the oxygen saturation level can be below a threshold, which can cause the presentation of visual alert indicator(s) in the graphical user interface 2408.

Figure 24F:
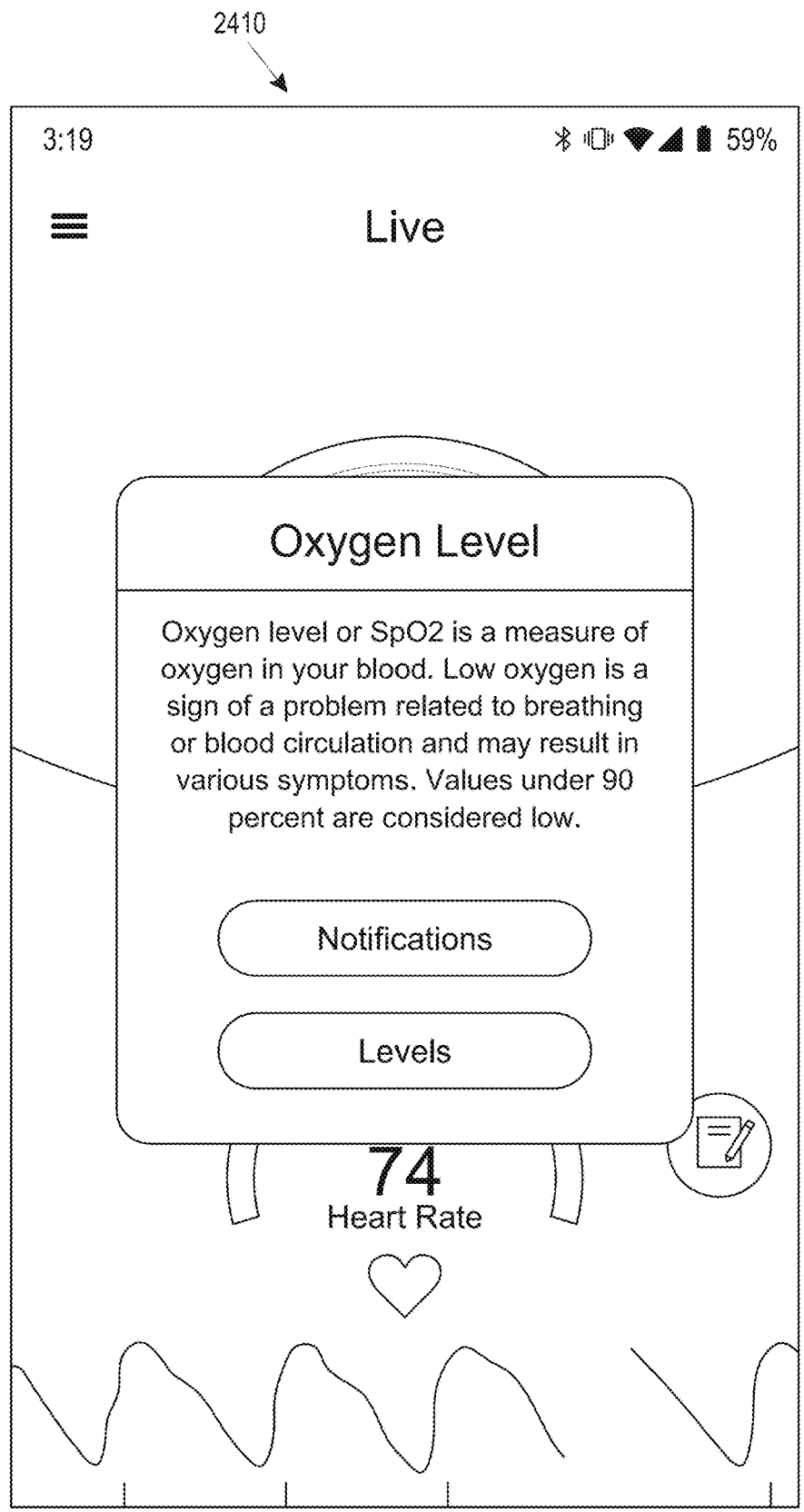

FIG. 24F illustrates a graphical user interface 2410 of the patient user computing device 102 for configuring notifications and/or threshold levels for a physiological parameter. For example, a user can configure the type of notifications, the frequency of notifications, and/or recipients of the notifications for a particular physiological parameter. As used herein, the terms "alerts," "alarms" and "events" can be used interchangeably. In some embodiments, a user can manually adjust the threshold levels for a physiological parameter for a notification to be sent.

Figure 24G:
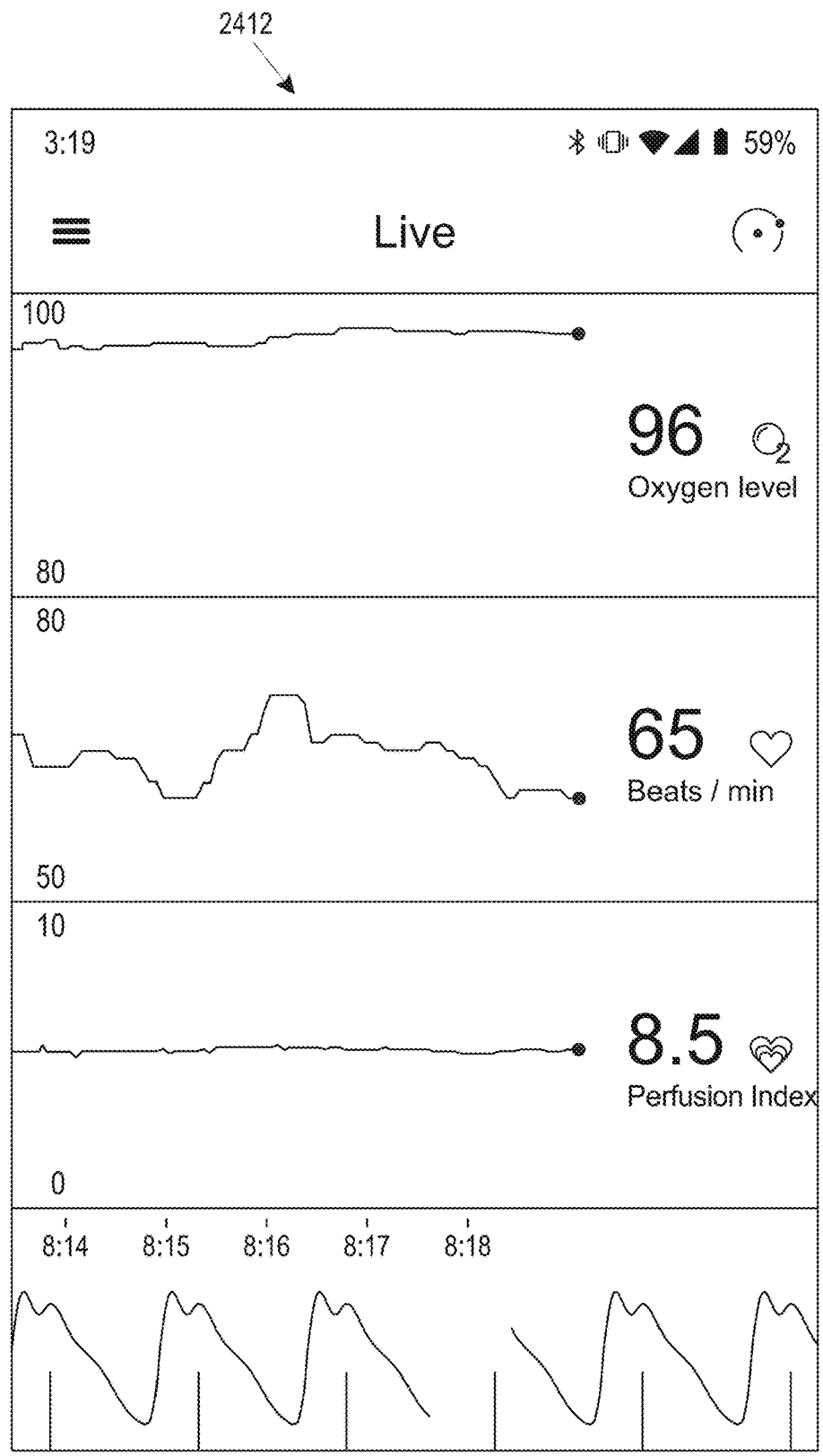

In FIG. 24G, yet another graphical user interface 2412 of the patient user computing device 102 is depicted that includes patient physiological parameters. The graphical user interface 2412 of FIG. 24G can be similar to the graphical user interface 2406 of FIG. 24D. However, in addition to the presentation of the patient physiological parameters shown in the graphical user interface 2406 of FIG. 24D, the graphical user interface 2412 of FIG. 24G can present an additional physiological parameter.

Figure 24H:
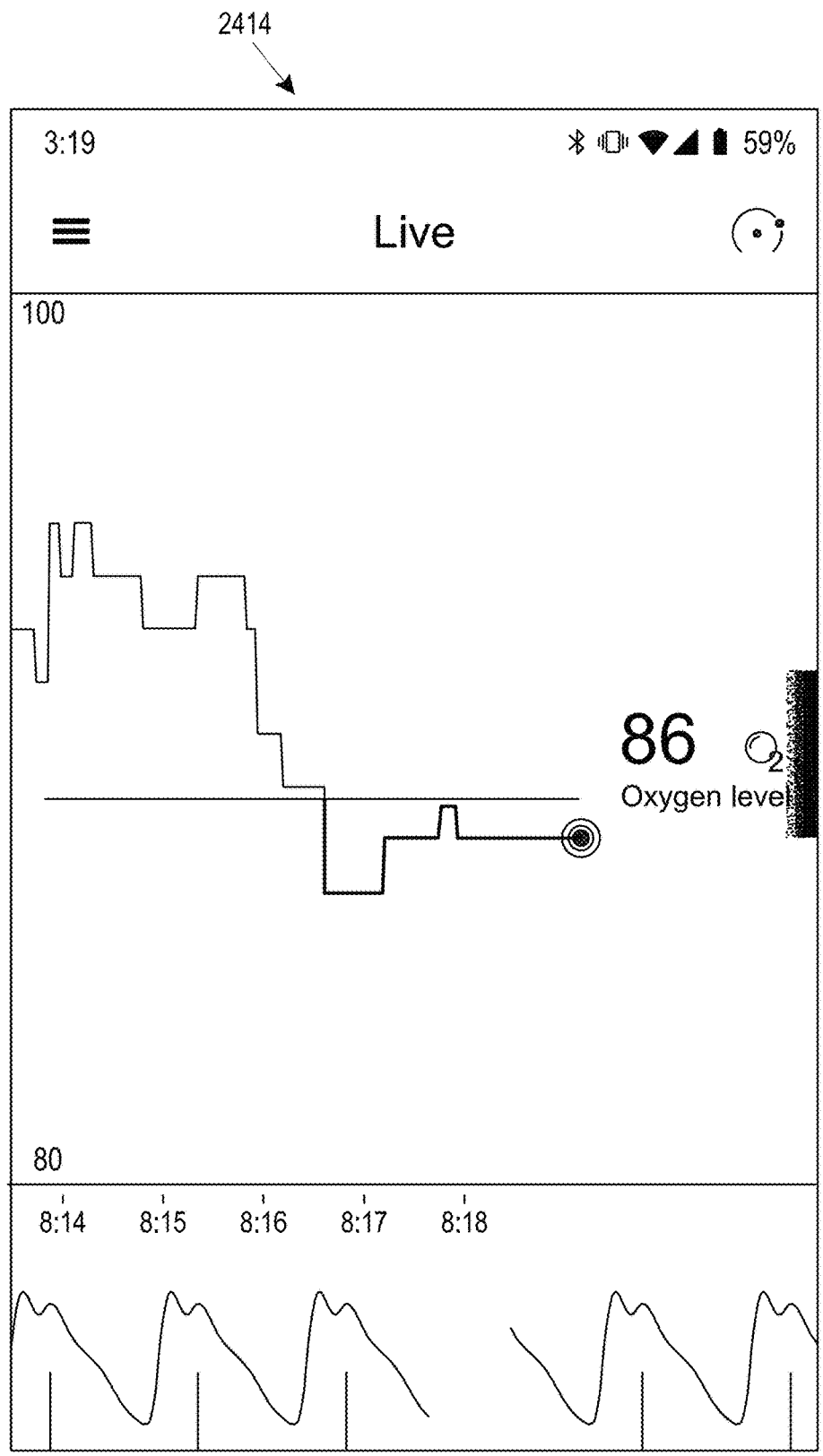

In FIG. 24H, yet another graphical user interface 2414 of the patient user computing device 102 is depicted that includes patient physiological parameters. The graphical user interface 2414 of FIG. 24G can be similar to the graphical user interface 2408 of FIG. 24E. However, unlike the presentation of the patient physiological parameters shown in the graphical user interface 2408 of FIG. 24E, the graphical user interface 2414 of FIG. 24H can present less patient physiological parameters.

Figure 24I:
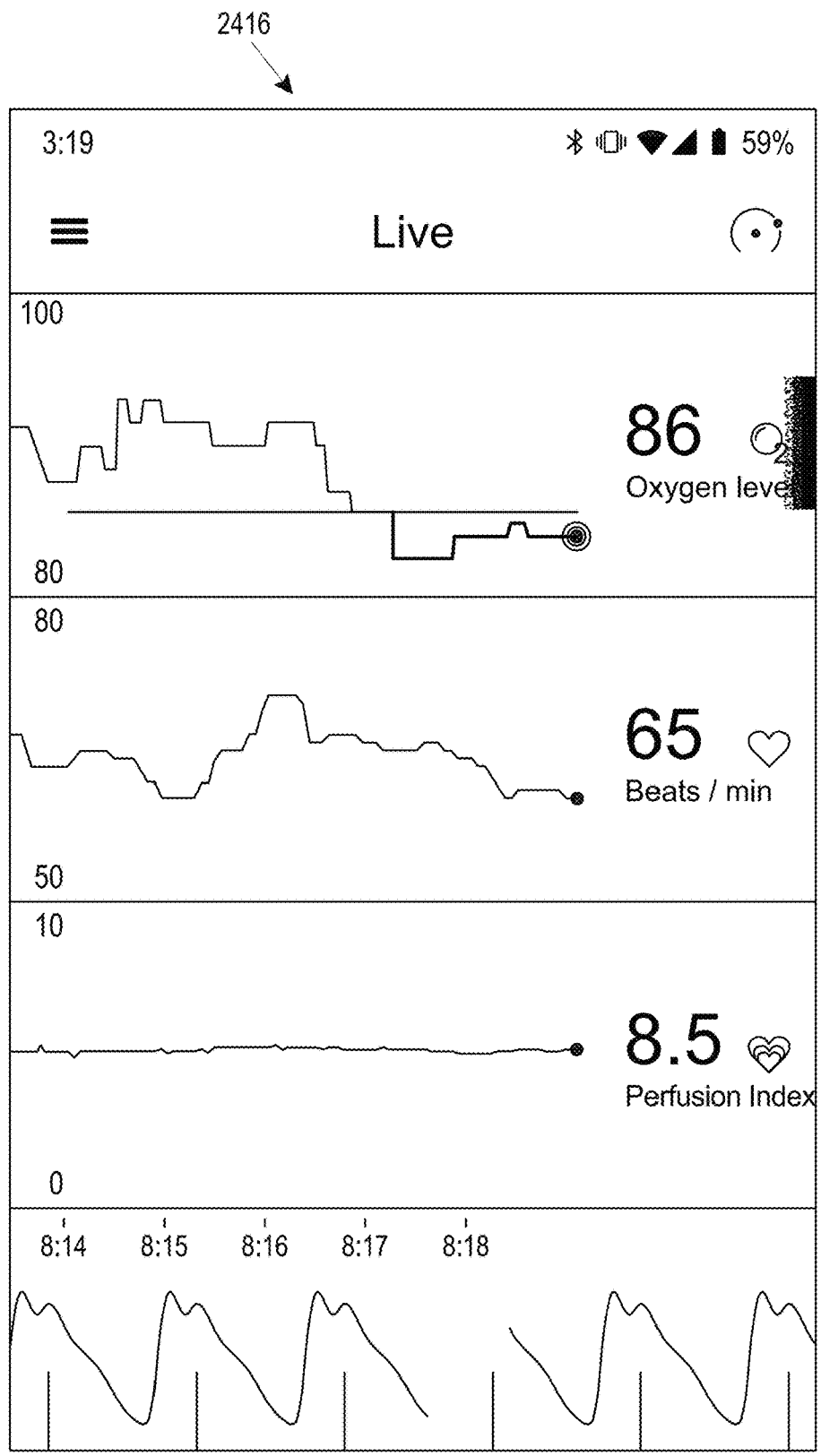

In FIG. 24I, yet another graphical user interface 2416 of the patient user computing device 102 is depicted that includes patient physiological parameters. The graphical user interface 2416 of FIG. 24I can be similar to the graphical user interface 2408 of FIG. 24E. However, in addition to the presentation of the patient physiological parameters shown in the graphical user interface 2408 of FIG. 24E, the graphical user interface 2416 of FIG. 24I can present an additional physiological parameter(s).

Figure 24J:
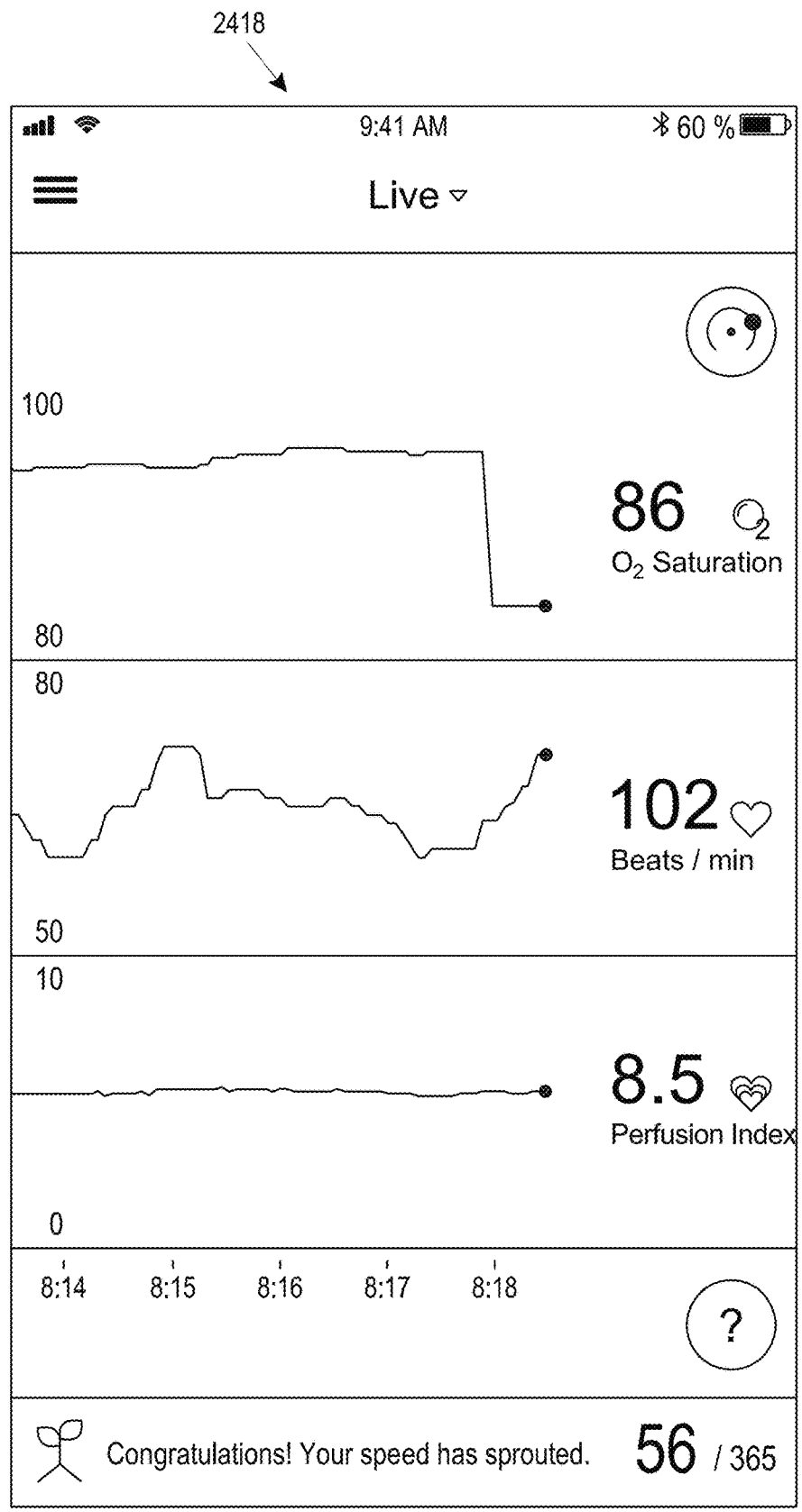

In FIG. 24J, yet another graphical user interface 2418 of the patient user computing device 102 is depicted that includes patient physiological parameters. The graphical user interface 2418 of FIG. 24J can be similar to the graphical user interface 2412 of FIG. 24G. However, in addition to the presentation of the patient physiological parameters, the graphical user interface 2418 of FIG. 24J can present a status indicator associated with patient action items, which is shown below the patient physiological parameters in this embodiment. The status indicator associated with patient action items can be used to facilitate patient engagement.

Figure 24K:
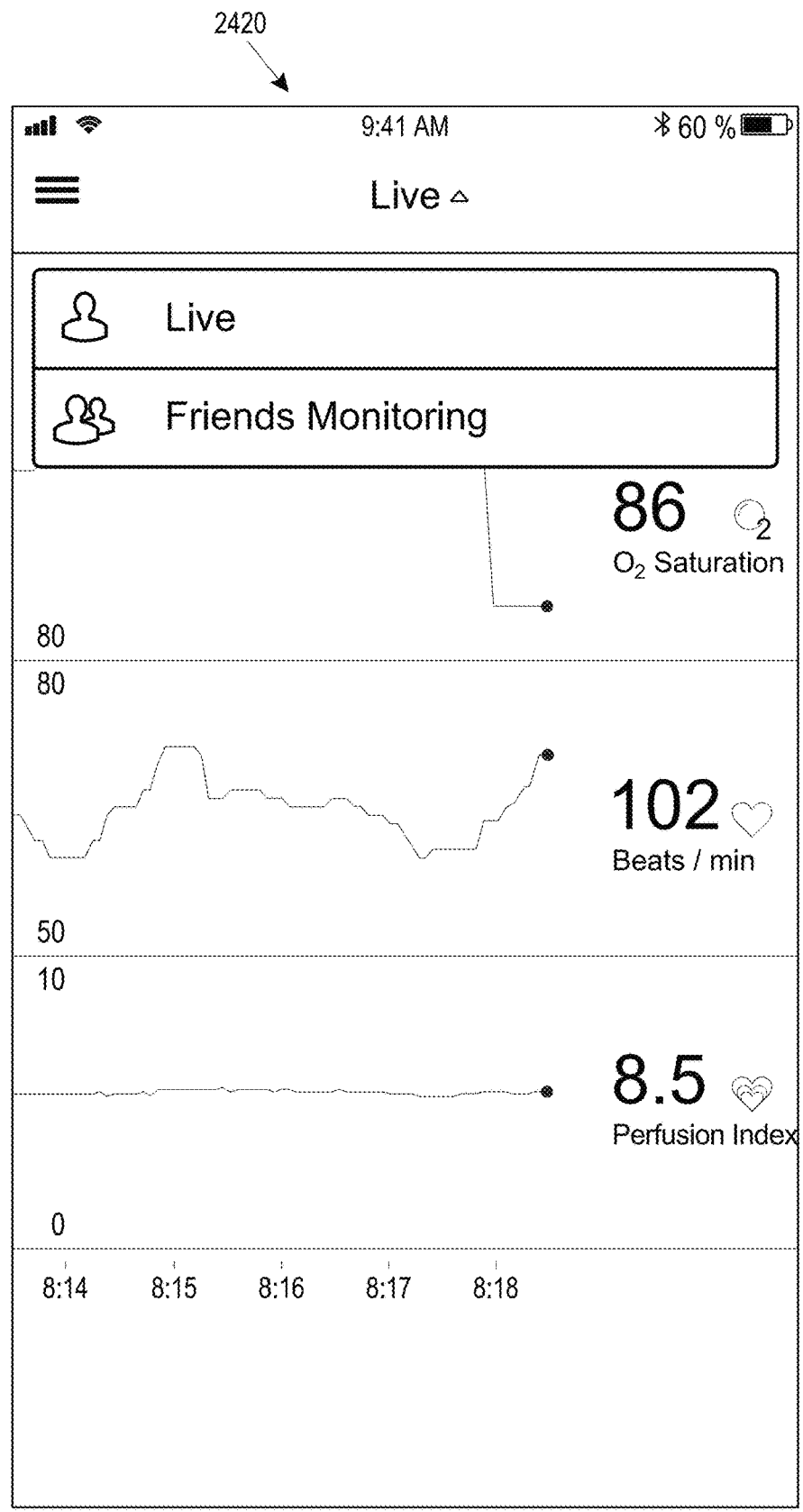

FIG. 24K illustrates a graphical user interface 2420 of the patient user computing device 102 for changing the source of patient physiological parameters. As shown, the graphical user interface 2420 can present source options, such as "Live" or "Friends Monitoring." For example, a first option can specify that the source of the physiological parameters is the patient of the patient user computing device 102. A second option can specify that the source of the physiological parameters is another patient that has shared their physiological data with the user.

Figure 24L:
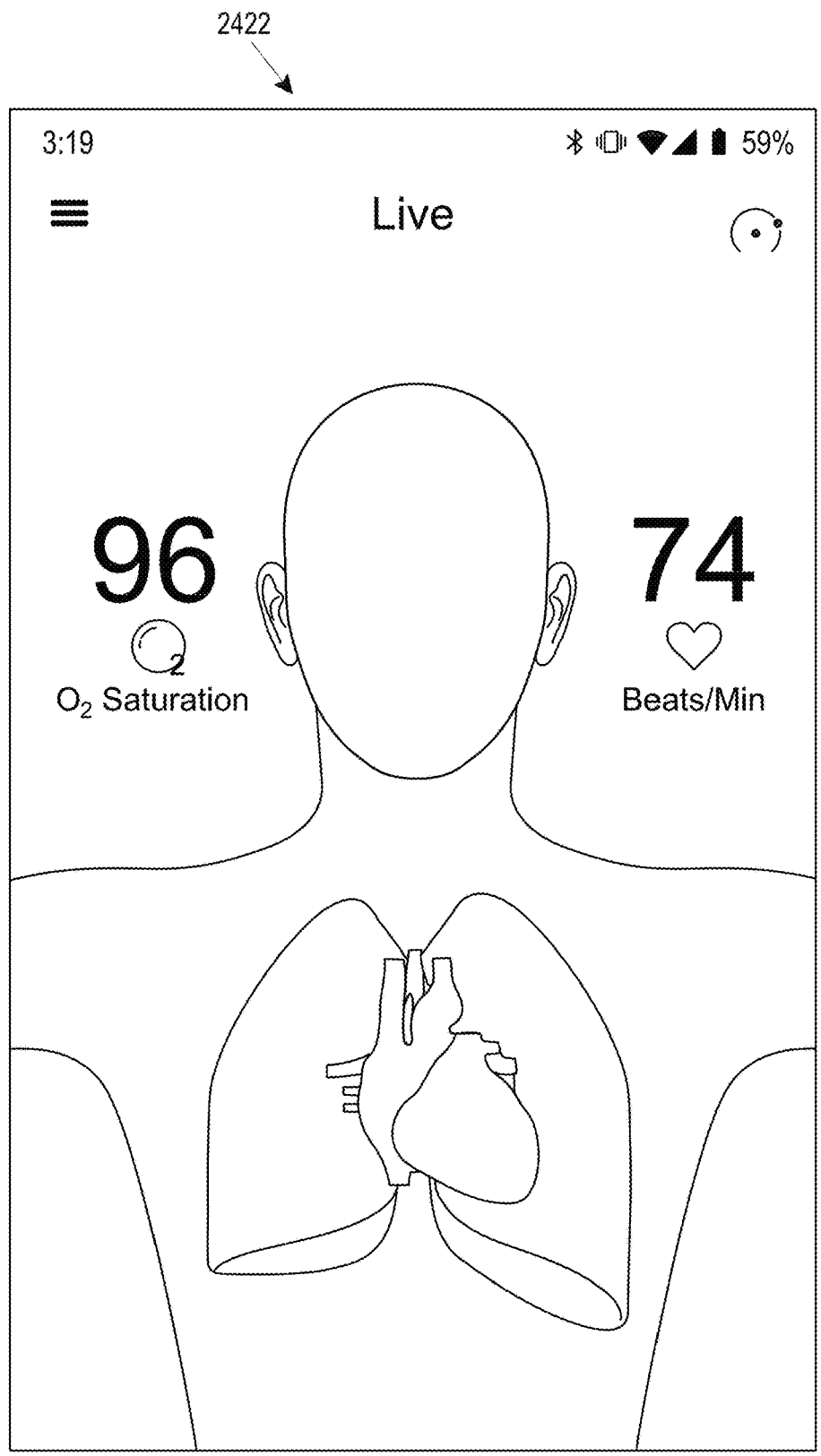
Figure 24M:
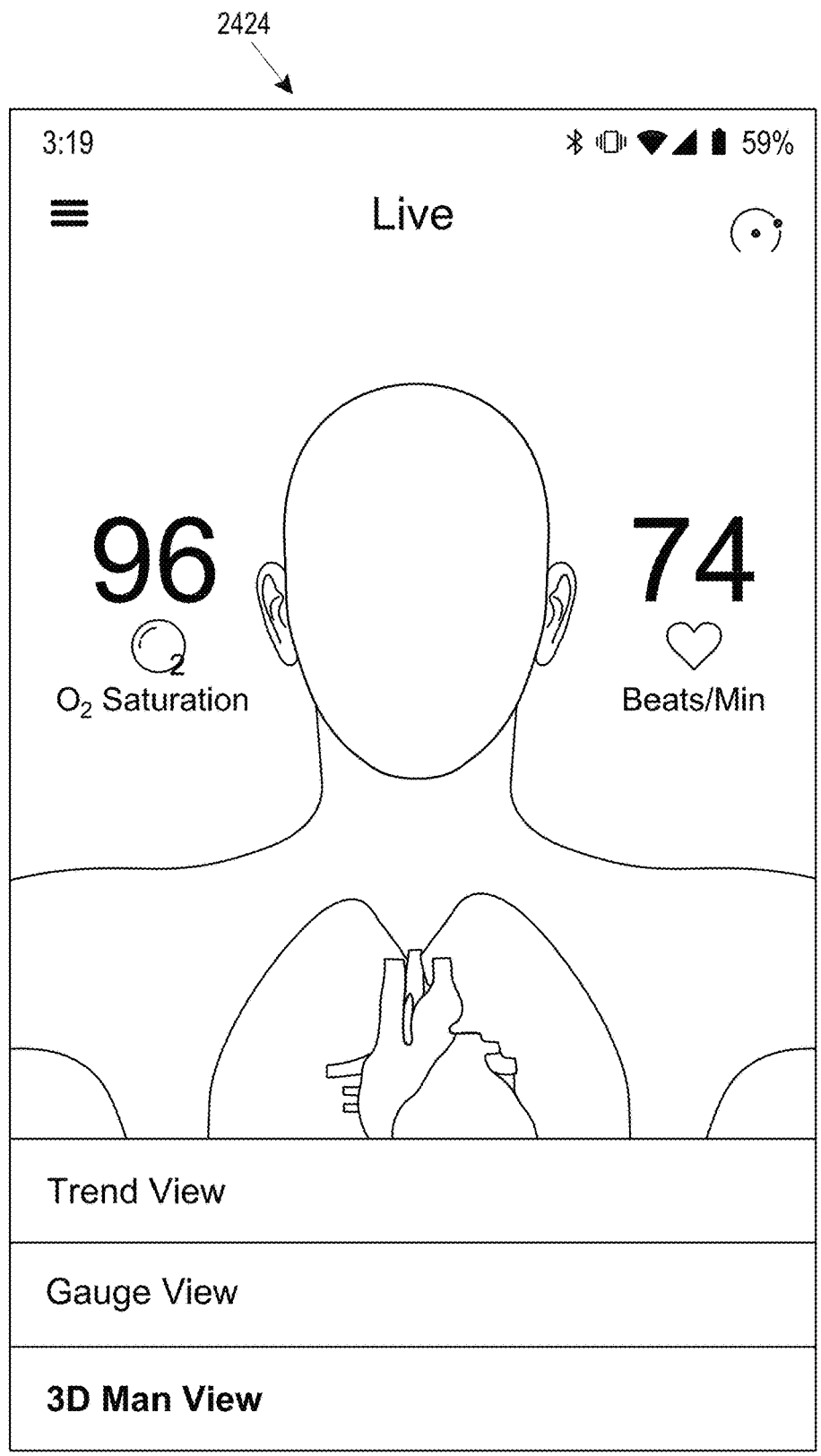

In FIG. 24L, yet another graphical user interface 2422 of the patient user computing device 102 is depicted that includes patient physiological parameters. The graphical user interface 2422 can present current values for patient physiological parameter(s). As shown, in addition to the current values for patient physiological parameter(s), the graphical user interface 2422 can present a visualization for a status of the patient. For example, the graphical user interface 2422 can present a visual representation of human organ(s) (e.g., heart and lungs) with visual indicators corresponding to the status of the patient. In the example, the visual representation of a human cardiovascular system can be color coded to match the status of the patient, such as green for nominal or red for an alert or alarm notification. In FIG. 24M, the graphical user interface 2424 of the patient user computing device 102 is depicted that allows a user to select an option to change the format of the user interface for presentation of patient physiological parameter(s).

Figure 24N:
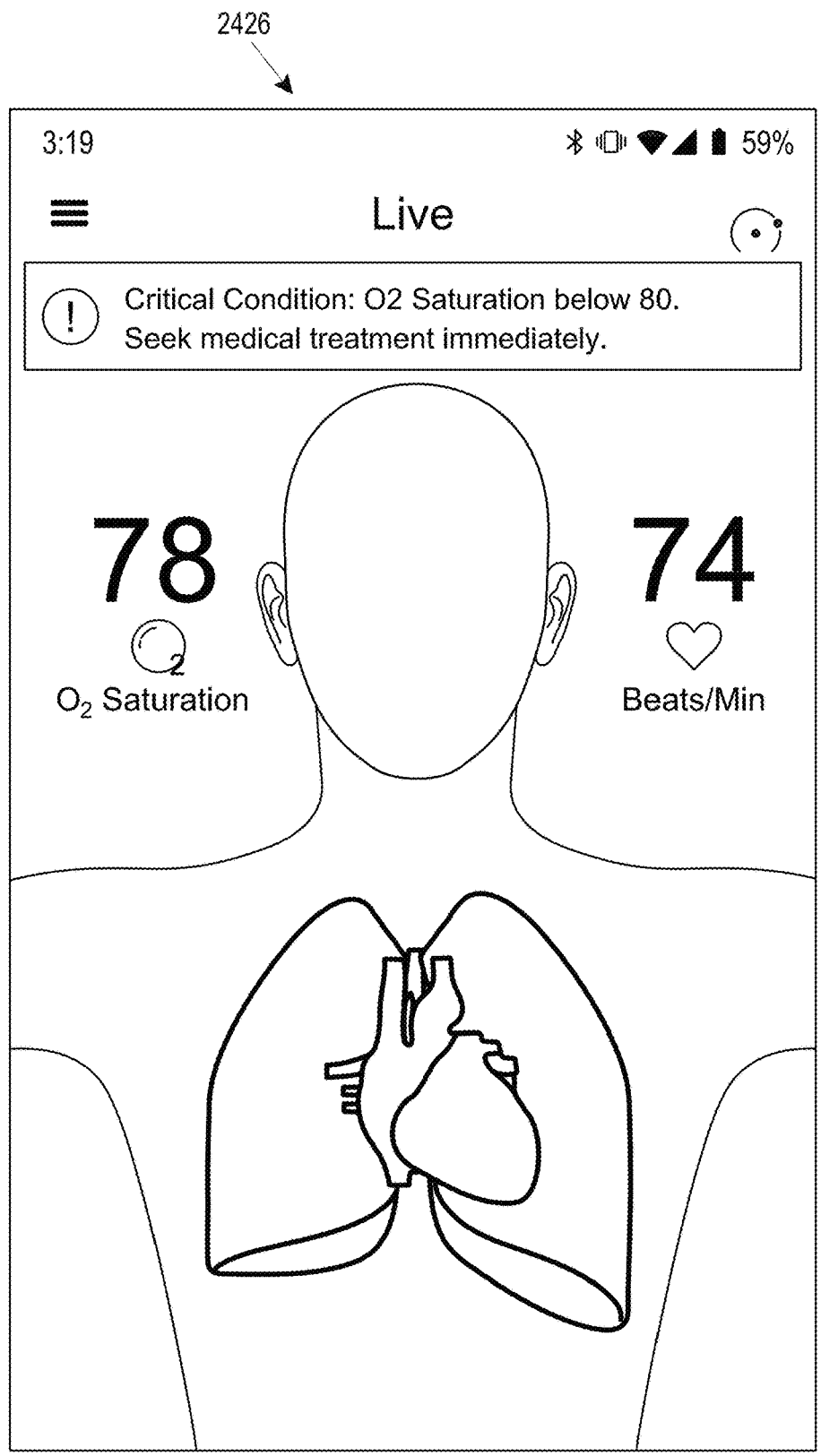

In FIG. 24N, yet another graphical user interface 2426 of the patient user computing device 102 is depicted that includes patient physiological parameters. The graphical user interface 2426 of FIG. 24N can be similar to the graphical user interface 2422 of FIG. 24L. However, in addition to the presentation of the current physiological parameters shown in the graphical user interface 2422 of FIG. 24L, the graphical user interface 2408 of FIG. 24E can include alert indicator(s). For example, in the graphical user interface 2426 of FIG. 24N, the oxygen saturation level can be below a threshold, which can cause the presentation of visual alert indicator(s) in the graphical user interface 2408. In particular, the graphical user interface 2422 can present a visual representation of human organ(s) (e.g., heart and lungs) with visual indicators corresponding to the alert(s). As shown, there can be an alert for oxygen saturation and the visually depicted lungs can be shown in red. As another example, if there is an alert for heartbeats then there can be visual alert indicator(s) for the heart, such as by showing the visual depiction of the heart in a red color.

Figure 24O:
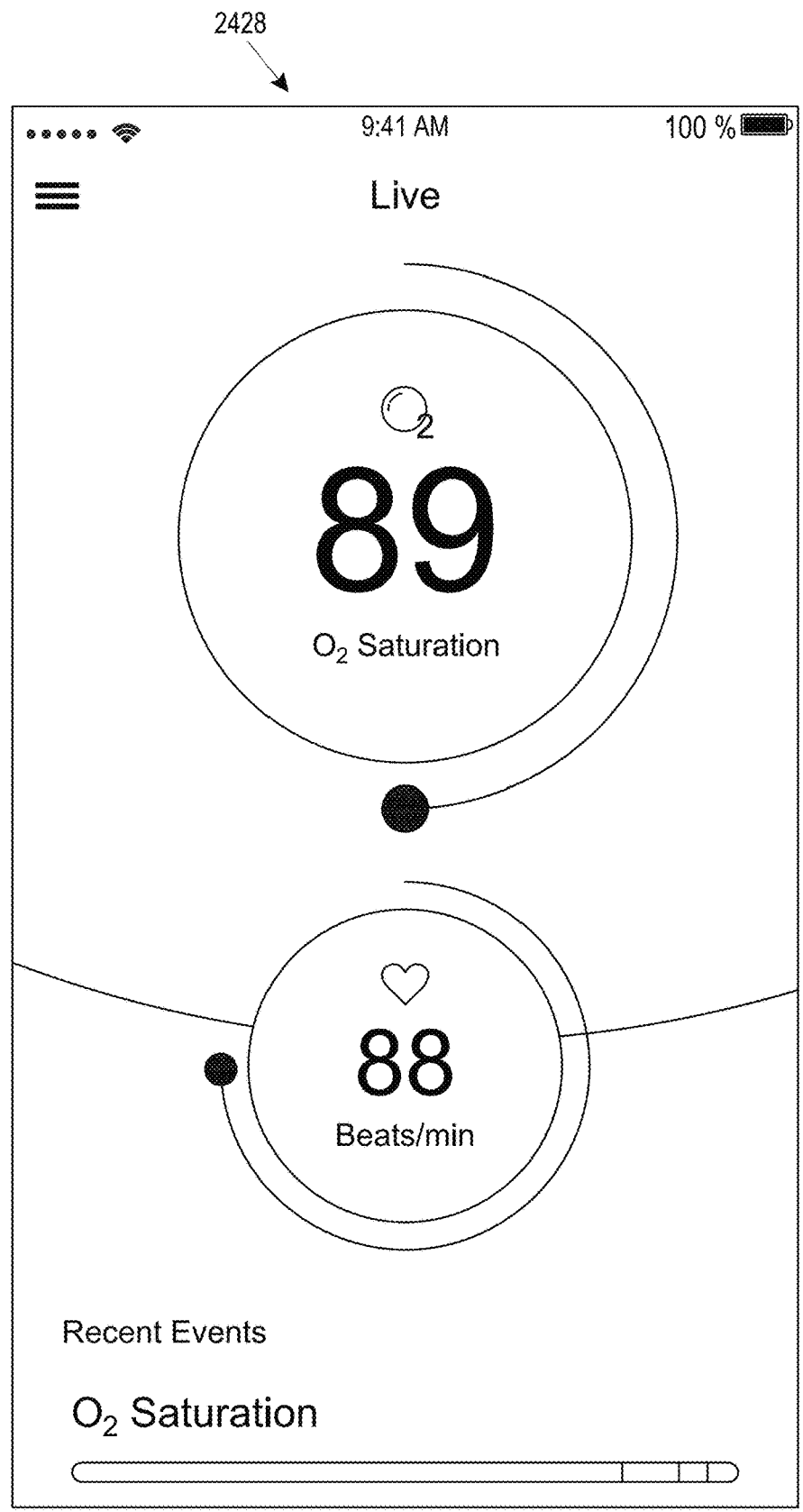

In FIG. 24O, yet another graphical user interface 2428 of the patient user computing device 102 is depicted that includes patient physiological parameters. The graphical user interface 2428 of FIG. 24O can be similar to the graphical user interface 2426 of FIG. 24N. However, instead of the visual depictions of organs shown in the graphical user interface 2426 of FIG. 24N, the graphical user interface 2408 of FIG. 24E can present current physiological parameters and alert indicator(s) without visual depictions of organs. Similar to other graphical user interfaces described herein, the alert indicator(s) can be color coded or otherwise show a severity or status of a physiological parameter. The graphical user interface 2428 of FIG. 24O can also include a recent events element that depicts a summary of events associated with a physiological parameter to indicate a quantity of events with various status levels, such as nominal, warning, cautionary, and/or critical statuses, for example.

Figure 24P:
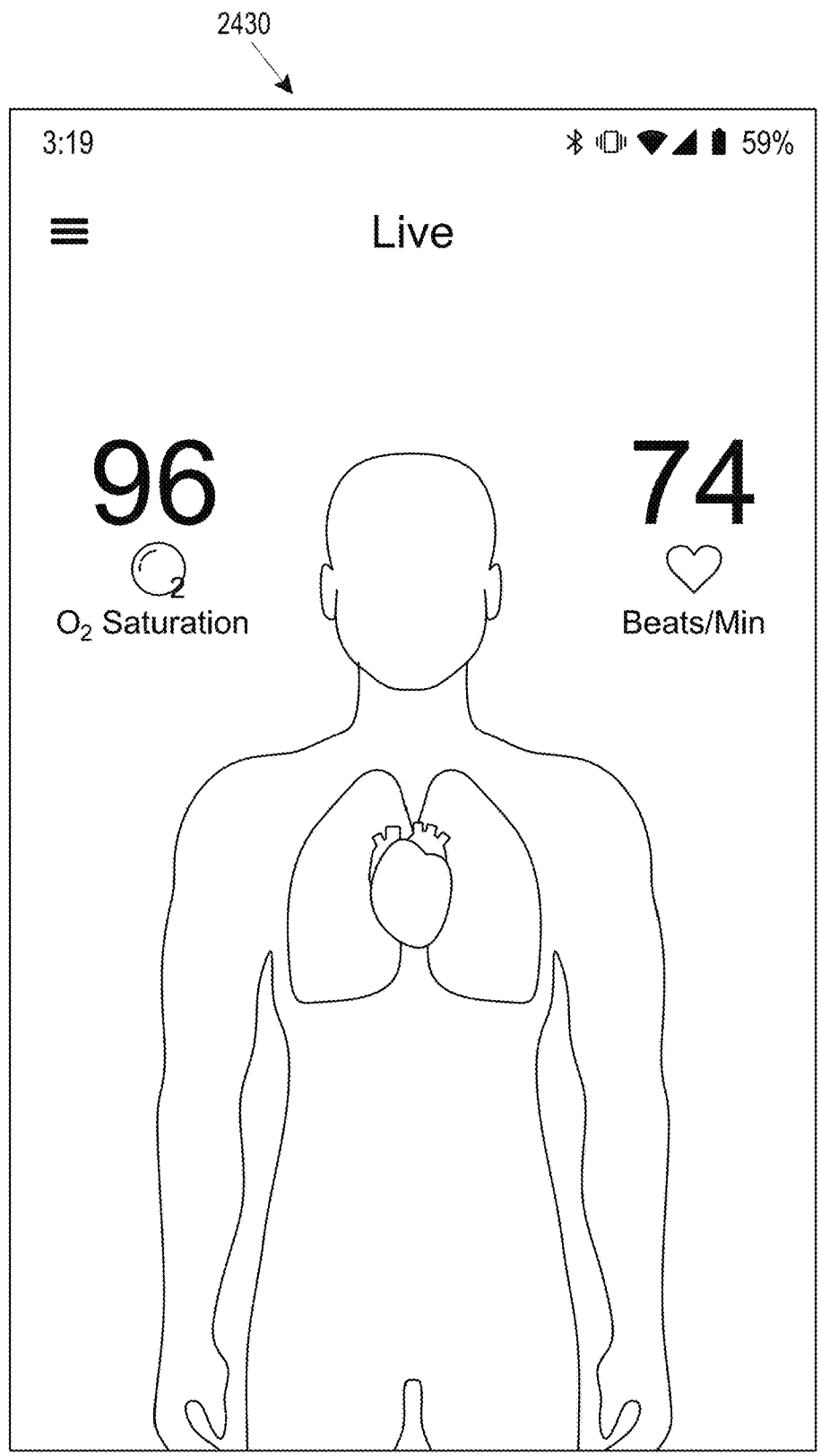

In FIG. 24P, yet another graphical user interface 2430 of the patient user computing device 102 is depicted that includes patient physiological parameters. The graphical user interface 2430 of FIG. 24P can be similar to the graphical user interface 2422 of FIG. 24L, such as by presenting current values for patient physiological parameter(s). The graphical user interface 430 of FIG. 24P can present another embodiment of a visual representation of human organ(s) (e.g., heart and lungs) with visual indicators corresponding to the status of the patient.

Figure 24Q:
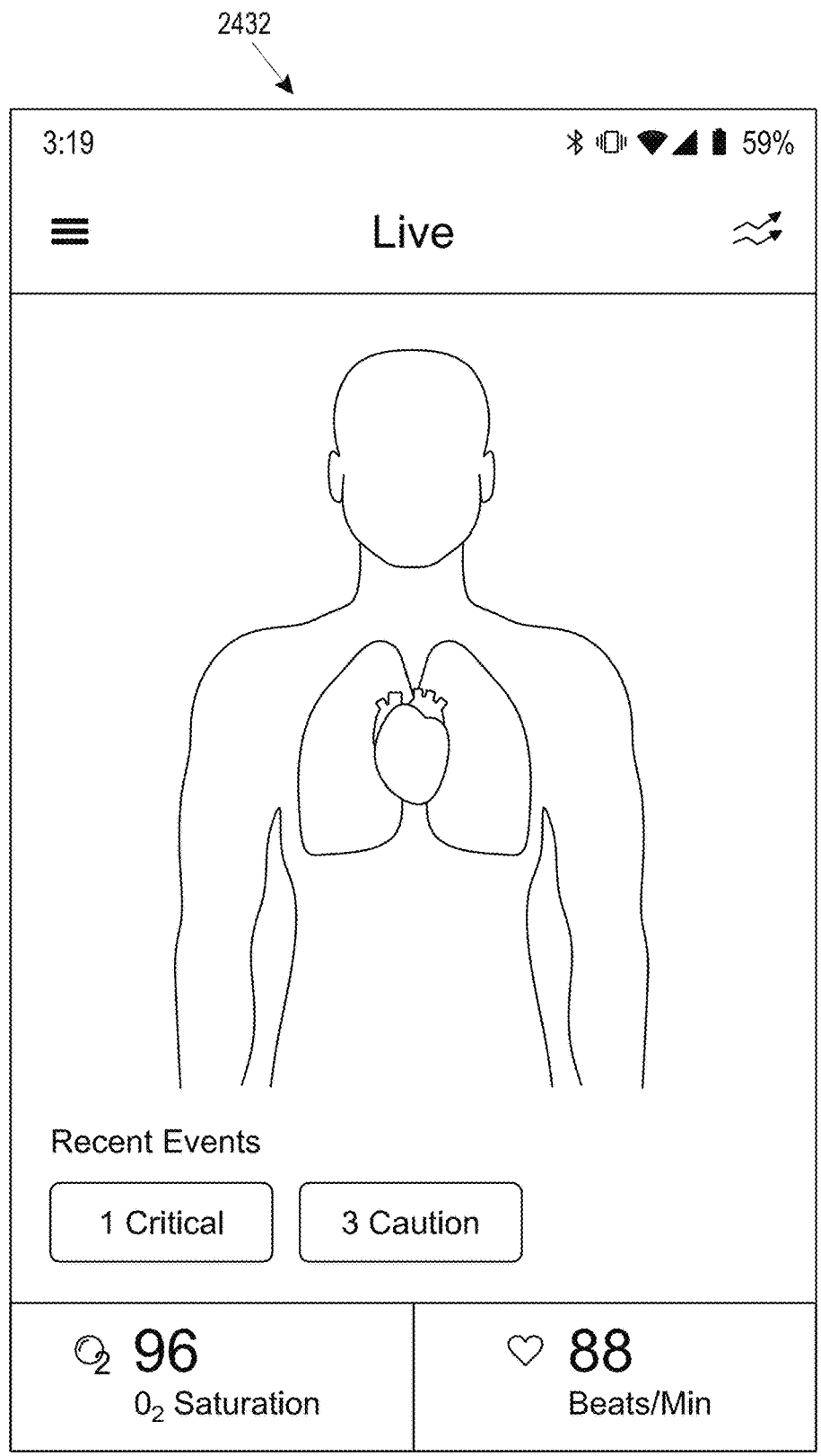
Figure 24R:
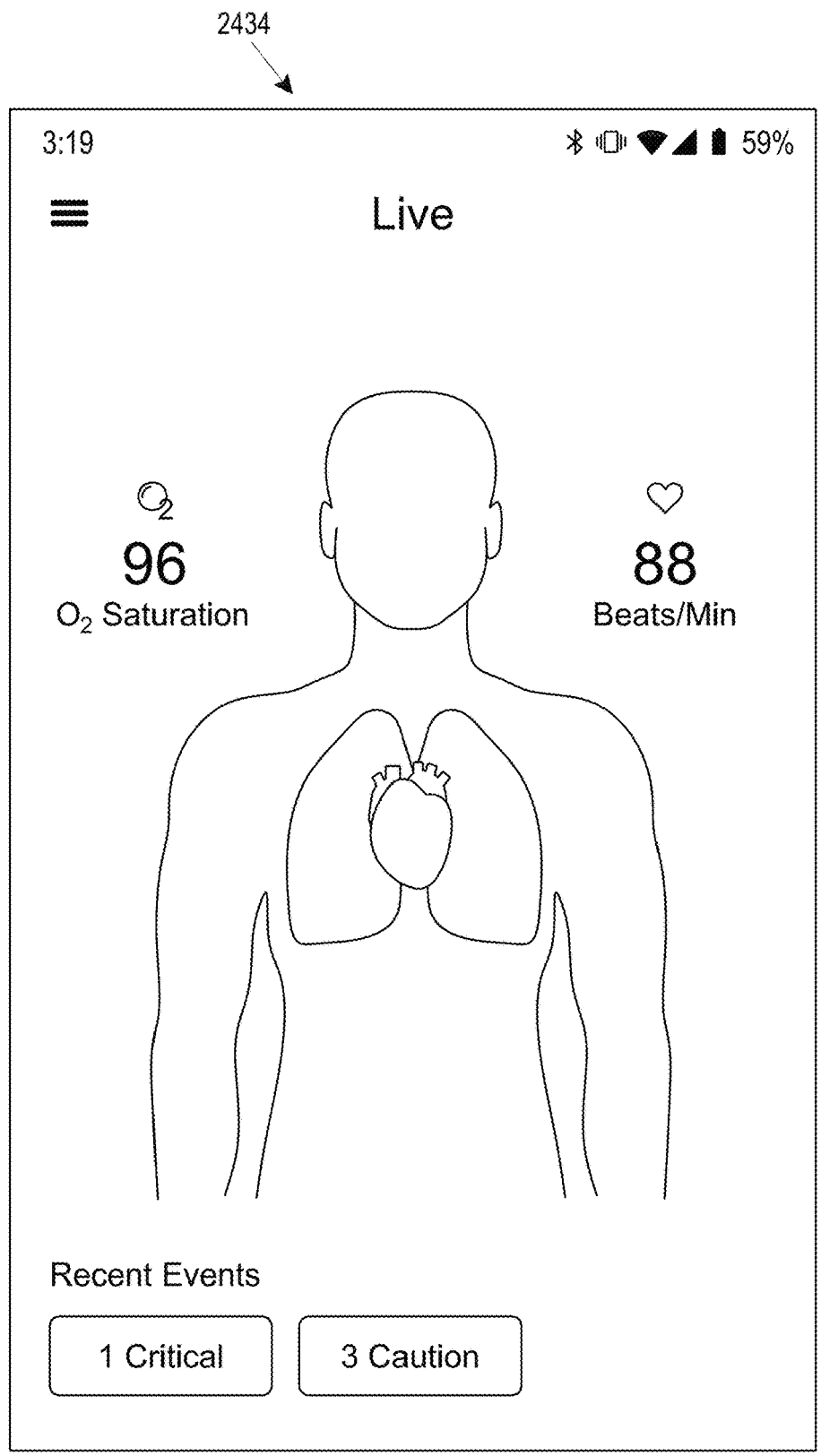

In FIG. 24Q, yet another graphical user interface 2432 of the patient user computing device 102 is depicted that includes patient physiological parameters. The graphical user interface 2432 of FIG. 24Q can be similar to the graphical user interface 2430 of FIG. 24P, such as by presenting current values for patient physiological parameter(s) and visual indicator(s) regarding a patient's status. In addition to the presentation of current values for patient physiological parameter(s) and visual indicator(s) regarding a patient's status, the graphical user interface 2432 of FIG. 24Q can present indicators of recent events, such as critical, cautionary, and/or warning events. In FIG. 24R, yet another graphical user interface 2434 of the patient user computing device 102 is depicted that includes patient physiological parameters. The graphical user interface 2434 of FIG. 24R can be similar to the graphical user interface 2432 of FIG. 24Q.

Figure 24S:
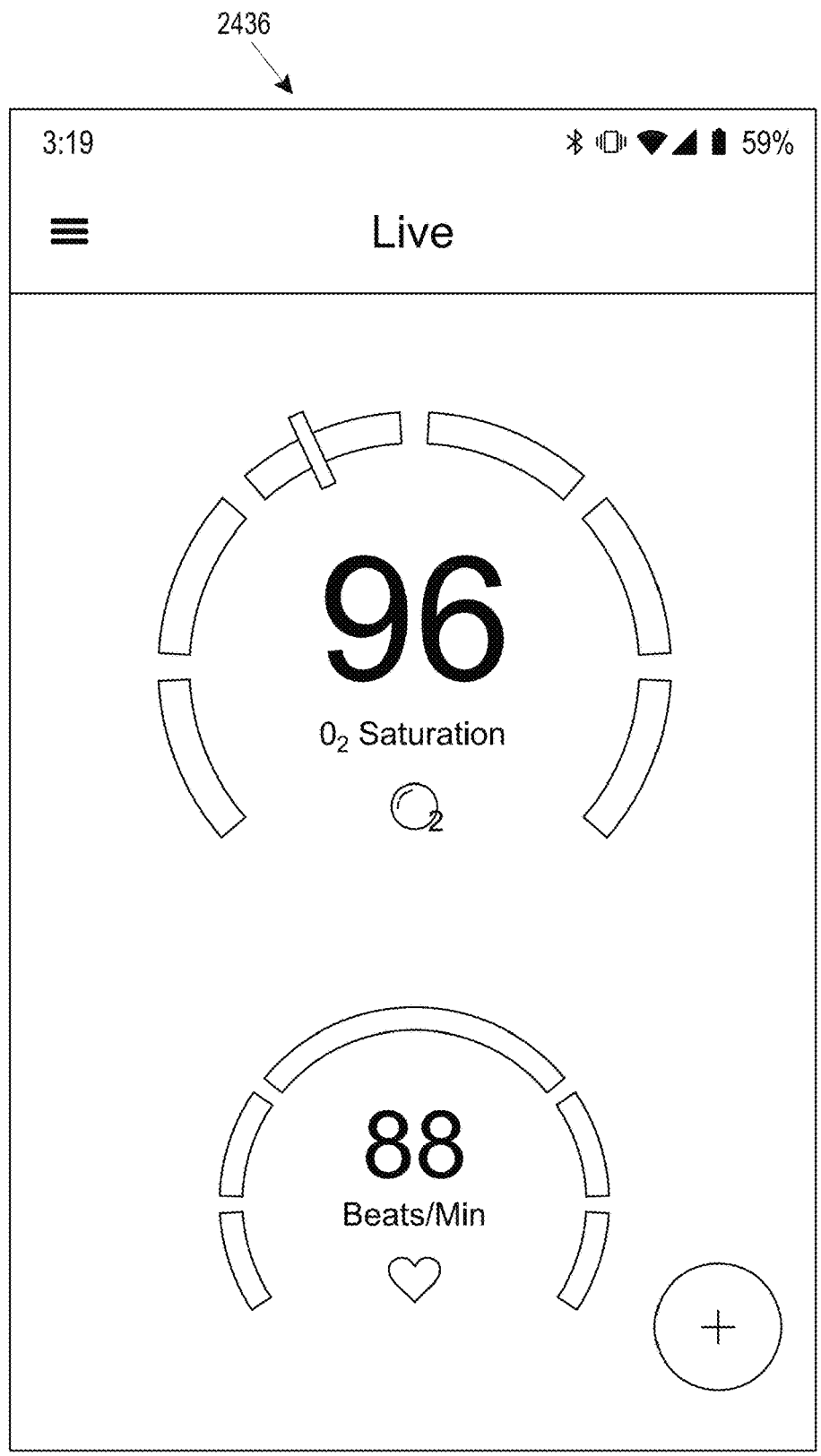
Figure 24T:
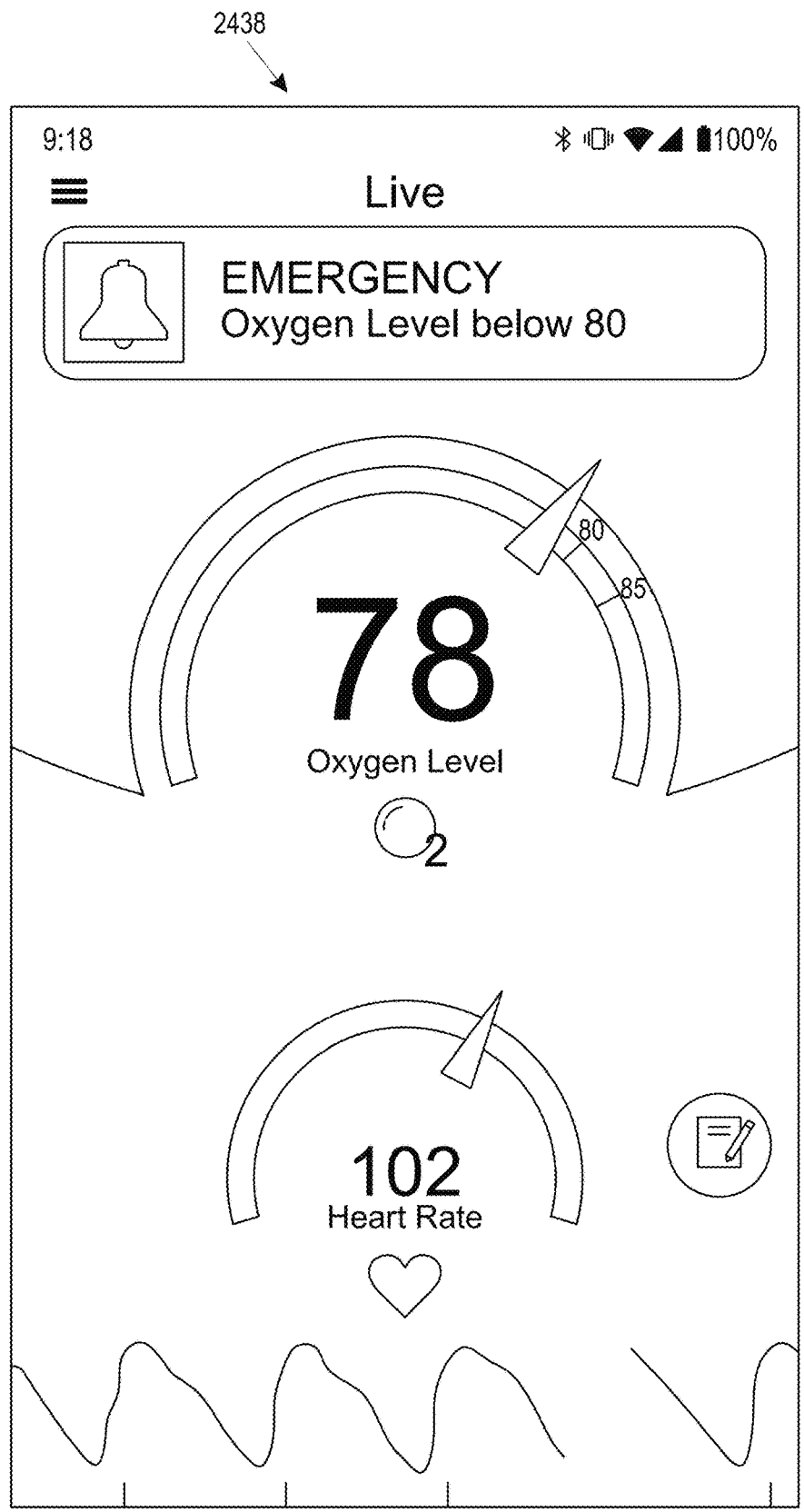

In FIG. 24S, yet another graphical user interface 2436 of the patient user computing device 102 is depicted that includes patient physiological parameters. The graphical user interface 2436 of FIG. 24S can be similar to the graphical user interface 2428 of FIG. 24O, such as by presenting current patient physiological parameter(s). In addition to the presentation of current patient physiological parameter(s), the graphical user interface 2436 of FIG. 24S can present indicator(s) that visually indicate a status of the parameters and various status ranges for each parameter. In FIG. 24T, yet another graphical user interface 2438 of the patient user computing device 102 is depicted that includes patient physiological parameters. The graphical user interface 2438 of FIG. 24T can be similar to the graphical user interface 2436 of FIG. 24S. In the embodiment of the graphical user interface 2438 of FIG. 24T, visual alert and/or alarm indicator(s) can be presented.

Figure 24U:
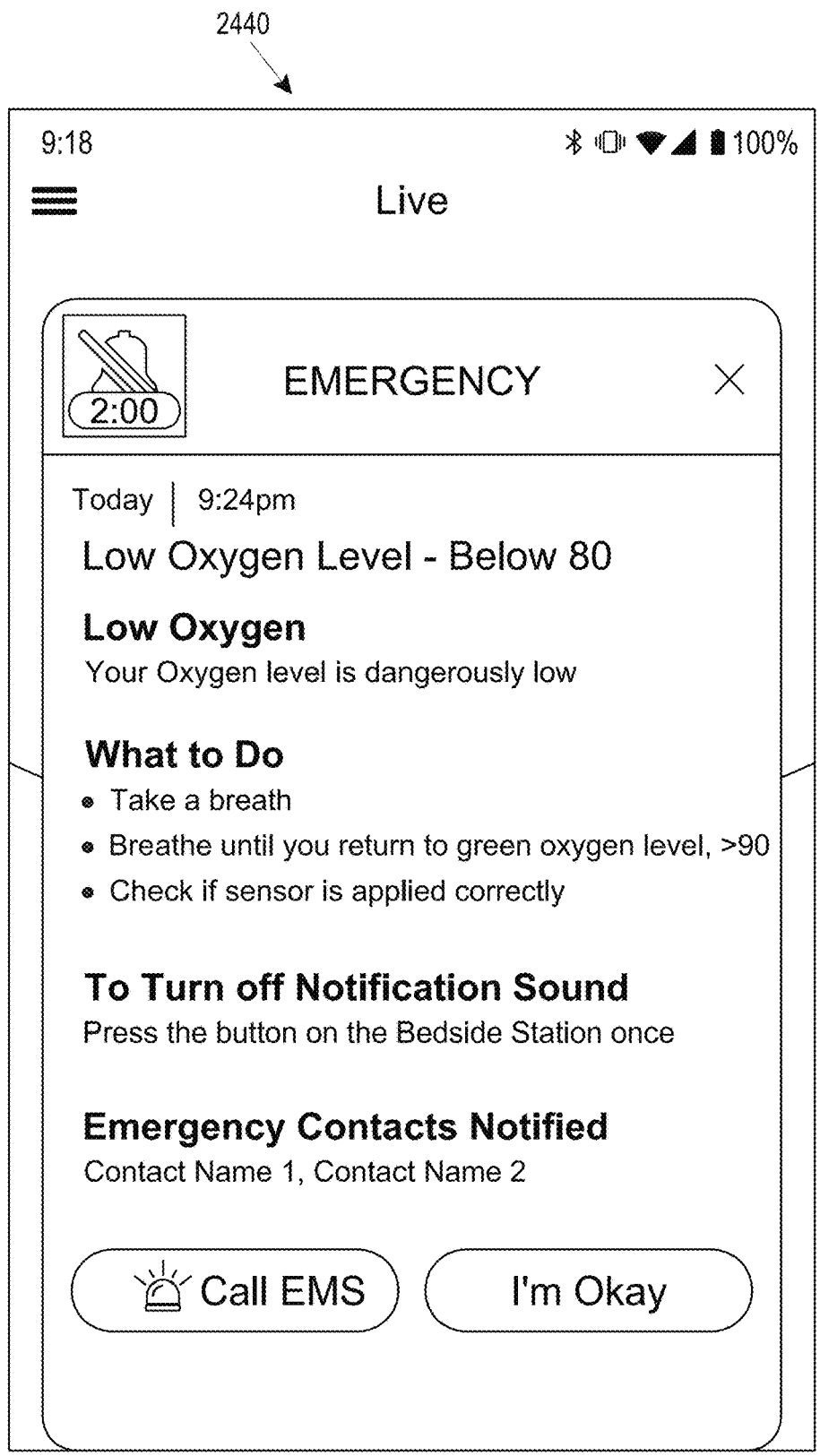
Figure 24W:
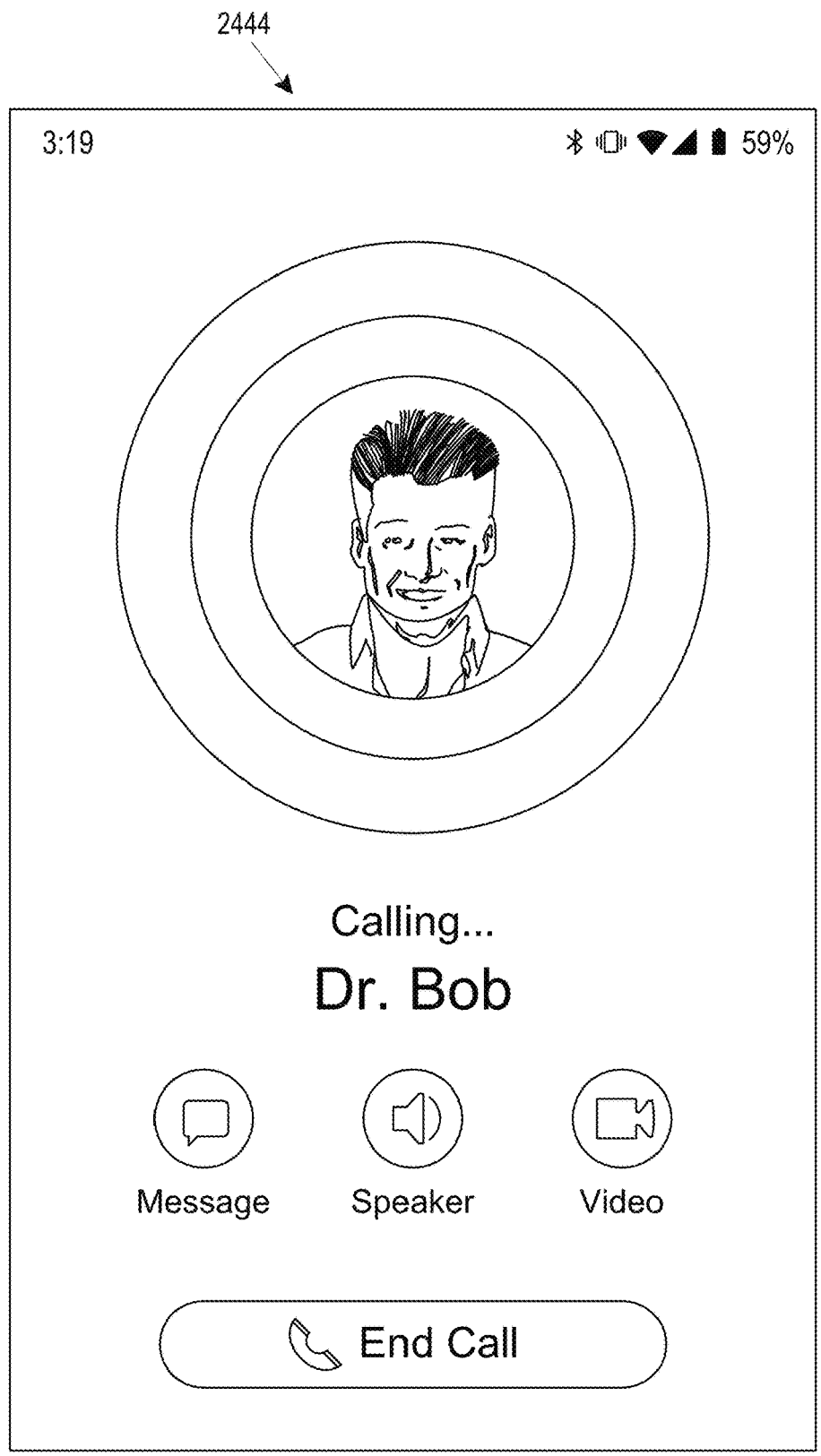

FIG. 24U illustrates a graphical user interface 2440 of the patient user computing device 102 for presenting an alert. The alert shown in the graphical user interface 2440 of FIG. 24U can correspond to the alert shown in the graphical user interface 2436 of FIG. 24S. The alert element in the graphical user interface 2440 can present alert information to a patient. The alert element in the graphical user interface 2440 can provide an option to contact an emergency contact and/or emergency services. FIG. 24V illustrates a graphical user interface 2442 of the patient user computing device 102 for confirming or cancelling notifying emergency services. Additionally or alternatively, a patient can contact their care provider and/or a clinician through the patient user computing device 102 regarding their physiological parameters. FIG. 24W illustrates a graphical user interface 2444 of the patient user computing device 102 for contacting a care provider and/or a clinician.

Figure 24X:
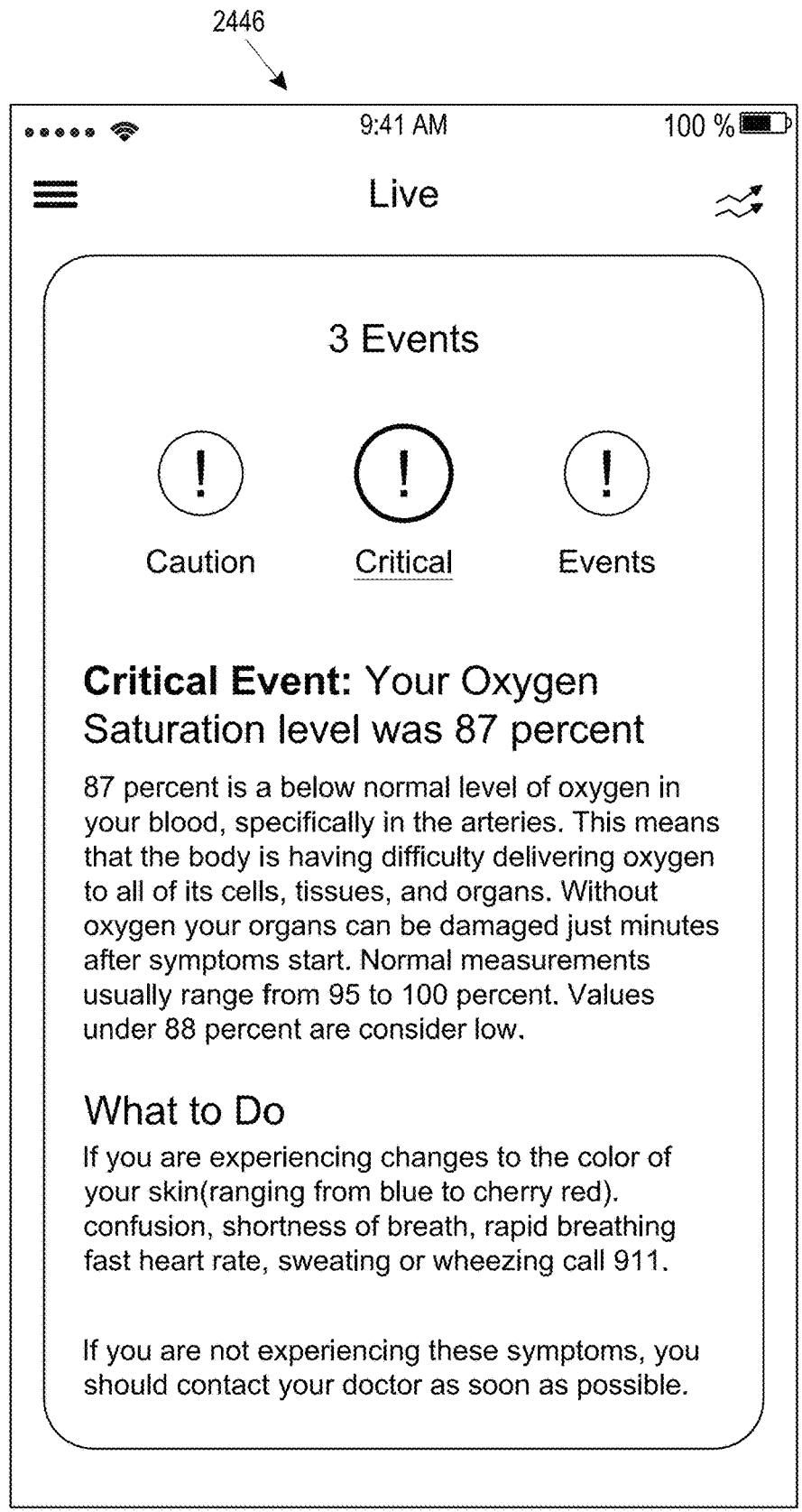
Figure 24Y:
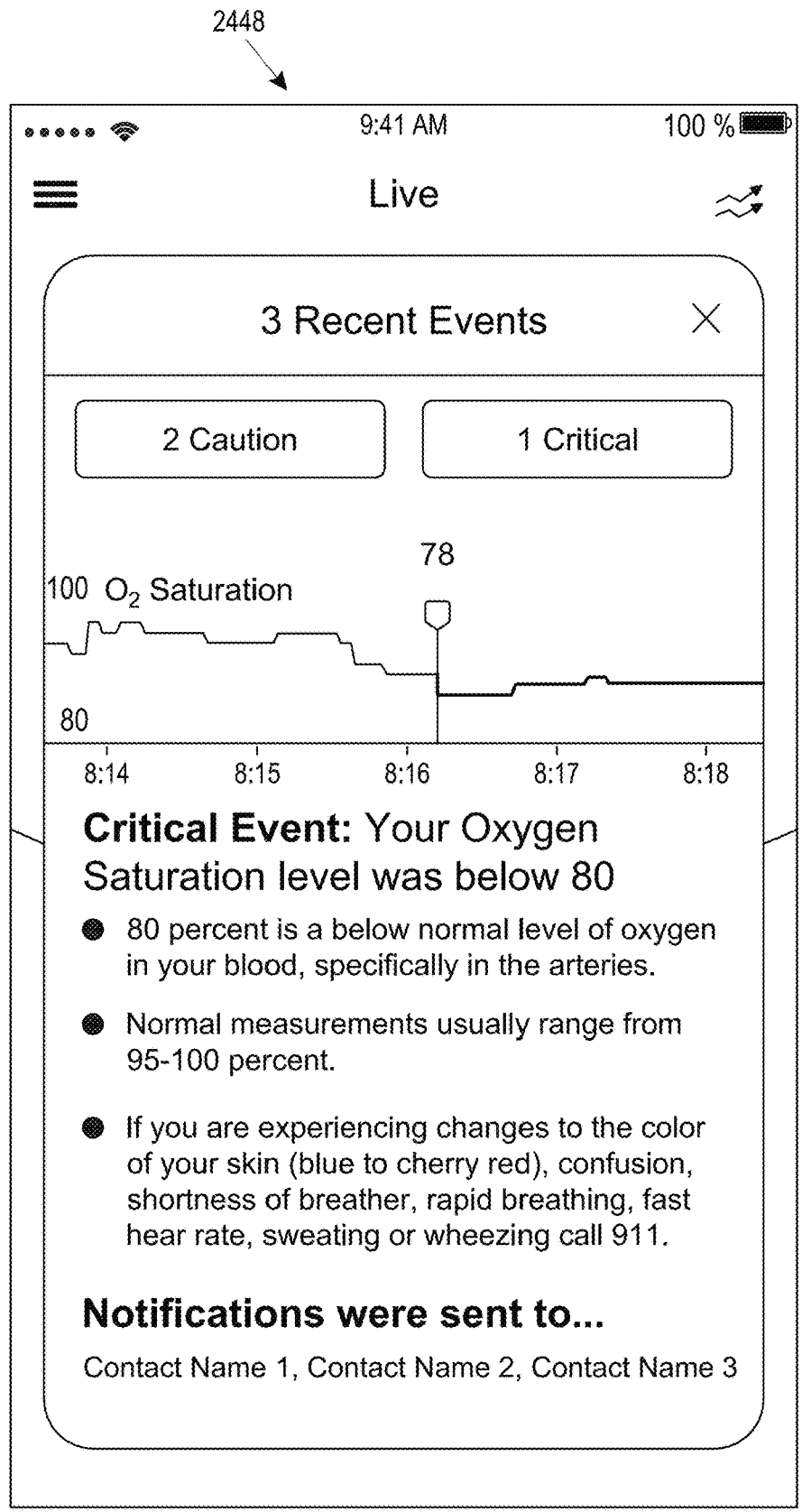

FIG. 24X illustrates another graphical user interface 2446 of the patient user computing device 102 for presenting an event. The graphical user interface 2446 of FIG. 24X can be similar to the graphical user interface 2440 of FIG. 24U, such as by presenting information regarding an event and/or alert for a physiological parameter. FIG. 24Y illustrates yet another graphical user interface 2448 of the patient user computing device 102 for presenting an event. The graphical user interface 2448 of FIG. 24Y can be similar to the graphical user interface 2446 of FIG. 24X, such as by presenting information regarding an event. However, in addition to the presentation of a description of an event associated with a physiological parameter, the graphical user interface 2448 of FIG. 24Y can present a visualization showing historical values associated with a physiological parameter and/or indications that notifications were sent to one or more recipients.

Figure 25A:
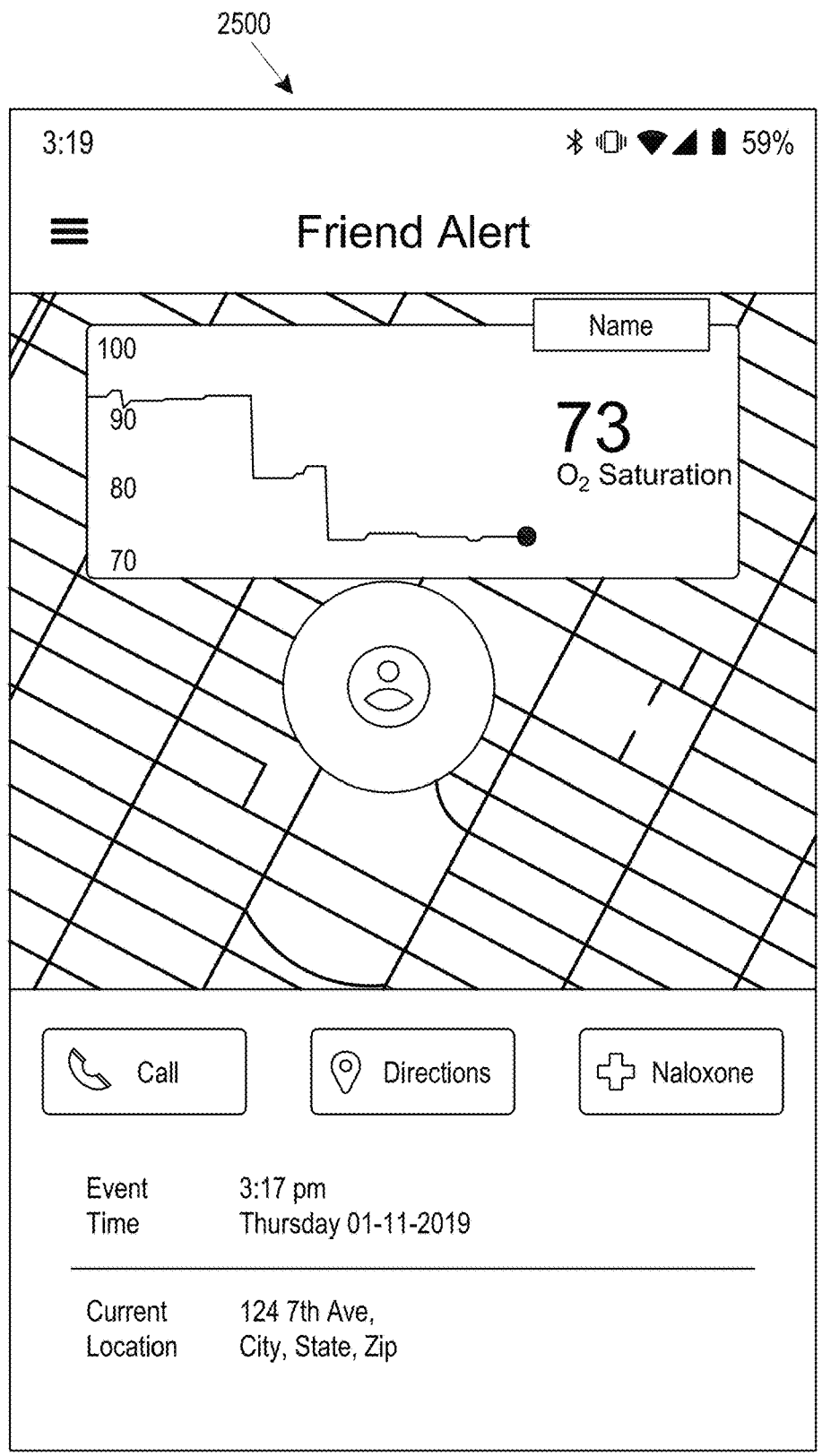

FIG. 25A illustrates a graphical user interface 2500 for viewing a patient alert. As described herein, a patient can specify contacts, such as friends or family, to receive patient data such as patient alerts. Accordingly, an authorized-user can use the graphical user interface 2500 to view the patient alert. As shown, the graphical user interface 2500 can display a map showing the location of the patient and a status of the patient. The graphical user interface 2500 can further include element(s) to call the patient, get directions to the patient's location, and/or to cause administration of medication.

Figure 25B:
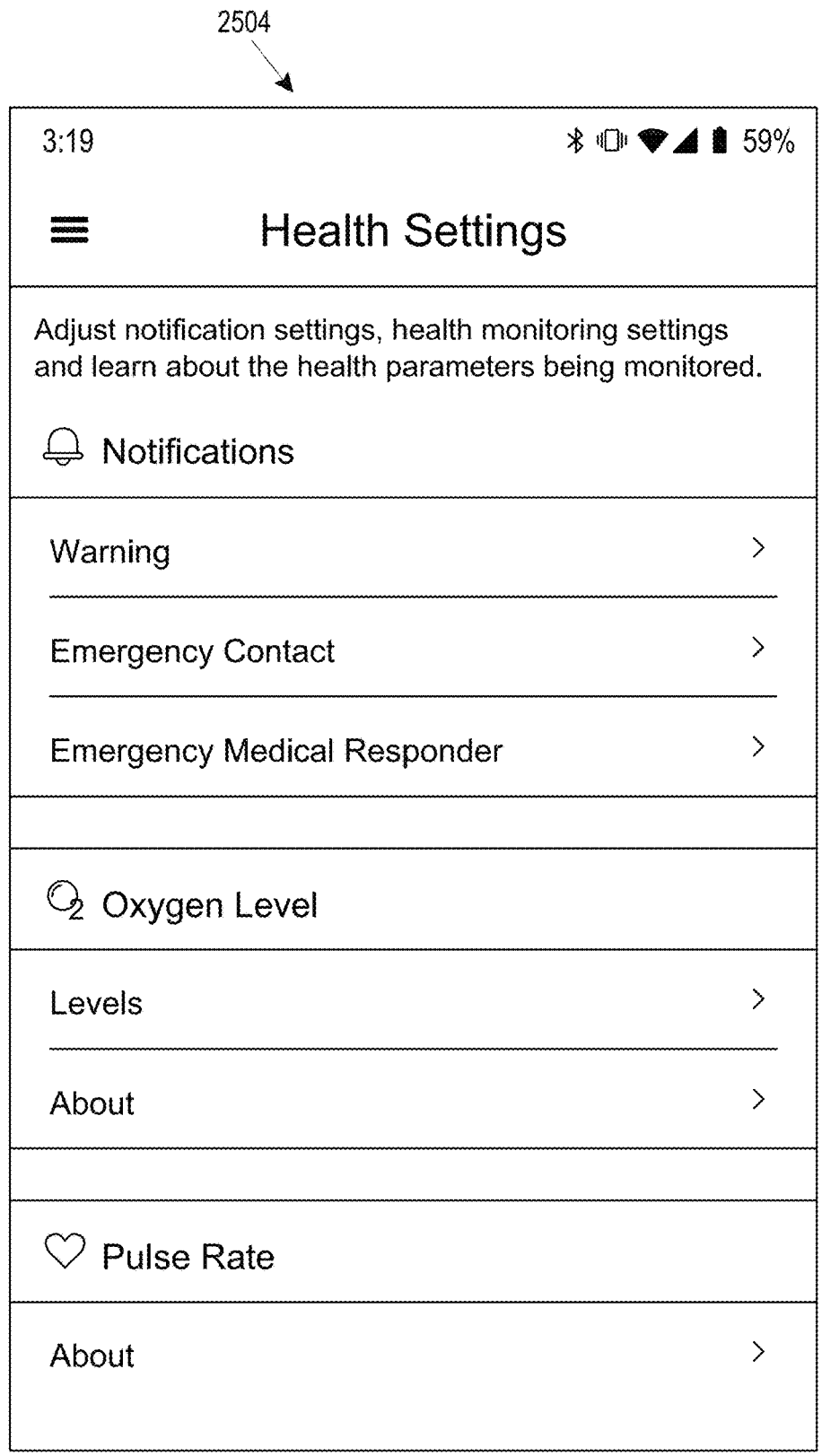

FIG. 25B illustrates a graphical user interface 2504 of the patient user computing device 102 for managing settings. Example settings can include notification and/or monitoring settings. The graphical user interface 2504 can enable a patient to configure the recipients of the notifications (such as emergency contacts and/or emergency services). The graphical user interface 2504 can enable a patient to con- figure monitoring settings for physiological parameters, such as the alarm levels for one or more physiological parameters.

Figure 25C:
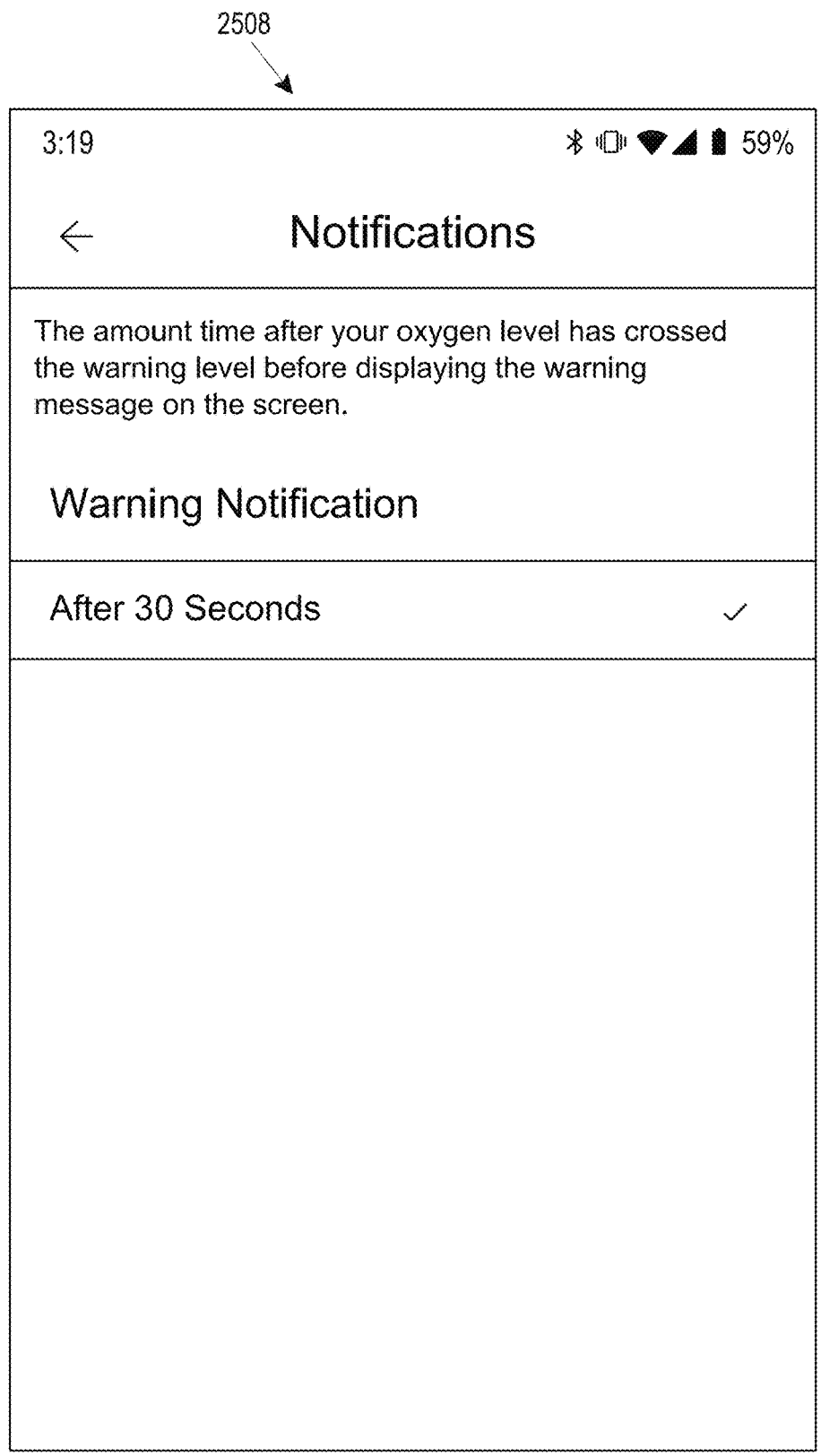

FIG. 25C illustrates a graphical user interface 2508 of the patient user computing device 102 for configuring notification settings. In the graphical user interface 2508, a patient can specify an amount of time after a physiological parameter has violated a warning level before the patient user computing device 102 generates a notification for the patient. In some embodiments, the amount of time can be configurable. An example amount of time can be thirty seconds. For example, if a physiological parameter violates a warning level for thirty seconds, then the patient user computing device 102 can generate a notification for the patient. As described below, additional or alternative graphical user interfaces can allow a patient to configure contact notifications and/or emergency service notifications.

Figure 25D:
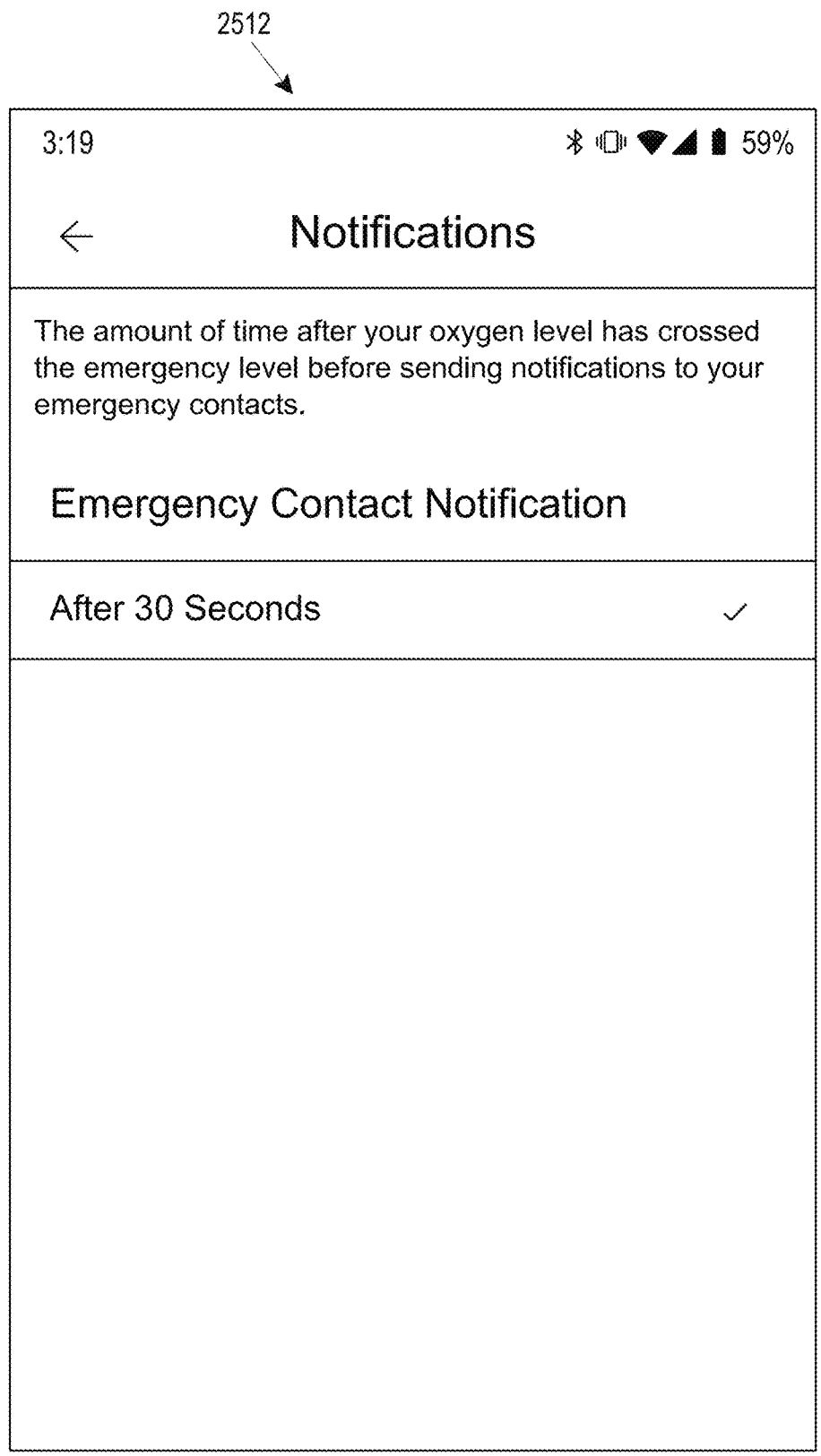

FIG. 25D illustrates another graphical user interface 2512 of the patient user computing device 102 for configuring notification settings. The graphical user interface 2512 of FIG. 25D can be similar to the graphical user interface 2508 of FIG. 25C, such as by allowing a patient to configure notification settings. However, instead of allowing configuration of notification settings for notifications destined for a patient, as shown in the graphical user interface 2508 of FIG. 25C, the graphical user interface 2512 of FIG. 25D can allow configuration of contact notifications. For example, if a physiological parameter violates a warning level for thirty seconds, then the patient user computing device 102 can generate a notification for a contact.

Figure 25E:
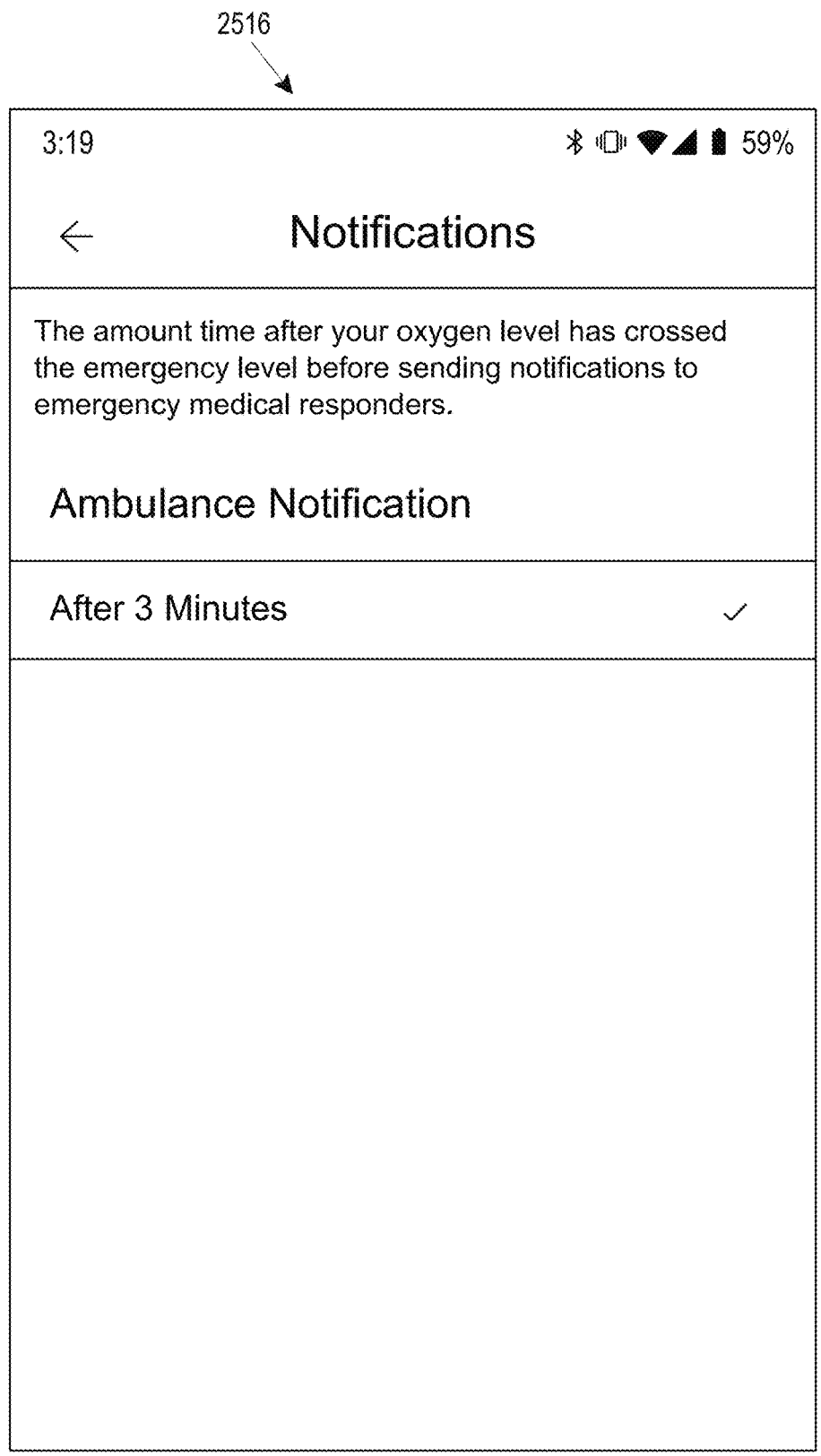

FIG. 25E illustrates yet another graphical user interface 2516 of the patient user computing device 102 for configuring notification settings. The graphical user interface 2516 of FIG. 25D can be similar to the graphical user interface 2508 of FIG. 25C, such as by allowing a patient to configure notification settings. However, instead of allowing configuration of notification settings for notifications destined for a patient, as shown in the graphical user interface 2508 of FIG. 25C, the graphical user interface 2516 of FIG. 25E can allow configuration of emergency service notifications. For example, if a physiological parameter violates a warning level for three minutes or longer, then the patient user computing device 102 can generate a notification emergency services.

Figure 25F:
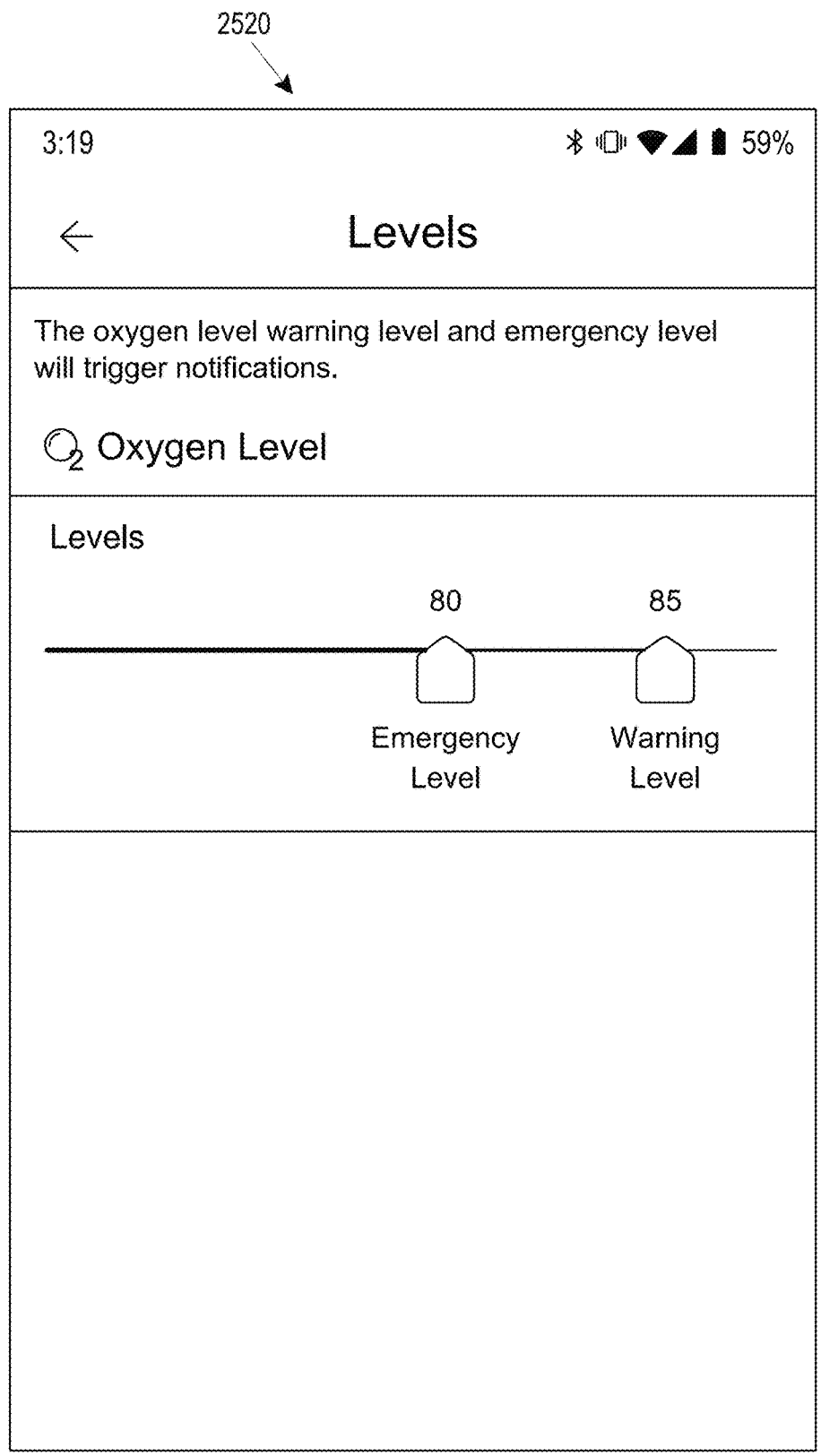

FIG. 25F illustrates a graphical user interface 2520 of the patient user computing device 102 for configuring alarm threshold levels. The graphical user interface 2520 can allow a patient to set one or more threshold levels for causing the patient user computing device 102 to generate a notification. For example, if a first level is violated, then the patient user computing device 102 can cause an emergency notification to be generated. As another example, if a second level is violated, then the patient user computing device 102 can cause a warning notification to be generated.

Figure 25G:
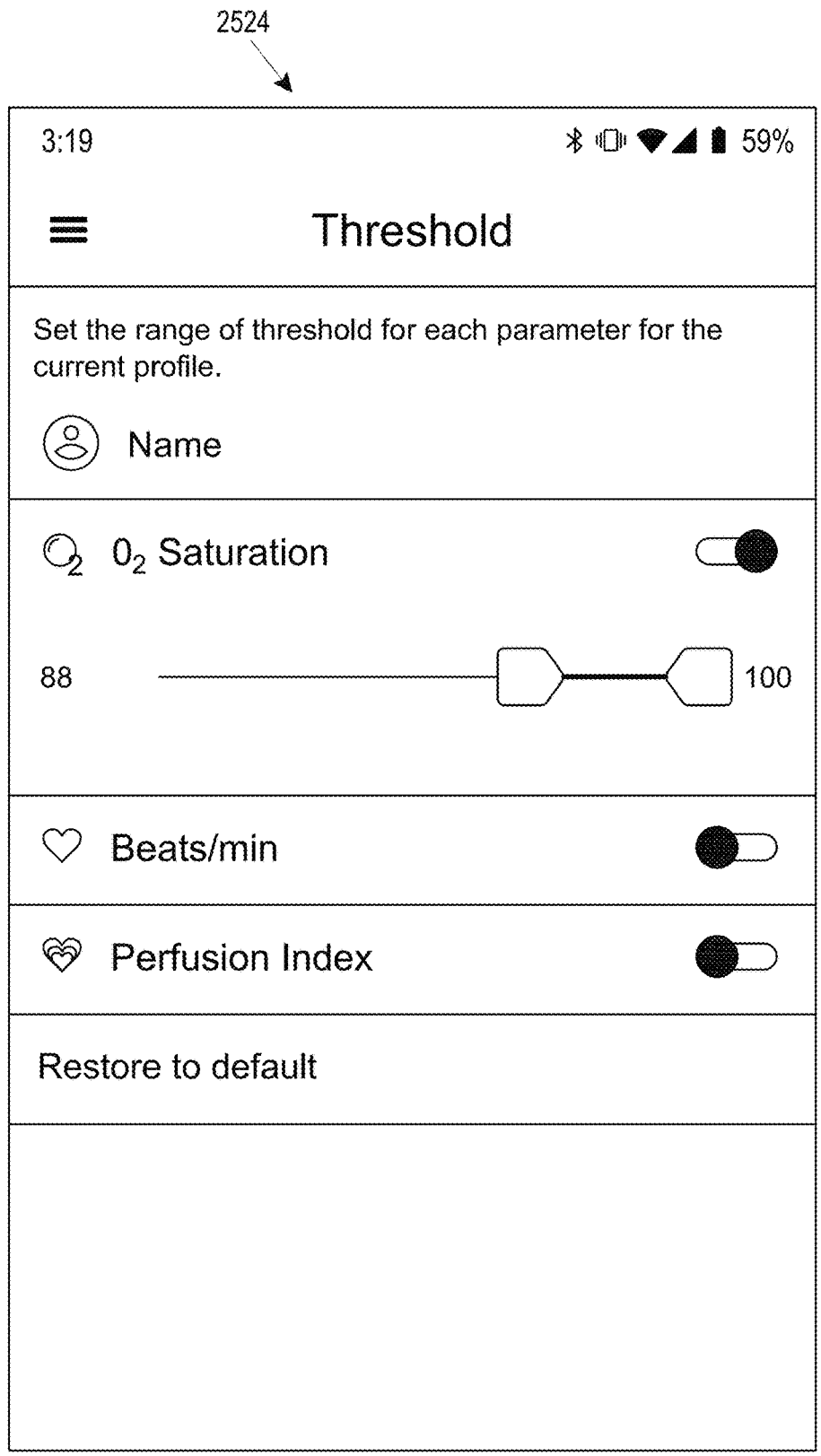

FIG. 25G illustrates another graphical user interface 2524 of the patient user computing device 102 for configuring alarm threshold levels. The graphical user interface 2524 of FIG. 25G can be similar to the graphical user interface 2520 of FIG. 25F, such as by allowing a patient to configure an alarm threshold. Moreover, the graphical user interface 2524 of FIG. 25G can allow a patient to configure multiple physiological parameter alarm levels. As shown, the physiological parameter alarm(s) can be activated or deactivated by the patient.

Figure 25H:
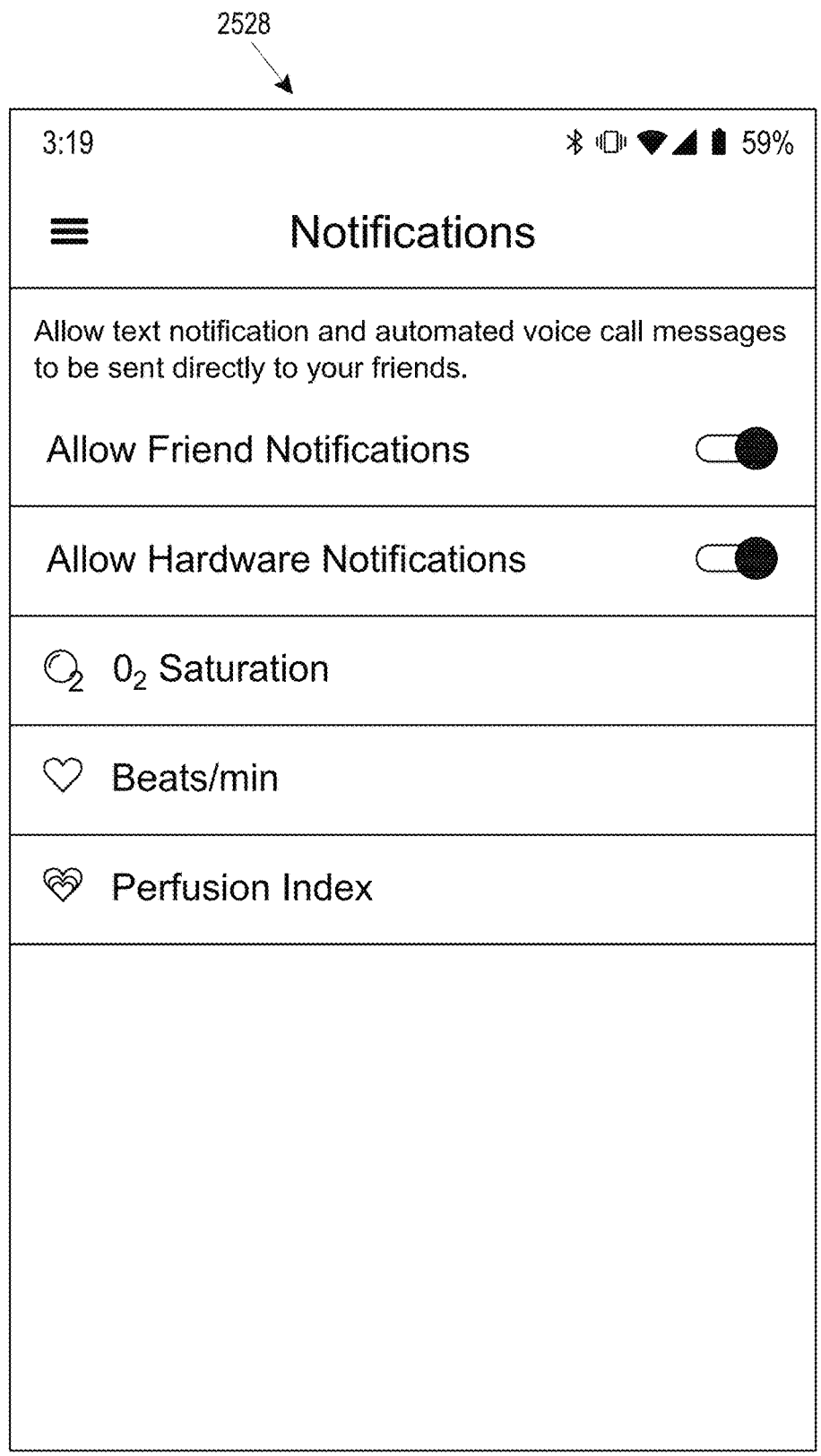

FIG. 25H illustrates yet another graphical user interface 2528 of the patient user computing device 102 for configuring notification settings. For example, in the graphical user interface 2528, a patient can activate or deactivate notifications for the patient's contacts. As another example, in the graphical user interface 2528, a patient can activate or deactivate notifications for the patient user computing device 102, which can cause the or notifications to the patient user computing device 102.

Figure 25I:
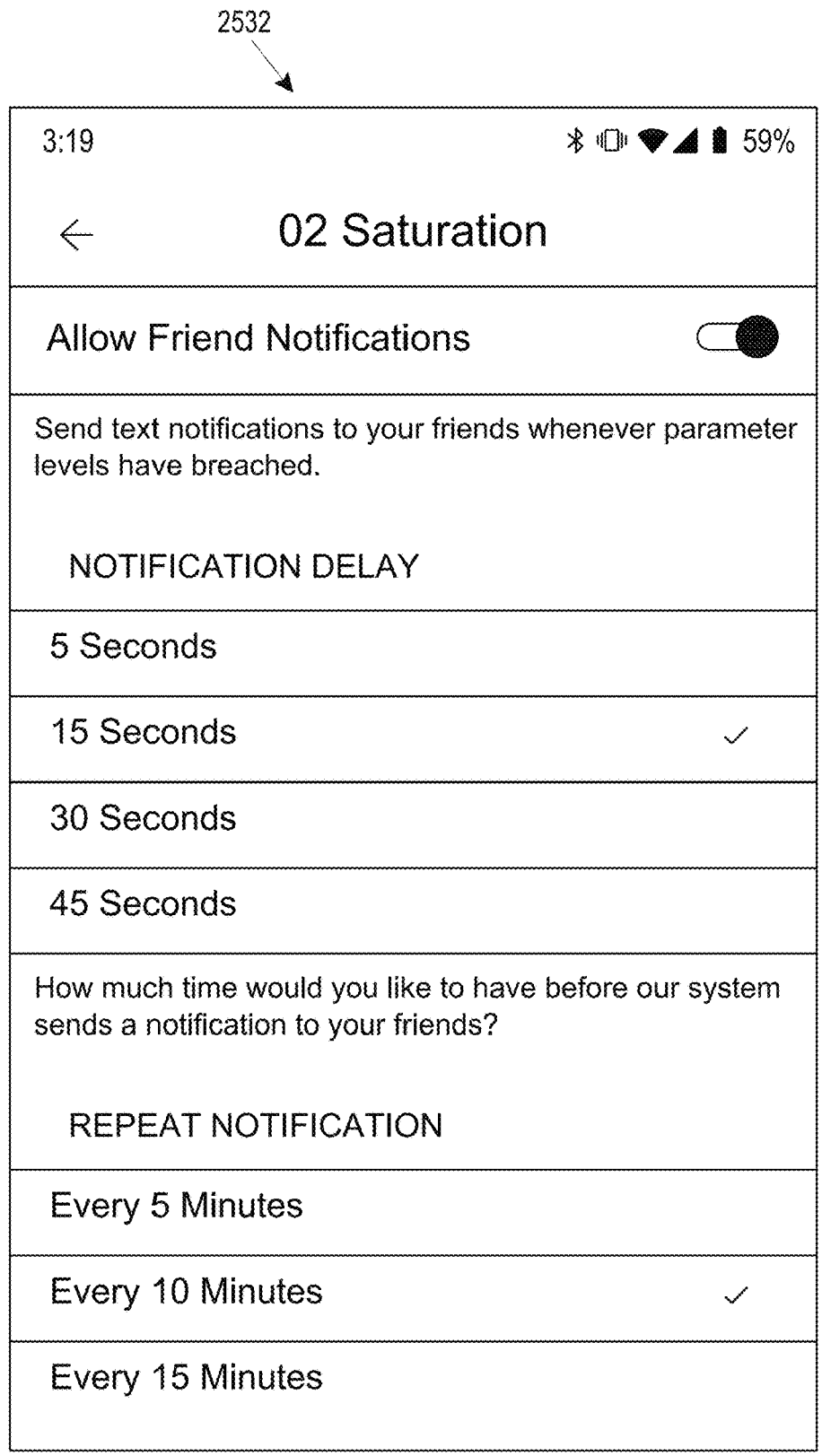

FIG. 25I illustrates yet another graphical user interface 2532 of the patient user computing device 102 for configuring notification settings. For example, in the graphical user interface 2532, a patient can configure the notification delay, which can be a configurable amount of time to delay a notification.

Figure 25J:
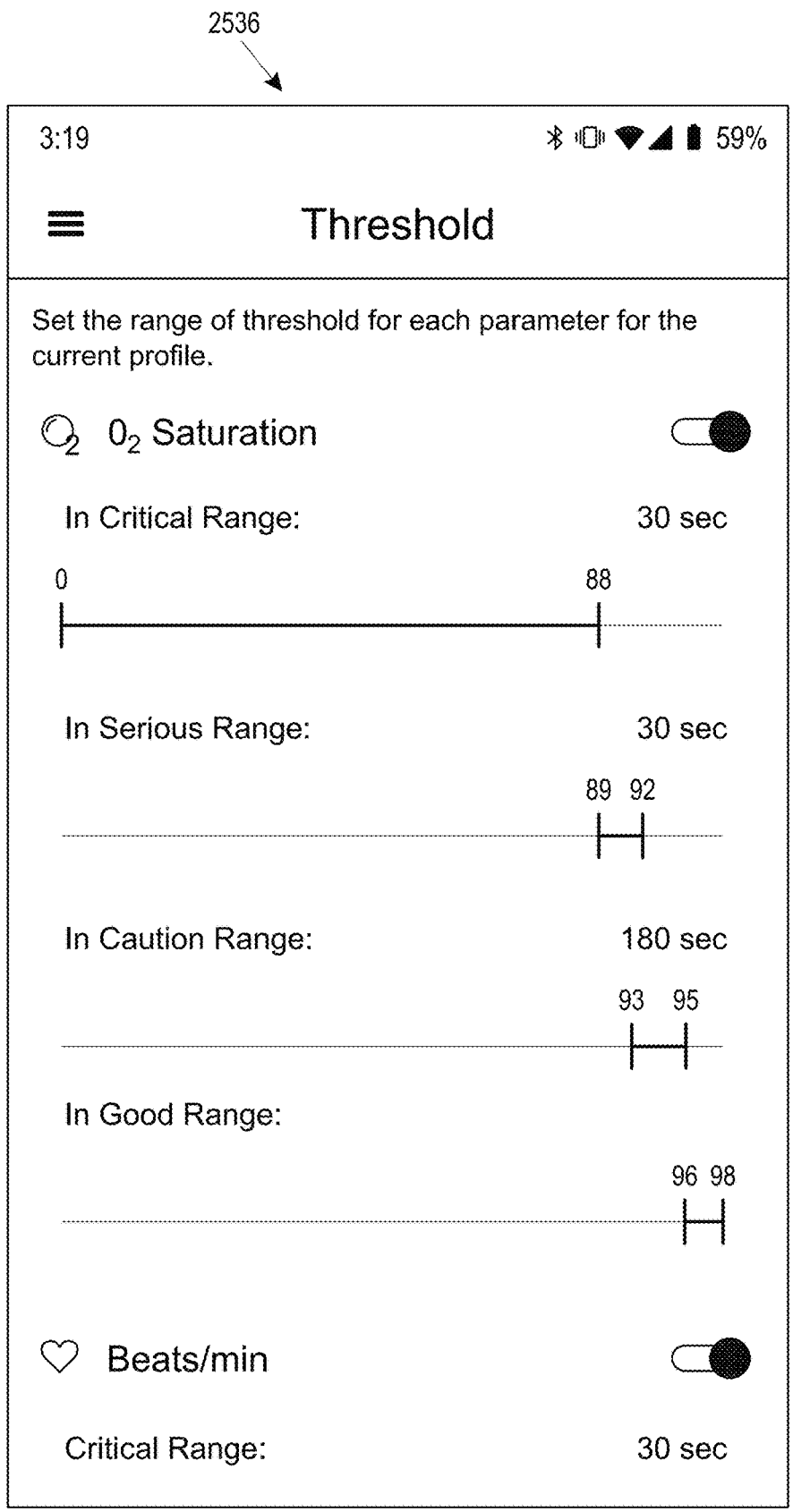

FIG. 25J illustrates yet another graphical user interface 2536 of the patient user computing device 102 for configuring alarm threshold levels. The graphical user interface 2536 of FIG. 25I can be similar to the graphical user interface 2520 of FIG. 25F, such as by allowing a patient to configure threshold range levels for particular physiological parameters. In particular, the example threshold ranges shown in FIG. 25J can correspond to a "Good Range," a "Caution Range," and a "Serious Range." As shown, the graphical user interface 2536 can allow a user to configure multiple alarm threshold levels.

Additional Patient Monitoring Methods

Figure 26:
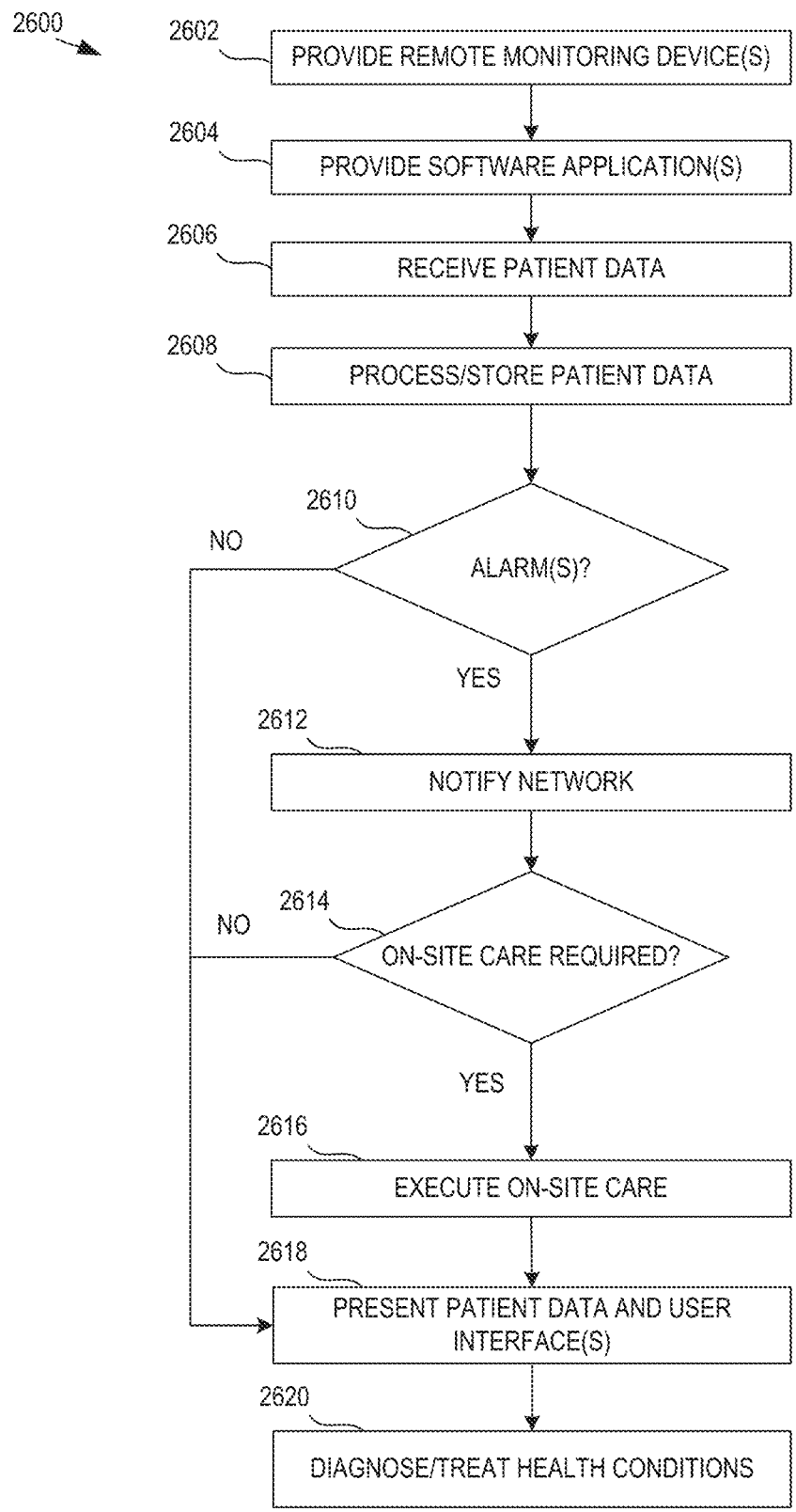
FIG. 26 is another flowchart of a method for patient monitoring, according to some embodiments of the present disclosure.

FIG. 26 is another flowchart of a method 2600 for patient monitoring, according to some embodiments of the present disclosure. The method 2600 provides additional example approaches regarding patient monitoring. As described herein, the patient user computing device 102, the connectivity hub device 106, the patient sensor devices 104, and/or additional device 114A, 114B may implement aspects of the method 2600 as described herein. As described herein, the patient management and monitoring system 110 of FIG. 1B may include various devices, services, and/or applications, some of which may implement aspects of the method 2600 as described herein. Depending on the embodiment, the method 2600 may include fewer or additional blocks and/or the blocks may be performed in order different than is illustrated.

Beginning at block 2602, one or more remote monitoring devices can be provided to a patient. An organization, such as a company or a care provider, can provide a remote monitoring kit to the patient. In some embodiments, the remote monitoring kit can include a reusable device 250 and a disposable device 220. The reusable device 250 can be configured to engage the disposable device 220 to form a wearable sensor assembly. The wearable sensor assembly can be configured to measure one or more physiological parameters, such as, but not limited to, blood oxygen saturation (SpO$_2$), pulse rate, perfusion index, pleth variability index, temperature, and/or respiration rate, of the patient over a monitoring period. The patient can be monitored at the patient's place of residence. The remote monitoring kit can include a connectivity hub device 106 that is configured to transmit the physiological parameters, such as the patient's blood oxygen saturation and the temperature measurements, over the monitoring period to the care provider. As described herein, the wearable sensor assembly can be configured to be disposed on at least one of the patient's finger, wrist, chest, or forehead.

In some embodiments, an organization can provide a wearable device to respective patients having symptoms of a health condition (such as an infectious disease or an opioid addiction) in a non-clinical space. As described herein, the wearable device can be configured to measure one or more physiological parameters (such as, but not limited to, blood oxygen saturation) over a monitoring period. An organization can further provide a connectivity hub device 106 that is configured to (i) wirelessly connect with respective wearable devices and (ii) transmit the measured physiological parameter(s) over the monitoring period.

In some embodiments, a remote monitoring kit can include a package and a pulse oximetry sensor device. The package can be configured to be mailed. Additional details regarding remote monitoring kits can be described herein, such as with respect to FIG. 7C. The pulse oximetry sensor device can include a wireless communications device, a memory device configured to store instructions, and a hardware processor configured to execute the instructions. The pulse oximetry sensor device can be configured to pair, via the wireless communications device, with a patient user computing device 102 through a downloadable application. The pulse oximetry sensor device can further include a removable chip 250. The removable chip 250 can include the wireless communications device, the memory device, and the hardware processor.

In some embodiments, the remote monitoring kit can further include multiple sensors, which can be in the package. Each of the sensors can be configured to receive the removable chip. The remote monitoring kit can include one or more scannable codes. The scannable code can encode a link to download the downloadable application. For example, a patient can take a picture of the scannable code with their patient user computing device 102, which can cause the patient user computing device 102 to download the downloadable application. Additionally or alternatively, a scannable code can be used for other purposes. For example, as described above with respect to FIG. 24A, the downloadable application can be configured to receive input data (such as an image of the scannable code) associated with the scannable code. Receipt of the input data by the downloadable application can cause the downloadable application to initiate pairing with a patient sensor device 104, such as the pulse oximetry sensor device. In some embodiments, the scannable code can initiate an ordering process for a prescription.

In some embodiments, the remote monitoring kit can further include a connectivity hub device 106, which can be in the package. The connectivity hub device 106 can be configured to communicate with the pulse oximetry sensor device and a remote server, such as a server of the patient management and monitoring system 110.

In some embodiments, an organization can provide a pulse oximetry sensor device to a patient. The pulse oximetry sensor device can be configured to measure blood oxygen saturation (and/or other physiological parameters such as, but not limited to, blood pressure, respiratory rate, total hemoglobin, carboxyhemoglobin, methemoglobin, oxygen content, pulse rate, perfusion index, and pleth variability index) of the patient over a monitoring period. The pulse oximetry sensor device can be configured to wirelessly connect with a patient user computing device 102.

In some embodiments, the remote monitoring kit can further include a medication applicator device. As described herein, a software application can be configured to instruct the medication applicator device to administer medication to the patient. The software application can be configured to instruct the medication applicator device to administer medication to the patient based on a physiological parameter, such as the patient's blood oxygen saturation over the monitoring period. An example medication applicator device is described above with respect to FIG. 2I.

In some embodiments, a user monitoring kit can include a wearable device one or more sensors. The wearable device can be configured to process sensor signals to determine measurement values of blood oxygen saturation of the user over a monitoring period. Additionally or alternatively, the wearable device can be configured to process sensor signals to determine measurement values of a temperature of the user over a monitoring period. The kit can further include a disposable battery and disposable sensor and a reusable processor and reusable wireless device.

At block 2604, one or more software applications can be provided. An organization can provide a software application to the patient. The software application can be configured to be installed on the patient user computing device 102. A wearable sensor assembly can be configured to wirelessly connect with the patient user computing device 102. The software application of the user computing device 102 can be configured to aggregate medical information of the user. The medical information can include received measurement values of blood oxygen saturation and/or received measurement values of a temperature of the user. The organization can provide another software application to a care provider. For example, graphical user interfaces of the software application for the care provider can be made available to clinicians of the care provider. In some embodiments, a clinician can use a web browser application to access the graphical user interfaces of the software application for the care provider. As described herein, the software application can enable the care provider to monitor the patient's physiological condition over the monitoring period without coming in close proximity with the patient.

In some embodiments, the software application of the care provider can be configured to receive medical information from the software application on the user computing device. The software application of the care provider can be further configured to process the medical information. The software application of the care provider can be further configured to output to a display viewable by the care provider, which can include indicia that is responsive to the measurement values of the blood oxygen saturation and temperature of the user during the monitored period. The indicia can include a variance from a baseline for the user at least when the user should receive further screening for the contagious respiratory infection.

A patient can configure one or more alerts, alarms, notifications, and/or emergency services using the software application on the patient user computing device 102, Example graphical user interfaces for configuring one or more alerts, alarms, notifications, and/or emergency services are described above in further detail with respect to FIGS. 24B, 24C, 24F, and 25B-25J.

At block 2606, patient data can be received. The block 2606 of FIG. 26 for receiving patient data can be similar to block 2214 of FIG. 22 for receiving physiological data and/or block 2302 of FIG. 23 for receiving patient data. In some embodiments, a software application can receive physiological parameter values generated from one or more patient sensor devices 104. The software application can receive physiological parameter values, such as, but not limited to, blood oxygen saturation ($SpO_2$), pulse rate, perfusion index, pleth variability index, and/or respiration rate. For example, as reflected in FIG. 24D, the software application can receive an oxygen saturation value of 97% and a heart rate of 65 beats-per-minute generated by patient sensor device(s) 104. As described herein, the patient user computing device 102 and/or the connectivity hub device 106 can transmit patient data to a remote server, such as a server of the patient management and monitoring system 110. The remote server, such as a server of the patient management and monitoring system 110, can receive patient data, which can include the physiological parameter values.

As described herein, example patient data can include answers to a questionnaire. Example questions, which can be used to identify a health condition (such as a respiratory infection/the novel coronavirus), can include, but are not limited to, one or more of the following questions. In the last twenty-four hours have you: Developed a cough? Experienced shortness of breath? Experienced chills? Experienced muscle pain? Lost the sense of taste or smell? Experienced nausea, vomiting, or diarrhea? Experienced loss of appetite? Experienced fatigue? The patient data can include yes/no answers to the questions.

At block 2608, patient data can be processed and/or stored. For example, the software application on the patient user computing device 102 can process and/or store the patient data. The software application can store historical physiological parameter values for a period of time. As described herein, in some embodiments, the software application can process the physiological parameters and determine if an alarm, alert, or notification is applicable. In some embodiments, the software application can store patient data on a storage device of the patient user computing device 102 in an encrypted format. The block 2608 of FIG. 26 for processing and/or storing patient data can be similar to block 2304 of FIG. 23 for processing and/or storing patient data. In some embodiments, a remote server can process and/or store patient data.

At block 2610, it can be determined whether any applicable alarm(s) and/or alert(s) are triggered. The block 2610 of FIG. 26 for determining any applicable alarm(s) and/or alert(s) can be similar to block 2306 of FIG. 23 for determining any applicable alarm(s). However, in addition or alternative to the patient monitoring service 136 checking for an alarm or alert, the patient user computing device 102 can determine whether any applicable alarm(s) and/or alert(s) are triggered. As described herein, example alerts can include measurement alerts (such as alerts associated with physiological parameter values for a user), low battery alerts, and/or sensor off alerts. For example, if blood oxygen saturation drops below eighty percent, then the patient user computing device 102 can cause one or more notifications can be sent and/or presented, as described herein. In some embodiments, there can be more than one threshold level to trigger an alert. For example, in the context of blood oxygen saturation, anything below eighty-five percent can trigger a warning notification and anything below eighty percent can trigger an emergency notification. In some embodiments, a user can adjust the threshold level(s) via the software application on the patient user computing device 102. If an alarm and/or alert is triggered, the method 2600 can proceed to the block 2612 for transmitting notifications. Otherwise, if an alarm and/or alert is not triggered, the method 2600 can proceed to the block 2618 for presenting patient data and user interface(s).

At block 2612, a network can be notified. The block 2612 of FIG. 26 for notifying a network can be similar to block 2308 of FIG. 23 for notifying a network. However, in addition or alternative to the patient monitoring service 136 notifying a network, the patient user computing device 102 can cause notification of the network. In particular, the software application on the patient user computing device 102 (and/or the patient monitoring service 136) can cause presentation of a notification in a graphical user interface, which can be based at least on a physiological parameter (such as the patient's blood oxygen saturation and/or temperature measurements) over the monitoring period.

Example notifications in graphical user interfaces are described herein, such as with respect to FIGS. 24E, 24H, 24I, 24N, 24T, 24U, 24X, and 24Y. The patient user computing device 102 can also cause a notification to be sent to the patient's network. As described herein, an example patient network can include one or more selected person(s), friends, family, caregivers, doctors, and/or clinicians. For example, the selected person(s) can receive a notification on their user computing device(s). Example notifications to a friend are described herein, such as with respect to FIG. 25A. In some embodiments, the patient monitoring service 136 can notify the care provide to contact the patient.

In some embodiments, the patient user computing device 102 can alert emergency services. As described above with respect to FIG. 24V, a patient can be prompted in a graphical user interface to confirm whether emergency services should be notified. The patient user computing device 102 and/or the patient monitoring service 136 can notify emergency medical services based at least on the patient's physiological parameters (such as blood oxygen saturation and/or temperature measurements) over the monitoring period.

At block 2614, it can be determined whether on-site care is required. The block 2614 of FIG. 26 for determining whether on-site care is required can be similar to block 2310 of FIG. 23 for determining whether on-site care is required. However, in addition or alternative to the patient monitoring service 136 determining whether on-site care is required, the patient user computing device 102 can determine whether on-site care is required. In particular, the software application on the patient user computing device 102 can determine based at least on the patient's physiological parameters (such as blood oxygen saturation) over the monitoring period, to instruct a medication applicator device to administer medication to the patient, as descried herein. For example, one or more physiological parameters can be used to detect an opioid overdose event. If on-site care is required, the method 2300 can proceed to the block 2616 for executing on-site care. Otherwise, if on-site care is not required, the method 2300 can proceed to the block 2618 for presenting patient data and user interface(s).

At block 2616, on-site care can be executed. The block 2616 of FIG. 26 for executing on-site care can be similar to block 2312 of FIG. 23 for executing on-site care. In some embodiments, the software application on the patient user computing device 102 and/or the connectivity hub device 106 can instruct the additional device(s) 114A, 114B to deliver medication in response to the indication of health event, such as an opioid overdose event. As described herein, a medication applicator device can administer an opioid receptor antagonist in response to the indication of an opioid overdose event.

At block 2618, patient data and/or user interface(s) can be presented. The block 2616 of FIG. 26 for presenting patient data can be similar to block 2314 of FIG. 23 for presenting patient data. However, in addition or alternative to the frontend server 130 presenting patient data to clinician user computing device(s) 124, the software application of the patient user computing device 102 can presenting patient data in one or more graphical user interface. Example graphical user interfaces of the software application on the patient user computing device 102 for presenting patient data can be described herein, such as with respect to FIGS. 24D-24U, 24X, 24Y, and 25A. The software application provided to a care provider can enable the care provider to view the patient's physiological parameters (such as, but not limited to, blood oxygen saturation and/or temperature measurements) over the monitoring period. Example graphical user interfaces of the software application for the care provider can be described herein, such as with respect to FIGS. 18, 19A-19B, and 20.

At block 2620, a patient can be diagnosed and/or treated for a health condition. For example, a clinician can review and/or a system can process the patient data and make a determination whether a health condition is present. For example, a preliminary indication of whether a patient has the coronavirus can be determined based on physiological parameters such as blood oxygen saturation and/or temperature measurements. A clinician can treat the patient based on the patient's physiological parameters (such as blood oxygen saturation and/or the temperature measurements) over the monitoring period. In some embodiments, a system can make a treatment recommendation based on the physiological parameters for review by a clinician. Treating the patient can include ordering mechanical ventilation for the patient. Treating the patient can include prescribing a drug to the patient. In the case of the novel coronavirus, example drugs that can be prescribed can include at least one of remdesivir, dexamethasone, azithromycin, tocilizumab, lopinavir, ritonavir, or oseltamivir. A clinician or a system can diagnose the patient with a respiratory virus. Example respiratory viruses can include SARS-COV-2, SARS-COV, or influenza. In other embodiments, a clinician or a system can diagnose the patient with an opioid addiction.

In some embodiments, the method 2600 can be used to establish a monitoring environment for a user suspected of having a contagious respiratory infection. As described herein, the user can be monitored remotely from a care provider. The monitoring environment can include one or more sensors worn by the user, a wearable device worn by the user configured to communicate with the one or more sensors and to process information responsive to output from the one or more sensors. The monitoring environment can further include a user computing device configured to wirelessly communicate with the wearable device and to communicate with a remote care provider system over a network. The care provider system can be configured to be monitored by the care provider.

In some embodiments, any of the systems or methods described herein can also be applied to and/or used in conjunction with a health monitoring system that can assist organizations to manage infectious diseases. As described herein, additional health monitoring systems and use cases are described in the health monitoring application. For example, any of the systems or methods described herein can also be applied to and/or used in conjunction with risk states and/or proximity data described in paragraphs [0007]-[0009], [0011]-[0012], [0014]-[0017], [0019]-[0022], [0024]-[0026], [0128]-[0132], [0142]-[0146], [0221], [0225]-[0226], [0228], [0223], among others, of the '794 Application.

Additional Implementation Details

Figure 27:
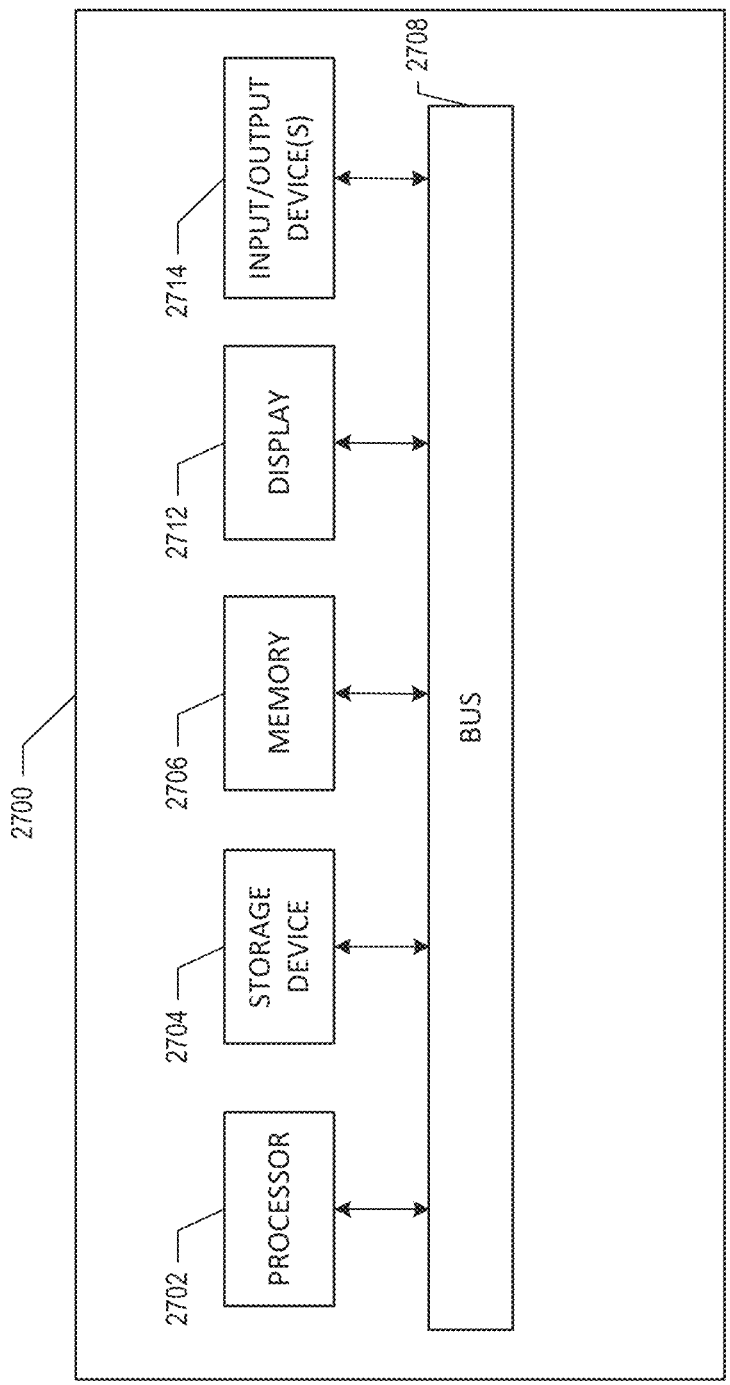
FIG. 27 illustrates a block diagram of an example computing device that may implement one or more aspects of the present disclosure, according to various embodiments of the present disclosure.

FIG. 27 is a block diagram that illustrates example components of a computing device 2700. The computing device 2700 can implement aspects of the present disclosure, and, in particular, aspects of the patient management and monitoring system 110, such as the frontend server 130, the patient data service 132, the patient care management service 134, and/or the patient monitoring service 136. The computing device 2700 can communicate with other computing devices.

The computing device 2700 can include a hardware processor 2702, a data storage device 2704, a memory device 2706, a bus 2708, a display 2712, and one or more input/output devices 2714. A processor 2702 can also be implemented as a combination of computing devices, e.g., a combination of a digital signal processor and a microprocessor, a plurality of microprocessors, one or more microprocessors in conjunction with a digital signal processor, or any other such configuration. The processor 2702 can be configured, among other things, to process data, execute instructions to perform one or more functions, such as process one or more physiological signals to obtain one or measurements, as described herein. The data storage device 2704 can include a magnetic disk, optical disk, or flash drive, etc., and is provided and coupled to the bus 2708 for storing information and instructions. The memory 2706 can include one or more memory devices that store data, including without limitation, random access memory (RAM) and read-only memory (ROM). The computing device 2700 may be coupled via the bus 2708 to a display 2712, such as a LCD display or touch screen, for displaying information to a user, such as a clinician. The computing device 2700 may be coupled via the bus 2708 to one or more input/output devices 2714. The input device 2714 can include, but is not limited to, a keyboard, mouse, digital pen, microphone, touch screen, gesture recognition system, voice recognition system, imaging device (which may capture eye, hand, head, or body tracking data and/or placement), gamepad, accelerometer, or gyroscope.

Additional Patient Management and Monitoring Embodiments

Additional patient management and monitoring embodiments are described in the following paragraphs. For example, a patient management system can be designed to help clinicians care for patients remotely over a period of time. As described herein, an example patient management system may be Masimo SafetyNet. The patient management system can advantageously adapt non-clinical spaces into advanced care environments with a range of sensors and vital signs monitors as described below.

Figure 28A:
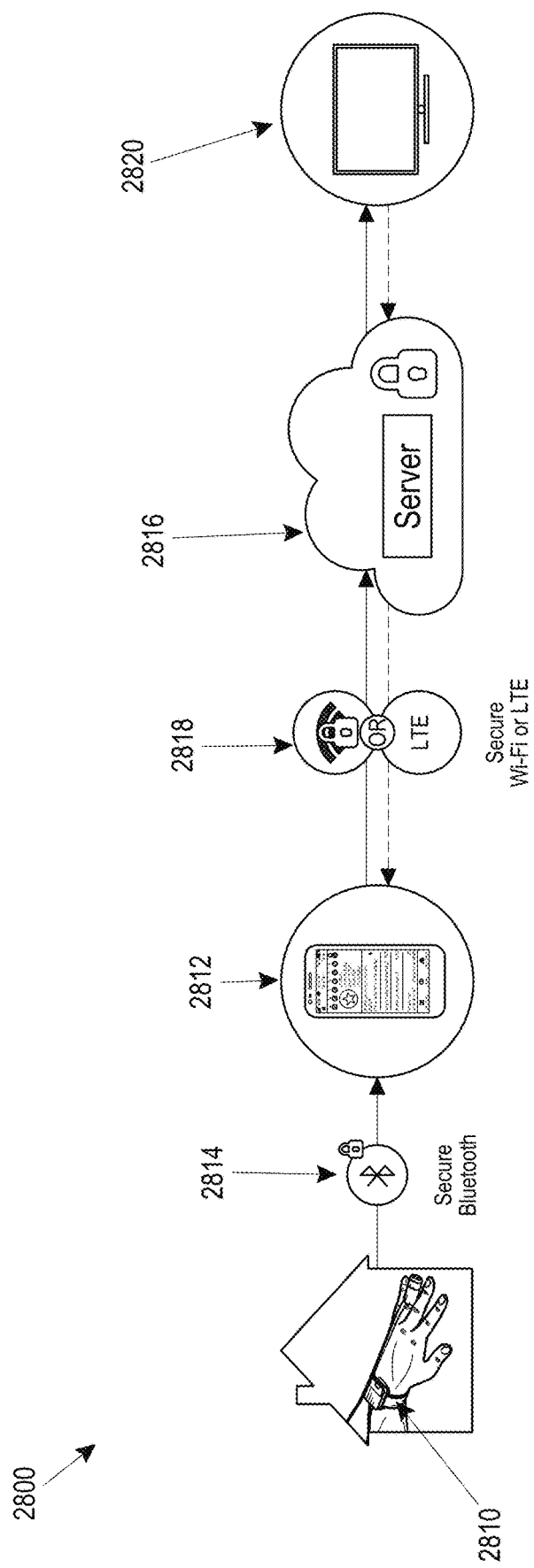
FIG. 28A illustrates a network architecture 2800 for enabling remote management of patients, according to some embodiments of the present disclosure.

FIG. 28A illustrates a network architecture 2800 for enabling remote management of patients. The network architecture 2800 can include a wireless sensor system 2810 that is capable of transmitting data to a mobile computing device 2812 such as iOS or Android™ enabled smartphones or another mobile computing device via a wireless link 2814. In some examples, the wireless link 2814 is a Bluetooth link. Other wireless links, such as NFC or WiFi can also be used for connection between the wireless sensor system 2810 and the mobile computing device 2812. The mobile computing device 2812 may communicate with a remote patient management system (RPMS) 2850 (see FIG. 28C) that can display the collected data from wireless sensor system 2810 in a format that is readable by a patient or a user of the mobile computing device 2812. The RPMS 2850 can generate customized user interfaces as shown in more detail below. The mobile computing device 2812 in combination with the RPMS 2850 may enable transmission of the collected data to a server 2816 via a network connection link 2818. In some examples, the network connection link 2818 can include WiFi or other wireless broadband communication systems.

In some examples, the mobile computing device 2812 can be replaced with a connectivity hub that enables data collection from the wireless sensor system 2810 and transmits the collected data to the server 2816 via the communication link 2818. Not all users have access to a smart phone or mobile computing devices. Accordingly, the connectivity hub as shown in FIG. 28B can enable collection and transmission of data.

A care provider monitoring system 2820 can access the collected data from the server 2816. The care provider monitoring system 2820 can include a computing system associated with a hospital, a caregiver (such as a primary provider), or a user (friends or family) that have permission to access the patient's data.

Figure 28B:
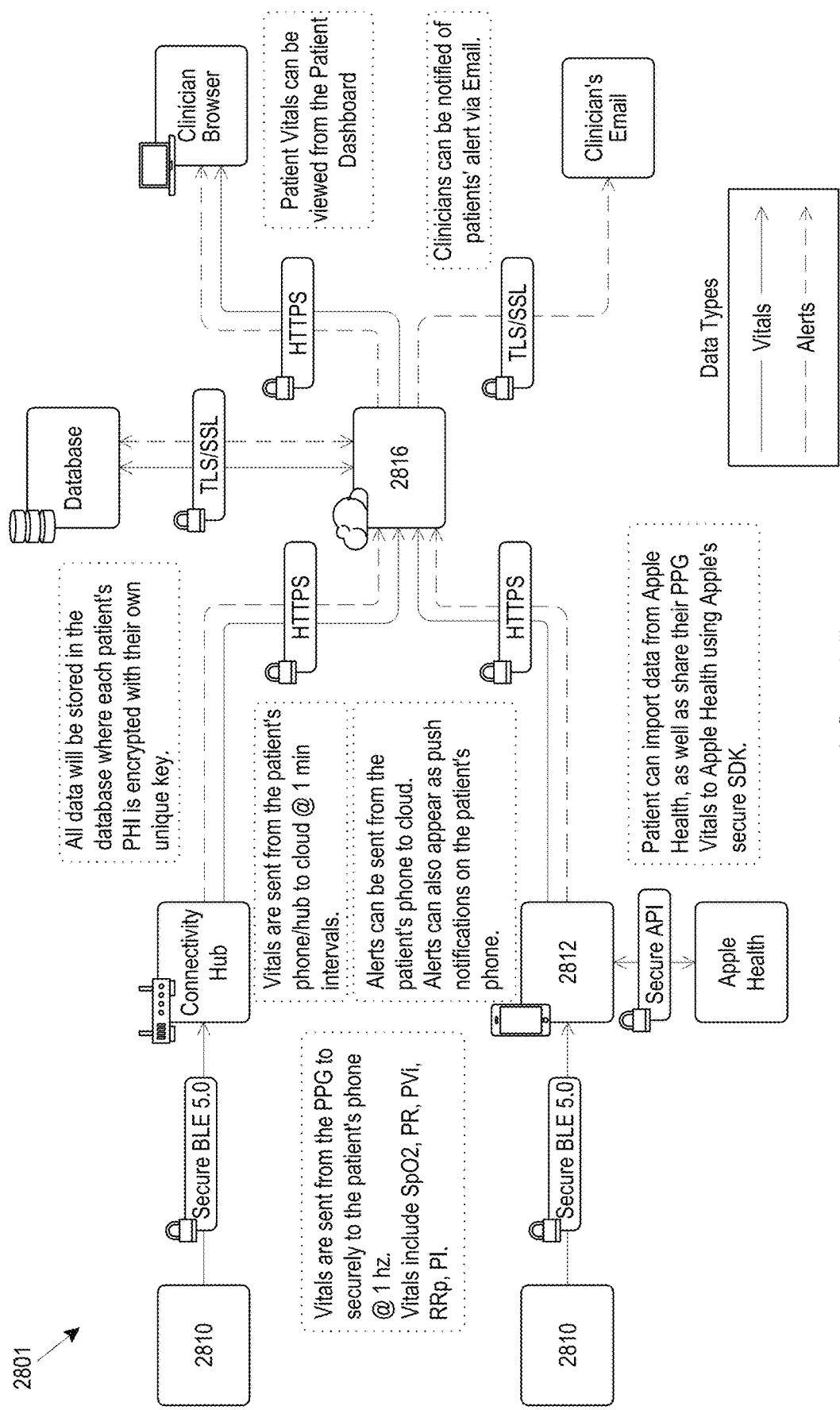
FIG. 28B illustrates an extended architecture, supplementing the architecture of FIG. 28A, according to some embodiments of the present disclosure.

FIG. 28B shows an extended architecture 2801, supplementing the architecture 2800 discussed above with respect to FIG. 28A. The wireless sensor system 2810 can collect physiological data. In some instances, the wireless sensor system 2810 can store 96 hours of data. This data can be streamed directly to the mobile computing device 2812. In some instances, when the mobile computing device 2812 is offline or not in the vicinity, data can be transferred when the mobile computing device 2812 is connected back with the wireless sensor system 2810. Accordingly, the wireless sensor system 2810 can keep monitoring and transmit when the mobile computing device 2812 is available.

The mobile computing device 2812 can associate the collected physiological data with patient identification information and transmit the data to the server 2816 as discussed above with respect to FIG. 28A. Likewise, connectivity hub can also transmit the collected data to the server 2816. In some instances, the database is part of the server 2816, that it is located within same networking environment. The clinicians can access the collected patient data with a web browser. The clinicians can monitor one patient or multiple patients in a dashboard. The clinicians can access trend chart of the patients. Moreover, clinicians can obtain patient alerts via email. In some instances, patient data may be replicated on clinician's mobile computing device using Masimo's Replica™ System, available from Masimo Corporation, Irvine, CA. In some examples, users can integrate their monitored data with Apple Health and/or Google Fit™ interfaces via the RPMS 2850 as discussed below.

While FIGS. 28A and 28B show a cloud based system, in some instances, connectivity between the wireless sensor system 2810 may be enabled inside the hospital using a network system, such as Masimo's Patent SafetyNet. During a contagion management situation, it may be ideal for caregivers to not come in close contact with patients on frequent basis. Accordingly, ad hoc remote monitoring system can be created at the hospital. The wireless sensor system 2810 (such as the Radius PPG available from Masimo Corporation and shown in FIG. 29) can be paired with a receiver. In some examples, the receiver can enable transmission of data to a patient monitor which in turn transmits the data to a hospital server. In other examples, the receiver is a communication hub that can directly transmit the data to the hospital server. Accordingly, caregivers can monitor multiple patients from a central location or even outside of a particular patient's hospital room, thereby limiting the interactions. This can also be useful in field hospitals that are set up on demand. A central monitoring station can be set up to monitor many patients through a local ad-hoc network.

Figure 28C:
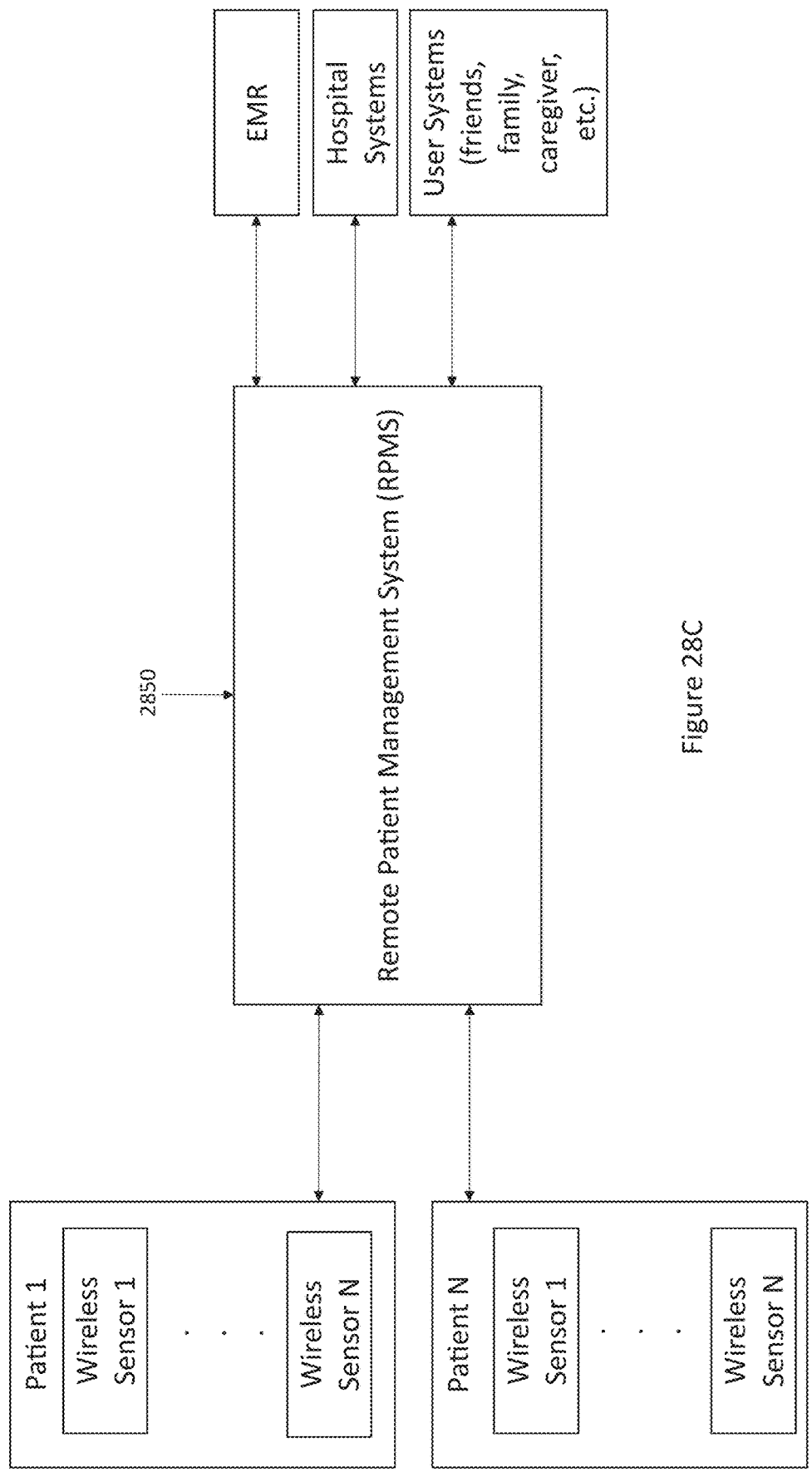
FIG. 28C illustrates a block diagram of the remote patient management system, according to some embodiments of the present disclosure.

FIG. 28C illustrates a block diagram of the RPMS 2850. The RPMS 2850 can be a software application including multiple engines that can be implemented across multiple devices, such as the mobile computing device 2812, the server 2816, and the care provider monitoring system 2820. The RPMS 2850 can collect data from multiple wireless sensor systems associated with a patient. The RPMS 2850 can further collect data from multiple patients that are monitored in different locations. The RPMS 2850 can collect data periodically for transmission to the server 2816. The RPMS 2850 can generate user interfaces for presenting the collected data and reports associated with the collected data.

Figure 29:
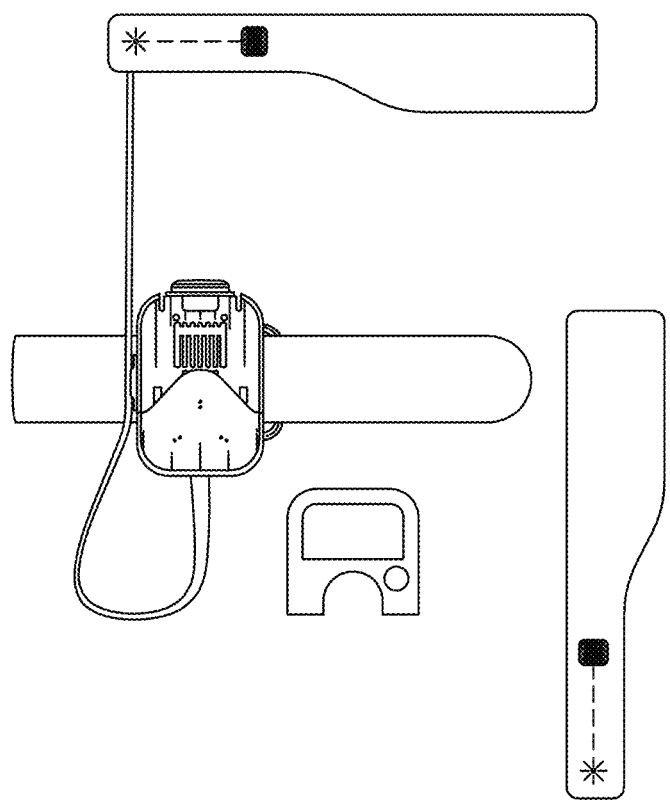
FIG. 29 illustrates an example wireless sensor system, according to some embodiments of the present disclosure.

FIG. 29 illustrates an example wireless sensor system 2810. Further details on the wireless sensor system 2810, including pairing to the mobile computing device 2812, can be found in the Dual Communication reference.

As shown in FIG. 28B, the RPMS 2850 can additionally or alternatively include a different wireless sensor system from the system shown in FIG. 29. In some instances, the wireless sensor system 2810 can include Masimo's MightySat™ available from Masimo Corporation, Irvine, CA. In some instances, multiple wireless sensors systems 2810 can be part of the network architecture 100. For example, additional wireless sensors systems 2810 can include a temperature monitoring system (described below), an ECG monitoring system, a blood pressure monitoring system, an acoustic sensor monitoring system, and any other physiological monitoring system capable of communication using the wireless link 2814.

In some implementations, the wireless sensor system(s) 2810 may include a pulse oximetry sensor with respiration rate monitoring. The pulse oximetry sensor can provide continuous respiration rate and oxygen saturation monitoring. The pulse oximetry sensor can also monitor the patient's pulse rate, pleth variability index, perfusion, index, among other physiological parameters. Alternatively or additionally, the wireless sensor system(s) 2810 may include a temperature monitoring system worn on the patient's body for measuring temperature. An example of such a temperature monitoring system 104 is shown in the FIGS. 2G-2H. Such a temperature monitoring system 104 is described in U.S. Pat. No. 10,226,187, issued on Mar. 12, 2019, titled "PATIENT-WORN WIRELESS PHYSIOLOGICAL SENSOR," which is hereby incorporated by reference in its entirety. The temperature monitoring system 104 can include a patch to secure it on the patient's body, such as the patient's chest. The temperature monitoring system 104 can provide continuous temperature monitoring. The temperature monitoring system 104 can connect directly to a mobile computing device 2800 via the wireless link 2814 discussed above.

In some implementations, the remote patient monitoring system may include a digital discussion platform that may incorporate questions and possible answers to direct a patient consultation. Further details of the remote patient monitoring system can be found in U.S. Patent Application Publication No. 2017/0024748, titled "GUIDED DISCUSSION PLATFORM FOR MULTIPLE PARTIES," which is hereby incorporated by reference in its entirety.

In some implementations, the remote patient management system may incorporate a secured data sharing to allow the remote patient surveillance system to share patient physiological data with others, for example, care providers, without the surveillance system gaining access to data. The secured data sharing may incorporate multiple layers of encryption with multiple entry points to some of the layers. Further details of the secured data sharing can be found in U.S. Patent Application Publication No. 2018/0013562, titled "SECURE AND ZERO KNOWLEDGE DATA SHARING FOR CLOUD APPLICATIONS," which is hereby incorporated by reference in its entirety.

The RPMS 2850 may offer care providers a single-platform solution that couples a secure, cloud-based monitoring platform with patient sensors that can monitor blood oxygen saturation ($SpO_2$), pulse rate, perfusion index, pleth variability index, and respiration rate from the photoplethysmograph, and the like. Optionally, the system can also monitor the patient's body temperature. The sensor monitoring can be continuous or periodic.

Patients can be sent home with one or more of wireless patient sensors 2810 along with access to a secure, home-based, remote patient surveillance system. In some examples, patients may receive a multi-day supply of sensors. For example, the wireless patient sensor 2810 can be a Radius PPG sensor, a sensor available at Masimo Corporation, Irvine, CA, and/or other suitable wireless sensors. Examples user interfaces provided by the RPMS 2850 can include user interfaces from the SafetyNet mobile application. The RPMS 2850 can include the Doctella™ mobile application, a home-based patient engagement and remote care automation platform available at Masimo Corporation, Irvine, CA. The RPMS 2850 may be designed to provide easy, intuitive patient use via a digital home-care plan. The RPMS 2850 can provide a dashboard user interface for a care provider to monitor multiple patient simultaneously. In some instances, the patients can be monitored for respiratory distress. Further, in some instances, the patients can be monitored during virus outbreaks. The RPMS 2850 may generate alerts when the patient may need urgent attention, including admission in the hospital based on monitoring a trend in physiological parameters. For example, if the patient's temperature is above normal for a substantial period of time and the blood oxygenation is decreasing, it may be an indication of the progression of a disease (such as COVID-19). In some instances, an alert is triggered by the RPMS 2850 when the blood oxygenation falls below 93 for more than 5 minutes.

In some implementations, the RPMS 2850 may offer programs or regimes that are digital replacement for traditional home-care plans and may be delivered to patients' smartphones. Programs can include for example, contagious disease monitoring, glucose monitoring, blood pressure monitoring, and other health condition monitoring and compliance. The programs can be predefined and selectable by the clinicians. The programs can be dynamically modified by changing government guidelines. The RPMS 2850 can actively remind patients to follow their regimen, automatically capture monitoring data from the wireless sensor system, and securely push (or transmit) the data to clinicians at the hospital for evaluation. In some implementations, the digital home-care plan may follow CDC and WHO guidance for monitoring suspected COVID-19 or other communicable disease subjects, which can be easily updated at any time to accommodate evolving guidance or hospital protocol. The patient management system can provide support during a surge in demand for medical care. The system can expand the ability of healthcare professionals to monitor conditions of patients that need non-urgent medical care (for example, patients with mild or moderate symptoms) and care for those patient remotely, while saving the limited hospital beds and urgent care facilities (for example, the intensive care units) for patients who are in more critical conditions, such as needing intubation and/or assisted breathing. Conditions of the patients who are experiencing mild or moderate symptoms, or suspected of having been infected by virus or bacteria can be more accurately and/or more timely monitored using the patient management system, for example, as compared to asking the patient to self-report breathlessness, fever, or other medical conditions. In times of an epidemic or pandemic, patients who otherwise need their vital signs monitored by a healthcare professional can also receive medical care using the patient management system. The reduction in need for patients to visit the hospital or other clinical setting unless in urgent situations can also facilitate in reducing cross-contamination (among patients, healthcare professionals, and other care takers) during epidemics or pandemics.

Additionally and/or optionally, the RPMS 2850 may collect other physiological data, for example, temperature, heart rate, and the like from user inputs via interactive user interfaces. For example, the RPMS 2850 may notify patients to answer questions such as, "are you having trouble breathing?" and "what is your temperature?", and securely push patient responses to those questions to care providers for evaluation. Such questions may be displayed on a screen or be read aloud to patients depending on accessibility options provided by care providers or patients. Alternatively, physiological data such as the temperature, heart rate, or others, can be measured automatically by the wireless sensor system worn by the patient. For example, the sensor system can include a temperature sensor 104 that is in thermal contact with the patient's skin, for example, through thermally conductive materials between the temperature sensor and the patient's skin. The temperature sensor can be configured to measure the patient's core body temperature using a technique by which deep tissue temperature can be measured from the skin surface. The technique can involve, for example, insulating the skin surface at and around the point at which the skin temperature is measured, thereby blocking heat from escaping the insulated skin surface. The temperature gradient between the body core and the skin surface can therefore decrease. The skin temperature under the insulated area can rise until reaching equilibrium with the warmest region (that is, the body core) under the insulation, thereby approaching the body core temperature. When equilibrium is reached, the skin temperature measured by the temperature sensor can be equal to the core body temperature. Alternatively, such a temperature sensor and the core body temperature sensing technique can be incorporated into the tetherless pulse oximetry sensor disclosed herein. Additionally and/or optionally, the remote patient surveillance system can transmit the patient responses along with physiological monitoring data. In some implementations, the remote patient surveillance system can proactively notify patients to submit status updates or request patients to submit status updates based at least in part on physiological data collected from the patient.

The RPMS 2850 may include a secured online portal that may allow care providers to easily track patient compliance, helping the care providers to identify when intervention may be needed, as well as providing insight to prioritize patients. With advanced automation features, institutions can more easily deploy home care monitoring at scale while ensuring clinicians stay informed of important developments in a patient's condition. In some implementations, the RPMS 2850 can be fully customizable to accommodate each institution's protocols, each patient's needs, and any changes in guidance. Additionally and/or optionally, the remote patient surveillance system can be updated through the cloud by providers even after being deployed, for maximum flexibility as situations evolve.

In some implementations, the digital home-care plan generated by RPMS 2850 may enable providers to monitor suspected COVID-19 patients at home until they recover or require hospital admission. The digital home-care plan may collect vital patient information by pulling data from the wireless sensor system and proactively notifying patients to submit status updates. For patients who need to visit the hospital or another clinical setting, the wireless sensor system disclosed herein can allow a healthcare professional to monitor (for example, continuously monitor) the patient from outside the room in which the patient is located, for example, via a patient monitor wirelessly connected to the sensor system or the healthcare professional's mobile computing device. Keeping the distance and/or physical barrier between the patient and the healthcare professional can further reduce the risks of cross-contamination.

Figure 30:
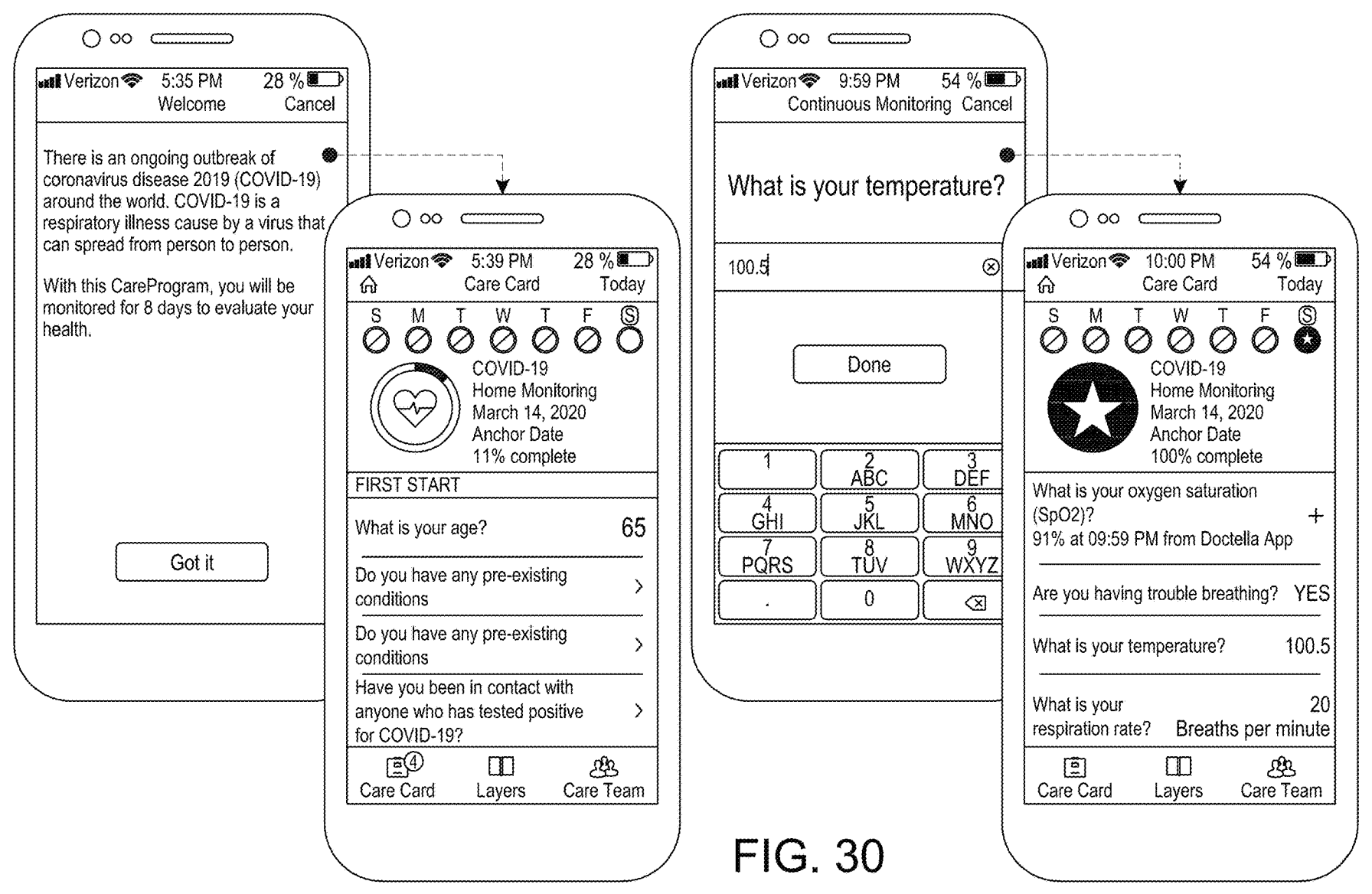

The RPMS 2850 can, for example, upon initialization, provide patients with descriptions of the digital home-care plan and a series of initial questions. An example graphical user interface providing patients with descriptions of the digital home-care plan and a series of initial questions is shown in FIG. 30.

Additionally and/or alternatively, the RPMS 2850 can periodically provide, as described herein, a series of questions that can be used to determine patient status. Such questions may include: "What is your oxygen saturation?" "What is your respiration rate?" "What is your temperature" (which may optionally be replaced and/or supplemented by the measurement from the temperature sensor disclosed herein) and "Are you having trouble breathing?" Example graphical user interfaces providing a series of questions to patients is shown in FIG. 30. In some implementations, the questions may be provided as directed or a certain number of times per day.

Figure 31:
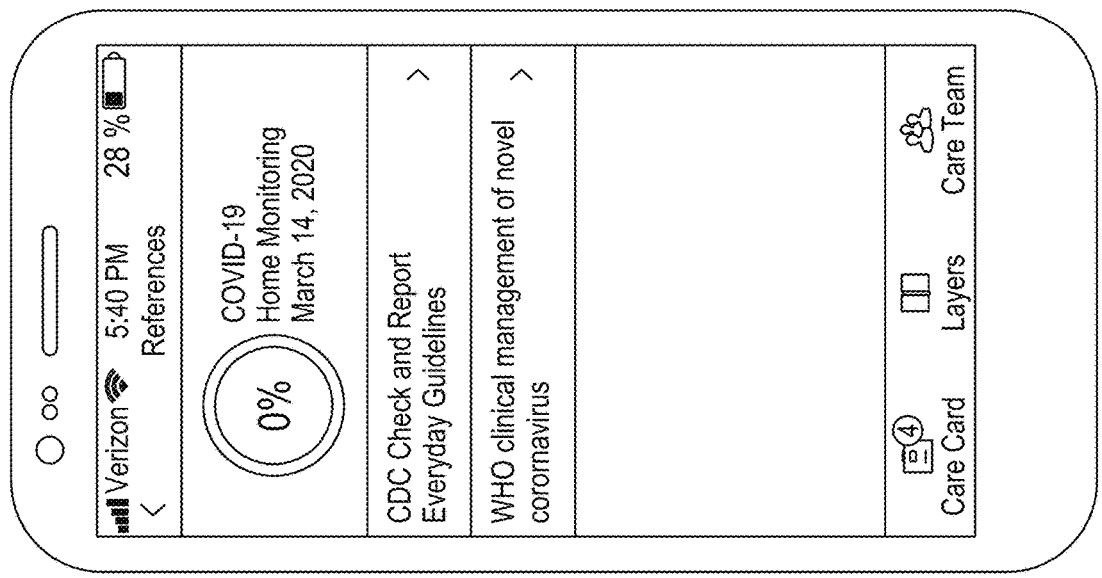
FIG. 31 illustrates an example graphical user interface providing resources to users, according to some embodiments of the present disclosure.

In some implementations, the RPMS 2850 can include a resource library with guidance on, for example, checking temperature, applying the wireless sensor system, manually gathering data from the wireless sensor system, checking heart rate, and the like. An example graphical user interface providing resources to users is shown in FIG. 31.

In some implementations, the RPMS 2850 can generate and provide displays of patient physiological data via, for example graphical user interfaces. Such displays can be made available to the user and/or care providers. To ensure privacy and security of such data, the RPMS 2850 may request users and care providers to provide authentication prior to providing and displaying patient physiological data.

Additional Client Graphical User Interfaces

Figure 32A:
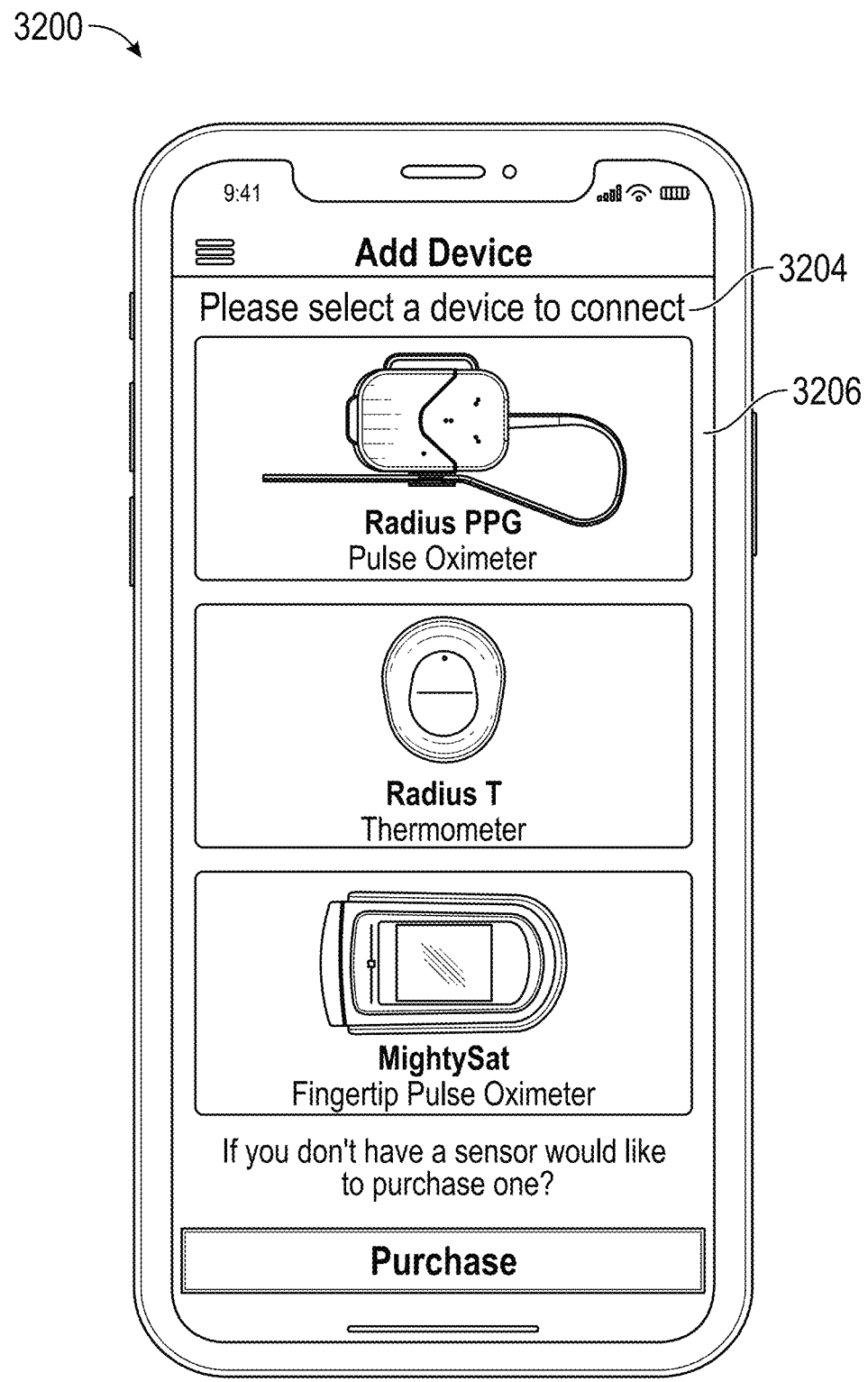
FIGS. 32A-32C illustrate additional example graphical user interfaces of a patient care application, according to some embodiments of the present disclosure.
Figure 32B:
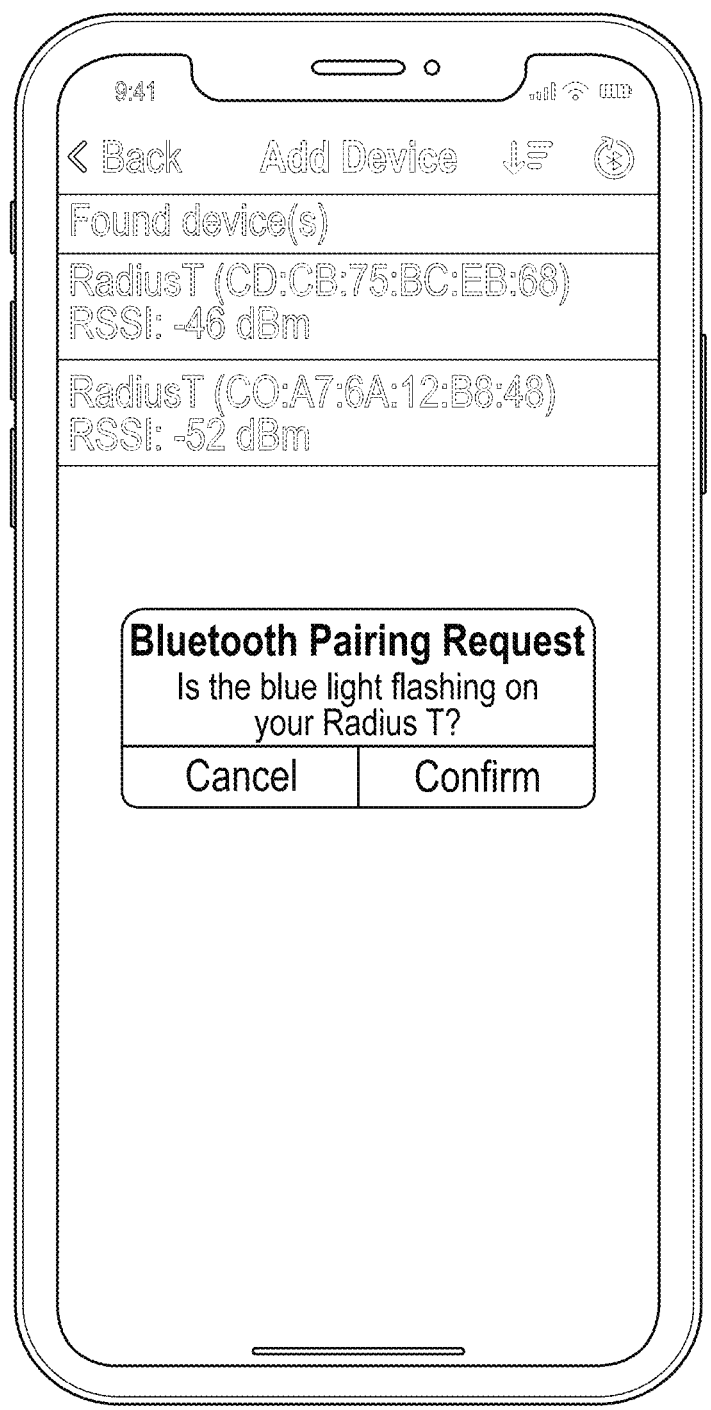
Figure 32C:
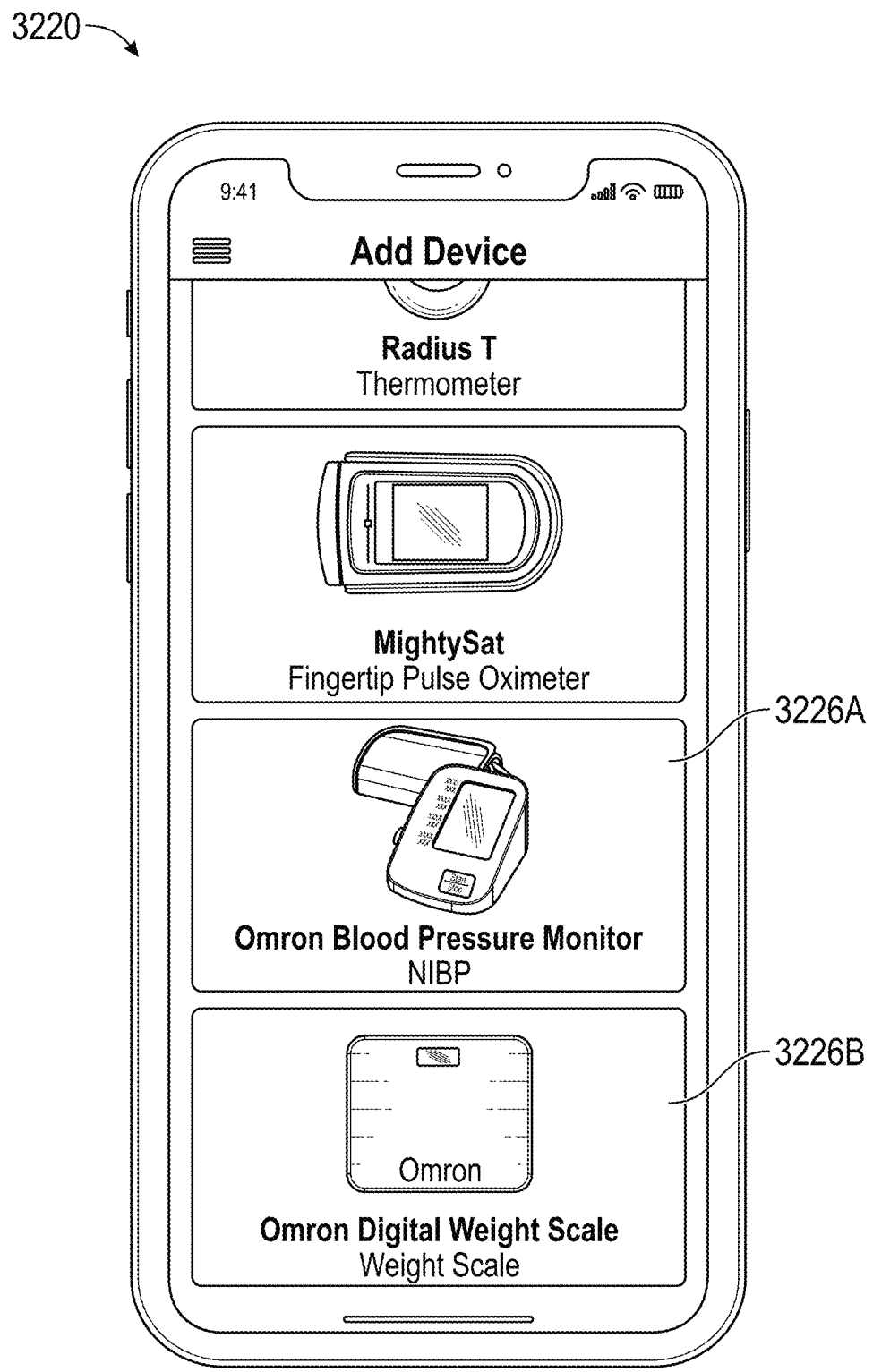

FIGS. 32A-32C illustrate additional example graphical user interfaces of a patient care application 120, according to some embodiments of the present disclosure. In various embodiments, aspects of the user interfaces may be rearranged from what is shown and described below, and/or particular aspects may or may not be included. The patient care application 120 can execute on the patient user computing device 102 to present the graphical user interfaces of FIGS. 32A-32C.

FIG. 32A illustrates a graphical user interface 3200 of the patient care application 120. The graphical user interface 3200 can include a list of device items 3204. The graphical user interface 3200 can be presented to a user as part of the setup process of a patient care user interface, which can include configuring patient sensor devices. For example, a user can select the pulse oximeter element 3206 to begin a pulse oximeter setup process. As another example, a user can select a thermometer element to begin a thermometer setup process.

FIG. 32B illustrates another graphical user interface 3210 of the patient care application 120. The graphical user interface 3210 can present a list of patient sensor devices. In some cases, such as a hospital setting or a setting that is using health monitoring systems, there can be multiple patient sensor devices in a vicinity. Thus, the graphical user interface 3210 can present the list of patient sensor devices sorted by signal strength, such as a Bluetooth signal strength. For example, patient sensor devices can be sorted by Received Signal Strength Indicator for Bluetooth devices.

FIG. 32C illustrates another graphical user interface 3220 of the patient care application 120. The graphical user interface 3220 of FIG. 32C can be similar to the graphical user interface 3200 of FIG. 32A. However, unlike the list of device items 3204 of FIG. 32A, the list of device items of the graphical user interface 3220 of FIG. 32C can include a blood pressure monitor element 3226A and a digital weight scale element 3226B.

Additional Embodiments and Terminology

While the present disclosure discusses example connectors in the medical device and/or patient monitoring context, the apparatuses, systems, and methods described herein may be agnostic to the particular context, and, therefore, may be used in any connector environment. Further, while the present disclosure discusses advantages of the example connectors as including water resistance, other embodiments of devices, apparatuses, systems, and/or methods described herein may not necessarily be water resistant and may have other advantages, as described herein.

As used herein, in addition to its ordinary meaning, the term "patient" can refer to any person that is monitored using the systems, methods, devices, and/or techniques described herein. As used herein, a "patient" is not required-to be admitted to a hospital, rather, the term "patient" can refer to a person that is being monitored. As used herein, in some cases the terms "patient" and "user" can be used interchangeably.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conditional language used herein, such as, among others, "can," "might," "may," "e.g.," "for example," and the like, unless specifically stated otherwise, or otherwise understood within the context as used, is generally intended to convey that certain embodiments include, while other embodiments do not include, certain features, elements, or states. Thus, such conditional language is not generally intended to imply that features, elements or states are in any way required for one or more embodiments.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Such disjunctive language is not generally intended to, and should not, imply that certain embodiments require at least one of X, at least one of Y, or at least one of Z to each be present. Thus, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The terms "comprising," "including," "having," and the like are synonymous and are used inclusively, in an open-ended fashion, and do not exclude additional elements, features, acts, operations, and so forth.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A method of reducing demand on medical facilities by monitoring a patient continuously in a home environment using medical devices, the method performed by at least one medical monitor, the method comprising:

pairing a mobile device of the patient with a wireless wearable patient monitoring device by the mobile device or the wireless wearable patient monitoring device generating and transmitting a pairing signal, wherein the pairing signal includes energy to enable nearby devices to transmit pairing parameters in response to the pairing signal, the wireless wearable patient monitoring device configured to measure at least blood oxygen saturation of the patient wearing the wireless wearable patient monitoring device over a monitoring period;

wirelessly receiving measurement data from the wireless wearable patient monitoring device;

on a processor, determining based at least on the patient's measured blood oxygen saturation over the monitoring period that the patient is experiencing a worsening medical condition and may need to be moved to a clinical facility for treatment;

electronically transmitting and causing to be displayed on a display of the mobile device of the patient an indication of the patient's worsening condition and providing instructions to the patient on appropriate steps to be taken by the patient;

electronically transmitting and causing to be displayed an alert to a mobile device of a designated family member or friend, the alert indicating the patient is experiencing a worsening medical condition and may need to be moved to a clinical facility for treatment, the alert providing patient status, patient location and an indication the patient may need to be moved to a clinical facility; and electronically transmitting to an electronic device of a care provider the patient's physiological condition over the monitoring period.

2. The method of claim 1, further comprising:
diagnosing the patient with one or more of a respiratory virus or an overdose event.

3. The method of claim 2, wherein the respiratory virus comprises at least one of severe acute respiratory syndrome coronavirus 2 (SARS-COV-2), severe acute respiratory syndrome-related coronavirus (SARS-COV), or influenza.

4. The method of claim 1, further comprising:
providing each of a plurality of patients a software application that is configured to be installed on a respective patient user computing device, said wireless wearable patient monitoring device configured to wirelessly connect with respective patient user computing devices.

5. The method of claim 1, wherein the processor is further configured to provide an alert based on the patient's measured blood oxygen saturation over the monitoring period.

6. The method of claim 1, further comprising:
providing treatment options to the patient based at least on the patient's measured blood oxygen saturation over the monitoring period.

7. The method of claim 1, further comprising:
notifying emergency medical services based at least on the patient's measured blood oxygen saturation over the monitoring period.

8. The method of claim 1, wherein the medical monitor is further configured to monitor and transmit patient temperature measurements over the monitoring period.

9. The method of claim 1, wherein the wireless wearable patient monitoring device is further configured to measure the patient's respiratory rate over the monitoring period.

10. The method of claim 1, wherein electronically transmitting to an electronic device of a care provider the patient's physiological condition over the monitoring period further comprising electronically transmitting direct patient contact information with the patient's physiological condition.

11. The method of claim 1, further comprising varying a strength of the pairing signal.

12. The method of claim 1, wherein the pairing parameters comprise identification information for the wireless wearable patient monitoring device.

13. The method of claim 12, wherein the identification information for the wireless wearable patient monitoring device comprises a serial number, a stock number, a lot number, or a batch number.

* * * * *

UNITED STATES PATENT AND TRADEMARK OFFICE
CERTIFICATE OF CORRECTION

PATENT NO. : 12,064,217 B2
APPLICATION NO. : 17/207447
DATED : August 20, 2024
INVENTOR(S) : Omar Ahmed et al.

It is certified that error appears in the above-identified patent and that said Letters Patent is hereby corrected as shown below:

In the Specification

Column 1, Line 5, delete "Ai" and insert -- AI --.

Column 2, Line 64, delete "Ai" and insert -- AI --.

Column 6, Line 59, delete "COV" and insert -- CoV --.

Column 6, Line 61, delete "COV" and insert -- CoV --.

Column 7, Line 65, delete "COV" and insert -- CoV --.

Column 7, Line 66, delete "COV" and insert -- CoV --.

Column 13, Line 32, delete "COV" and insert -- CoV --.

Column 13, Line 50, delete "COV" and insert -- CoV --.

Column 27, Line 45, delete "(IOT)" and insert -- (IoT) --.

Column 50, Line 28, above "FIG. 22" insert -- Patient Care User Interface Implementation Methods --.

Column 66, Line 24, delete "COV" and insert -- CoV --.

Column 66, Line 24, delete "COV" and insert -- CoV --.

Signed and Sealed this
Seventeenth Day of December, 2024

Derrick Brent
*Acting Director of the United States Patent and Trademark Office*

In the Claims

Column 75, Line 6, in Claim 3, delete "COV" and insert -- CoV --.

Column 75, Line 7, in Claim 3, delete "COV" and insert -- CoV --.